US010259796B2

(12) United States Patent
Vath et al.

(10) Patent No.: US 10,259,796 B2
(45) Date of Patent: Apr. 16, 2019

(54) OXASPIRO[2.5]OCTANE DERIVATIVES AND ANALOGS

(71) Applicant: Zafgen, Inc., Boston, MA (US)

(72) Inventors: James E. Vath, Lynnfield, MA (US); Stuart Chaffee, Wellesley, MA (US)

(73) Assignee: Zafgen, Inc., Boston, MA (US)

( * ) Notice: Subject to any disclaimer, the term of this patent is extended or adjusted under 35 U.S.C. 154(b) by 0 days.

(21) Appl. No.: 15/609,813

(22) Filed: May 31, 2017

(65) Prior Publication Data

US 2018/0354924 A1  Dec. 13, 2018

Related U.S. Application Data

(63) Continuation of application No. 15/068,942, filed on Mar. 14, 2016, now abandoned, which is a continuation of application No. 14/003,906, filed as application No. PCT/US2012/028068 on Mar. 7, 2012, now Pat. No. 9,328,082.

(60) Provisional application No. 61/450,301, filed on Mar. 8, 2011.

(51) Int. Cl.
| | |
|---|---|
| C07D 303/38 | (2006.01) |
| C07D 303/46 | (2006.01) |
| C07D 491/107 | (2006.01) |
| C07B 59/00 | (2006.01) |
| C07D 303/40 | (2006.01) |
| C07D 493/10 | (2006.01) |
| C07D 491/10 | (2006.01) |
| C07D 453/02 | (2006.01) |
| C07D 405/14 | (2006.01) |
| C07D 303/36 | (2006.01) |
| C07D 303/34 | (2006.01) |
| C07D 303/32 | (2006.01) |
| C07D 303/22 | (2006.01) |

(52) U.S. Cl.
CPC .......... *C07D 303/46* (2013.01); *C07B 59/004* (2013.01); *C07D 303/22* (2013.01); *C07D 303/32* (2013.01); *C07D 303/34* (2013.01); *C07D 303/36* (2013.01); *C07D 303/38* (2013.01); *C07D 303/40* (2013.01); *C07D 405/14* (2013.01); *C07D 453/02* (2013.01); *C07D 491/10* (2013.01); *C07D 491/107* (2013.01); *C07D 493/10* (2013.01); *C07B 2200/05* (2013.01)

(58) Field of Classification Search
None
See application file for complete search history.

(56) References Cited

U.S. PATENT DOCUMENTS

| | | |
|---|---|---|
| 5,164,410 A | 11/1992 | Kishimoto et al. |
| 5,166,172 A | 11/1992 | Kishimoto et al. |
| 5,180,735 A | 1/1993 | Kishimoto et al. |
| 5,180,738 A | 1/1993 | Kishimoto et al. |
| 5,196,406 A | 3/1993 | Kamei et al. |
| 5,204,345 A | 4/1993 | Kishimoto et al. |
| 5,288,722 A | 2/1994 | Kishimoto et al. |
| 5,290,807 A | 3/1994 | Folkman et al. |
| 5,422,363 A | 6/1995 | Yanai et al. |
| 5,536,623 A | 7/1996 | Ohmachi et al. |
| 5,698,586 A | 12/1997 | Kishimoto et al. |
| 5,767,293 A | 6/1998 | Oku et al. |
| 5,846,562 A | 12/1998 | Yanai et al. |
| 5,900,431 A | 5/1999 | Molina et al. |
| 6,017,949 A | 1/2000 | D'Amato et al. |
| 6,017,954 A | 1/2000 | Folkman et al. |
| 6,040,337 A | 3/2000 | Hong, II et al. |
| 6,063,812 A | 5/2000 | Hong et al. |
| 6,180,626 B1 | 1/2001 | Shimomura et al. |
| 6,207,704 B1 | 3/2001 | Liu et al. |
| 6,306,819 B1 | 10/2001 | Rupnick et al. |
| 6,323,228 B1 | 11/2001 | BaMaung et al. |
| 6,383,471 B1 | 5/2002 | Chen et al. |
| 6,548,477 B1 | 4/2003 | Olson et al. |
| 6,566,541 B2 | 5/2003 | Liu et al. |
| 6,664,244 B1 | 12/2003 | Furuse et al. |
| 6,803,382 B2 | 10/2004 | Eustache et al. |
| 6,989,392 B2 | 1/2006 | Collins et al. |
| 7,084,108 B2 | 8/2006 | Olson et al. |
| 7,268,111 B2 | 9/2007 | Olson et al. |
| 7,718,695 B2 | 5/2010 | Kim et al. |
| 8,367,721 B2 | 2/2013 | Hughes et al. |
| 9,328,082 B2 | 5/2016 | Lane et al. |
| 2004/0067266 A1 | 4/2004 | Toppo |
| 2004/0116495 A1 | 6/2004 | Marino, Jr. et al. |
| 2004/0204472 A1 | 10/2004 | Briggs et al. |

(Continued)

FOREIGN PATENT DOCUMENTS

| | | |
|---|---|---|
| EP | 0682020 A1 | 11/1995 |
| WO | WO-1999/059986 A1 | 11/1999 |

(Continued)

OTHER PUBLICATIONS

Issued U.S. Pat. No. 9,328,082, Issued on May 3, 2016; U.S. Appl. No. 14/003,906; published as US 2015-0045427 A1, on Feb. 12, 2015, Oxaspiro[2.5]Octane Derivatives and Analogs, Oct. 29, 2014.
Anderson, "The Use of Fumagillin in Amoebiasis" Ann N Y Acad Sci. Dec. 30, 1952;55(6):1118-24.
Benny et al., "An Orally Delivered Small-Molecule Formulation with Antiangiogenic and Anticancer Activity" Nat Biotechnol. Jul. 2008;26(7):799-807. doi: 10.1038/nbt1415. Epub Jun. 29, 2008.
Bernier et al., "Fumagillin class inhibitors of methionine aminopeptidase-2" Drugs of the Future 30(5):497-500, 2005.
Brakenhielm et al., "Angiogenesis Inhibitor, TNP-470, Prevents Diet-Induced and Genetic Obesity in Mice" Circulation Research, http://circres.ahajournals.org (accessed on Feb. 8, 2007), 2004.

(Continued)

*Primary Examiner* — Samantha L Shterengarts
(74) *Attorney, Agent, or Firm* — Goodwin Procter LLP

(57) ABSTRACT

The invention provides oxaspiro[2.5]octane derivatives and analogs, methods for preparation thereof, intermediates thereto, pharmaceutical compositions, and uses thereof in the treatment of various disorders and conditions, such as overweight and obesity.

9 Claims, 4 Drawing Sheets

(56) References Cited

U.S. PATENT DOCUMENTS

| | | |
|---|---|---|
| 2005/0037994 A1 | 2/2005 | Kim et al. |
| 2005/0239878 A1 | 10/2005 | Thompson et al. |
| 2006/0045865 A1 | 3/2006 | Jacob et al. |
| 2006/0069161 A1 | 3/2006 | Lee et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2009/0148396 A1 | 6/2009 | Akullian et al. |
| 2010/0016425 A1 | 1/2010 | Vath |
| 2010/0111894 A1 | 5/2010 | Benny-Ratsaby et al. |
| 2012/0004162 A1 | 1/2012 | Vath |
| 2012/0010259 A1 | 1/2012 | Vath |
| 2012/0010290 A1 | 1/2012 | Vath |
| 2012/0034233 A1 | 2/2012 | Hughes et al. |

FOREIGN PATENT DOCUMENTS

| | | |
|---|---|---|
| WO | WO-1999/059987 A1 | 11/1999 |
| WO | WO-2000/064876 A1 | 11/2000 |
| WO | WO-2003/027104 A1 | 4/2003 |
| WO | WO-2004/033419 A1 | 4/2004 |
| WO | WO-2005/082349 A1 | 9/2005 |
| WO | WO-2006/080591 A1 | 8/2006 |
| WO | WO-2010/009374 A1 | 1/2010 |
| WO | WO-2010/042163 A2 | 4/2010 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |
| WO | WO-2011/150338 A1 | 12/2011 |
| WO | WO-2012/012642 A1 | 1/2012 |
| WO | WO-2012/051318 A1 | 4/2012 |
| WO | WO-2012/074968 A1 | 6/2012 |
| WO | WO-2012/075020 A1 | 6/2012 |
| WO | WO-2012/075026 A1 | 6/2012 |
| WO | WO-2012/103333 A1 | 8/2012 |
| WO | WO-2012/154676 A1 | 11/2012 |
| WO | WO-2012/154678 A1 | 11/2012 |
| WO | WO-2012/154679 A1 | 11/2012 |

OTHER PUBLICATIONS

Braunwald et al, "Obesity" in Harrison's Principles of Internal Medicine, 15th Ed., McGraw Hill (new York) pp. 479-486, 2001.
Chinese Office Action for Application No. 201280022154.X dated Apr. 30, 2015 (7 pages).
Database Registry Chemical Abstracts Service, Columbus, Ohio, Accession No. RN 129298-86-8 and RN 129298-87-9, Entered STN: Sep. 14, 1990.
Didier et al. "Antimicrosporidial Activities of Fumagillin, TNP-470, Ovalicin, and Ovalicin Derivatives in Vitro and In Vivo" Antimicrob Agents Chemother. Jun. 2006;50(6):2146-55.
DiPaolo et al. "Studies on the Carcinolytic Activity of Fumagillin and Some of its Derivatives," Antibiot Annu. 1958-1959;6:541-6.
Drevs et al. "Antiangiogenic Potency of FK866/K22.175, a New Inhibitor of Intracellular NAD Biosynthesis, in Murine Renal Cell Carcinoma" Anticancer Res. Nov.-Dec. 2003;23(6C):4853-8.
Dumas et al., "Synthesis and Structure Activity Relationships of Novel Small Molecule Cathepsin D Inhibitors" Bioorg Med Chem Lett. Sep. 6, 1999;9(17):2531-6.
Eder et al., "Phase 1 Dose Escalation Safety & Tolerance Study of PPI-2458 in Subjects with Non-Hodgkin's Lymphoma or Solid Tumors" (Presented on Nov. 7-10, 2006 at EORTC-NCI-AACR Symposium on "Molecular Targets and Cancer Therapeutics.") 2006.
European Search Report for EP 09798793 dated Oct. 11, 2011, 9 pages.
Everhart "Contributions of Obesity and Weight Loss to Gallstone Disease" Ann Intern Med. Nov. 15, 1993;119(10):1029-35.
Examination Report for Application No. EP12709761.6 dated Jun. 23, 2015 (4 pages).

Garrabrant et al. "Small molecule inhibitors of methionine aminopeptidase type 2 (MetAP-2) fail to inhibit endothelial cell proliferation or formation of microvessels from rat aortic rings in vitro" Angiogenesis. 2004;7(2):91-6.
Ingber et al. "Synthetic analogues of fumagillin that inhibit angiogenesis and suppress tumour growth" Nature. Dec. 6, 1990;348(6301):555-7.
International Search Report and Written Opinion for International Application No. PCT/US2012/028068 dated May 22, 2012,10 pages.
Ito et al., "A Medium-term Rat Liver Bioassay for Rapid in vivo Detection of Carcinogenic Potential of Chemicals," Cancer Sci, 2003, 94(1):3-8.
Jeong et al, "Total synthesis and antiangiogenic activity of cyclopentane analogues of fumagillol" Bioorg Med Chem Lett. Aug. 1, 2005;15(15):3580-3.
Kim et al. "Assessment of the Anti-Obesity Effects of the TNP-470 Analog, CKD-732" J Mol Endocrinol. Apr. 2007;38(4):455-65.
Kruger, "TNP-470: An Angiogenesis Inhibitor in Clinical Development for Cancer" Expert Opin Investig Drugs. Jun. 2000;9(6):1383-96.
Lijnen et al. "Fumagillin Reduces Adipose Tissue Formation in Murine Models of Nutritionally Induced Obesity" Obesity (Silver Spring). Dec. 2010;18(12):2241-6. doi: 10.1038/oby.2009.503. Epub Jan. 21, 2010.
Marui et al., "Chemical modification of fumagillin. I. 6-O-acyl, 6-O-sulfonyl, 6-O-alkyl, and 6-O-(N-substituted-carbamoyl)fumagillols" Chem Pharm Bull (Tokyo). Jan. 1992;40(1):96-101.
Masiero et al. "New Anti-angiogenesis Agents: Review of the Clinical Experience with Carboxyamido-Triazole (CAI), Thalidomide, TNP-470 and Interleukin-12" Angiogenesis. 1997;1(1):23-35.
McCowen et al., "Fumagillin (H-3), a New Antibiotic with Amebicidal Properties" Science. Feb. 23, 1951(2930):202-3.
Milkowski et al., "TNP-470" *Antiangiogenic Agents in Cancer Therapy*, Chapter 22 pp. 385-398, 1999.
Molina et al. "Potential Efficacy of Fumagillin in Intestinal Microsporidiosis Due to Enterocytozoon Bieneusi in Patients with HIV Infection: Results of a Drug Screening Study" AIDS. Nov. 1997;11(13):1603-10.
Molina et al. "Fumagillin Treatment of Intestinal Microsporidiosis" N Engl J Med. Jun. 20, 2002;346(25):1963-9.
Molina, et al. "Trial of Oral Fumagillin for the Treatment of Intestinal Microsporidiosis in Patients with HIV Infection" AIDS. Jul. 7, 2000;14(10):1341-8.
Naganuma et al. "Metronomic doxifluridine chemotherapy combined with the anti-angiogenic agent TNP-470 inhibits the growth of human uterine carcinosarcoma xenografts" Cancer Sci. Aug. 2011;102(8):1545-52. doi: 10.1111/j.1349-7006.2011.01998.x. Epub Jul. 3, 2011.
National Task Force on the Prevention and Treatment of Obesity "Very low-calorie diets. National Task Force on the Prevention and Treatment of Obesity, National Institutes of Health" JAMA. Aug. 25, 1993;270(8):967-74.
Noel et al. "Increased Risk of Acute Pancreatitis and Biliary Disease Observed in Patients with Type 2 Diabetes" Diabetes Care. May 2009;32(5):834-8. doi: 10.2337/dc08-1755. Epub Feb. 10, 2009.
Pagliarulo et al. "Gallstone disease and related risk factors in a large cohort of diabetic patients" Dig Liver Dis. Feb. 2004;36(2):130-4.
Picoul et al. "Progress in fumagillin synthesis" *Pure Appl. Chem.* 75(2-3): 235-249, 2003.
Rupnick "Adipose Tissue Mass Can be Regulated Through the Vasculature" Proc Natl Acad Sci U S A. Aug. 6, 2002;99(16):10730-5. Epub Jul. 29, 2002.
Seneca et al. "Amebiasis: a review. II. Laboratory diagnosis, differential diagnosis and therapy" Am J Dig Dis. Jul. 1956;1(7):310-22.
Shin, "A Phase I Pharmacokinetic and Pharmacodynamic Stdy of CKD-732, an Antiangiogenic Agent, in Patients with Refractory Solid Cancer" Invest New Drugs. Oct. 2010;28(5):650-8.
Teicher, et al (1999) "Antiangiogenic Agents in Cancer Therapy" pp. 385-398.
Weinsier et al. "Gallstone Formation and Weight Loss" Obes Res. Jan. 1993;1(1):51-6.

(56) References Cited

OTHER PUBLICATIONS

Weinsier et al. "Medically Safe Rate of Weight Loss for the Treatment of Obesity: A Guideline Based on Risk of Gallstone Formation" Am J Med. Feb. 1995;98(2):115-7.

Winter et al. "Endothelial anb3 Integrin-Targeted Fumagillin Nanoparticles Inhibit Angiogenesis in Atherosclerosis" Arterioscler Thromb Vasc Biol. Sep. 2006;26(9):2103-9. Epub Jul. 6, 2006.

Yanai et al. "Antitumor Effect of Arterial Administration of a Medium-Chain Triglyceride Solutionof an Angiogenesis Inhibitor, TNP-470, in Rabbits Bearing VX-2 Carcinoma" Pharm Res. May 1995;12(5):653-7.

Yanai et al., "Antitumor activity of a medium-chain triglyceride solution of the angiogenesis inhibitor TNP-470 (AGM-1470) when administered via the hepatic artery to rats bearing Walker 256 carcinosarcoma in the liver" J Pharmacol Exp Ther. Dec. 1994;271(3):1267-73.

THXI (1-6) MVKLIE

OXASPIRO[2.5]OCTANE DERIVATIVES AND ANALOGS

CROSS REFERENCE TO RELATED APPLICATIONS

This application is a continuation of U.S. patent application Ser. No. 15/068,942, filed Mar. 14, 2016; which is a continuation of U.S. patent application Ser. No. 14/003,906, filed Oct. 29, 2014; which is a national stage filing under U.S.C. § 371 of PCT/US2012/028068, filed Mar. 7, 2012; which claims priority to U.S. Provisional Patent Application No. 61/450,301 filed Mar. 8, 2011; all of which are hereby incorporated by reference in their entirety.

BACKGROUND

Over 1.1 billion people worldwide are reported to be overweight. Obesity is estimated to affect over 90 million people in the United States alone. Twenty-five percent of the population in the United States over the age of twenty is considered clinically obese. While being overweight or obese presents problems (for example restriction of mobility, discomfort in tight spaces such as theater or airplane seats, social difficulties, etc.), these conditions, in particular clinical obesity, affect other aspects of health, i.e., diseases and other adverse health conditions associated with, exacerbated by, or precipitated by being overweight or obese. The estimated mortality from obesity-related conditions in the United States is over 300,000 annually (O'Brien et al. Amer J Surgery (2002) 184:4S-8S; and Hill et al. (1998) Science, 280:1371).

There is no curative treatment for being overweight or obese. Traditional pharmacotherapies for treating an overweight or obese subject, such as serotonin and noradrenergic re-uptake inhibitor, noradrenergic re-uptake inhibitors, selective serotonin re-uptake inhibitors, intestinal lipase inhibitors, or surgeries such as stomach stapling or gastric banding, have been shown to provide minimal short-term benefits or significant rates of relapse, and have further shown harmful side-effects to patients.

MetAP2 encodes a protein that functions at least in part by enzymatically removing the amino terminal methionine residue from certain newly translated proteins such as glyceraldehyde-3-phosphate dehydrogenase (Warder et al. (2008) J Proteome Res 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al. (2003) Cancer Res 63:7861) and infectious diseases such as microsporidiosis, leishmaniasis, and malaria (Zhang et al. (2002) J Biomed Sci. 9:34). Notably, inhibition of MetAP2 activity in obese and obese-diabetic animals leads to a reduction in body weight in part by increasing the oxidation of fat and in part by reducing the consumption of food (Rupnick et al. (2002) Proc Natl Acad Sci USA 99:10730).

Such MetAP2 inhibitors may be useful as well for patients with excess adiposity and conditions related to adiposity including type 2 diabetes, hepatic steatosis, and cardiovascular disease (via e.g. by ameliorating insulin resistance, reducing hepatic lipid content, and reducing cardiac workload). Accordingly, compounds capable of modulating MetAP2 are needed to address the treatment of obesity and related diseases as well as other ailments favorably responsive to MetAP2 modulator treatment

SUMMARY

The disclosure provides, for example, compounds which may be modulators of MetAP2, and their use as medicinal agents, processes for their preparation, pharmaceutical compositions containing them as an active ingredient both alone or in combination with other agents, to their use as medicaments and to their use in the manufacture of medicaments for the use in the inhibition of MetAP2 activity in warm-blooded animals such as humans. In particular this invention relates to compounds useful for the treatment of obesity, type 2 diabetes, and other obesity-associated conditions. Also provided are pharmaceutical compositions comprising at least one disclosed compound and a pharmaceutically acceptable carrier.

DETAILED DESCRIPTION

Figure 1:
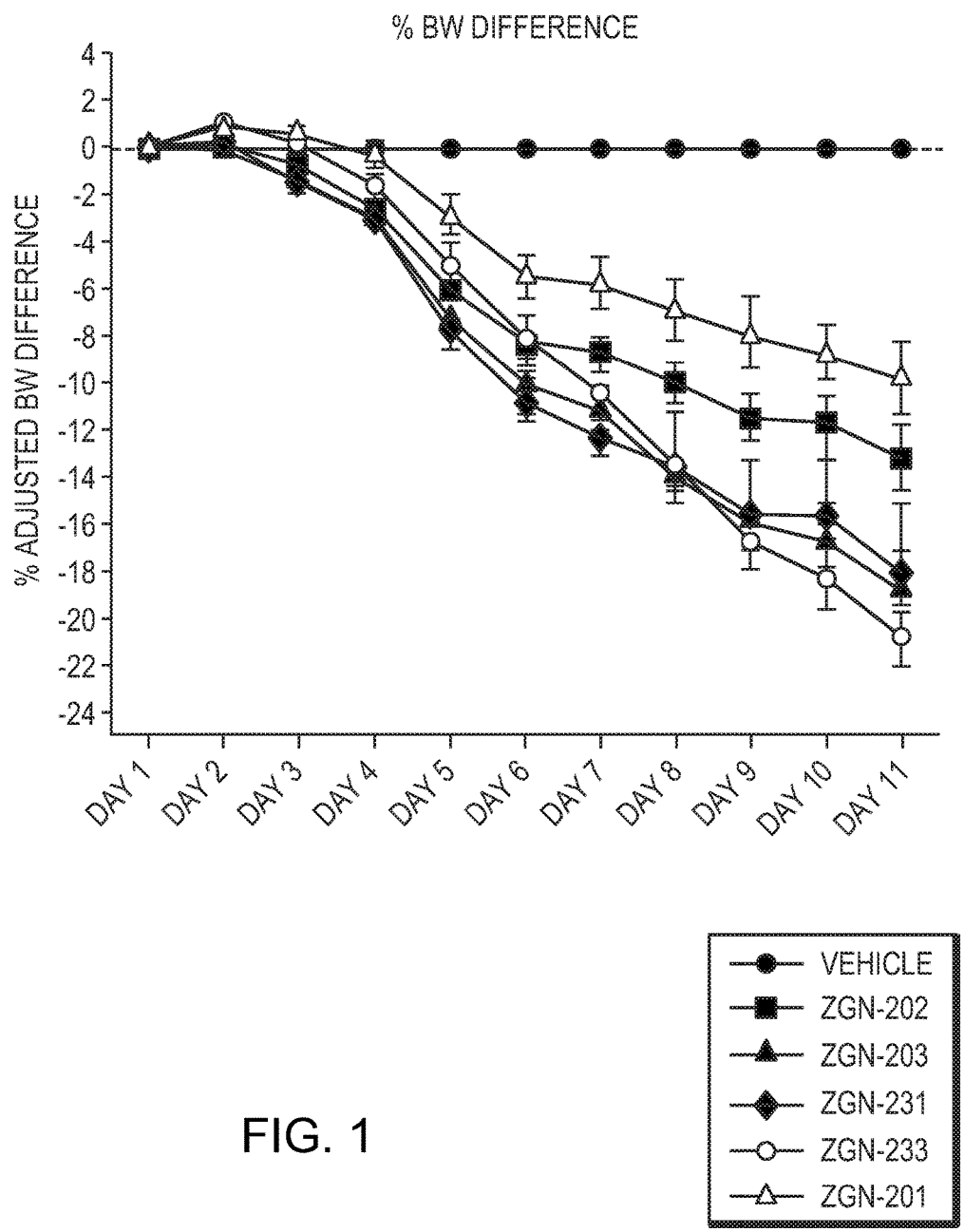
FIG. 1 depicts body weight % difference in mice dosed PO once a day for 10 days with 3 mg/kg of compound 201, 202, 203, 231 or 233.

The features and other details of the disclosure will now be more particularly described. Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

Definitions

"Treating" includes any effect, e.g., lessening, reducing, modulating, or eliminating, that results in the improvement of the condition, disease, disorder and the like.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment of obesity, or weight loss is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in weight loss.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, acetate, tartrate, oleate, fumarate, formate, benzoate, glutamate, methanesulfonate, benzenesulfonate, and p-toluenesulfonate salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

The compounds of the disclosure may contain one or more chiral centers and/or double bonds and, therefore, exist as geometric isomers, enantiomers or diastereomers. The enantiomer and diastereomers may be designated by the symbols "(+)," "(−)." "R" or "S," depending on the configuration of substituents around the stereogenic carbon atom, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds of the present invention. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "stereoisomers" when used herein consist of all geometric isomers, enantiomers or diastereomers. The present invention encompasses various stereoisomers of these compounds and mixtures thereof.

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using steroselective chemical or enzymatic reagents. Racemic mixtures can also be resolved into their component enantiomers by well known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}$Cl, respectively. For example, a compound of the invention may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence form a contemplated alternative embodiment. Isotopically labeled compounds of the invention can generally be prepared by following procedures analogous to those disclosed in the e.g., Examples herein by substituting an isotopically labeled reagent for a non-isotopically labeled reagent.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described herein may be substituted or unsubstituted, branched or unbranched, cyclic or acyclic, and wherein any of the aryl or heteroaryl substituents described above and herein may be substituted or unsubstituted.

The term "alkyl", as used herein, refers to a saturated linear or branched (including cyclic) hydrocarbon free radical, unsubstituted (i.e., with corresponding number of carbon and hydrogen atoms), or optionally substituted with substituents known to those skilled in the art.

The term "(C$_1$-C$_6$) alkyl or C$_1$-C$_6$ alkyl," as used herein, refers to a saturated linear or branched free radical consisting essentially of 1 to 6 carbon atoms (i.e., 1, 2, 3, 4, 5, or 6 carbon atoms) and a corresponding number of hydrogen atoms. Exemplary (C$_1$-C$_6$) alkyl groups include methyl, ethyl, n-propyl, isopropyl, n-butyl, isobutyl, etc. Of course, other (C$_1$-C$_6$) alkyl groups will be readily apparent to those of skill in the art given the benefit of the present disclosure.

The term "(C$_3$-C$_{10}$) cycloalkyl or C$_3$-C$_{10}$ cycloalkyl," as used herein, refers to a nonaromatic saturated free radical forming at least one ring consisting essentially of 3 to 10 carbon atoms and a corresponding number of hydrogen atoms. As such, (C$_3$-C$_{10}$) cycloalkyl groups can be monocyclic or multicyclic. Individual rings of such multicyclic cycloalkyl groups can have different connectivities, e.g., fused, bridged, spiro, etc. in addition to covalent bond substitution. Exemplary (C$_3$-C$_{10}$) cycloalkyl groups include cyclopropyl, cyclobutyl, cyclopentyl, cyclohexyl, norbornanyl, bicyclo[3.2.1]octanyl, octahydro-pentalenyl, spiro[4.5]decanyl, cyclopropyl substituted with cyclobutyl, cyclobutyl substituted with cyclopentyl, cyclohexyl substituted with cyclopropyl, etc. Of course, other (C$_3$-C$_{10}$) cycloalkyl groups will be readily apparent to those of skill in the art given the benefit of the present disclosure.

The term "(C$_2$-C$_9$) heterocycloalkyl or C$_2$-C$_9$ heterocycloalkyl," as used herein, refers to a nonaromatic free radical having 3 to 10 atoms (i.e., ring atoms) that form at least one ring, wherein 2 to 9 of the ring atoms are carbon and the remaining ring atom(s) (i.e., hetero ring atom(s)) is selected from the group consisting of nitrogen, sulfur, and oxygen. As such, (C$_2$-C$_9$) heterocycloalkyl groups can be monocyclic or multicyclic. Individual rings of such multicyclic heterocycloalkyl groups can have different connectivities, e.g., fused, bridged, spiro, etc. in addition to covalent bond substitution. Exemplary (C$_2$-C$_9$) heterocycloalkyl groups include pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl 2-azaspiro[4.4]nonanyl, 7-oxa-1-azaspiro[4.4]nonanyl, 7-azabicyclo[2.2.2]heptanyl, octahydro-1H-indolyl, etc. In general, the (C$_2$-C$_9$) heterocycloalkyl group typically is attached to the main structure via a carbon atom or a nitrogen atom. Of course, other (C$_2$-C$_9$) heterocycloalkyl groups will be readily apparent to those of skill in the art given the benefit of the present disclosure.

The term "(C$_2$-C$_9$) heteroaryl or C$_2$-C$_9$ heteroaryl," as used herein, refers to an aromatic free radical having 5 to 10 atoms (i.e., ring atoms) that form at least one ring, wherein 2 to 9 of the ring atoms are carbon and the remaining ring atom(s) (i.e., hetero ring atom(s)) is selected from the group consisting of nitrogen, sulfur, and oxygen. As such, (C$_2$-C$_9$) heteroaryl groups can be monocyclic or multicyclic. Individual rings of such multicyclic heteroaryl groups can have different connectivities, e.g., fused, etc. in addition to covalent bond substitution. Exemplary (C$_2$-C$_9$) heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydroquinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl, etc. In general, the ($C_2$-$C_9$) heteroaryl group typically is attached to the main structure via a carbon atom, however, those of skill in the art will realize when certain other atoms, e.g., hetero ring atoms, can be attached to the main structure. Of course, other ($C_2$-$C_9$) heteroaryl groups will be readily apparent to those of skill in the art given the benefit of the present disclosure.

The term "($C_6$-$C_{10}$) aryl or $C_6$-$C_{10}$ aryl," as used herein, refers to phenyl or naphthyl. As used herein, the term "halo" means fluorine, chlorine, bromine, or iodine. As used herein, the term "amino" means a free radical having a nitrogen atom and 1 to 2 hydrogen atoms. As such, the term amino generally refers to primary and secondary amines. In that regard, as used herein and in the appended claims, a tertiary amine is represented by the general formula $R_aR_a'N$—, wherein $R_a$ and $R_a'$ are carbon radicals that may or may not be identical. Nevertheless, the term "amino" generally may be used herein to describe a primary, secondary, or tertiary amine, and those of skill in the art will readily be able to ascertain the identification of which in view of the context in which this term is used in the present disclosure.

This disclosure provides in part, oxaspiro[2.5]octane derivatives and analogs that have useful properties, such as pharmaceutical properties (e.g. as MetAP-2 inhibitors) Another aspect of this disclosure provides methods of modulating the activity of MetAP2. Such methods comprise exposing said receptor to a compound described herein. The ability of compounds described herein to modulate or inhibit MetAP2 can be evaluated by procedures known in the art and/or described herein. Another aspect of the invention provides methods of treating a disease associated with expression or activity of MetAP2 in a patient. For example, a contemplated method includes administering a disclosed compound in an amount sufficient to establish inhibition of intracellular MetAP2 effective to increase thioredoxin production in the patient and to induce multi organ stimulation of anti-obesity processes in the subject, for example, by administering a disclosed compound in an amount insufficient to reduce angiogenesis in the patient.

In certain embodiments, the disclosure provides a method of treating and or ameliorating obesity in a patient by administering an effective amount of a disclosed compound. Also provided herein are methods for inducing weight loss in a patient in need thereof.

Other contemplated methods of treatment include method of treating or ameliorating an obesity-related condition or co-morbidity, by administering a compound disclosed herein to a subject. For example, contemplated herein are methods for treating type 2 diabetes in a patient in need thereof.

Exemplary co-morbidities or other disorders that may be treated by a disclosed compound may include cardiac disorders, endocrine disorders, respiratory disorders, hepatic disorders, skeletal disorders, psychiatric disorders, metabolic disorders, metabolic disorders, and reproductive disorders.

Exemplary cardiac disorders include hypertension, dyslipidemia, ischemic heart disease, cardiomyopathy, cardiac infarction, stroke, venous thromboembolic disease and pulmonary hypertension. Exemplary endocrine disorders include type 2 diabetes and latent autoimmune diabetes in adults. Exemplary respiratory disorders include obesity-hyperventilation syndrome, asthma, and obstructive sleep apnea. An exemplary hepatic disorder is nonalcoholic fatty liver disease. Exemplary skeletal disorders include back pain and osteoarthritis of weight-bearing joints. Exemplary metabolic disorders include Prader-Willi Syndrome and polycystic ovary syndrome. Exemplary reproductive disorders include sexual dysfunction, erectile dysfunction, infertility, obstetric complications, and fetal abnormalities. Exemplary psychiatric disorders include weight-associated depression and anxiety.

In particular, in certain embodiments, the disclosure provides a method of treating the above medical indications comprising administering to a subject in need thereof a therapeutically effective amount of a compound described herein.

Obesity or reference to "overweight" refer to an excess of fat in proportion to lean body mass. Excess fat accumulation is associated with increase in size (hypertrophy) as well as number (hyperplasia) of adipose tissue cells. Obesity is variously measured in terms of absolute weight, weight:height ratio, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using either of the formulas: weight(kg)/height$^2$ (m$^2$) (SI) or 703×weight(lb)/height$^2$(in$^2$) (US).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. Obesity can also refer to patients with a waist circumference of about 102 cm for males and about 88 cm for females. For children, the definitions of overweight and obese take into account age and gender effects on body fat. Patients with differing genetic background may be considered "obese" at a level differing from the general guidelines, above.

The disclosed compounds may also be useful for reducing the risk of secondary outcomes of obesity, such as reducing the risk of left ventricular hypertrophy. Methods for treating patients at risk of obesity, such as those patients who are overweight, but not obese, e.g. with a BMI of between about 25 and 30 kg/m$^2$, are also contemplated, for example, patients at this lower BMI but with a co-morbidity such as diabetes. In certain embodiments, a patient is a human.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity.

A minimum WHR indicative of central obesity has been variously set, and a centrally obese adult typically has a WHR of about 0.85 or greater if female and about 0.9 or greater if male.

Methods of determining whether a subject is overweight or obese that account for the ratio of excess adipose tissue to lean body mass involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink.

In another aspect, the disclosure provides methods for treating an overweight or obese subject involving determining a level of at least one biomarker related to being overweight or obese in the subject, and administering an effective amount of a disclosed compound to achieve a target level in the subject. Exemplary biomarkers include body weight, Body Mass Index (BMI), Waist/Hip ratio WHR, plasma adipokines, and a combination of two or more thereof.

In one aspect, the invention is generally related to a compound of Formula I:

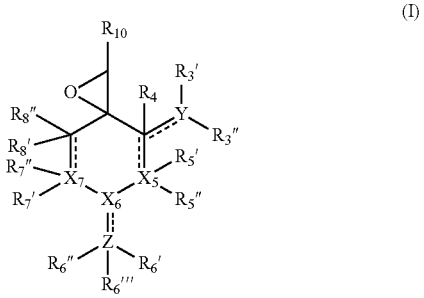

(I)

or a pharmaceutically acceptable salt, ester or pro-drug thereof;
wherein
each of $X_5$ and $X_7$ independently is a C, O, N or S atom, and one or more of $R_5$, $R_5$, $R_7$, and $R_7$ is absent when $X_5$ or $X_7$ is a O, S, or N at the respective positions;
$X_6$ is a C, O, or N atom;
Z is a C, O, S or N, and the bond between $X_6$ and Z is a single bond or a double bond, wherein when Z is a O, S, or N, or when the bond between $X_6$ and Z a double bond, one or more of $R_6$, $R_6$, $R_6$ is absent;
Y is a C, O, N or S atom, and one or more of $R_3$, and $R_3$ is absent when Y is a O or S and wherein $R_3$, and $R_3$ may together with atoms attached thereto form a cyclic, heterocyclic, aromatic cyclic, or aromatic heterocyclic group;
$R_4$ is a H, —OH, a halogen, a $C_1$-$C_6$ alkyl;
each of $R_6$, $R_6$ and $R_6$ is independently H, alkyl, aryl, halogen, —OH, alkoxy, carbamoyl, carbonyldioxyl, thiohydroxyl, amino, alkylamino, dialkylamino, ureido, lower alkoxy, a substituted alkanoyl group, a cyclic or aromatic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether, and two of $R_6$, $R_6$ and $R_6$ may together form a closed ring;

each of $R_3$, $R_3$, $R_5$, $R_5$, $R_7$, $R_7$, $R_8$, and $R_8$ is independently H, alkyl, aryl, halogen, —OH, alkoxy, carbamoyl, carbonyldioxyl, thiohydroxyl, amino, alkylamino, dialkylamino, ureido, lower alkoxy, a substituted alkanoyl group, a cyclic or aromatic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether, and wherein $R_3$, and $R_3$ may together form a closed ring; $R_5$, and $R_5$ may together form a closed ring; $R_7$, and $R_7$ may together form a closed ring; and $R_8$, and $R_8$ may together form a closed ring; and $R_{10}$ is a H, a halogen, —OH, or a $C_1$-$C_6$ alkyl group.

In certain embodiments, contemplated compounds may be represented by have Formula IIa or IIb:

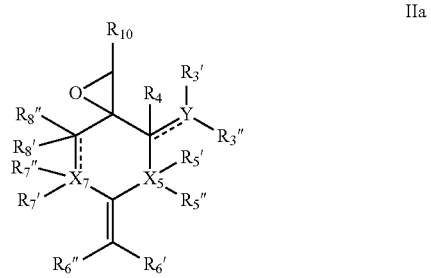

(IIa)

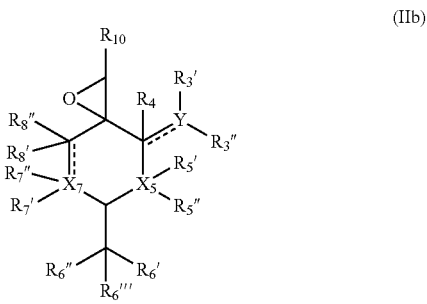

(IIb)

In certain other embodiments, contemplated compounds are represented by:

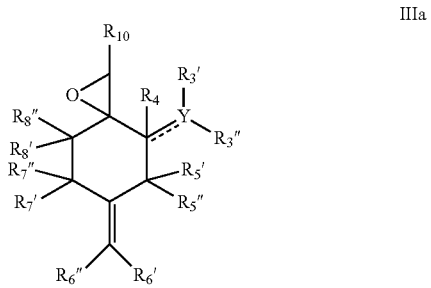

IIIa

-continued (IIIb)

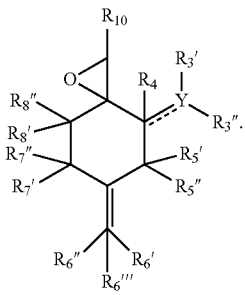

Also contemplated here are compound represented by Formula IVa:

(IVa)

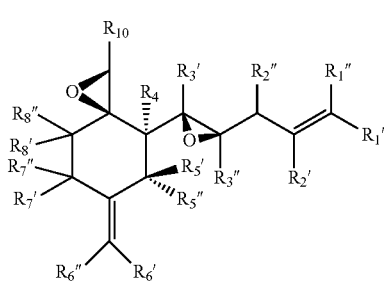

wherein each of $R_1$', $R_1$''', $R_2$', $R_2$''', $R_3$', $R_3$''', $R_4$', $R_5$', and $R_5$''' is independently H, $C_1$-$C_6$ alkyl, halogen, —OH, or $C_1$-$C_6$ alkoxy. For example, $R_5$' may be H and $R_5$''' is —OCH$_3$. In some embodiments, $R_4$ is H. In some embodiments, $R_3$' is $C_1$-$C_3$ alkyl, such as a methyl or ethyl. In some preferred embodiments, each of $R_7$', $R_7$''', $R_8$', and $R_8$''' is independently H, $C_1$-$C_3$ alkyl, halogen, —OH, or $C_1$-$C_3$ alkoxy. In some embodiments, one of $R_6$' and $R_6$''' is

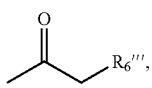

wherein $R_6$''' is H, alkyl, aryl, halogen, —OH, alkoxy, carbamoyl, carbonyldioxyl, thiohydroxyl, amino, alkylamino, dialkylamino, ureido, lower alkoxy, a substituted alkanoyl group, a cyclic or aromatic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether.

Exemplary compounds include:

IVa1

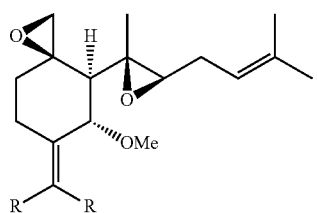

-continued

IVa2

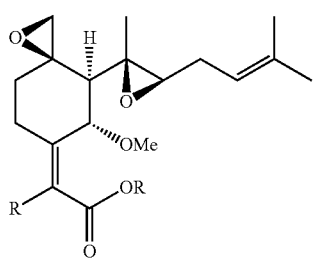

IVa3

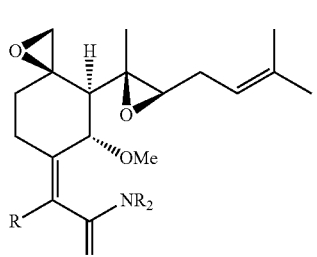

IVa4

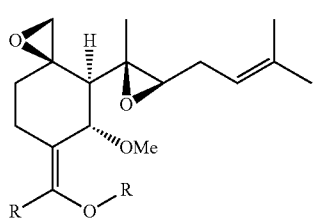

wherein each R is independently a H or an unsubstituted or substituted $C_1$-$C_{12}$alkyl, $C_1$-$C_{12}$alkenyl, or $C_1$-$C_{12}$alkoxy group, optionally substituted with —COOH, or —O$C_{1-6}$alkyl. For example, provided herein are the structures:

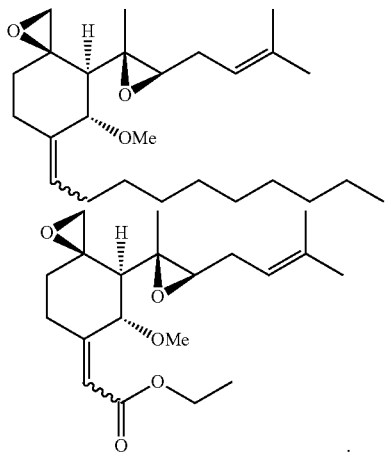

Exemplary compounds include compounds having Formula IVb:

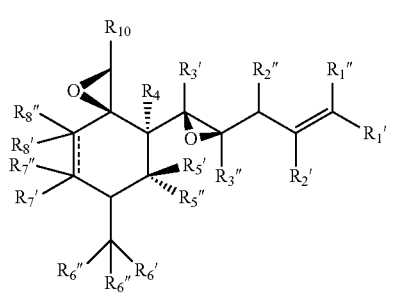
(IVb)

wherein each of $R_{1'}$, $R_{1'''}$, $R_{2'}$, $R_{2'''}$, $R_{3'}$, $R_{3'''}$, $R_{4'}$, $R_{5'}$ and $R_{5'''}$ is independently H, $C_1$-$C_6$ alkyl, halogen, —OH, or $C_1$-$C_6$ alkoxy. In some preferred embodiments, $R_{5'}$ is H and $R_{5'''}$ is —OCH$_3$. In some preferred embodiment, $R_4$ is H. In some preferred embodiment, $R_{3'}$ is $C_1$-$C_3$ alkyl, such as a methyl or ethyl. In some preferred embodiments, each of $R_{7'}$, $R_{7'''}$, $R_{8'}$ and $R_{8'''}$ is independently H, $C_1$-$C_3$ alkyl, halogen, —OH, or $C_1$-$C_3$ alkoxy. In some preferred embodiments, one of $R_{6'}$ and $R_{6'''}$ is

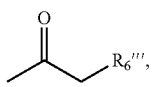

wherein $R_{6'''}$ is H, alkyl, $C_1$-$C_{12}$alkyl (optionally substituted by —COOH or —COOR$_{20}$, wherein $R_{20}$ is $C_1$-$C_6$alkyl), $C_1$-$C_{12}$alkenyl, or $C_1$-$C_{12}$alkoxy group, optionally substituted with carboxyl.aryl, halogen, —OH, alkoxy, carbamoyl, carbonyldioxyl, thiohydroxyl, amino, alkylamino, dialkylamino, ureido, lower alkoxy, a substituted alkanoyl group, a cyclic or aromatic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether.

Exemplary compounds provided herein include:
wherein each R is independently a H or an unsubstituted or substituted $C_1$-$C_{12}$alkyl, $C_1$-$C_{12}$alkenyl, or $C_1$-$C_{12}$alkoxy group, each independently and optionally substituted with $C_1$-$C_{12}$alkoxy group, optionally substituted with carboxyl, or —OC$_{1-6}$alkyl.

Exemplary compounds include

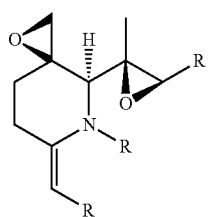
VIIa1

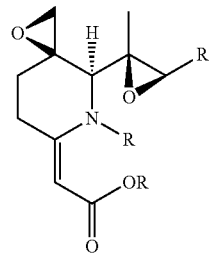
VIIa2

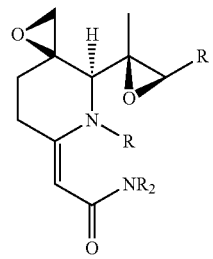
VIIa3

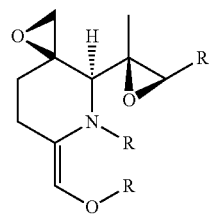
VIIa4

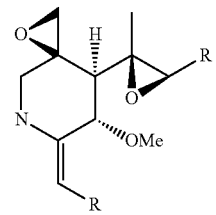
VIa1

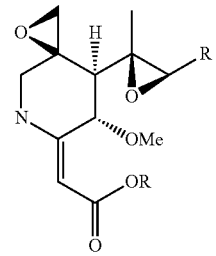
VIa2

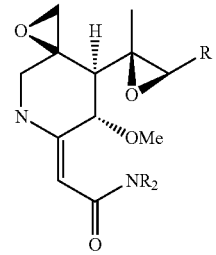
VIa3

-continued

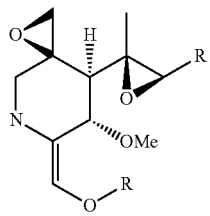

VIa4 wherein each R is independently a H or an unsubstituted or substituted $C_1$-$C_8$ alkyl or alkoxy group.

Exemplary compounds include compound such as:

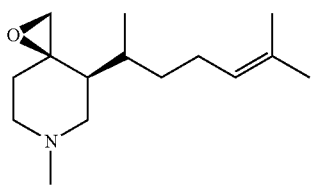

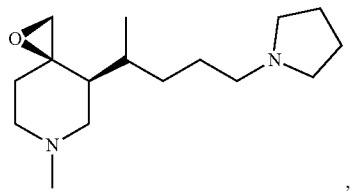

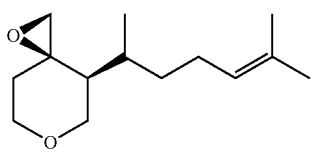

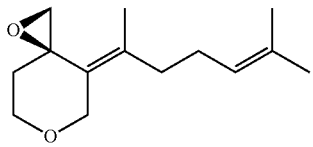

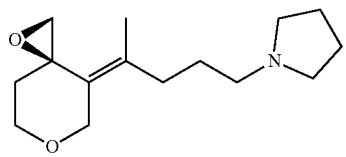

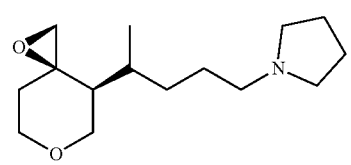

In another embodiment, compounds are provided such as:

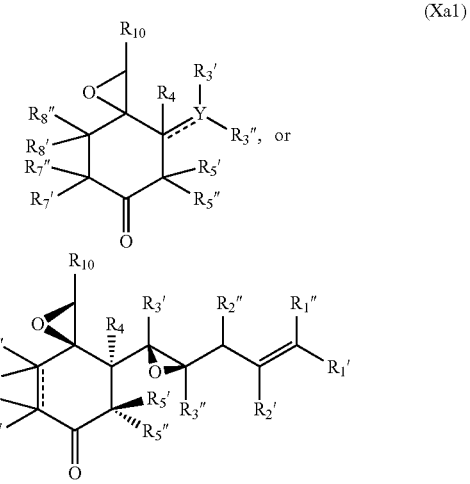

(Xa1)

wherein each of $R_{1'}$, $R_{1'''}$, $R_{2''}$, $R_{2'''}$, $R_{3''}$, $R_{3'''}$, $R_{4'}$, $R_{5'}$ and $R_{5''}$ is independently H, $C_1$-$C_6$ alkyl, halogen, —OH, or $C_1$-$C_6$ alkoxy. In some preferred embodiments, $R_{5'}$ is H and $R_{5''}$ is —OCH$_3$. In some preferred embodiment, $R_4$ is H. In some preferred embodiment, $R_{3'}$ is $C_1$-$C_3$ alkyl, such as a methyl or ethyl. In some preferred embodiments, each of $R_{7'}$, $R_{7''}$, $R_{8'}$ and $R_{8''}$ is independently H, $C_1$-$C_3$ alkyl, halogen, —OH, or $C_1$-$C_3$ alkoxy. In some preferred embodiments, one of $R_{6'}$ and $R_{6''}$ is

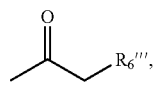

wherein $R_{6'''}$ is H, alkyl, aryl, halogen, —OH, alkoxy, carbamoyl, carbonyldioxyl, thiohydroxyl, amino, alkylamino, dialkylamino, ureido, lower alkoxy, a substituted alkanoyl group, a cyclic or aromatic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether.

Exemplary compounds include:

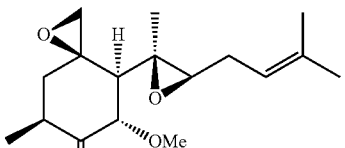

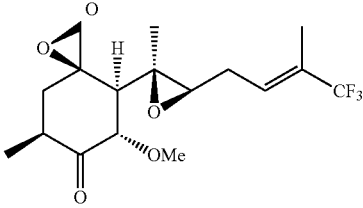

17
-continued
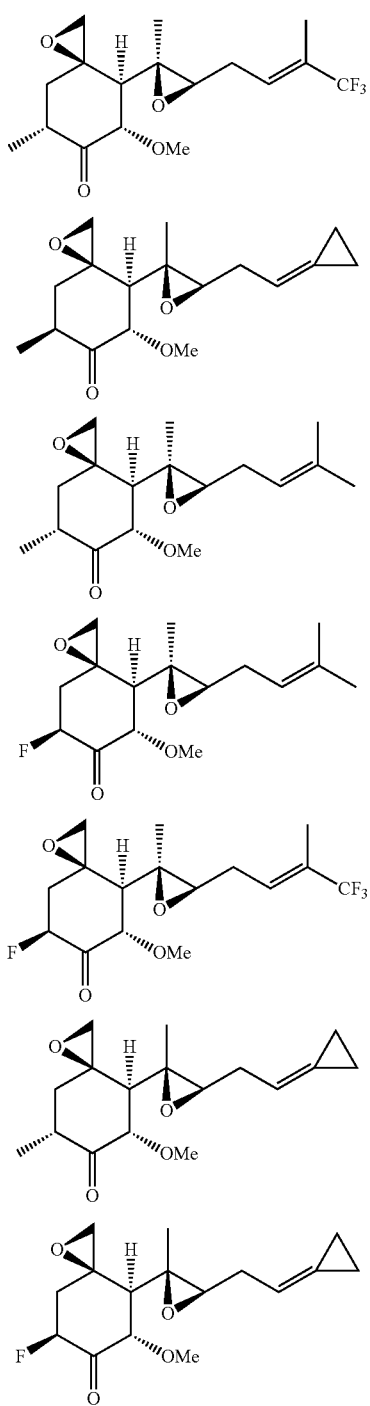
Exemplary compounds also include:
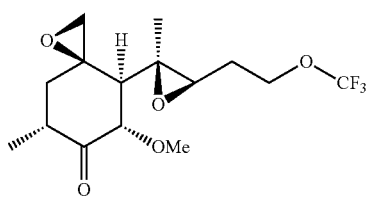
18
-continued
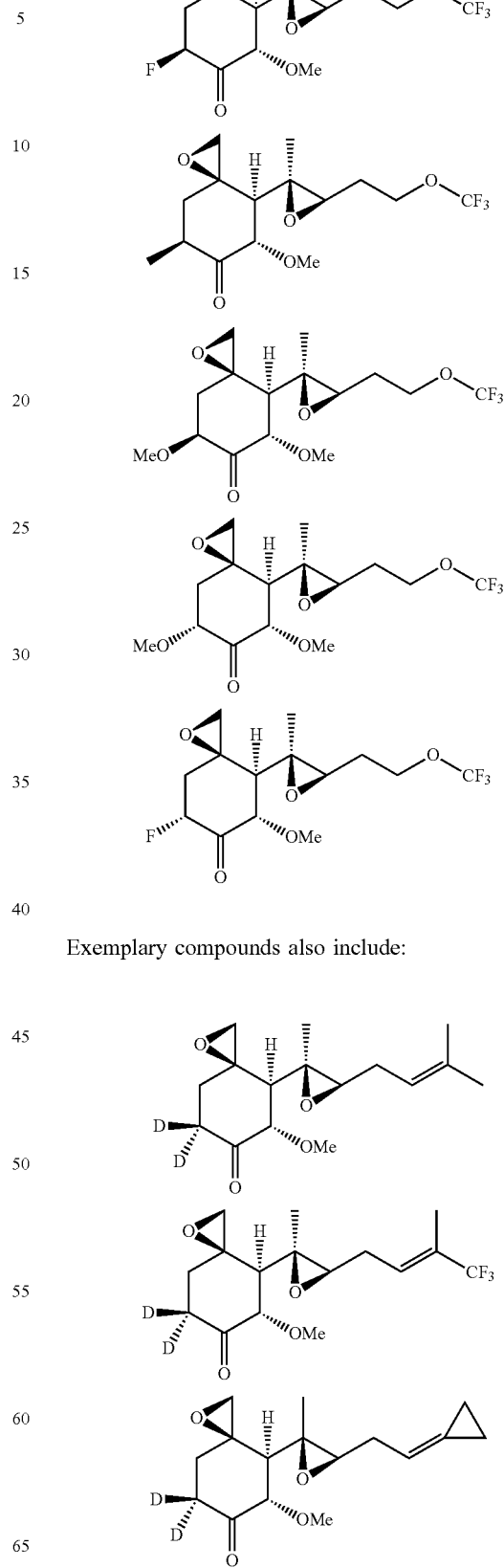
Exemplary compounds also include:
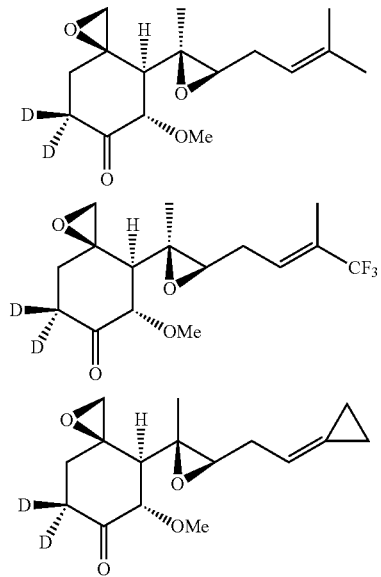

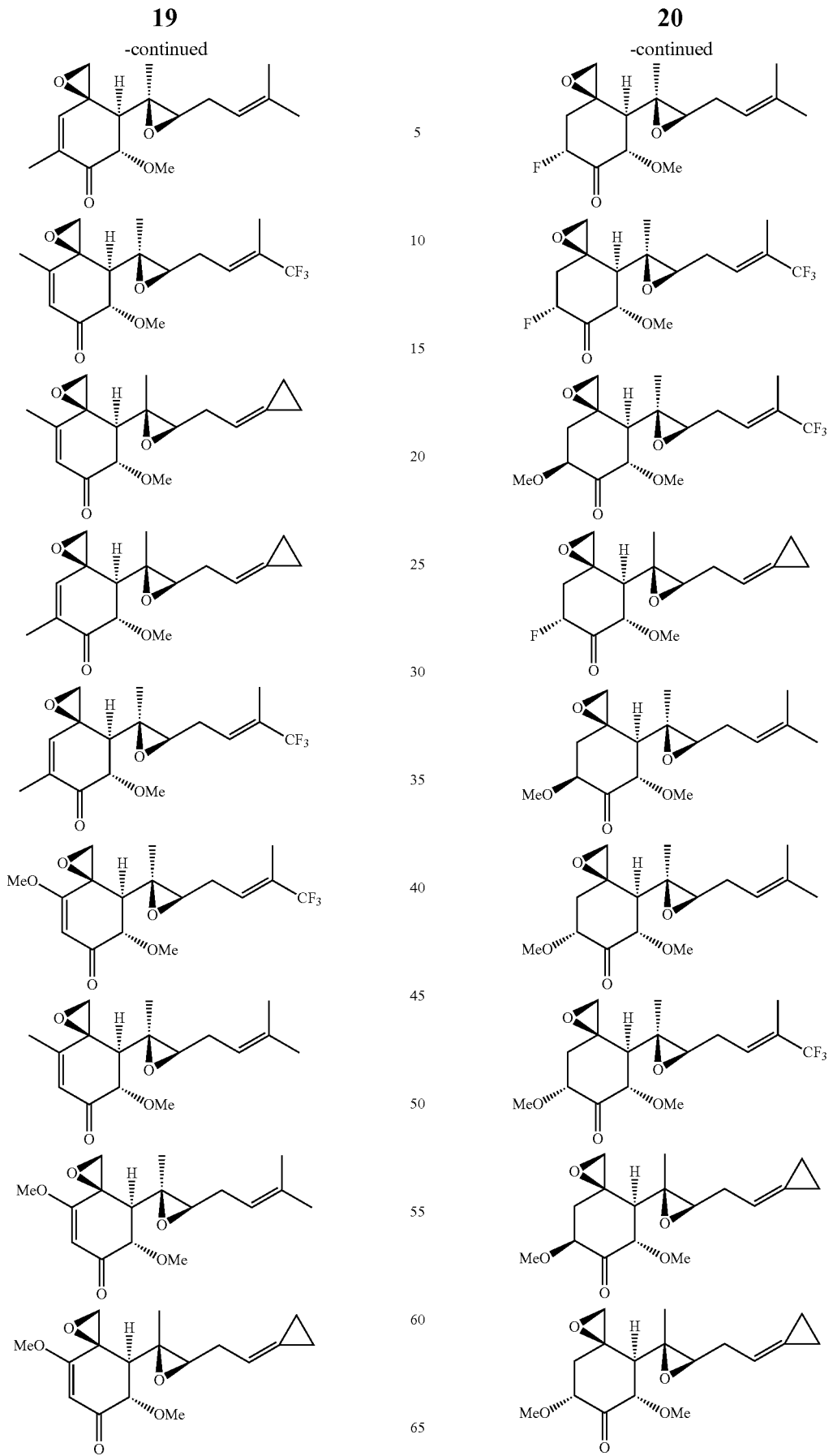

-continued
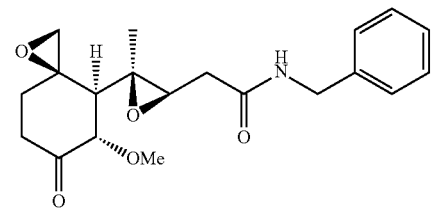
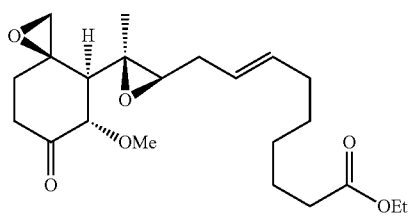
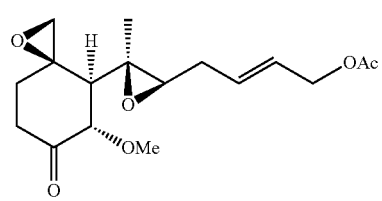
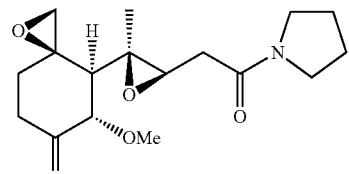
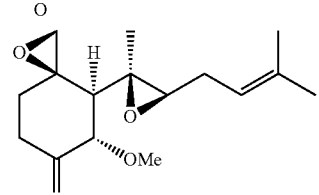
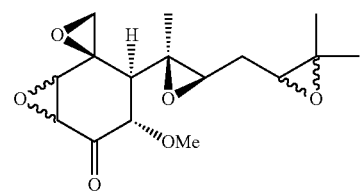
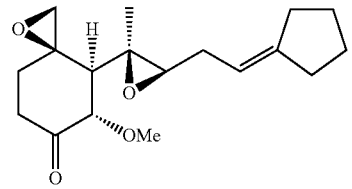
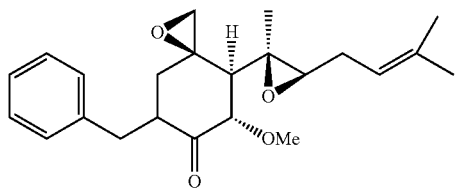
In certain embodiments, the compounds of the invention have Formula XI:
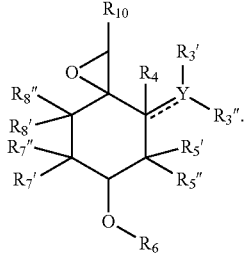
(XI)
In some embodiments, the compounds of the invention have Formula XIa:
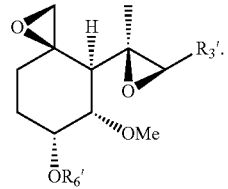
(XIa)
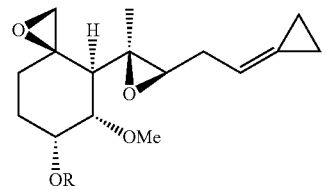
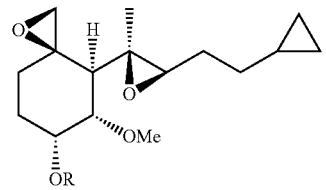
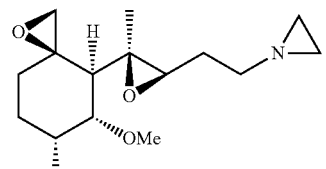
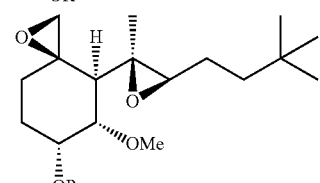
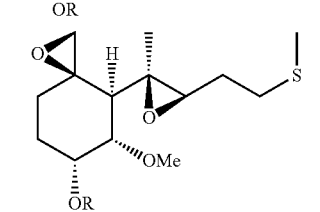

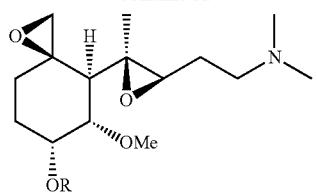
In some embodiments, the compounds of the invention have Formula XIb:
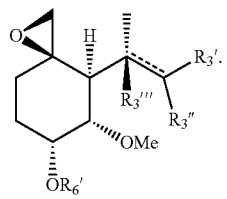
(XIb)
Exemplary compounds also include:
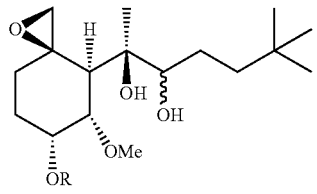
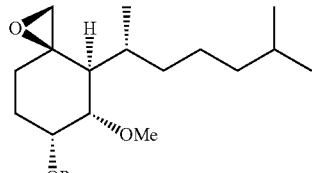
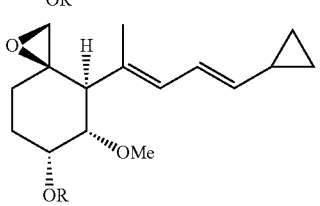
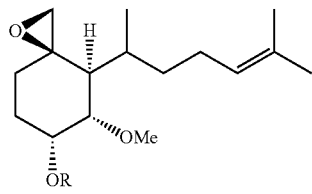
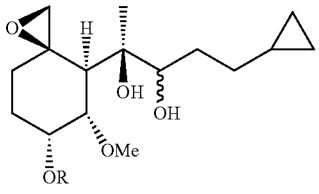
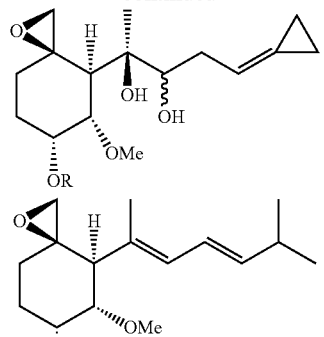
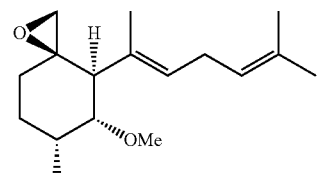
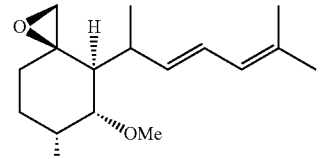
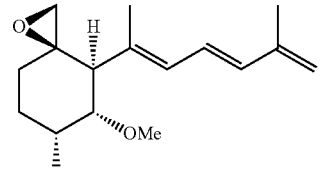
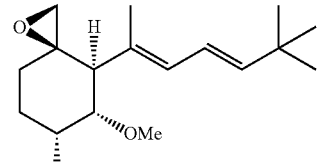
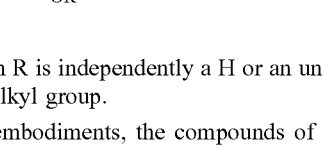
wherein each R is independently a H or an unsubstituted or substituted alkyl group.
In some embodiments, the compounds of the invention have Formula XIc:
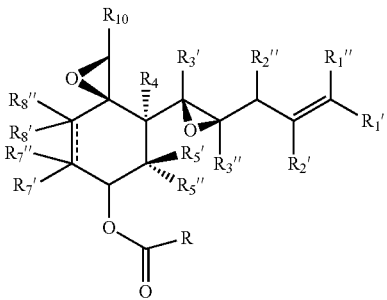
(XIc)
wherein R is $(C_1-C_{20})$alkyl or $(C_1-C_{20})$alkene.

Exemplary compounds include:
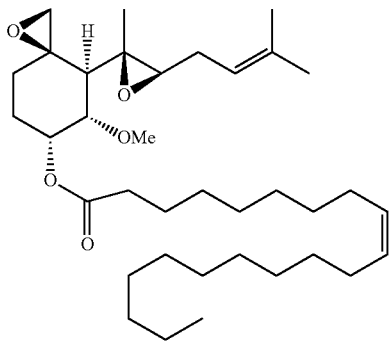
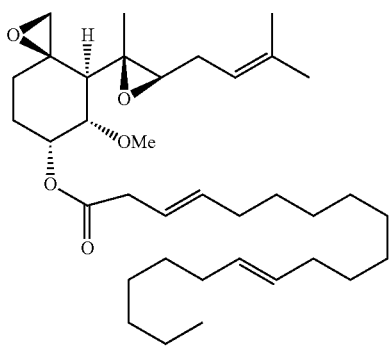
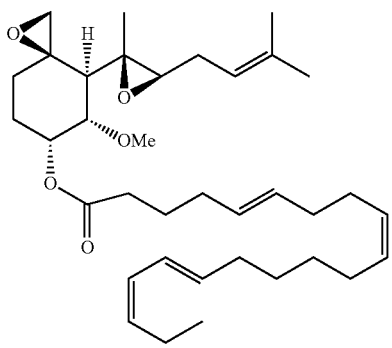
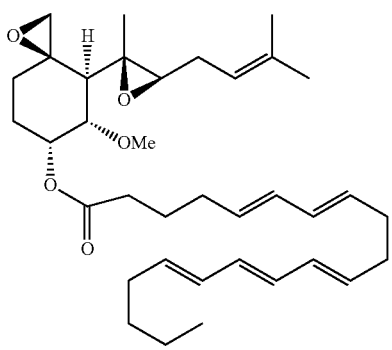
-continued
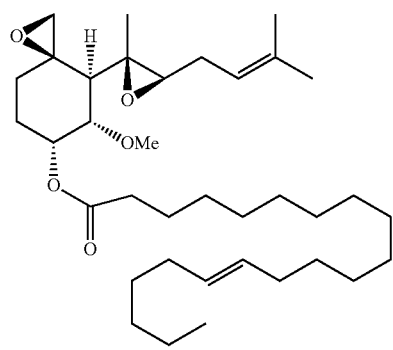
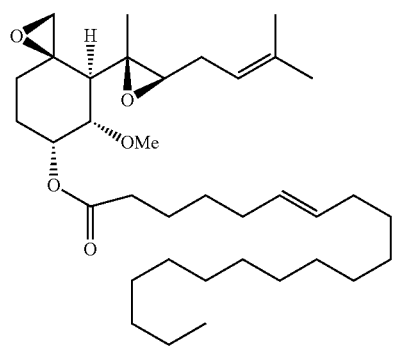
Additional exemplary compounds having two epoxy moieties include:
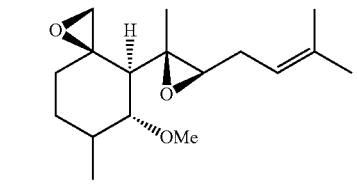
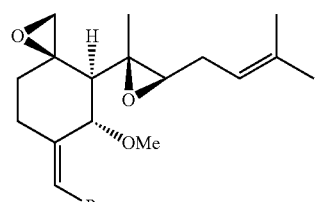
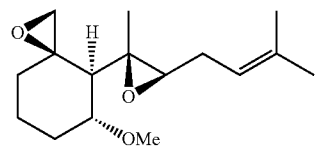
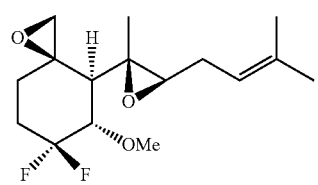

27
-continued
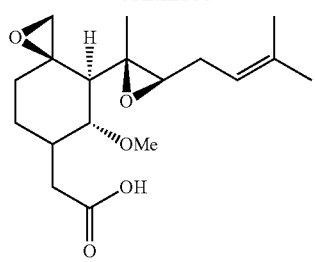
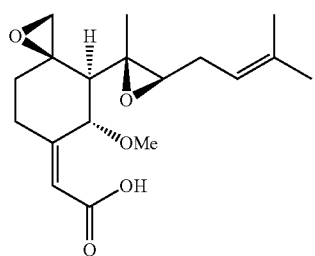
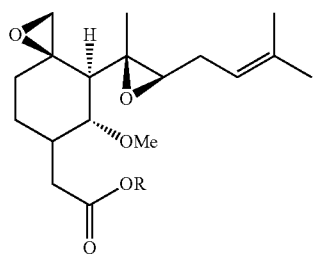
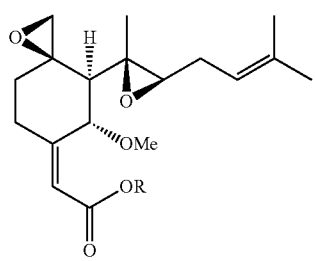
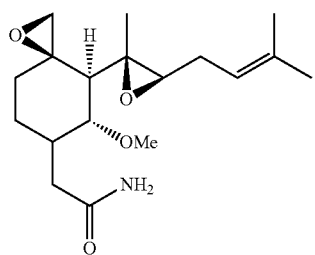
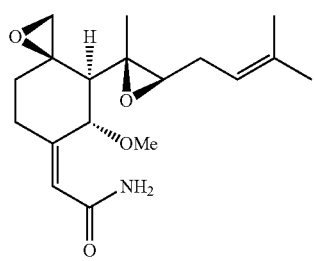
28
-continued
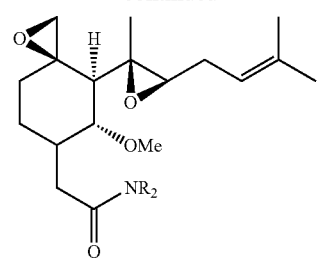
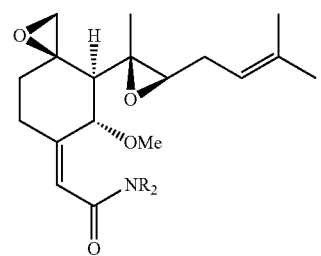
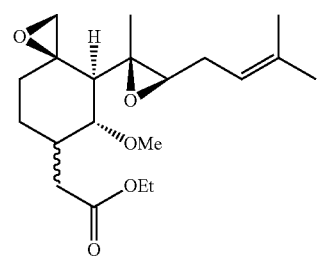
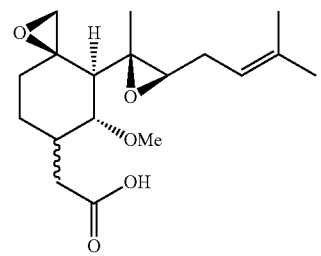
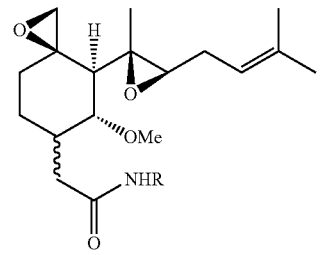
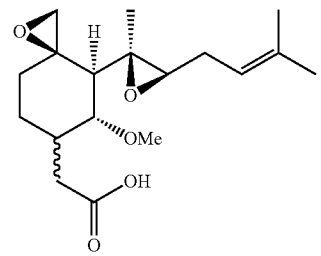

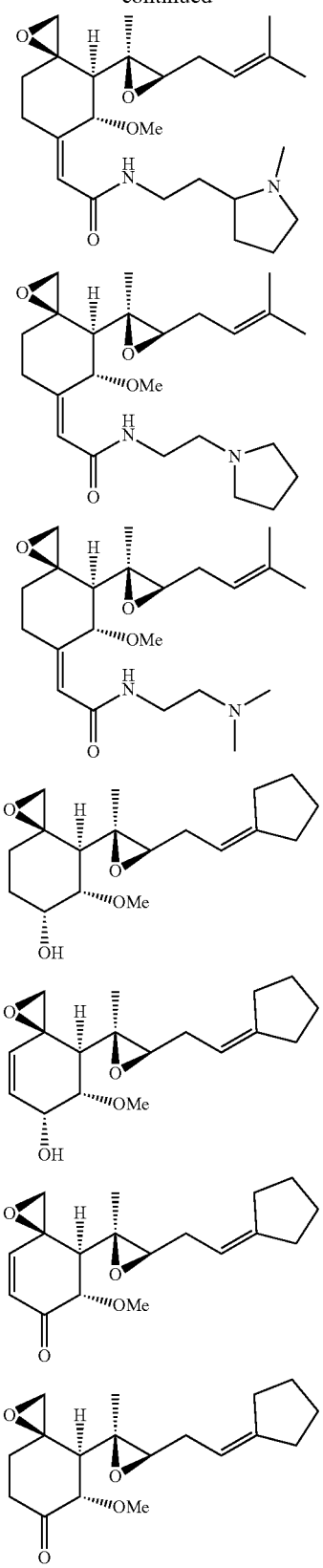
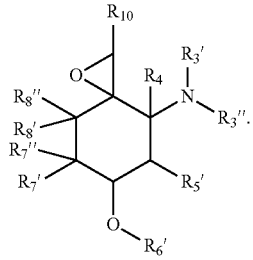
Exemplary compounds include those that have Formula (XIc1):
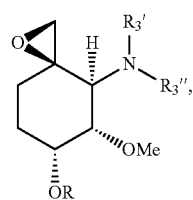
for example,
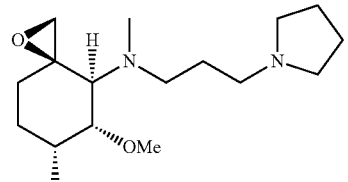
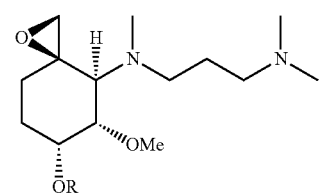
Exemplary compounds also include those that have Formula (XIc2):
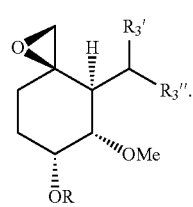
In certain other embodiments, preferred compounds have Formula XIc:

Exemplary compounds include:
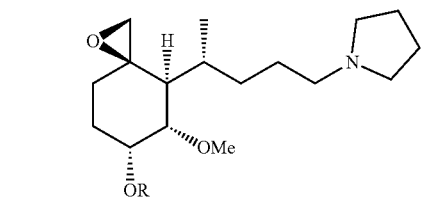
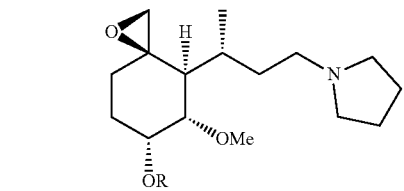
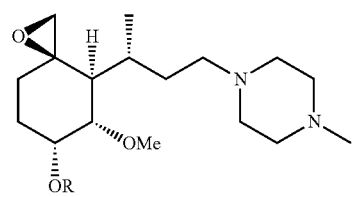
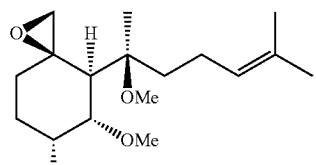
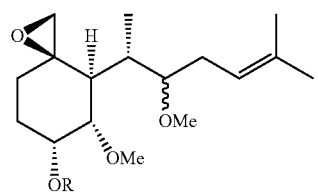
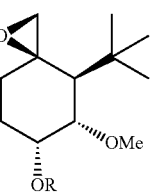
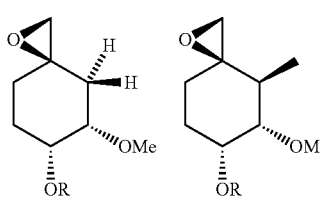
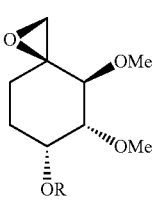
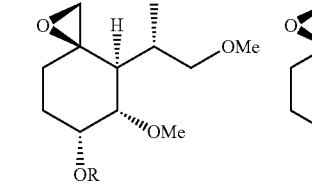
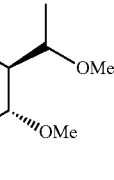
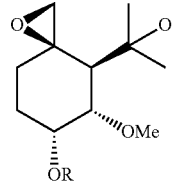
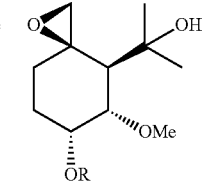
In certain other embodiments, preferred compounds have Formula XIIa or XIIb:
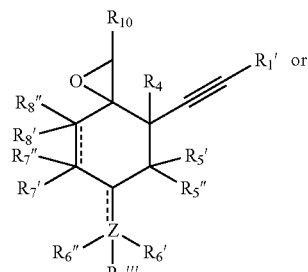
(XIIa)
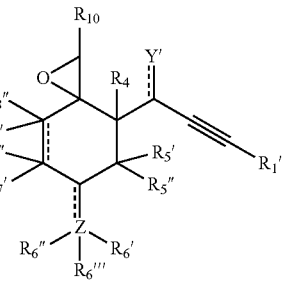
(XIb)
wherein Y' is a H, an alkyl, or a carbonyl O. Examples include:
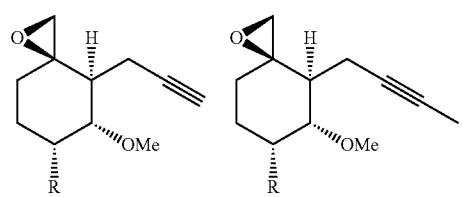
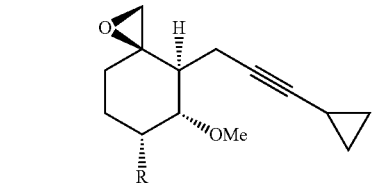
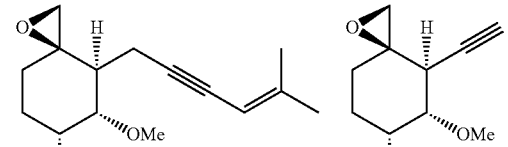
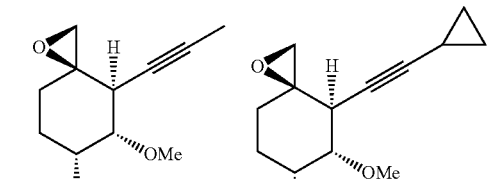
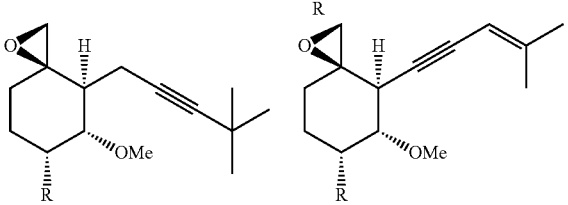

-continued

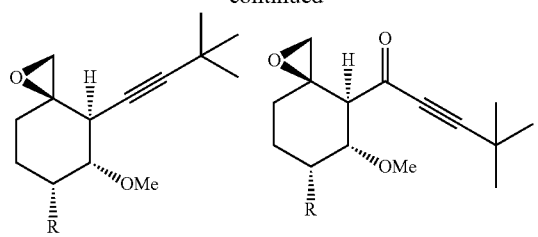

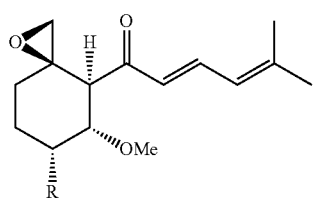

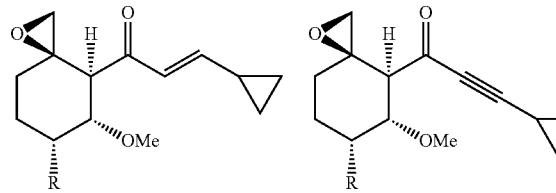

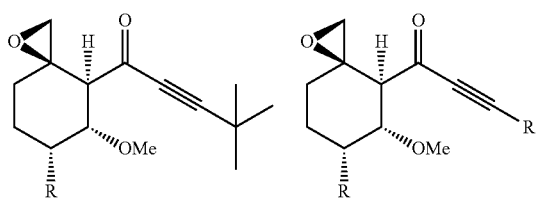

Examples also include compounds:

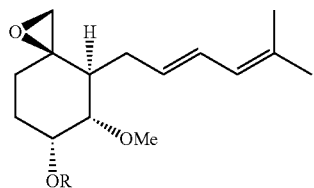

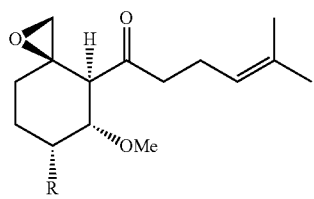

In certain embodiments, the preferred $R_{10}$ is H, F or Cl. In certain embodiments, the preferred $R_{10}$ is H. In some embodiments, the H at $R_{10}$ is preferred to be at least predominantly D.

(Ia)

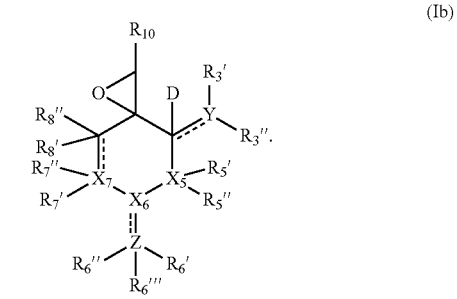

In some embodiments, $R_{10}$ is a $C_1$-$C_3$ alkyl group.

In certain embodiments, the preferred $R_4$ is H, F or Cl. In certain embodiments, the preferred $R_4$ is H. In some embodiments, the H at $R_4$ is preferred to be at least predominantly D.

(Ib)

In some embodiments, $R_4$ is a $C_1$-$C_3$ alkyl group.

Exemplary compounds also include:

(XIII)

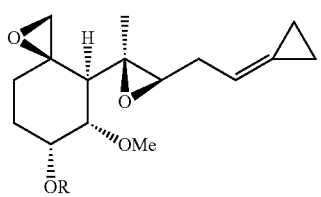

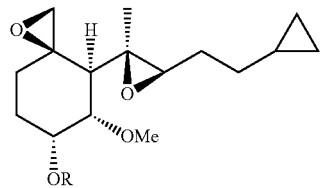

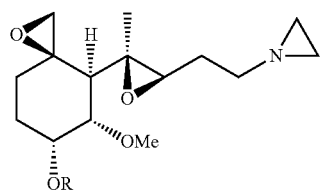

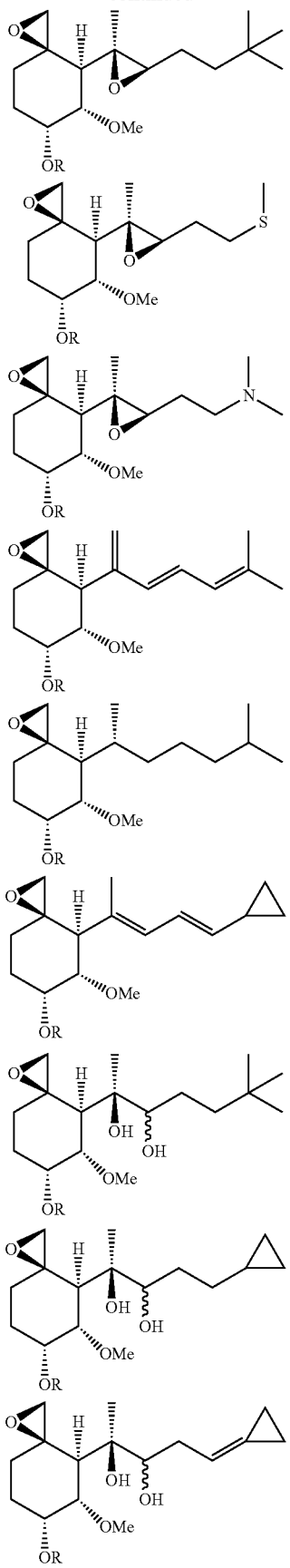
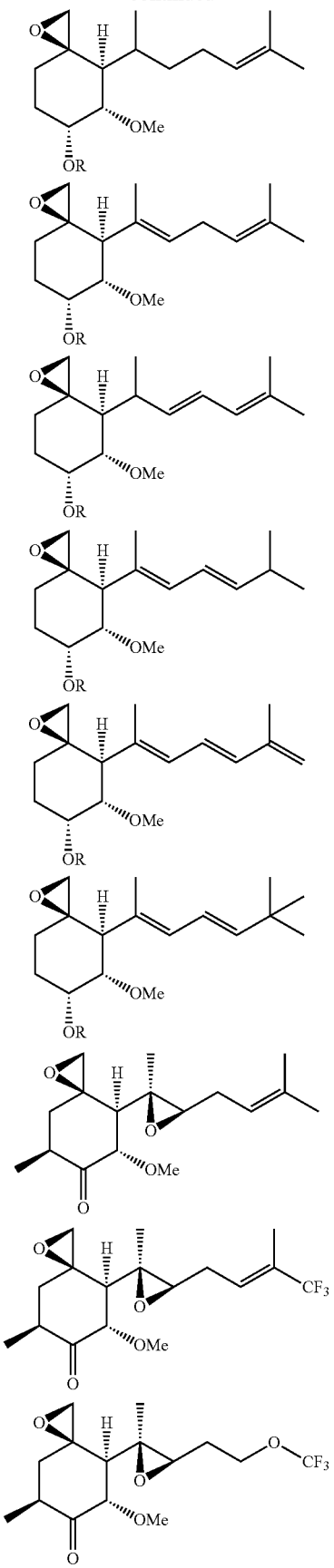

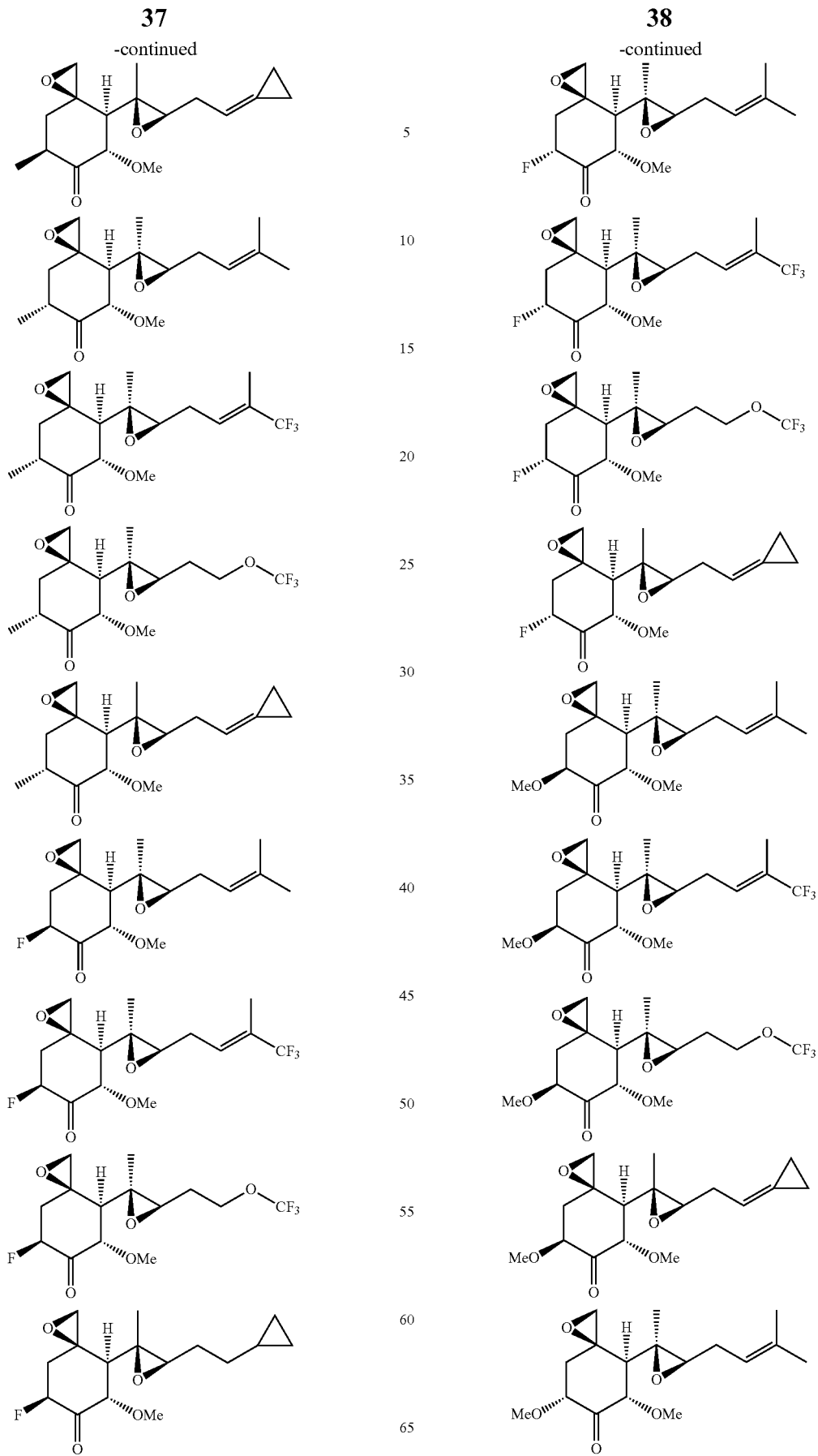

39
-continued
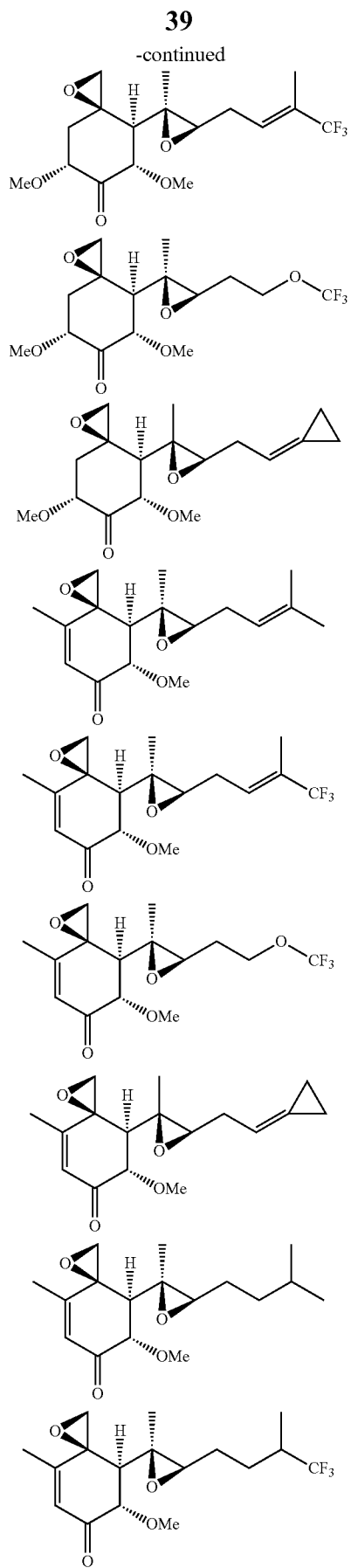
40
-continued
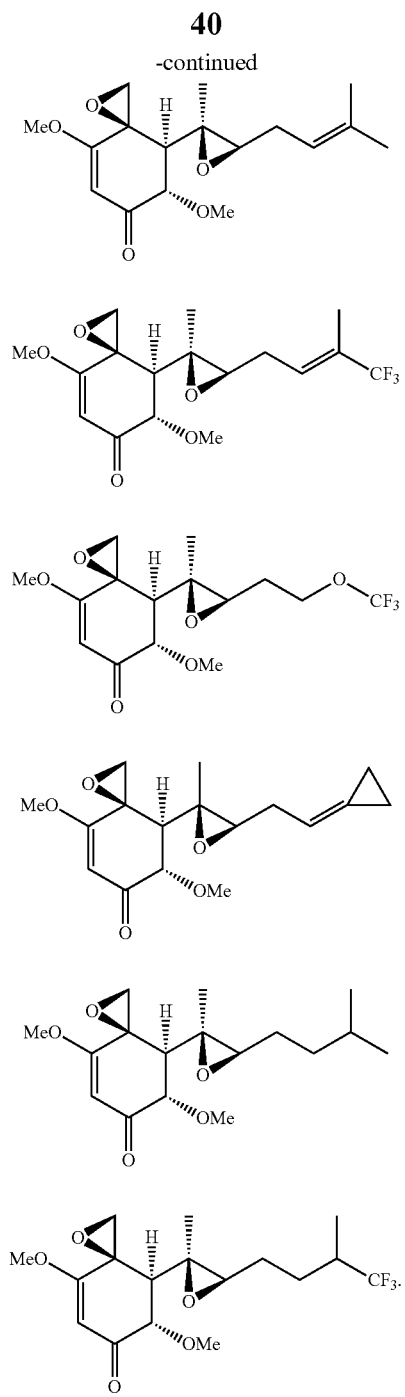
Other contemplated compounds include:
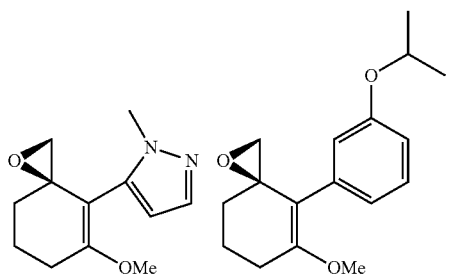

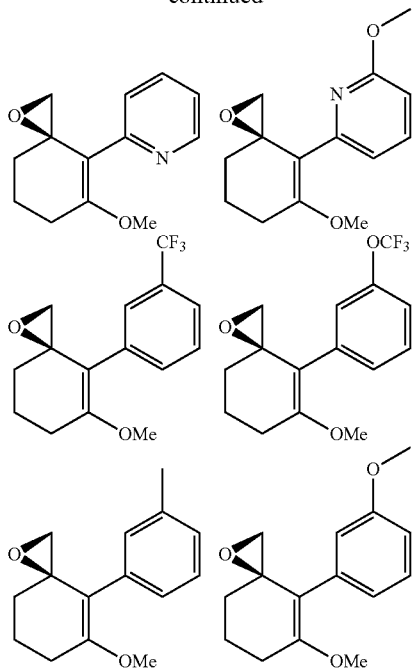

In another aspect, the invention generally relates to a method of making a compound of Formula I,

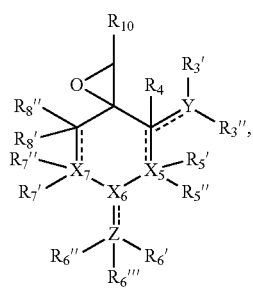

comprising for example, one or more steps, and/or intermediates:

Another aspect of this disclosure provides methods of modulating the activity of MetAP2. Such methods comprise exposing said receptor to a compound described herein. The ability of compounds described herein to modulate or inhibit MetAP2 can be evaluated by procedures known in the art and/or described herein. Another aspect of the invention provides methods of treating a disease associated with expression or activity of MetAP2 in a patient. For example, a contemplated method includes administering a disclosed compound in an amount sufficient to establish inhibition of intracellular MetAP2 effective to increase thioredoxin production in the patient and to induce multi organ stimulation of anti-obesity processes in the subject, for example, by administering a disclosed compound in an amount insufficient to reduce angiogenesis in the patient.

In certain embodiments, the disclosure provides a method of treating and or ameliorating obesity in a patient by administering an effective amount of a disclosed compound. Also provided herein are methods for inducing weight loss in a patient in need thereof.

Other contemplated methods of treatment include method of treating or ameliorating an obesity-related condition or co-morbidity, by administering a compound disclosed herein to a subject. For example, contemplated herein are methods for treating type 2 diabetes in a patient in need thereof.

Exemplary co-morbidities or other disorders that may be treated by a disclosed compound may include cardiac disorders, endocrine disorders, respiratory disorders, hepatic disorders, skeletal disorders, psychiatric disorders, metabolic disorders, metabolic disorders, and reproductive disorders.

Exemplary cardiac disorders include hypertension, dyslipidemia, ischemic heart disease, cardiomyopathy, cardiac infarction, stroke, venous thromboembolic disease and pulmonary hypertension. Exemplary endocrine disorders include type 2 diabetes and latent autoimmune diabetes in adults. Exemplary respiratory disorders include obesity-hyperventilation syndrome, asthma, and obstructive sleep apnea. An exemplary hepatic disorder is nonalcoholic fatty liver disease. Exemplary skeletal disorders include back pain and osteoarthritis of weight-bearing joints. Exemplary metabolic disorders include Prader-Willi Syndrome and polycystic ovary syndrome. Exemplary reproductive disorders include sexual dysfunction, erectile dysfunction, infertility, obstetric complications, and fetal abnormalities. Exemplary psychiatric disorders include weight-associated depression and anxiety.

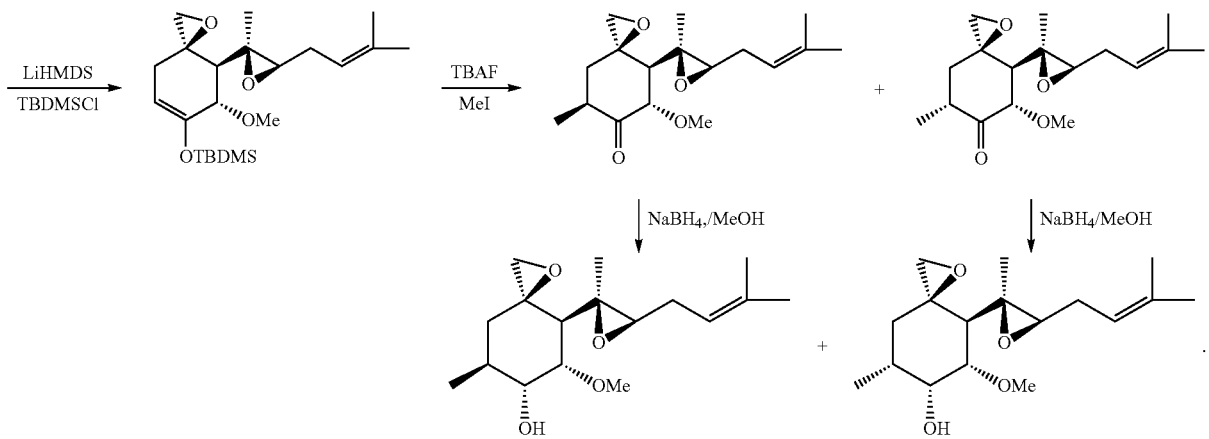

In particular, in certain embodiments, the disclosure provides a method of treating the above medical indications comprising administering to a subject in need thereof a therapeutically effective amount of a compound described herein. Disclosed methods may be for the treatment of diseases in humans and other animals including domesticated animals. Any mode of administration including oral, topical, transdermal, intravenous, intramuscular, inhalational, and parenteral administration of the pharmaceutical compositions may be used. In certain embodiments, the compounds of the invention may be useful in medical devices or in coatings for medical devices.

Other contemplated embodiments include methods of treating a patient suffering from cancer, e.g. colorectal cancer and/or other cancers (e.g. Kaposi's sarcoma, lung cancer, breast cancer, prostate cancer, head and neck cancer, liver cancer, ovarian, or laryngeal or mouth cancer; e.g. disclosed compounds, for example, at certain dosages, may suppress tumor angiogenesis), that include administering an effective amount of a disclosed compound.

Disclosed compounds may also be used as e.g. an antimicrobial, antifungal, and/or antiprotozoal compound, e.g. disclosed herein are methods of treating an animal (e.g. an insect (e.g. bee), fish, mammal, amphipian, bird or reptile) suffering from a microbial or protozoal infection that include administering a disclosed compound to the animal. For example, provided herein are method of treating a protozoal, myxozoan or bacterial infection (e.g. by *Nosema apis*) in bees or in fish (e.g. a method of treating an infection caused by *T. bryosalmonae, H. carassii, S. renicola, Myxobolus* sp., *T. wuhanensis*, and/or *M. giardi*.)

The compounds of the invention may be administered to patients (animals (e.g. cats, dogs, and/or other companion animals or humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound of this invention may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

In certain embodiments, the compounds of the invention may be administered orally or parenterally at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.001 mg/kg to about 4 mg/kg, from about 0.1 mg/kg to about 10 mg/kg, from about 1 mg/kg to about 25 mg/kg, of subject body weight, administered daily, one or more times a day, every other day, every third or fourth day, every week, every two weeks, every three weeks, or every four weeks. In certain embodiments, the desired dosage may be delivered using multiple administrations (e.g., two, three, four, five, six, seven, eight, nine, or ten administrations).

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a weight loss target, is achieved. A treatment regimen can include a corrective phase, during which dose sufficient to provide reduction of weight is administered, and can be followed by a maintenance phase, during which a e.g. over dose sufficient to weight gain is administered. A suitable maintenance dose is likely to be found in the lower parts of the dose ranges provided herein, but corrective and maintenance doses can readily be established for individual subjects by those of skill in the art without undue experimentation, based on the disclosure herein. Maintenance doses can be employed to maintain body weight in subjects whose body weight has been previously controlled by other means, including diet and exercise, bariatric procedures such as bypass or banding surgeries, or treatments employing other pharmacological agents.

Another aspect of the disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may bemixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the invention provides enteral pharmaceutical formulations including a disclosed compound an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum.

The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleat, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e. g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present invention.

Advantageously, the invention also provides kits for use by a e.g. a consumer in need of weight loss. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Also contemplated herein are methods and compositions that include a second active agent, or administering a second active agent. For example, in addition to being overweight or obese, a subject or patient can further have overweight- or obesity-related co-morbidities, i.e., diseases and other adverse health conditions associated with, exacerbated by, or precipitated by being overweight or obese. Contemplated herein are disclosed compounds in combination with at least one other agent that has previously been shown to treat these overweight- or obesity-related conditions.

For example, Type II diabetes has been associated with obesity. Certain complications of Type II diabetes, e.g., disability and premature death, can be prevented, ameliorated, or eliminated by sustained weight loss (Astrup, A. Pub Health Nutr (2001) 4:499-5 15). Agents administered to treat Type II diabetes include sulfonylureas (e.g., Chlorpropamide, Glipizide, Glyburide, Glimepiride); meglitinides (e.g., Repaglinide and Nateglinide); biguanides (e.g., Metformin); thiazolidinediones (Rosiglitazone, Troglitazone, and Pioglitazone); dipeptidylpeptidase-4 inhibitors (e.g., Sitagliptin, Vildagliptin, and Saxagliptin); glucagon-like peptide-1 mimetics (e.g., Exenatide and Liraglutide); and alpha-glucosidase inhibitors (e.g., Acarbose and Miglitol).

Cardiac disorders and conditions, for example hypertension, dyslipidemia, ischemic heart disease, cardiomyopathy, cardiac infarction, stroke, venous thromboembolic disease and pulmonary hypertension, have been linked to overweight or obesity. For example, hypertension has been linked to obesity because excess adipose tissue secretes substances that are acted on by the kidneys, resulting in hypertension. Additionally, with obesity there are generally higher amounts of insulin produced (because of the excess adipose tissue) and this excess insulin also elevates blood pressure. A major treatment option of hypertension is weight loss. Agents administered to treat hypertension include Chlorthalidone; Hydrochlorothiazide; Indapamide, Metolazone; loop diuretics (e.g., Bumetanide, Ethacrynic acid, Furosemide, Lasix, Torsemide); potassium-sparing agents (e.g., Amiloride hydrochloride, benzamil, Spironolactone, and Triamterene); peripheral agents (e.g., Reserpine); central alpha-agonists (e.g., Clonidine hydrochloride, Guanabenz acetate, Guanfacine hydrochloride, and Methyldopa); alpha-blockers (e.g., Doxazosin mesylate, Prazosin hydrochloride, and Terazosin hydrochloride); beta-blockers (e.g., Acebutolol, Atenolol, Betaxolol, Bisoprolol fumarate, Carteolol hydrochloride, Metoprolol tartrate, Metoprolol succinate, Nadolol, Penbutolol sulfate, Pindolol, Propranolol hydrochloride, and Timolol maleate); combined alpha- and beta-blockers (e.g., Carvedilol and Labetalol hydrochloride); direct vasodilators (e.g., Hydralazine hydrochloride and Minoxidil); calcium antagonists (e.g., Diltiazem hydrochloride and Verapamil hydrochloride); dihydropyridines (e.g., Amlodipine besylate, Felodipine, Isradipine, Nicardipine, Nifedipine, and Nisoldipine); ACE inhibitors (benazepril hydrochloride, Captopril, Enalapril maleate, Fosinopril sodium, Lisinopril, Moexipril, Quinapril hydrochloride, Ramipril, Trandolapril); Angiotensin II receptor blockers (e.g., Losartan potassium, Valsartan, and Irbesartan); Renin inhibitors (e.g., Aliskiren); and combinations thereof. These compounds are administered in regimens and at dosages known in the art.

Carr et al. (The Journal of Clinical Endocrinology & Metabolism (2004) Vol. 89, No. 6 2601-2607) discusses a link between being overweight or obese and dyslipidemia. Dyslipidemia is typically treated with statins. Statins, HMG-CoA reductase inhibitors, slow down production of cholesterol in a subject and/or remove cholesterol buildup from arteries. Statins include mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin. These compounds are administered in regimens and at dosages known in the art. Eckel (Circulation (1997) 96:3248-3250) discusses a link between being overweight or obese and ischemic heart disease. Agents administered to treat ischemic heart disease include statins, nitrates (e.g., Isosorbide Dinitrate and Isosorbide Mononitrate), beta-blockers, and calcium channel antagonists. These compounds are administered in regimens and at dosages known in the art.

Wong et al. (Nature Clinical Practice Cardiovascular Medicine (2007) 4:436-443) discusses a link between being overweight or obese and cardiomyopathy. Agents administered to treat cardiomyopathy include inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers. These compounds are administered in regimens and at dosages known in the art. Yusef et al. (Lancet (2005) 366(9497): 1640-1649) discusses a link between being overweight or obese and cardiac infarction. Agents administered to treat cardiac infarction include ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase). These compounds are administered in regimens and at dosages known in the art.

Suk et al. (Stroke (2003) 34:1586-1592) discusses a link between being overweight or obese and strokes. Agents administered to treat strokes include anti-platelet agents (e.g., Aspirin, Clopidogrel, Dipyridamole, and Ticlopidine), anticoagulant agents (e.g., Heparin), and thrombolytic agents. Stein et al. (The American Journal of Medicine (2005) 18(9):978-980) discusses a link between being overweight or obese and venous thromboembolic disease. Agents administered to treat venous thromboembolic disease include anti-platelet agents, anticoagulant agents, and thrombolytic agents. Sztrymf et al. (Rev Pneumol Clin (2002) 58(2):104-10) discusses a link between being overweight or obese and pulmonary hypertension. Agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil. Respiratory disorders and conditions such as obesity-hypoventilation syndrome, asthma, and obstructive sleep apnea, have been linked to being overweight or obese. Elamin (Chest (2004) 125:1972-1974) discusses a link between being overweight or obese and asthma. Agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex.

Kessler et al. (Eur Respir J (1996) 9:787-794) discusses a link between being overweight or obese and obstructive sleep apnea. Agents administered to treat sleep apnea include Modafinil and amphetamines.

Hepatic disorders and conditions, such as nonalcoholic fatty liver disease, have been linked to being overweight or obese. Tolman et al. (Ther Clin Risk Manag (2007) 6:1153-1163) discusses a link between being overweight or obese and nonalcoholic fatty liver disease. Agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents.

Skeletal disorders and conditions, such as, back pain and osteoarthritis of weight-bearing joints, have been linked to being overweight or obese. van Saase (J Rheumatol (1988) 15(7):1152-1158) discusses a link between being overweight or obese and osteoarthritis of weight-bearing joints. Agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid.

Metabolic disorders and conditions, for example, Prader-Willi Syndrome and polycystic ovary syndrome, have been linked to being overweight or obese. Cassidy (Journal of Medical Genetics (1997) 34:917-923) discusses a link between being overweight or obese and Prader-Willi Syndrome. Agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax).

Hoeger (Obstetrics and Gynecology Clinics of North America (2001) 28(1):85-97) discusses a link between being overweight or obese and polycystic ovary syndrome. Agents administered to treat polycystic ovary syndrome include insulin-sensitizers, combinations of synthetic estrogen and progesterone, Spironolactone, Eflornithine, and Clomiphene. Reproductive disorders and conditions such as sexual dysfunction, erectile dysfunction, infertility, obstetric complications, and fetal abnormalities, have been linked to being overweight or obese. Larsen et al. (Int J Obes (Lond) (2007) 8:1189-1198) discusses a link between being overweight or obese and sexual dysfunction. Chung et al. (Eur Urol (1999) 36(1):68-70) discusses a link between being overweight or obese and erectile dysfunction. Agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone. Pasquali et al. (Hum Reprod (1997) 1:82-87) discusses a link between being overweight or obese and infertility. Agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Urofollitropin, Heparin, Follitropin alfa, and Follitropin beta.

Weiss et al. (American Journal of Obstetrics and Gynecology (2004) 190(4): 1091-1097) discusses a link between being overweight or obese and obstetric complications. Agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic.

Psychiatric disorders and conditions, for example, weight-associated depression and anxiety, have been linked to being overweight or obese. Dixson et al. (Arch Intern Med (2003) 163:2058-2065) discusses a link between being overweight or obese and depression. Agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate).

Simon et al. (Archives of General Psychiatry (2006) 63(7):824-830) discusses a link between being overweight or obese and anxiety. Agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers.

Another aspect of the invention provides methods for facilitating and maintaining weight loss in a subject involving administering to the subject an amount of a disclosed compound effective to result in weight loss in the subject; and administering a therapeutically effective amount of a different weight loss agent to maintain a reduced weight in the subject. Weight loss agents include serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, bromocriptine, lorcaserin, topiramate, or agents acting to modulate food intake by blocking ghrelin action, inhibiting diacylglycerol acyltransferase 1 (DGAT1) activity, inhibiting stearoyl CoA desaturase 1 (SCD1) activity, inhibiting neuropeptide Y receptor 1 function, activating neuropeptide Y receptor 2 or 4 function, or inhibiting activity of sodium-glucose cotransporters 1 or 2. These compounds are administered in regimens and at dosages known in the art.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance which can be adapted to the practice of this invention in its various embodiments and equivalents thereof.

EXAMPLES

The following examples illustrate the preparation and/or properties of exemplary disclosed compounds.

Example 1: General Methods

Starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds provided herein are produced by organic synthesis methods known to one of ordinary skill in the art as illustrated in the following Examples. Starting materials to synthesize the compounds of Formulas herein are commercially available from, for example, Sigma-Aldrich (Millwaukee, Wis.). Reactions were monitored by TLC (Silica Gel 60 $F_{254}$, EMD Chemicals) or HPLC (HP 1090). Compounds of Formulas herein and their intermediates were purified by crystallization or silica gel flash chromatography. Characterization of compounds and intermediates was done with nuclear magnetic resonance spectroscopy (NMR) and mass spectrometry (MS).

Example 2: General Process Conditions

The following applies in general to all processes mentioned herein before and hereinafter. All the above-mentioned process steps are carried out under reaction conditions that are well known in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the $H^+$ form, depending on the nature of the reaction and/or of the reactants at reduced, normal or elevated temperature, for example in a temperature range of from about −100° C. to about 190° C., including, for example, from about −80° C. to about 150° C., for example at from about −80 to about 60° C., at room temperature, at from about −20 to about 40° C. or at reflux temperature, under atmospheric pressure or in a closed vessel, where appropriate under pressure, and/or in an inert atmosphere, for example under an argon or nitrogen atmosphere.

At each stage of the reactions, mixtures of isomers that are formed can be separated into the individual isomers, for example diastereoisomers or enantiomers, or into any desired mixtures of isomers, for example racemates or mixtures of diastereoisomers.

The solvents include solvents suitable for a particular reaction that are selected among, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethylacetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in purifying or isolating the compounds herein, for example by chromatography or partitioning.

The compounds, including their salts, may also be obtained in the form of hydrates, or their crystals may, for example, include the solvent used for crystallization. Different crystalline forms may be present.

The invention encompasses also those forms of the process in which a compound obtainable as an intermediate at any stage of the process is used as starting material and the remaining process steps are carried out; or in which a starting material is formed under reaction conditions; or is used in the form of a derivative, for example, in a protected form or in the form of a salt; or a compound obtainable by the process according to the invention is produced under the process conditions and is processed further in situ.

Example 3

Compound 202

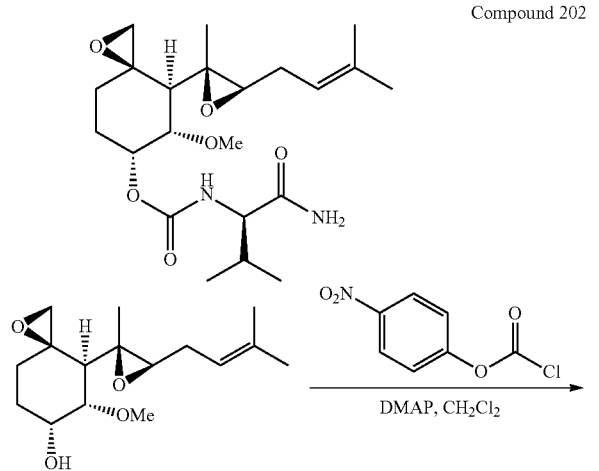

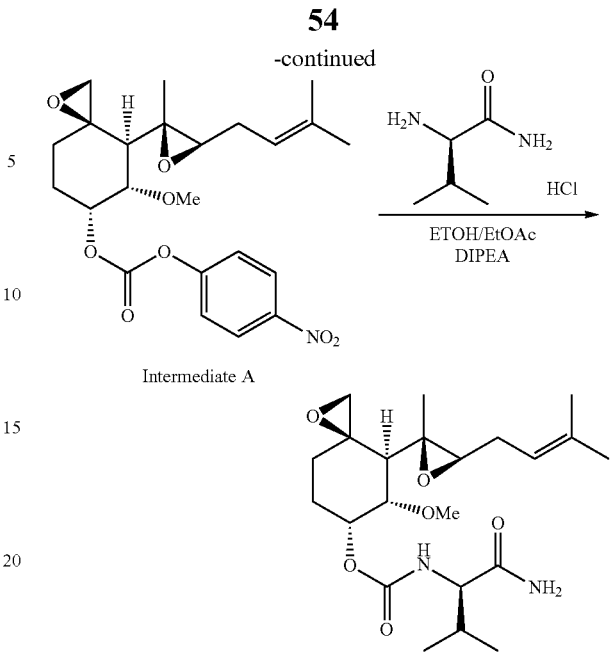

Intermediate A 1.4 g (4.9 mmol) of fumagillol is dissolved in 30 mL of dry $CH_2CL_2$ and cooled to 0° C. DMAP (1.2 g, 9.8 mmol) is added followed by 2 g (10 mmol) of p-nitrophenyl chloroformate. The mixture is allowed to warm up to room temperature overnight and then diluted with 100 mL of $CH_2CL_2$. The mixture is then washed with 2×100 mL of saturated $K_2CO_3$, 2×100 mL of water, and dried over $Na_2SO_4$. Purification by biotage flash chromatography (SiO2, EtOAc/Hexanes gradient) affords 1.7 g of the title compound contaminated with some p-nitrophenol. The material was further purified by dissolving in 100 mL of $CH_2CL_2$ and washing with 2×100 mL of saturated $K_2CO_3$. The material is then dried over $Na_2SO_4$ and condensed in vacuo to give 1.6 g (73%) of Intermediate A as a white amorphous solid.

3.5 g (7.8 mmol) of intermediate A is dissolved in a mixture of 75 mL of ETOH and 25 mL of EtOAc. DIPEA (8.2 mL, 46.9 mmol) and D-Valine amide (6 g, 39.3 mmol) are added and the reaction is allowed to stir at room temperature overnight. In the morning the solvent is removed on the rotovap and the resulting material is dissolved in 100 mL of EtOAc and washed with 2×60 mL of water and 2×50 mL of brine. The organic layer was dried over $Na_2SO_4$ and condensed in vacuo to give the crude product which was purified by biotage flash chromatography (SiO2, MeOH/$CH_2CL_2$ gradient) to give the pure product (2.7 g, 82%).

Example 4

Compound 205

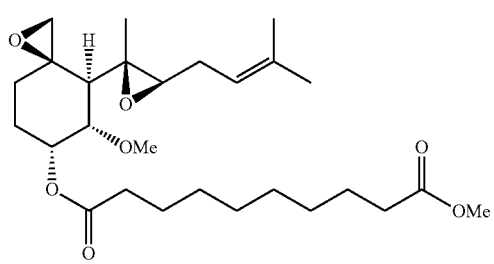

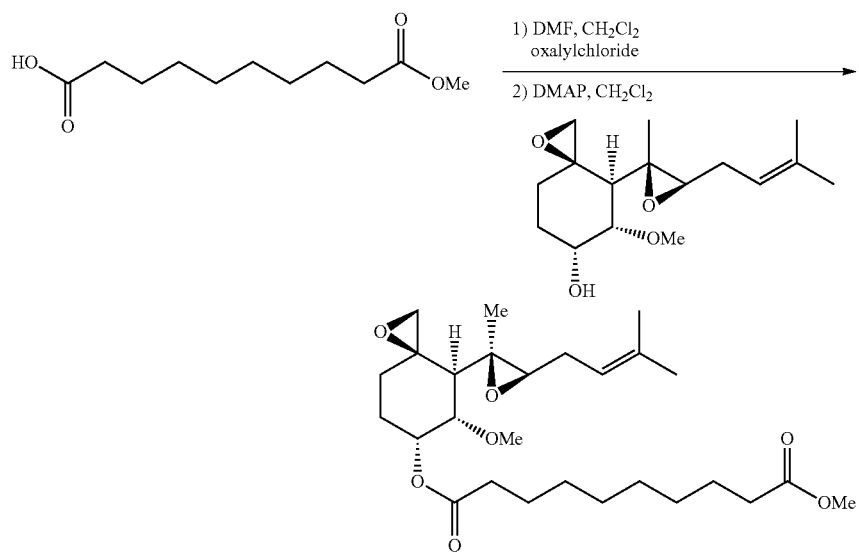

0.5 g (2.3 mmol) of Sebacic acid mono methyl ester is dissolved in 10 mL of dry CH$_2$CL$_2$. Then 0.39 mL (4.6 mmol) of oxallyl chloride is added followed by 3 drops of DMF. Gas evolution is observed and the reaction is allowed to go for 2 h at room temperature. The solvent and excess oxallyl chloride is removed in vacuo and the resulting yellow oil is dissolved in 10 mL of dry CH$_2$CL$_2$. Fumagillol (0.72 g, 2.6 mmol) is added followed by DMAP (0.57 g, 4.6 mmol) and the reaction is allowed to stir overnight at room temperature. In the morning the reaction is diluted with 50 mL of and washed with 2×100 mL of saturated NaHCO$_3$, 2×100 mL of water, and dried over Na$_2$SO$_4$. Purification by biotage flash chromatography (SiO2, EtOAc/Hexanes gradient) affords 0.732 g (67%) of the title compound.

Example 5

Compound 206

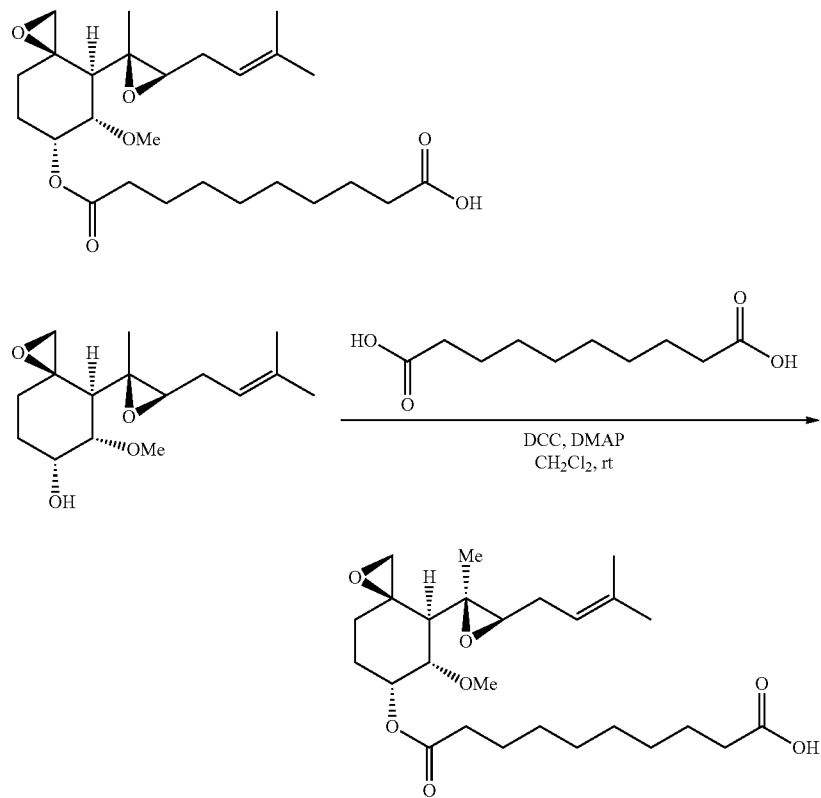

0.3 g (1.1 mmol) of fumagillol, 0.21 g (1.0 mmol) of Sebacic acid, and 0.027 g (0.21 mmol) of DMAP are dissolved in 5 mL of dry CH$_2$CL$_2$. DCC (0.22 g, 1.0 mmol) dissolved in 5 mL of dry CH$_2$CL$_2$ is added drop wise over 3 h with stirring at room temperature. After addition is complete the mixture is allowed to stir for 40 min and then diluted with 50 mL of CH$_2$CL$_2$, washed with 50 mL of water followed by 50 mL of brine, dried over Na$_2$SO$_4$ and condensed in vacuo. Purification by biotage flash chromatography (SiO2, EtOAc/Hexanes gradient) affords 110 mg (24%) of the title compound.

Example 6

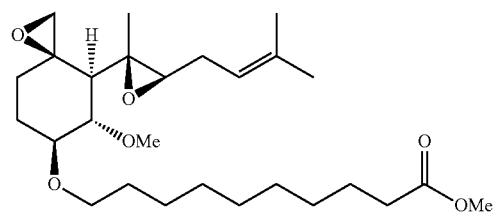

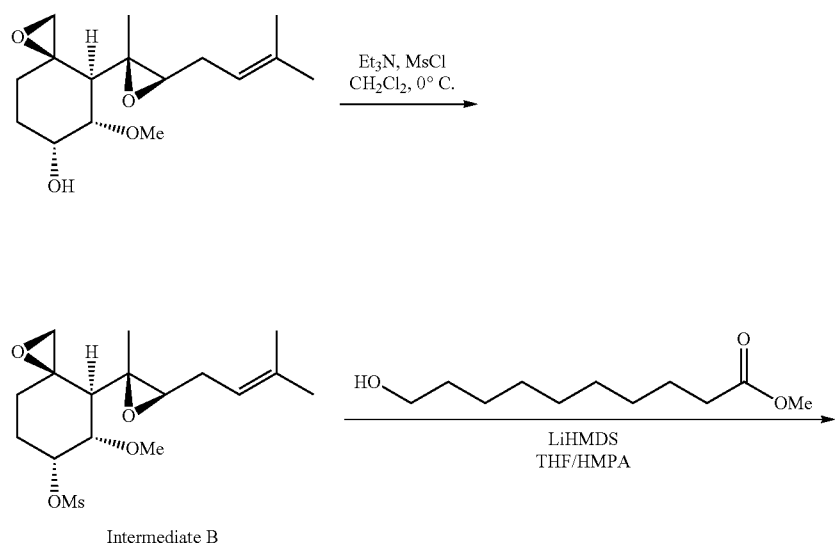

The reaction is allowed to warm up to room temperature overnight and then diluted with 50 mL of EtOAc, washed with 20 mL of saturated NaHCO$_3$, dried over Na$_2$SO$_4$ and condensed in vacuo. Purification by biotage flash chromatography (SiO2, EtOAc/Hexanes gradient) affords 0.100 mg (37%) of Intermediate B.

0.12 g (0.61 mmol) of 10-hydroxy decanoic acid methyl ester is dissolved in 5 mL of dry THF. Then 0.61 mL (0.65 mmol) of 1.06M LiHMDS is added drop wise. A yellow waxy precipitate forms and HMPA (0.75 ml is added). The mixture is stirred vigorously for 30 min. at room temperature followed by drop wise addition of a solution of Intermediate B (0.22 g, 0.57 mmol) in 1 mL of THF. Vigorous stirring is

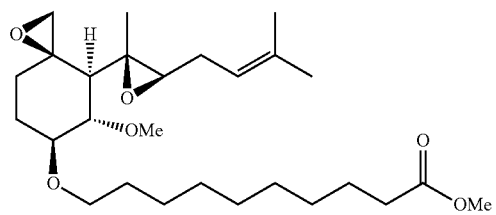

0.2 g (0.71 mmol) of fumagillol is dissolved in 4 mL of dry CH$_2$CL$_2$ and cooled to 0° C. Et3N (0.3 mL, 2.13 mmol) is added drop wise followed by MsCl (82 uL, 1.06 mmol) with stirring. The solution turns yellow and becomes cloudy.

continued overnight and in the morning the solution is diluted with 40 mL of EtOAc and washed with 2×50 mL of water, 50 mL of brine, and dried over Na$_2$SO$_4$. Purification by biotage flash chromatography (SiO$_2$, EtOAc/Hexanes gradient) affords 0.180 mg (64%) of the title compound.

Example 7

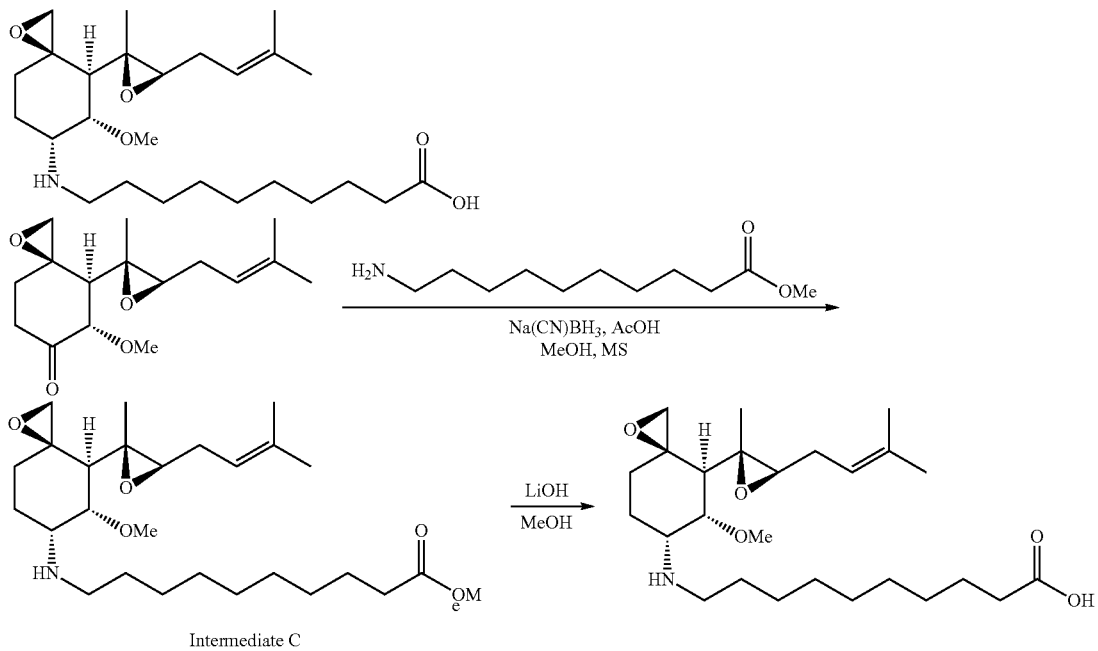

To a solution of 1 eq. of fumigilone (0.3 g, 1.07 mmol) in anhydrous methanol (10 ml) was added 1 eq. of amine (0.215 g, 1.07 mmol), 1.63 eq. of sodium cyanoborohydride (0.11 g, 1.75 mmol), a catalytic amount of acetic acid (0.12 ml) and some 3 A molecular sieves. The reaction was stirred under nitrogen at room temperature overnight. Next morning, the reaction was diluted with ethyl acetate and the organic layer was washed with saturated sodium bicarbonate and brine. The organic layer was dried over magnesium sulfate and concentrated in vacuo. The crude product was purified using a Biotage SP1 chromatography system using a 25M column and methanol/methylene chloride gradient to give 100 mg of pure Intermediate C.

To a solution of 1 eq. of Intermediate C (0.17 g, 0.37 mmol) in 5/1 methanol/water (3 ml) was added 5 eq. lithium hydroxide hydrate and the reaction mixture was stirred at OC overnight. Next morning, the reaction mixture was concentrated to dryness; the residue was diluted with water and washed with ethyl acetate. The aqueous layer was carefully titrated to pH 7 with 0.1 N HCl and was extracted with ethyl acetate (six times). The combined organic extracts were dried over magnesium sulfate and concentrated in vacuo to give thick oil. The oil was dissolved in a minimum amount of ethyl acetate and left in the fridge overnight. Next morning, the product (while solid) was isolated by filtration. 100 mg of pure product was obtained.

Example 8

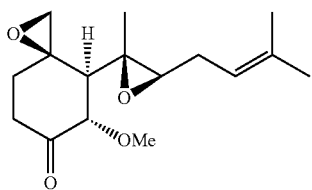

-continued

To a mixture of fumagillol (4.5 g, 17.7 mmol) and 4 A MS (40 g) in DCM (300 mL) was added PCC (10 g, 46 mmol) at 0° C. The mixture was stirred for 1 h at room temperature, followed by filtering through a pad of $Al_2O_3$. The filtrate was concentrated in vacuo. The resulting residue was purified on silica gel to afford fumagillin ketone (3.5 g, 92%) as a colorless oil: $^1$HNMR (500 MHz, $CDCl_3$) δ 5.19 (t, 1H, J=8 Hz), 4.08 (dd, 1H, J=1.0 Hz, J=10.5 Hz), 3.51 (s, 3H), 3.06 (d, 1H, J=4.5 Hz), 2.73 (d, 1H, J=4.5 Hz), 2.65-2.69 (m, 1H), ☐☐ 2.61 (t, 1H, J=6.0 Hz), 2.50-2.54 (m, 1H), ☐☐ 2.37-2.42 (m, 1H), ☐☐ 2.07-2.19 (m, 1H), ☐☐ 2.02-2.06 (m, 1H), ☐☐ 1.88 (d, 1H, J=10.5 Hz), 1.75 (s, 3H), 1.70-1.75 (m, 1H), ☐☐ ☐☐1.66 (s, 3H), 1.29 (s, 3H).

Example 9

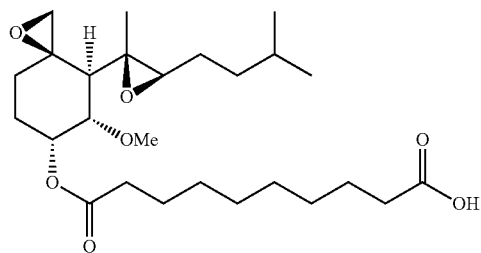

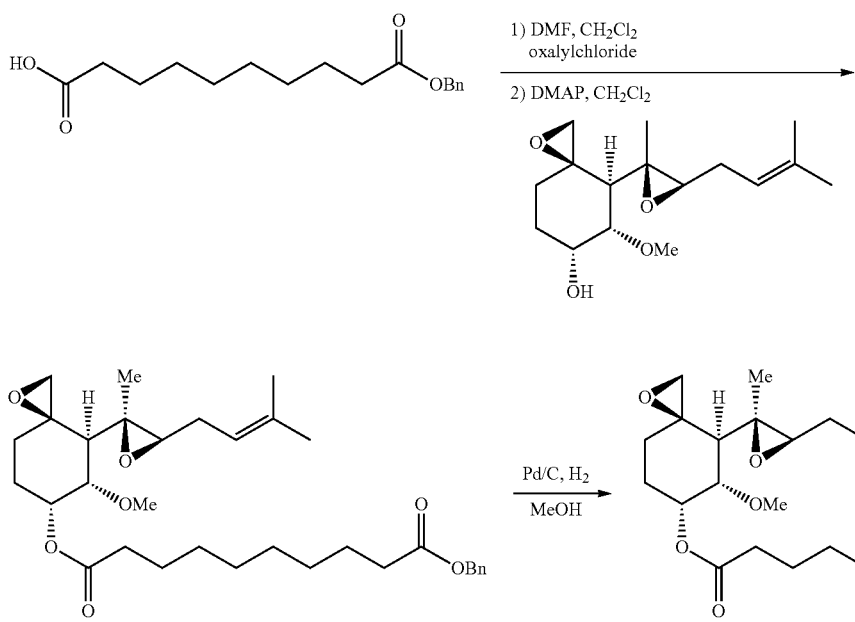

0.1 g (0.34 mmol) of Sebacic acid mono benzyl ester is dissolved in 4 mL of dry $CH_2CL_2$. Then 0.06 mL (0.71 mmol) of oxallyl chloride is added followed by 2 drops of DMF. Gas evolution is observed and the reaction is allowed to go for 2 h at room temperature. The solvent and excess oxallyl chloride is removed in vacuo and the resulting yellow oil is dissolved in 4 mL of dry $CH_2CL_2$. Fumagillol (0.97 g, 3.4 mmol) is added followed by DMAP (0.087 g, 0.68 mmol) and the reaction is allowed to stir overnight at room temperature. In the morning the reaction is diluted with 50 mL of and washed with 2×100 mL of saturated $NaHCO_3$, 2×100 mL of water, and dried over $Na_2SO_4$. Purification by biotage flash chromatography (SiO2, EtOAc/Hexanes gradient) affords 0.145 g (76%) of Intermediate D.

0.14 g (0.25 mmol) of intermediate D is dissolved in 1 mL of EtOH and 26 mg of 10% Pd on C is added. The flask is evacuated and backfilled with nitrogen 3 times and then evacuated and backfilled with hydrogen. The reaction is stirred under a balloon of hydrogen for 20 minutes and then the balloon is removed. The reaction vessel is evacuated and backfilled with nitrogen 3 times and then opened. The mixture is diluted with 20 mL of EtOH and filtered through a pad of celite. The reaction mixture is condensed in vacuo to give the title compound (82 mg, 71%).

Example 10

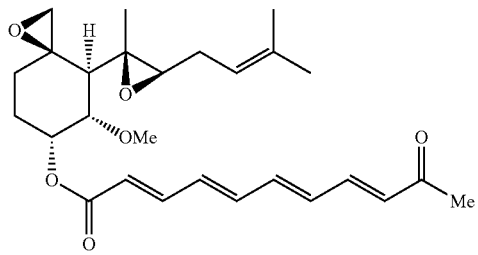

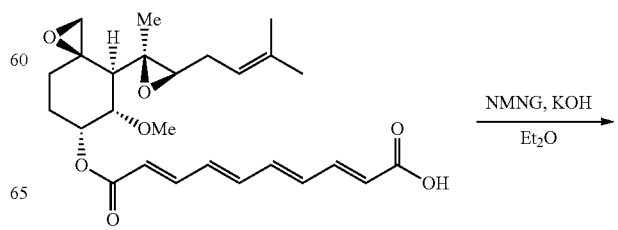

-continued

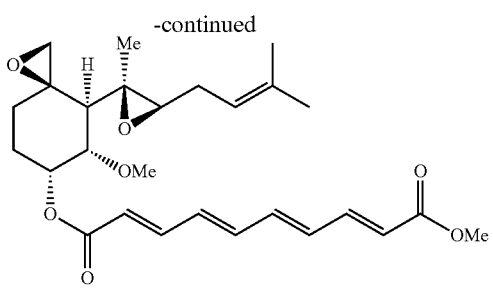

0.3 g (0.65 mmol) of fumagillin is dissolved in 4 mL of dry Et₂O with stirring. Then in an Erlenmeyer flask, solid KOH (~0.5 g) is added to a mixture of 10 mL of water and 20 mL of Et₂O and cooled in and ice bath. Solid N-Methyl-N-nitrosoguanidine is added in portions with swirling until a bright yellow solution of diazomethane is obtained. The diazo methane solution is add drop wise to the solution of fumagillin until a slight yellow color persists in the fumagillin solution. The mixture is allowed to stir for 1 h then excess diazomethane is quenched by addition of a few drops of acetic acid. The resulting material is condensed in vacuo to give the tile compound without further purification.

Example 11

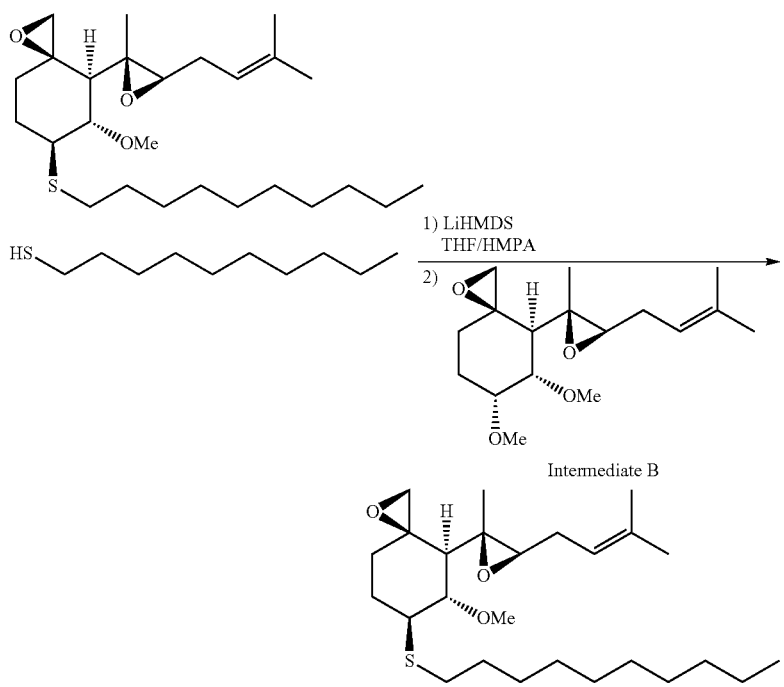

Intermediate B 0.03 g (0.17 mmol) of decane thiol is dissolved in 5 mL of dry THF and 0.1 mL of HMPA. Then 0.18 mL (0.19 mmol) of 1.06M LiHMDS is added drop wise. The mixture is stirred vigorously for 30 min. at room temperature followed by drop wise addition of a solution of Intermediate B (0.06 g, 0.17 mmol) in 1 mL of THF. Vigorous stirring is continued overnight and in the morning the solution is diluted with 40 mL of EtOAc and washed with 2×50 mL of water, 50 mL of brine, and dried over Na₂SO₄. Purification by biotage flash chromatography (SiO2, EtOAc/Hexanes gradient) affords 35 mg (47%) of the title compound.

Example 12

(Compound 216)

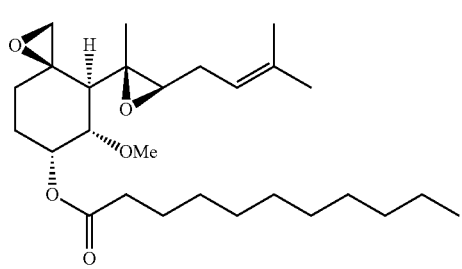

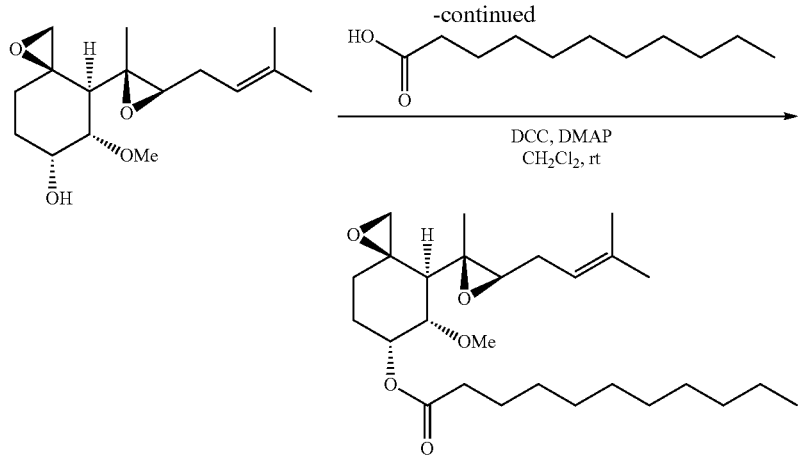

0.28 g (1.0 mmol) of fumagillol, 0.19 g (1.0 mmol) of undecanoic acid acid, and 0.011 g (0.1 mmol) of DMAP are dissolved in 5 mL of dry $CH_2CL_2$. DCC (0.21 g, 1.0 mmol) dissolved in 5 mL of dry $CH_2CL_2$ is added drop wise over 5 minutes with stirring at room temperature. After addition is complete the mixture is allowed to stir overnight and then diluted with 50 mL of $CH_2CL_2$, washed with 50 mL of water followed by 50 mL of brine, dried over $Na_2SO_4$ and condensed in vacuo. Purification by biotage flash chromatography (SiO2, EtOAc/Hexanes gradient) affords 160 mg (36%) of the title compound.

Example 13

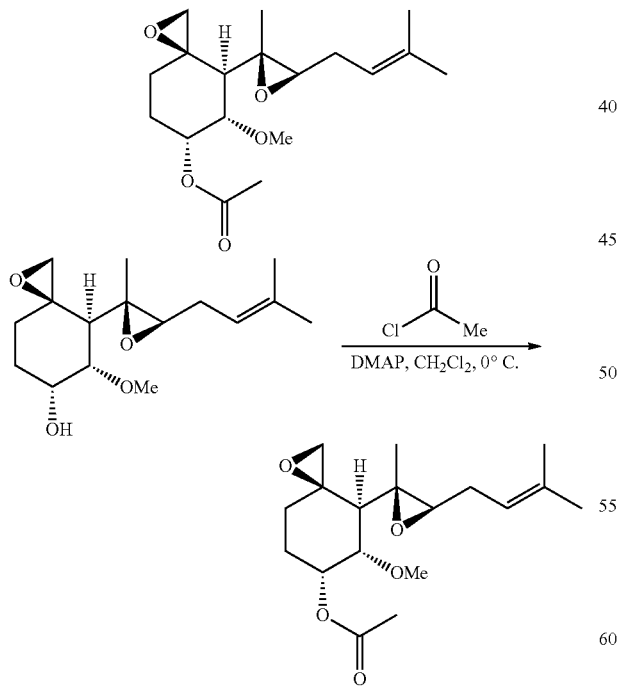

0.1 g (0.35 mmol) of fumagillol is dissolved in 3 mL of dry $CH_2Cl_2$ and cooled to 0° C. Then acetyl chloride (0.022 mL, 0.31 mmol) is added followed by DMAP (0.09 g, 0.71 mmol). The reaction is allowed to stir at 0° C. for 1 h and then warmed to room temperature and diluted with 30 mL of water. The mixture is then extracted with 3×30 mL of $CH_2Cl_2$, dried over $Na_2SO_4$ and condensed in vacuo. Purification by biotage flash chromatography (SiO2, EtOAc/Hexanes gradient) affords 30 mg (27%) of the title compound.

Example 14

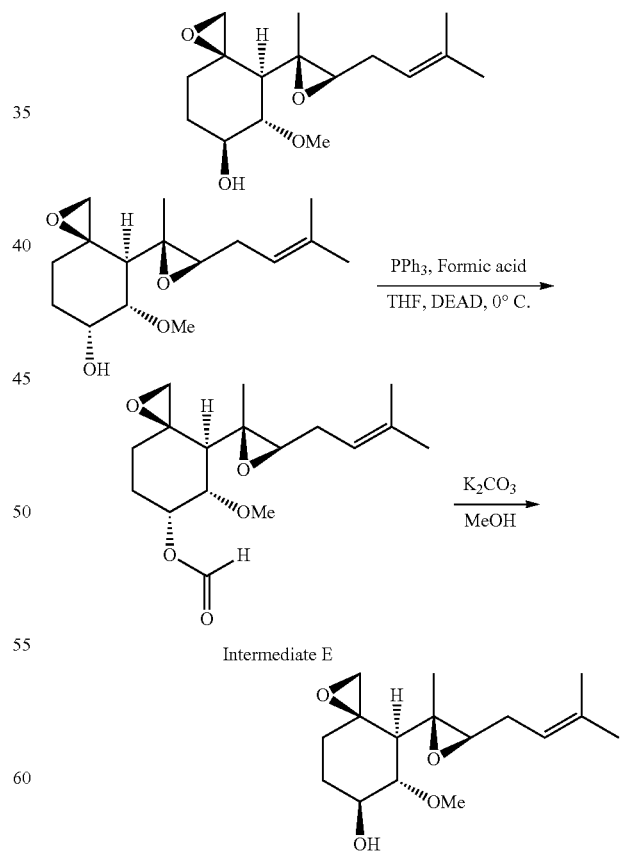

1 g (3.5 mmol) of fumagillol, 2.8 g (10.7 mmol) of triphenylphosphine, and 0.4 mL of formic acid are dissolved in 15 mL of dry THF and cooled to 0° C. Then DEAD (1.7 mL, 13.7 mmol) is added drop wise. The reaction is allowed to warm to room temperature overnight and diluted with 50 mL of EtOAc. The mixture is then washed with 3×30 mL of water, 30 mL of brine, dried over Na$_2$SO$_4$ and condensed in vacuo. Purification by biotage flash chromatography (SiO2, EtOAc/Hexanes gradient) affords 1.1 g (100%) of Intermediate E.

3 g (9.7 mmol) of Intermediate E is dissolved in 40 mL of MeOH and 3.2 g (19.4 mmol) of K$_2$CO$_3$ is added with stirring. The reaction is allowed to stir at room temperature for 4 hours and diluted with 100 mL of EtOAc. The mixture is then washed with 3×50 mL of water, 50 mL of brine, dried over Na$_2$SO$_4$ and condensed in vacuo. Purification by biotage flash chromatography (SiO2, EtOAc/Hexanes gradient) affords 2.2 g (81%) of the title compound.

Example 15

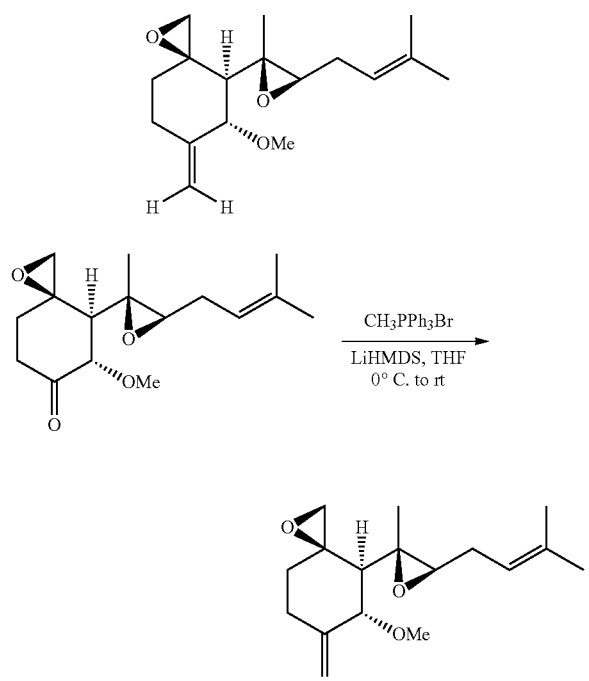

3.04 g (8.5 mmol) of methyl triphenylphosonium bromide is dissolved in THF (100 mL) and cooled to 0° C. Lithium hexamethyldisilazide (1.06 M in THF, 7.4 mL, 7.8 mmol) is added drop wise at 0° C. The solution turns orange and is allowed to stir at 0° C. for 1 h after which a solution of 6-ketofumagillol (2.0 g, 7.1 mmol in 10 mL of THF) is added drop wise at 0° C. The reaction is allowed to warm up to room temperature overnight and then diluted with EtOAc (150 mL) and washed with 3×100 mL of saturated NaHCO$_3$. The resulting solution is dried over Na$^2$SO$_4$ and concentrated in vacuo. Purification by flash chromatography (biotage, SiO$_2$, EtOAc/Hexane gradient) gave the desired product (1.3 g, 66%).

Example 16

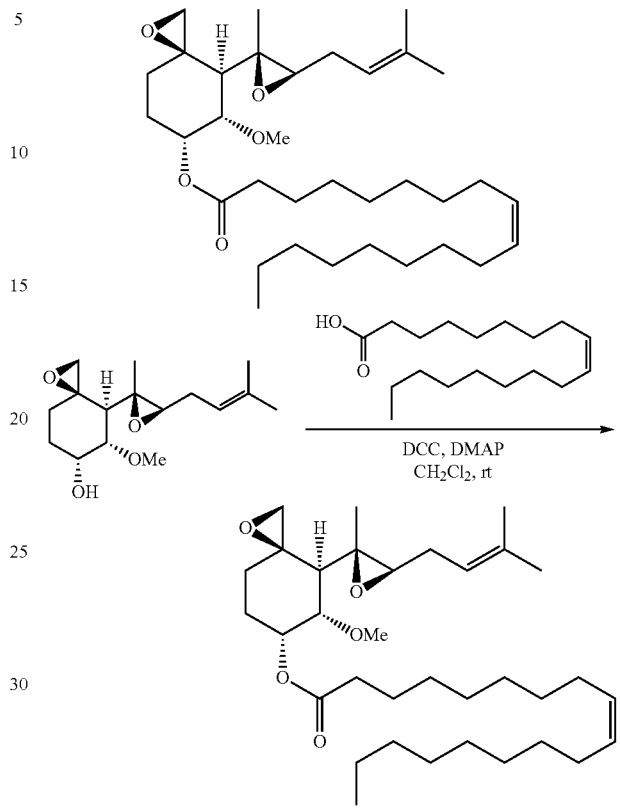

0.20 g (0.71 mmol) of fumagillol, 0.2 g (0.71 mmol) of oleic acid, and 0.009 g (0.07 mmol) of DMAP are dissolved in 5 mL of dry CH$_2$CL$_2$. DCC (0.15 g, 0.73 mmol) dissolved in 2 mL of dry CH$_2$CL$_2$ is added drop wise over 5 minutes with stirring at room temperature. After addition is complete the mixture is allowed to stir overnight and then diluted with 20 mL of CH$_2$CL$_2$, washed with 20 mL of water followed by 20 mL of brine, dried over Na$_2$SO$_4$ and condensed in vacuo. Purification by biotage flash chromatography (SiO2, EtOAc/Hexanes gradient) affords 175 mg (39%) of the title compound.

Example 17

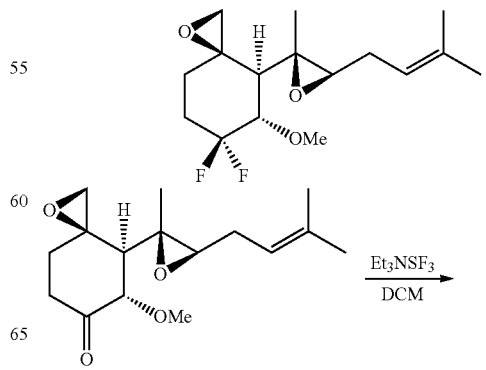

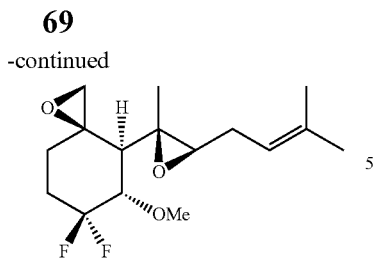

To a solution of 1 eq. of fumigilone (0.2 g, 0.71 mmol) in methylene chloride (5 ml) was added 1.5 eq. of thiethylaminosulfur trilfluoride (0.134 ml, 1.1 mmol) drop wise and the reaction mixture was stirred at room temperature overnight. Next morning, the reaction was diluted with ethyl acetate and was washed with saturated sodium bicarbonate and brine. The organic layer was dried over magnesium sulfate and concentrated in vacuo. The crude compound was purified using a Biotage SP1 chromatography system using a 25s column and ethyl acetate/hexane gradient to give 120 mg of pure product, obtained as a clear oil.

Example 18

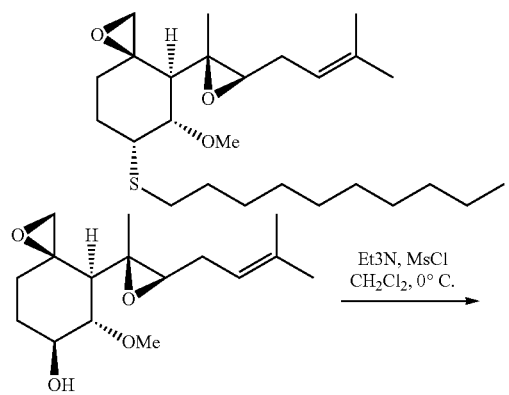

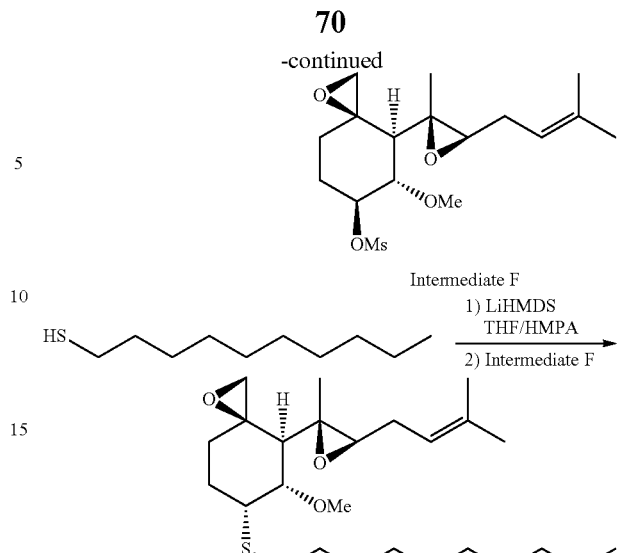

0.84 g (2.9 mmol) of epi-fumagillol, is dissolved in 15 mL of dry CH$_2$CL$_2$. and cooled to 0° C. Et3N (1.3 mL, 9.3 mmol) is added drop wise followed by MsCl (0.35 mL, 4.5 mmol) with stirring. The solution turns yellow and becomes cloudy. The reaction is allowed to warm up to room temperature overnight and then diluted with 100 mL of EtOAc, washed with 50 mL of saturated NaHCO$_3$, dried over Na$_2$SO$_4$ and condensed in vacuo. Purification by biotage flash chromatography (SiO2, EtOAc/Hexanes gradient) affords 618 mg (62%) of Intermediate F.

0.048 g (0.27 mmol) of decane thiol is dissolved in 2 mL of dry THF and 0.1 mL of HMPA. Then 0.28 mL (0.31 mmol) of 1.06M LiHMDS is added drop wise. The mixture is stirred vigorously for 30 min. at room temperature followed by drop wise addition of a solution of Intermediate F (0.1 g, 0.27 mmol) in 1 mL of THF. Vigorous stirring is continued overnight and in the morning the solution is diluted with 40 mL of EtOAc and washed with 2×50 mL of water, 50 mL of brine, and dried over Na$_2$SO$_4$. Purification by biotage flash chromatography (SiO2, EtOAc/Hexanes gradient) affords 73 mg (61%) of the title compound.

Example 19

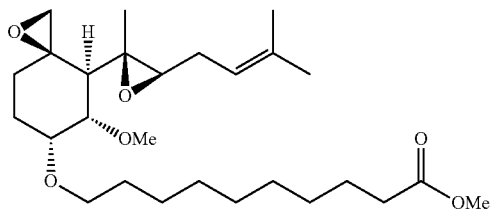

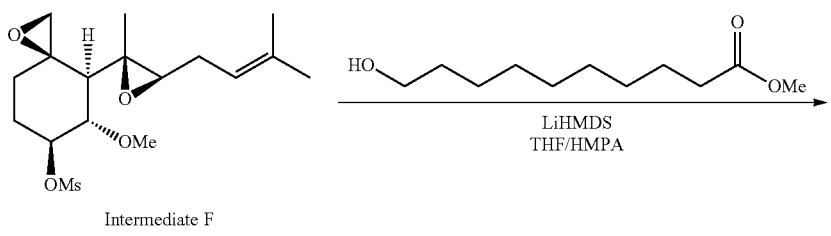

Intermediate F

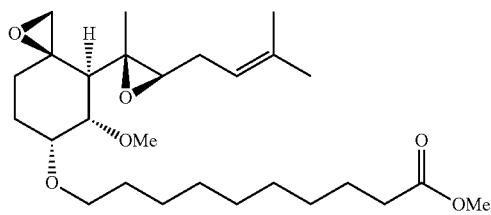

0.056 g (0.27 mmol) of 10-hydroxy decanoic acid methyl ester is dissolved in 2 mL of dry THF and 0.1 mL of HMPA. Then 0.29 mL (0.30 mmol) of 1.06M LiHMDS is added drop wise. The mixture is stirred vigorously for 30 min. at room temperature followed by drop wise addition of a solution of Intermediate F (0.1 g, 0.27 mmol) in 1 mL of THF. Vigorous stirring is continued overnight and in the morning the solution is diluted with 40 mL of EtOAc and washed with 2×50 mL of water, 50 mL of brine, and dried over $Na_2SO_4$. Purification by biotage flash chromatography (SiO2, EtOAc/Hexanes gradient) affords 57 mg (44%) of the title compound.

Example 20

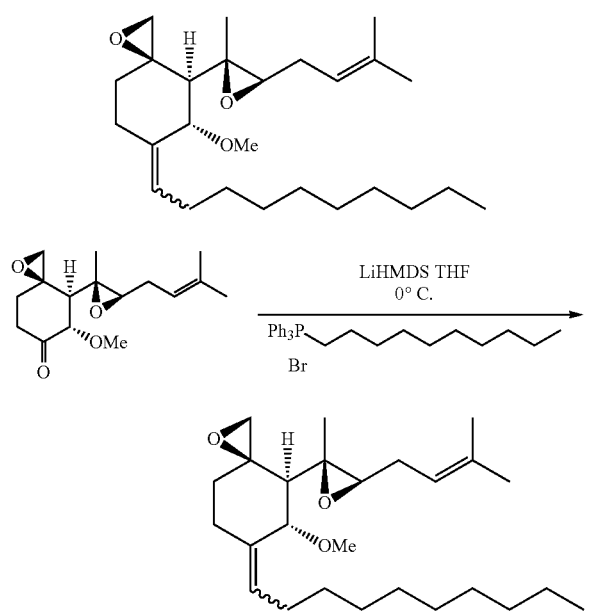

0.62 g (1.1 mmol) of decyl triphenylphosphonium bromide is dissolved in 5 mL of dry THF and cooled to 0° C. Then 0.12 mL (0.11 mmol) of 1.06M LiHMDS is added drop wise. The mixture is stirred at 0° C. for I hour followed by drop wise addition of a solution of fumagillol ketone (0.3 g, 0.11 mmol) in 1 mL of THF. The reaction is allowed to warm to room temperature overnight and in the morning the solution is diluted with 40 mL of EtOAc and washed with 2×50 mL of saturated sodium bicarbonate, 50 mL of brine, and dried over $Na_2SO_4$. Purification by biotage flash chromatography (SiO2, EtOAc/Hexanes gradient) affords 135 mg (32%) of the title compound.

Example 21

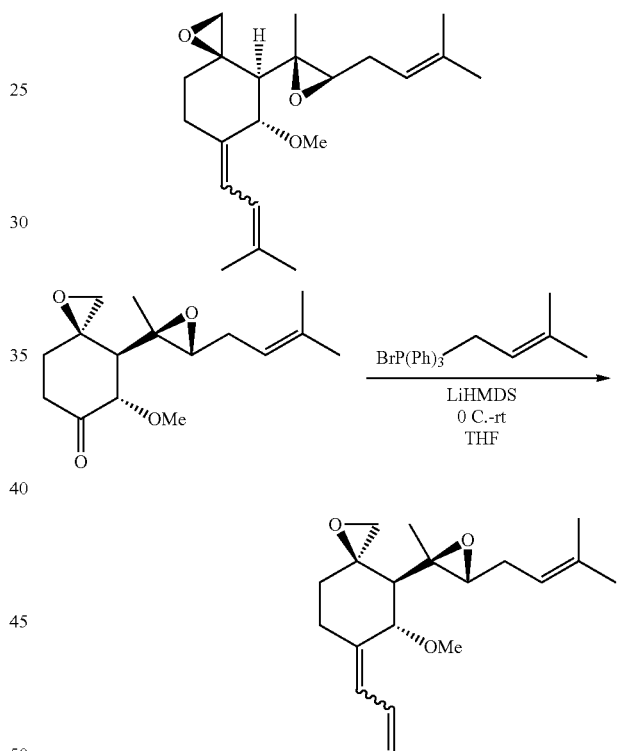

To a cold (0° C.) solution of 1.2 eq of 3-methyl but-2-ene triphenyl phosphonium bromide (0.73 g, 1.78 mmol) in anhydrous tetrahydrofuran (5 ml) was added 1.06 M LiHMDS (1.47 ml, 1.56 mmol) slowly. The reaction mixture turned yellow. The reaction mixture was stirred at OC for 1 hr, the 1 eq of fumigilone (0.40 g, 0.71 mmol), dissolved in 2 ml tetrahydrofuran was added. The reaction was allowed to warm to ambient temperature with stirring overnight. Next day, the reaction mixture was diluted with ethyl acetate, washed with sodium bicarbonate and dried over magnesium sulfate. The crude product was concentrated in vacuo and purified on a SP1 Biotage chromatography system, using a 25S column and ethyl acetate/hexane gradient. The pure product (47 mg) was isolated as clear oil.

Example 22

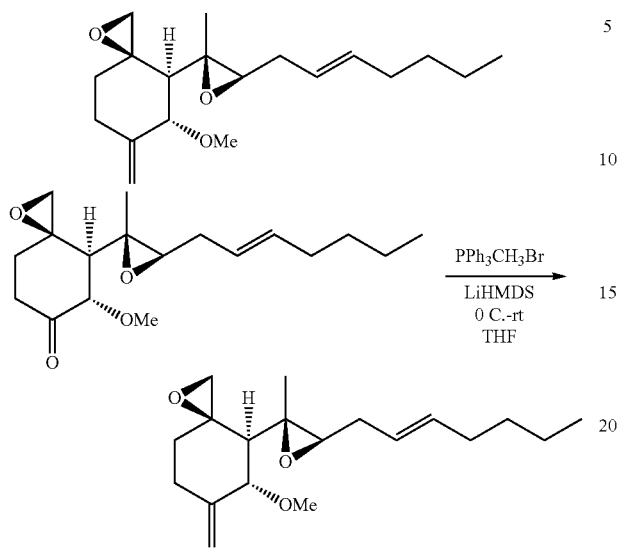

To a cold (0° C.) solution of 1.2 eq of methyl triphenyl phosphonium bromide (0.3 g, 0.85 mmol) in anhydrous tetrahydrofuran (5 ml) was added 1.06 M LiHMDS (0.74 ml, 0.78 mmol) slowly. The reaction mixture turned yellow. The reaction mixture was stirred at OC for 1 hr, the 1 eq of ZGN-229 (0.22 g, 0.71 mmol), dissolved in 2 ml tetrahydrofuran was added. The reaction was allowed to warm to ambient temperature with stirring overnight. Next day, the reaction mixture was diluted with ethyl acetate, washed with sodium bicarbonate and dried over magnesium sulfate. The crude product was concentrated in vacuo and purified on a SP1 Biotage chromatography system, using a 25S column and ethyl acetate/hexane gradient. The pure product (90 mg) was isolated as clear oil.

Example 23

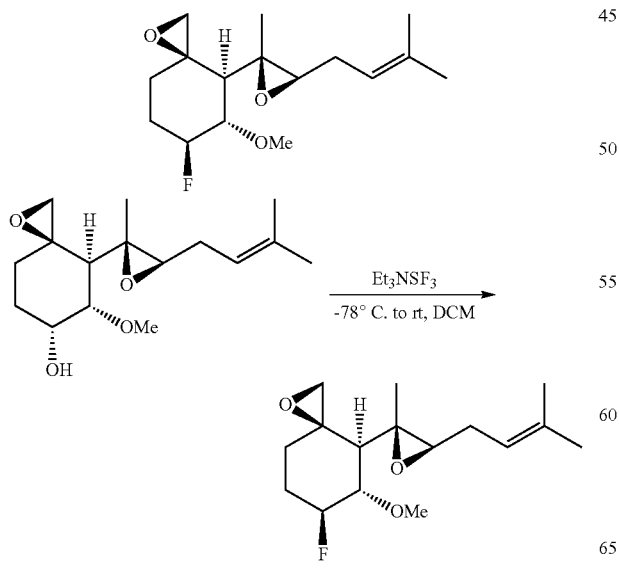

A solution of 1 eq of fumagillol (0.2 g, 0.71 mmol) in methylene chloride (3 ml) was cooled to −78° C. with a dry ice/acetone bath and afterwards 1 eq. of thiethylamino sulfur trifluoride (0.087 ml, 0.71 mmol) was added drop wise and the reaction mixture was warmed to room temperature and stirred for 1.5 h. Then the reaction was concentrated in vacuo and the residue purified using a Biotage SP1 chromatography system using a 25S column and ethyl acetate/hexane gradient to give 20 mg of pure product, obtained as a clear oil.

Example 24

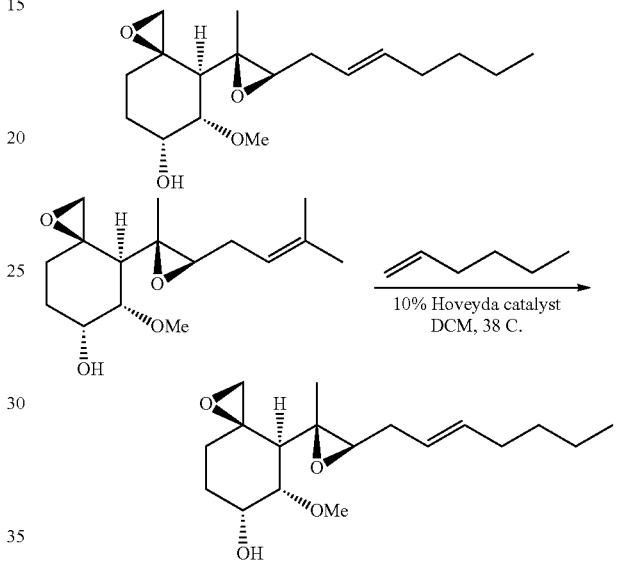

To a solution of 1 eq of fumagillol (0.1 g, 0.35 mmol) in methylene chloride (3 ml) was added 10 eq. of 1-hexene (0.29 g, 3.5 mmol) and 10 mol % of Grubbs-Hoveyda $2^{nd}$ generation metathesis catalyst (0.022 g, 0.035 mmol) and the reaction mixture was heated at reflux overnight. The next morning, the reaction was concentrated in vacuo. The crude compound was purified using a Biotage SP1 chromatography system using a 12M column and ethyl acetate/hexane gradient to give 20 mg of pure product, obtained as a light brown oil.

Example 25

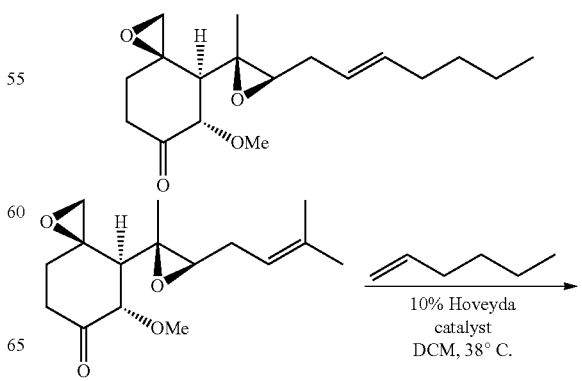

75

-continued

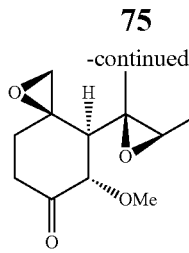

To a solution of 1 eq of fumigilone (0.1 g, 0.35 mmol) in methylene chloride (3 ml) was added 10 eq. of 1-hexene (0.29 g, 3.5 mmol) and 10 mol % of Grubbs-Hoveyda 2$^{nd}$ generation metathesis catalyst (0.022 g, 0.035 mmol) and the reaction mixture was heated at reflux overnight. The next morning, the reaction was concentrated in vacuo. The crude compound was purified using a Biotage SP1 chromatography system using a 25S column and ethyl acetate/hexane gradient to give 28 mg of pure product, obtained as a light brown oil.

Example 26

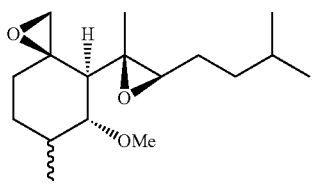

76

-continued

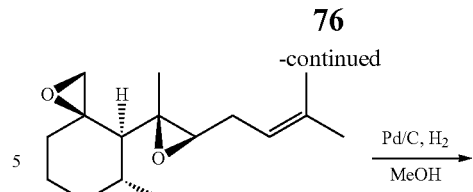

In a round bottom flask the substrate (0.15 g, 0.54 mmol) is dissolved in 5 ml of methanol and 0.057 g, 0.054 mmol) of 10% palladium on carbon is added carefully. The flask is evacuated and back filled with nitrogen three times and then evacuated and back filled with hydrogen from a balloon. The reaction is stirred at room temperature under hydrogen for 18 h. After 18 h the balloon is removed and the reaction vessel evacuated and back filed with nitrogen three times. The Pd/C is removed by filtration through Celite and the solvent is removed in vacuo. The product is purified by flash chromatography (Biotage, SiO2, EtOAc/Hex gradient) to give the desired product (0.078 g, 51%).

Example 27

(Compound 231)

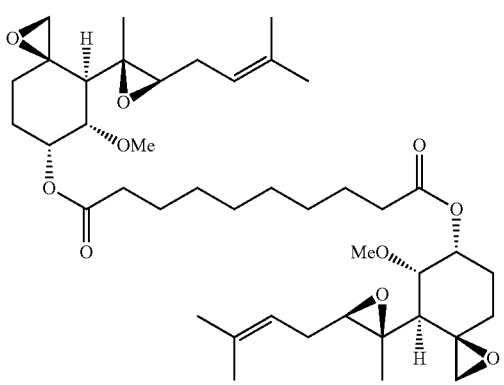

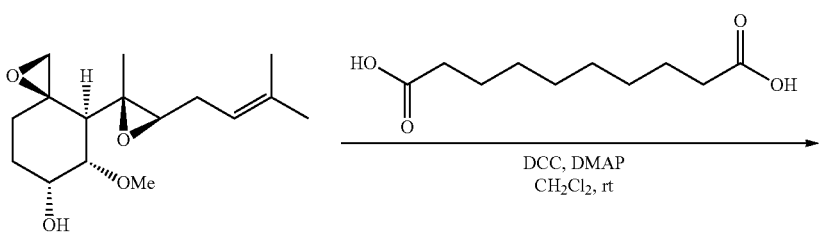

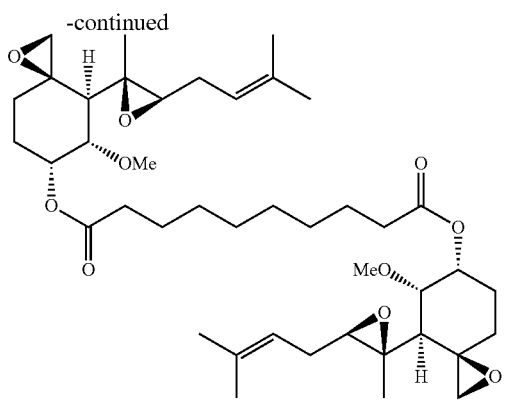

2.0 g (7.1 mmol) of fumagillol, 0.1.4 g (6.9 mmol) of Sebacic acid, and 0.18 g (1.4 mmol) of DMAP are dissolved in 5 mL of dry CH$_2$CL$_2$. DCC (0.22 g, 1.0 mmol) dissolved in 5 mL of dry CH$_2$CL$_2$ is added drop wise over 3 h with stirring at room temperature. After addition is complete the mixture is allowed to stir overnight and then diluted with 50 mL of CH$_2$Cl$_2$, washed with 50 mL of water followed by 50 mL of brine, dried over Na$_2$SO$_4$ and condensed in vacuo. Purification by biotage flash chromatography (SiO2, EtOAc/Hexanes gradient) affords 238 mg of the title compound.

Example 28

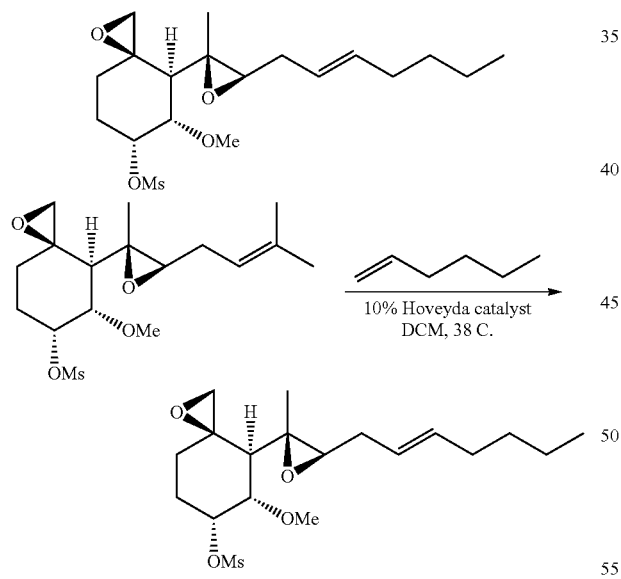

To a solution of 1 eq of fumagillol mesylate (0.1 g, 0.28 mmol) in methylene chloride (4 ml) was added 10 eq. of 1-hexene (0.29 g, 3.5 mmol) and 10 mol % of Grubbs-Hoveyda 2$^{nd}$ generation metathesis catalyst (0.022 g, 0.035 mmol) and the reaction mixture was heated at reflux overnight. The next morning, the reaction was concentrated in vacuo. The crude compound was purified using a Biotage SP1 chromatography system using a 12M column and ethyl acetate/hexane gradient to give 31 mg of pure product, obtained as yellow oil.

Example 29

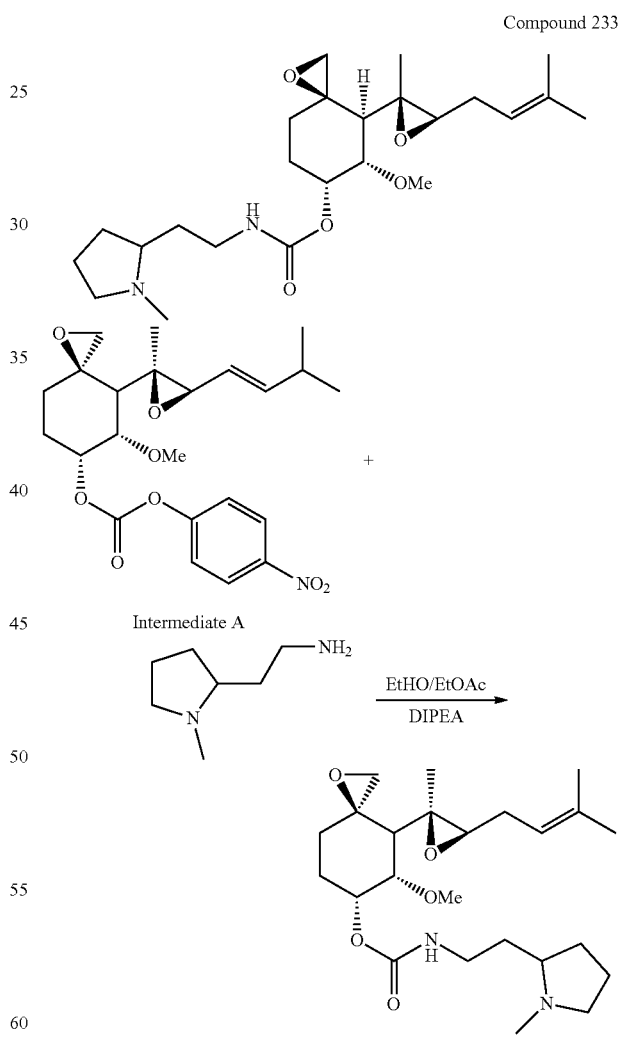

In a round bottom flask under nitrogen 150 mg (0.33 mmol) of Intermediate A was dissolved in 7.5 mL of ETOH and 2.5 Ml of EtOAc. 0.15 mL (1 mmol) of N-methyl-2-(aminoethyl)pyrrolidine was added followed by DIPEA (0.16 mL, 1 mmol). The mixture was allowed to stir overnight and then condensed in vacuo. The residue was dissolved in 20 mL of EtOAc and washed with 2×20 mL of water, 20 mL of brine, dried over $Na_2SO_4$ and condensed in vacuo. Purification by biotage flash chromatography (SiO2, MeOH/$CH_2Cl_2$/$Et_3N$ gradient) affords 12 mg of the title compound.

Example 30

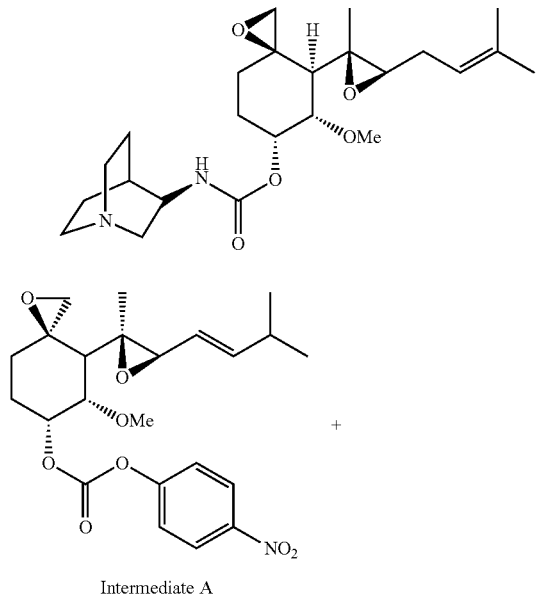

Intermediate A

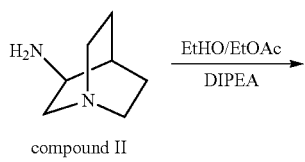

compound II

In a round bottom flask under nitrogen 150 mg (0.33 mmol) of intermediate A was dissolved in 7.5 mL of ETOH and 2.5 Ml of EtOAc. 0.2 g (1 mmol) of compound II was added followed by DIPEA (0.27 mL, 1.7 mmol). The mixture was allowed to stir overnight and then condensed in vacuo. The residue was dissolved in 20 mL of EtOAc and washed with 2×20 mL of water, 20 mL of brine, dried over $Na_2SO_4$ and condensed in vacuo. Purification by biotage flash chromatography (SiO2, MeOH/$CH_2Cl_2$/$Et_3N$ gradient) affords 10 mg of the title compound.

Example 31

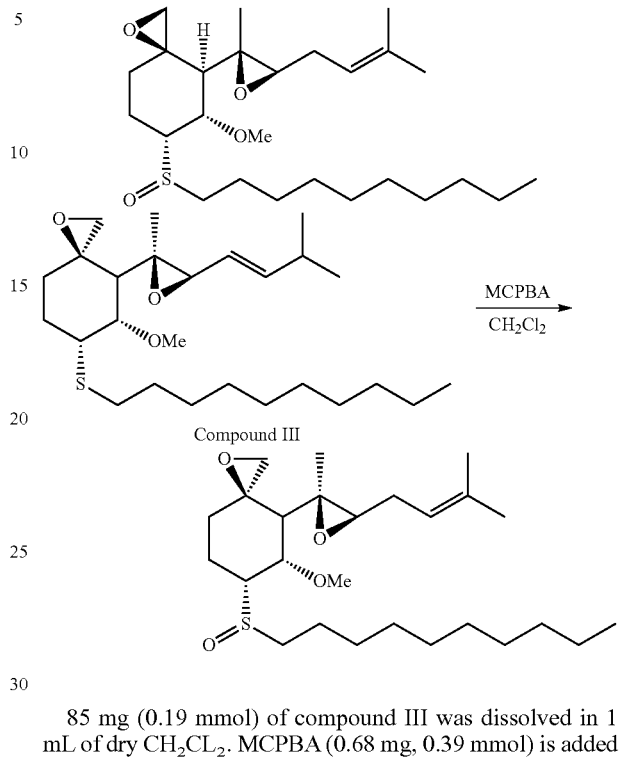

Compound III 85 mg (0.19 mmol) of compound III was dissolved in 1 mL of dry $CH_2CL_2$. MCPBA (0.68 mg, 0.39 mmol) is added with stirring at room temperature and the mixture is allowed to stir overnight. Next the mixture was diluted with 50 mL of EtOAc, washed with 2×50 mL of saturated $NaHCO_3$ followed by 50 mL of brine, dried over $Na_2SO_4$ and condensed in vacuo. Purification by biotage flash chromatography (SiO2, EtOAc/Hexanes gradient) affords 22 mg of the title compound.

Example 32

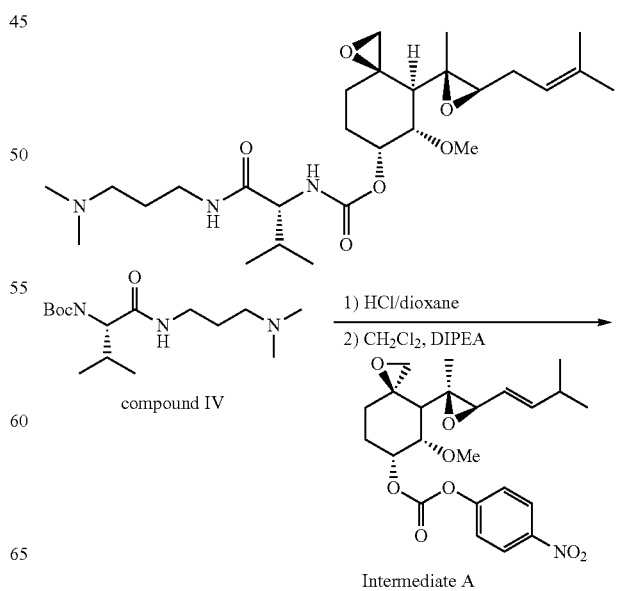

compound IV

Intermediate A

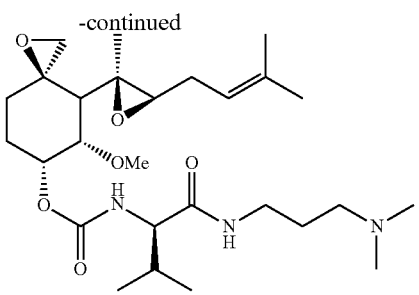

In a round bottom flask under nitrogen 50 mg (0.17 mmol) of compound IV was dissolved in 2 mL of 4N HCL in dioxane and allowed to stir for 30 min. The material was condensed in vacuo, and triturated with Et₂O. The resulting solid is dissolved in 5 mL of CH₂CL₂ and 70 mg (0.16 mmol) of Intermediate A was added followed by DIPEA (0.15 mL, 0.85 mmol). The mixture was allowed to stir overnight. The reaction was diluted with 20 mL of CH₂CL₂ and washed with 20 mL of saturated NaHCO₃, 2×20 mL of water, 20 mL of brine, dried over Na₂SO₄ and condensed in vacuo. Purification by biotage flash chromatography (SiO2, MeOH/CH₂Cl₂/Et₃N gradient) affords 14 mg of the title compound.

Example 33

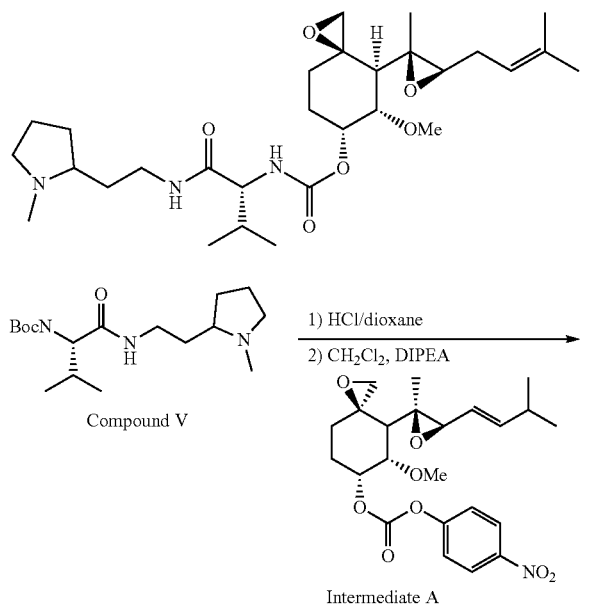

In a round bottom flask under nitrogen 100 mg (0.30 mmol) of compound V was dissolved in 10 mL of 4N HCL in dioxane and allowed to stir for 30 min. The material was condensed in vacuo, and triturated with Et₂O. The resulting solid is dissolved in 5 mL of CH₂Cl₂ and 140 mg (0.31 mmol) of Intermediate A was added followed by DIPEA (0.3 mL, 0.70 mmol). The mixture was allowed to stir overnight. The reaction was diluted with 20 mL of CH₂CL₂ and washed with 20 mL of saturated NaHCO₃, 2×20 mL of water, 20 mL of brine, dried over Na₂SO₄ and condensed in vacuo. Purification by biotage flash chromatography (SiO2, MeOH/CH₂Cl₂/Et₃N gradient) affords 12 mg of the title compound.

Example 35

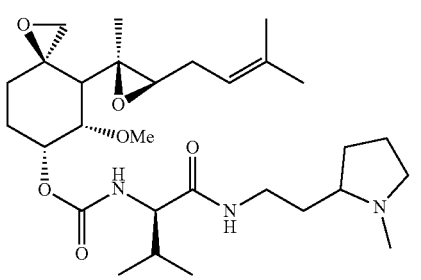

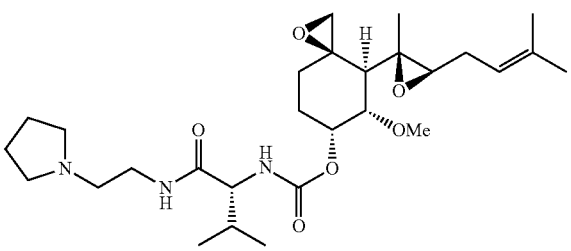

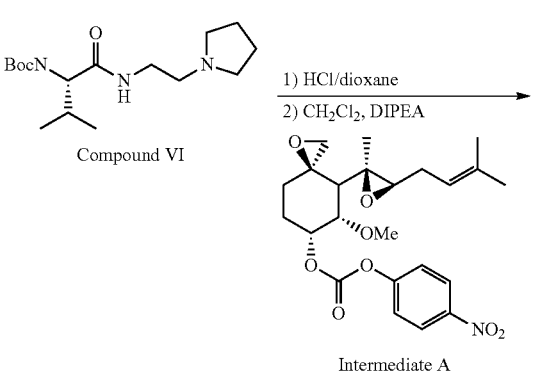

In a round bottom flask under nitrogen 100 mg (0.32 mmol) of compound VI was dissolved in 10 mL of 4N HCL in dioxane and allowed to stir for 30 min. The material was condensed in vacuo, and triturated with Et₂O. The resulting solid is dissolved in 5 mL of CH₂Cl₂ and 140 mg (0.31 mmol) of Intermediate A was added followed by DIPEA (0.3 mL, 0.70 mmol). The mixture was allowed to stir overnight. The reaction was diluted with 20 mL of CH₂CL₂ and washed with 20 mL of saturated NaHCO₃, 2×20 mL of water, 20 mL of brine, dried over Na₂SO₄ and condensed in vacuo. Purification by biotage flash chromatography (SiO2, MeOH/CH₂Cl₂/Et₃N gradient) affords 16 mg of the title compound.

Example 36

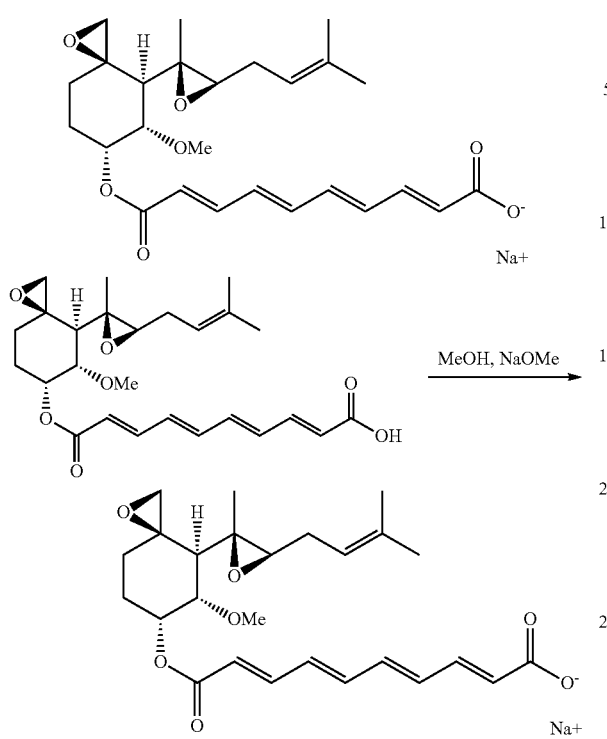

Pure fumagillin free acid (0.5 g, 1.1 mmol) was dissolved in 5 ml of anhydrous MeOH with heating. The solution is allowed to cool just to room temperature and then immediately treated with 0.235 g of sodium methoxide (25% in MeOH) at room temperature (Note**Fumagillin will crystallize out of MeOH if allowed to sit at room temperature) The solution darkens dramatically when the last of the acid is neutralized, thus the reaction can "titrated" with NaOMe by watching for the color change. The mixture is then concentrated on the rotovap to generate yellowish sticky oil. The oil is dissolved in hot EtOAc and Hexanes are added until precipitation occurs. The yellow precipitate is collected by vacuum filtration on a Buchner funnel and dried under vacuum. The yield is 345 mg (67%).

Example 37

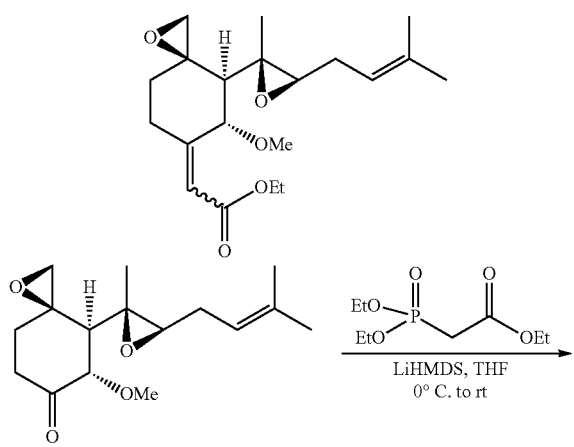

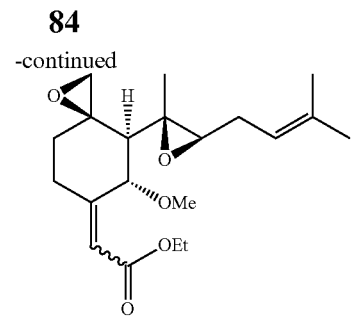

0.29 g (1.3 mmol) of triethyl phosphonoacetate is dissolved in THF (10 mL) and cooled to 0° C. Lithium hexamethyldisilazide (1.06 M in THF, 1.2 mL, 1.1 mmol) is added drop wise at 0° C. The solution is allowed to stir at 0° C. for 1 h after which a solution of 6-ketofumagillol (0.3 g, 1.1 mmol in 1 mL of THF) is added drop wise at 0° C. The reaction is allowed to warm up to room temperature overnight and then diluted with EtOAc (50 mL) and washed with 3×50 mL of saturated NaHCO₃. The resulting solution is dried over Na²SO₄ and concentrated in vacuo. Purification by flash chromatography (biotage, SiO₂, EtOAc/Hexane gradient) gave the desired product (0.25 g, 68%).

Example 38

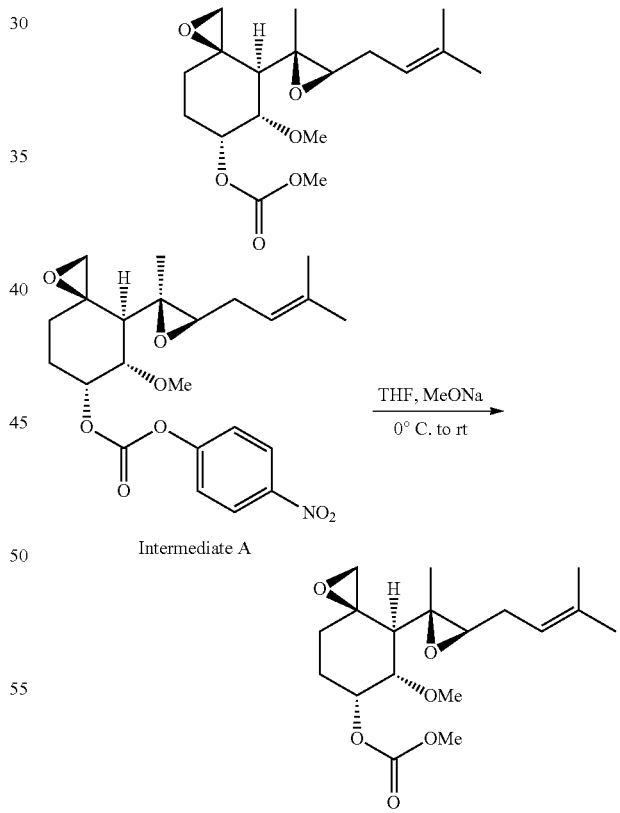

Intermediate A

In a round bottom flask under nitrogen 700 mg (1.6 mmol) of Intermediate A was dissolved in 10 mL of THF and cooled to 0° C. MeONa is added and the reaction is allowed to warm to room temperature overnight. The mixture is diluted with 20 mL of EtOAc and washed with 2×20 mL of water, 20 mL of brine, dried over Na₂SO₄ and condensed in vacuo.

Purification by biotage flash chromatography (SiO2, MeOH/CH₂Cl₂/Et₃N gradient) affords 335 mg of the title compound.

Example 39

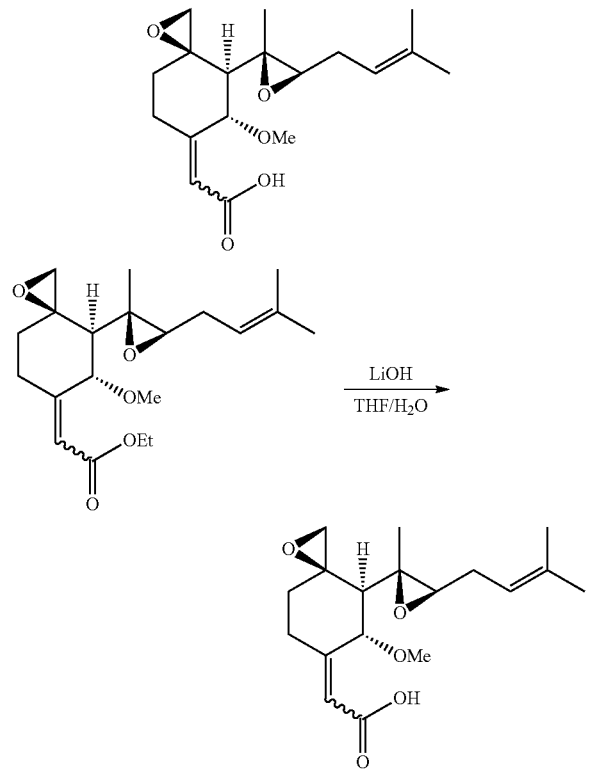

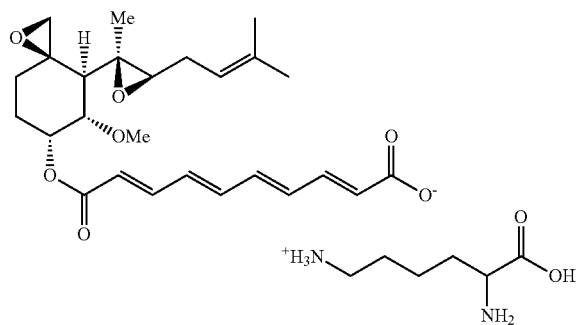

0.1 g (0.29 mmol) of ZGN-240 is dissolved in THF (0.5 mL) to which is added 24 mg (0.57 mmol) of LiOH mono hydrate dissolved in 0.5 mL of water. The solution is allowed to stir at room temperature for 5 h. The mixture is diluted with water (10 mL) and washed with 2×10 mL of EtOAc. The aqueous layer is then acidified to pH 1 with 1N HCl and extracted with 3×20 mL of CH₂Cl₂. The combined CH₂C₁ layers are dried over Na₂SO₄ and concentrated in vacuo.

Example 40

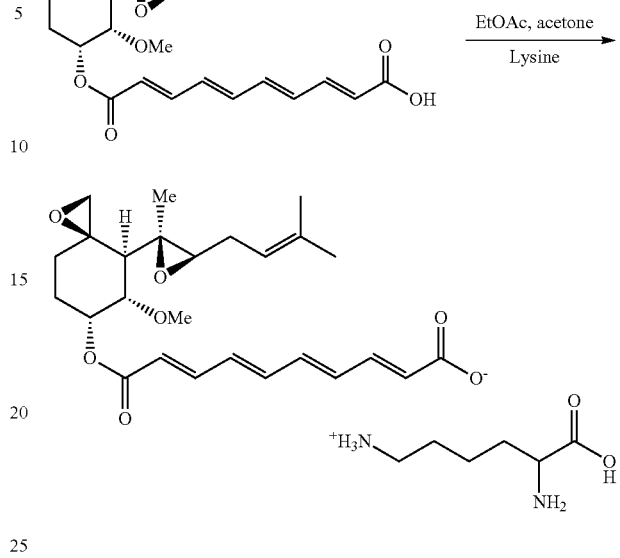

Pure fumagillin free acid (0.5 g, 1.1 mmol) was dissolved in 30 ml of anhydrous EtOAc with heating. The solution is allowed to cool just to room temperature and then immediately treated with a solution of 0.17 g of L (+) Lysine in a minimum of acetone at room temperature (Note**Fumagillin will crystallize out of MeOH if allowed to sit at room temperature) The solution darkens dramatically when the last of the acid is neutralized. A brown/orange precipitate form immediately which is collected by vacuum filtration on a Buchner funnel, washed with EtOAc, and dried under vacuum. The yield is 573 mg of product.

Example 41

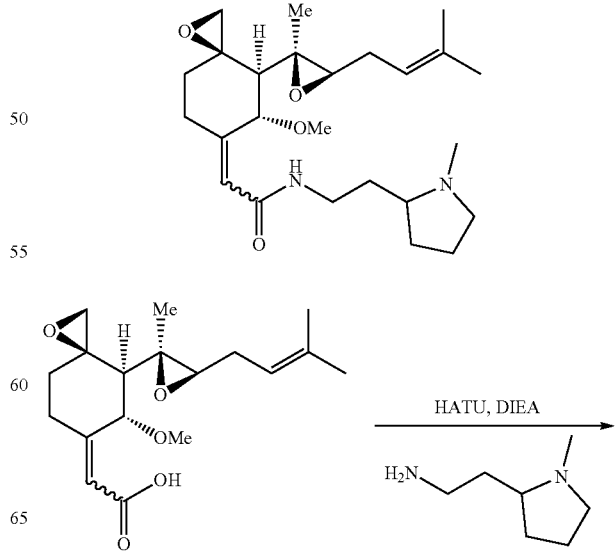

-continued

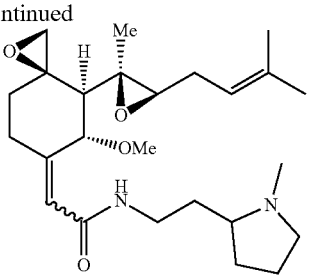

To a solution of the acid (1) in DCM (6 mL) (50 mg, 0.158 mmol, 1 eq), HATU (0.237 mmol, 90 mg, 1.5 eq) followed by DIEA (82.5 uL, 0.47 mmol, 3 eq) were added. The reaction mixture was stirred for few minutes then (2-(2-Aminoethyl)-1-methyl pyrrolidine) (33.92 uL, 0.237 mmol, 1.5 eq) was added The reaction was left stirring for a few hours and concentrated on the rotavap, product was purified on the 12M+ Biotage column using DCM:MeOH (9:1) Fractions containing the product were combined and evaporated to give 75.24 mg (95% yield) of product.

Example 42

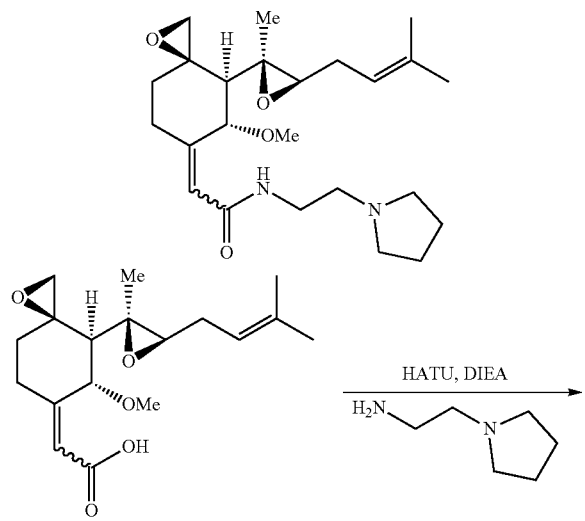

To a solution of the acid (1) in DCM (6 mL) (50 mg, 0.158 mmol, 1 eq), HATU (0.237 mmol, 90 mg, 1.5 eq) followed by DIEA (82.5 uL, 0.47 mmol, 3 eq) were added. The reaction mixture was stirred for few minutes then (1-(2-Aminoethyl)-pyrrolidine) (33.92 uL, 0.237 mmol, 1.5 eq) was added. The reaction was left stirring for a few hours and concentrated on the rotavap, product was purified on the 12M+ Biotage column using DCM:MeOH (9:1) Fractions containing the product were combined and evaporated to give quantitative yield of product.

Example 43

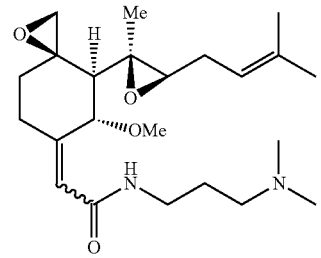

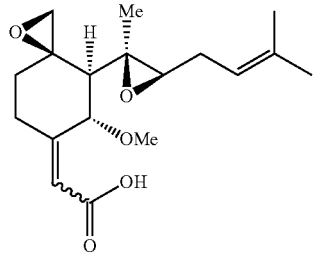
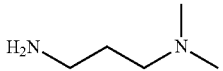
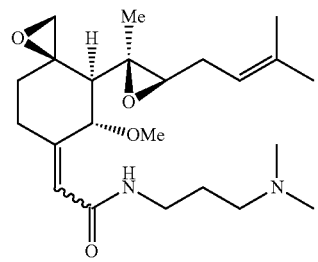

To a solution of the acid (1) in DCM (6 mL) (50 mg, 0.155 mmol, 1 eq), HATU (0.237 mmol, 90 mg, 1.5 eq) followed by DIEA (82.5 uL, 0.47 mmol, 3 eq) were added. The reaction mixture was stirred for few minutes then (2-(2-Aminoethyl)-1-methyl pyrrolidine) (33.92 uL, 0.237 mmol, 1.5 eq) was added The reaction was left stirring for a few hours and concentrated on the rotavap, product was purified on the 12M+ Biotage column using DCM:MeOH (9:1) Fractions containing the product were combined and evaporated to give 86.34 mg (86% yield) of product.

Example 44

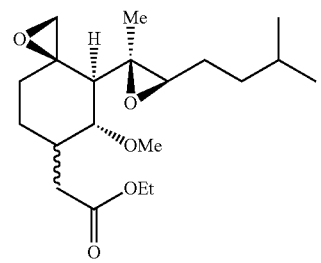

-continued

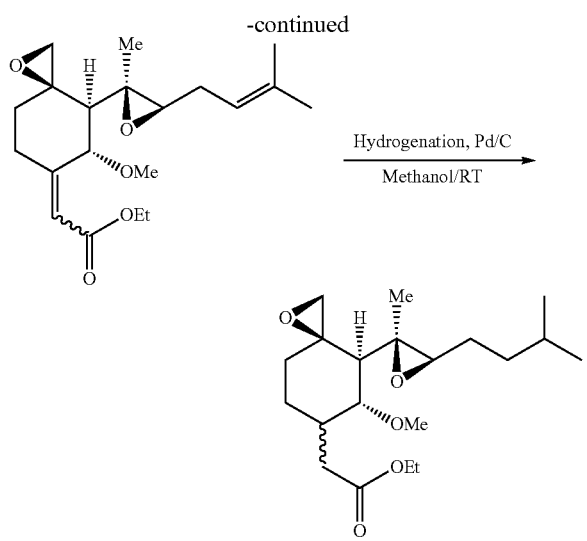

To a solution of the ester (54.4 mg, 0.155 mmol) in anhydrous methanol (1.5 mL) was added Pd/C (~29 mg) and the reaction slurry was evacuated several times to remove the air under nitrogen. A balloon filled with hydrogen was attached to the reaction vessel and the reaction was allowed to proceed for ~3.5 hours. The reaction was evacuated and checked by LC/MS and filtered through a pad of Celite and concentrated on the rotavap and purified on the Biotage column to obtain 52.73 mg (95%) of the title compound.

Example 45

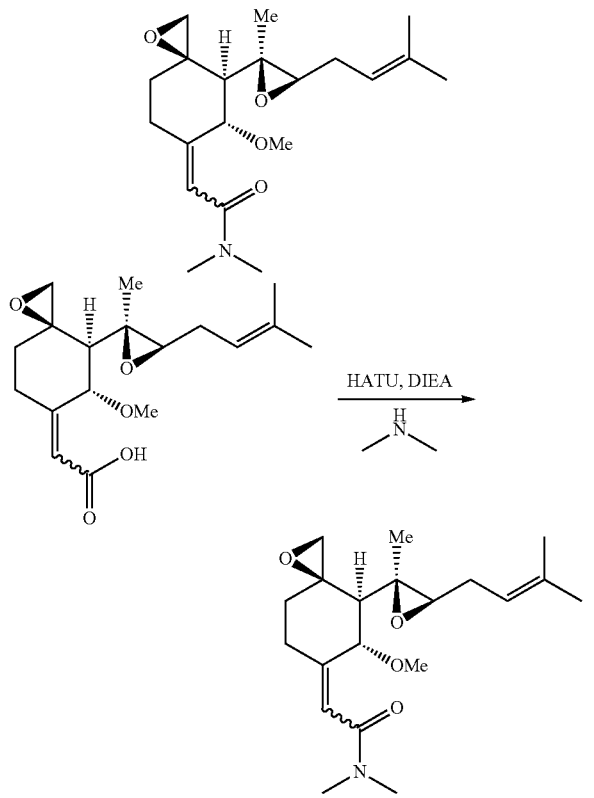

To a solution of the acid (1) in DCM (6 mL) (50 mg, 0.155 mmol, 1 eq), HATU (0.237 mmol, 90 mg, 1.5 eq) followed by DIEA (82.5 uL, 0.47 mmol, 3 eq) were added. The reaction mixture was stirred for few minutes then Dimethylamine (25 uL, 0.237 mmol, 3.35 eq) was added The reaction was left stirring for a few hours and concentrated on the rotavap, product was purified on the 12M+ Biotage column using DCM:MeOH (9:1) Fractions containing the product were combined and evaporated to give quantitative yield of product.

Example 46

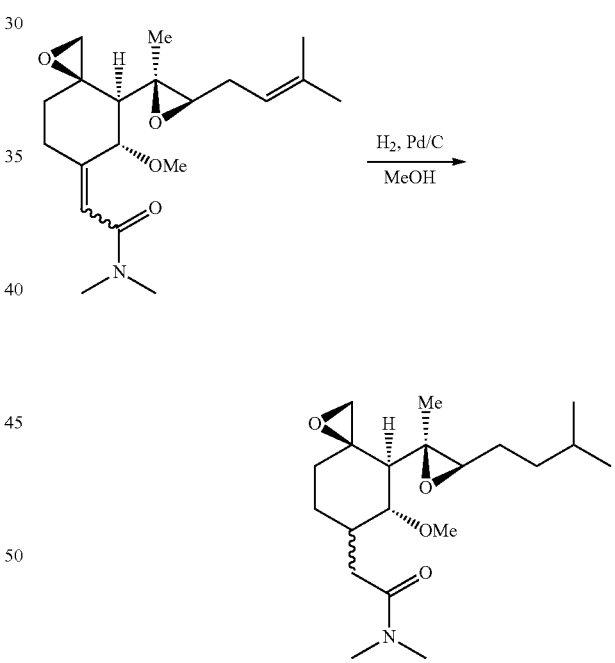

To a solution of a compound of Example 45 (50.5 mg, 0.144 mmol) in anhydrous methanol (1.5 mL) was added Pd/C (31.91 mg) and the reaction slurry was evacuated several times to remove the air under nitrogen. A balloon filled with hydrogen was attached to the reaction vessel and the reaction was allowed to proceed overnight. The next morning the reaction was evacuated and checked by LC/MS and filtered through a pad of Celite and concentrated on the rotavap to give 38.56 mg of product (76% yield).

Example 47

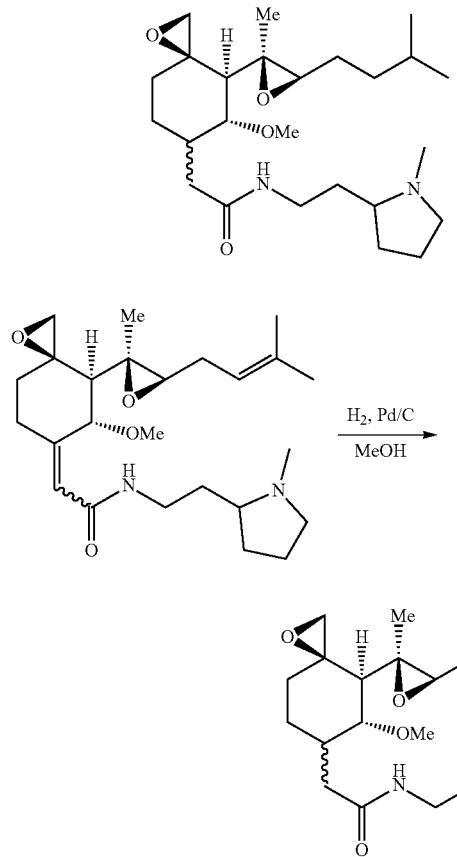

To a solution of a compound from Example 41 (99.14 mg, 0.229 mmol) in anhydrous methanol (3 mL) was added Pd/C (~60 mg) and the reaction slurry was evacuated several times to remove the air under nitrogen. A balloon filled with hydrogen was attached to the reaction vessel and the reaction was allowed to proceed overnight. The next morning the reaction was evacuated and checked by LC/MS and filtered through a pad of Celite and concentrated on the rotavap to give 76.1 mg of product (76% yield).

Example 48

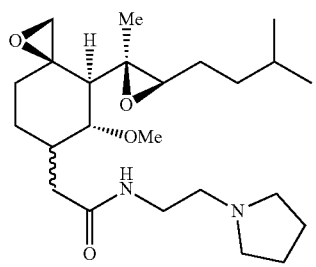

-continued

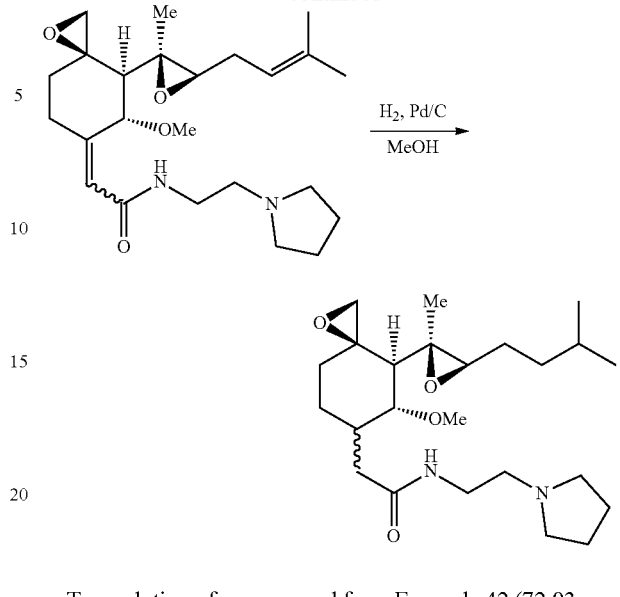

To a solution of a compound from Example 42 (72.03 mg, 0.17 mmol) in anhydrous methanol (3 mL) was added Pd/C (~60 mg) and the reaction slurry was evacuated several times to remove the air under nitrogen. A balloon filled with hydrogen was attached to the reaction vessel and the reaction was allowed to proceed overnight. The next morning the reaction was evacuated and checked by LC/MS and filtered through a pad of Celite and concentrated on the rotavap to give 70.7 mg of product (97% yield).

Example 49

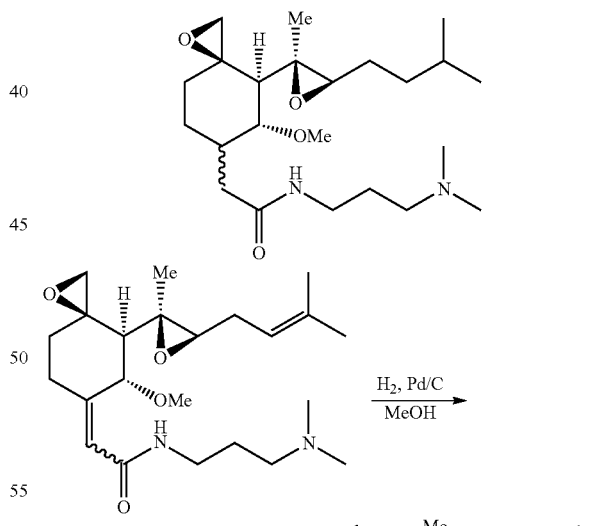

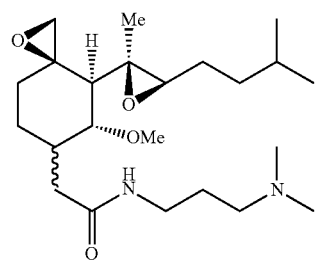

To a solution of a compound from Example 43 (70.26 mg, 0.17 mmol) in anhydrous methanol (3 mL) was added Pd/C (~60 mg) and the reaction slurry was evacuated several times to remove the air under nitrogen. A balloon filled with hydrogen was attached to the reaction vessel and the reaction was allowed to proceed overnight. The next morning the reaction was evacuated and checked by LC/MS and filtered through a pad of Celite and concentrated on the rotavap to give 71.62 mg of product in a quantitative yield.

Example 50

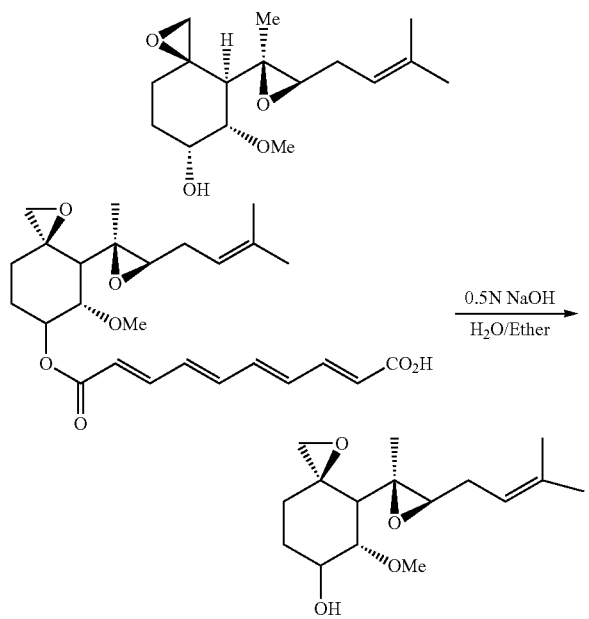

(3R,5S)-5-methoxy-4-((2R,3R)-2-methyl-3-(3-methylbut-2-enyl)oxiran-2-yl)-1-oxaspiro[2.5]octan-6-ol The mixture of fumagillin DCHA salt (10 g, 0.022 mol), 800 mL of 0.1 N NaOH solution in H$_2$O, and 800 mL of Et$_2$O was stirred at RT for 3 h. LC/Mass showed that the fumagillin had been consumed. The mixture was treated with 400 mL of Ether and the layers were separated. The water layer was extracted with ether (3×500 mL) and the combined organic layer was dried over anhydrous Na$_2$SO$_4$ and concentrated under reduced pressure. The crude product was purified on a Biotage (EtOAc/hexanes) to provide ANT-2970 (4.1 g, 6.16 g theoretical, 66%). $^1$H NMR (300 MHz, CDCl$_3$) δ 1.21 (s, 3H), 1.65 (s, 3H), 1.75 (s, 3H), 1.90-2.05 (m, 3H), 2.18-2.26 (m, 2H), 2.34-2.39 (m, 2H), 2.55 (d, 1H), 2.59 (t, 1H), 2.92 (m, 1H), 3.48 (s, 3H), 3.62 (dt, 1H), 4.38 (m, 1H), 5.21 (m, 1H); LC-MS 283 (M+1).

Example 51

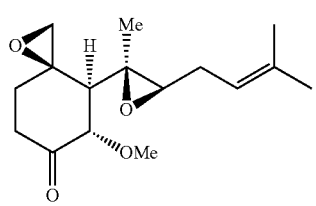

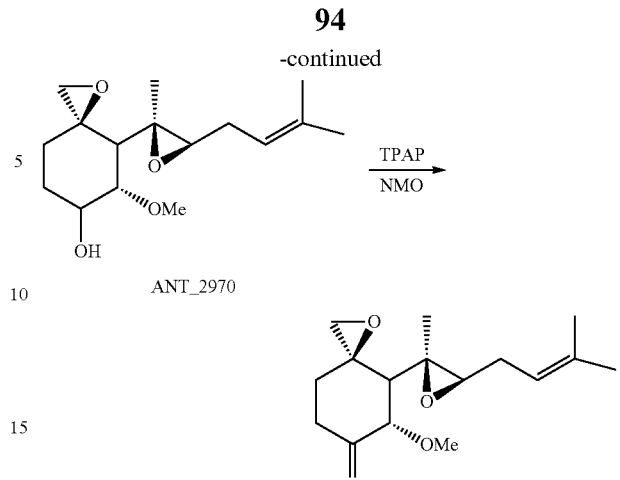

(3R,5S)-5-methoxy-4-((2R,3R)-2-methyl-3-(3-methylbut-2-enyl)oxiran-2-yl)-1-oxaspiro[2.5]octan-6-one (ANT-2971)

ANT_2970 (1.75 g, 6.18 mmol) was treated with dichloromethane (100 mL), dried 3 A° sieves (1.5 g), tetrapropylammonium perruthenate (TPAP, 53 mg, 0.151 mmol, 0.02 equiv.), and N-methylmorpholine N-oxide (1.76 g, 15.0 mmol, 2.5 equiv.). The reaction mixture was stirred at RT for 2.5 h and LC/Mass showed that the alcohol had been consumed. The mixture was treated with 100 mL of H$_2$O and the layers were separated. The water layer was extracted with DCM (3×50 mL) and the combined organic layer was dried over anhydrous Na$_2$SO$_4$ and concentrated under reduced pressure. The crude product was purified on a Biotage (EtOAc/hexanes) to provide ANT-2971 (1.38 g, 1.73 g theoretical, 80%). $^1$H NMR (300 MHz, CDCl$_3$) δ 1.23 (s, 3H), 1.65 (s, 3H), 1.75 (s, 3H), 1.80-1.88 (m, 1H), 1.98-2.18 (m, 2H), 2.32-2.74 (m, 5H), 3.15 (d, 1H), 3.48 (s, 3H), 4.14 (d, 1H), 4.38 (m, 1H), 5.15 (m, 1H); LC-MS 281 (M+1).

Example 52

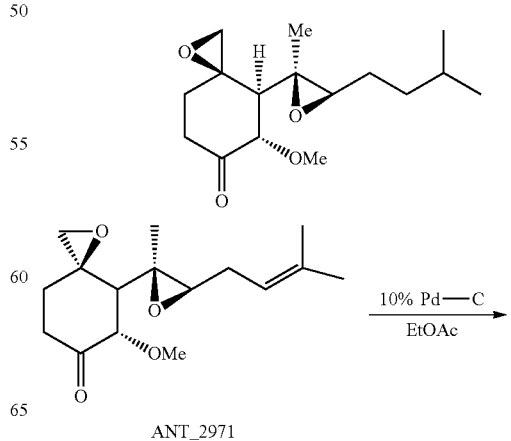

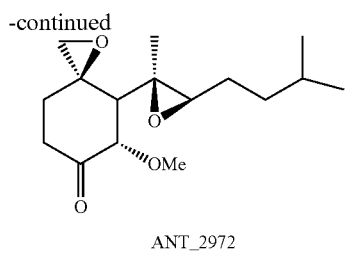

ANT_2972

(3R,5S)-4-((2R,3R)-3-isopentyl-2-methyloxiran-2-yl)-5-methoxy-1-oxaspiro[2.5]octan-6-one (ANT-2972)

ANT_2971 (80 mg, 0.286 mmol) was treated with EtOAc (10 mL), 10% palladium on carbon (8 mg), and a balloon of $H_2$. The reaction mixture was stirred at RT for 3 h and LC/Mass showed that the olefin had been consumed. The reaction mixture was filtered and concentrated under reduced pressure. The crude product was recrystallized from acetonitrile to provide ANT-2972 (23.6 mg, 81 mg theoretical, 29%). $^1$H NMR (300 MHz, CDCl$_3$) δ 0.981 (s, 3H), 0.983 (s, 3H), 1.21 (s, 3H), 1.22-1.65 (m, 5H), 1.81 (m, 1H), 2.92 (d, 1H), 3.15 (m, 1H), 2.50-2.75 (m, 3H), 2.85 (d, 1H), 2.98 (d, 1H), 3.50 (s, 3H), 4.14 (d, 1H); LC-MS 281 (M+1).

Example 53

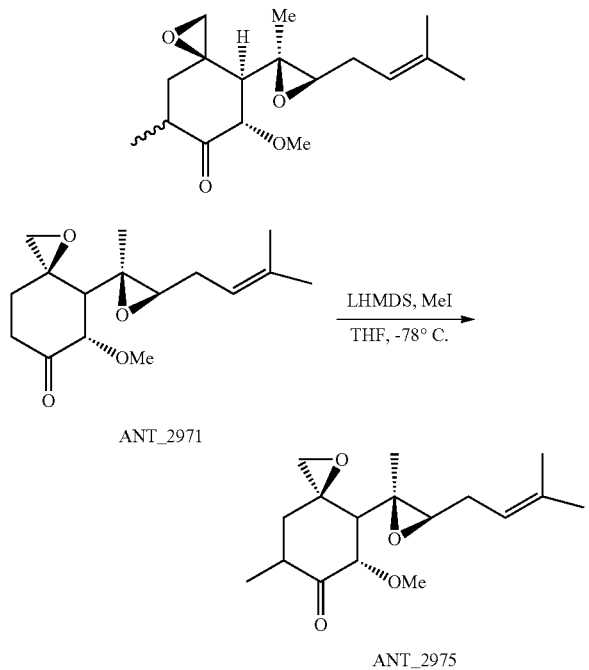

ANT_2975

(3R,5S)-5-methoxy-7-methyl-4-((2R,3R)-2-methyl-3-(3-methylbut-2-enyl)oxiran-2-yl)-1-oxaspiro[2.5]octan-6-one (ANT-2975)

ANT_2971 (60 mg, 0.214 mmol) was treated with THF (1 mL) and cooled to −78° C. under $N_2$. The reaction mixture was then treated with lithium bis(trimethylsilyl)amide (LHMDS, 1.0 M in THF, 0.54 mL, 2.5 equiv.) and stirred at −78° C. for 2 h. The reaction mixture was then treated with MeI (30 □L, 2.1 equiv.) and the reaction mixture was gradually warmed to RT over a 2 h period. The reaction mixture was then treated with saturated NH$_4$Cl solution in H$_2$O (3 mL) and extracted with EtOAc (3×5 mL). The combined organic layer was dried over anhydrous Na$_2$SO$_4$ and concentrated under reduced pressure. The crude product was purified on a Biotage (EtOAc/hexanes) to provide ANT-2975 (6 mg, 63 mg theoretical, 10%). $^1$H NMR (300 MHz, CDCl$_3$) δ 1.12 (s, 3H), 1.14 (s, 3H), 1.23 (s, 6H), 1.46-1.85 (m, 3H), 2.17 (m, 1H), 2.41 (m, 1H), 2.59 (m, 1H), 2.70 (m, 1H), 2.81 (m, 1H), 3.11 (m, 1H), 3.56 (s, 3H), 4.21 (d, 1H), 5.20 (m, 1H); LC-MS 295 (M+1).

Example 54

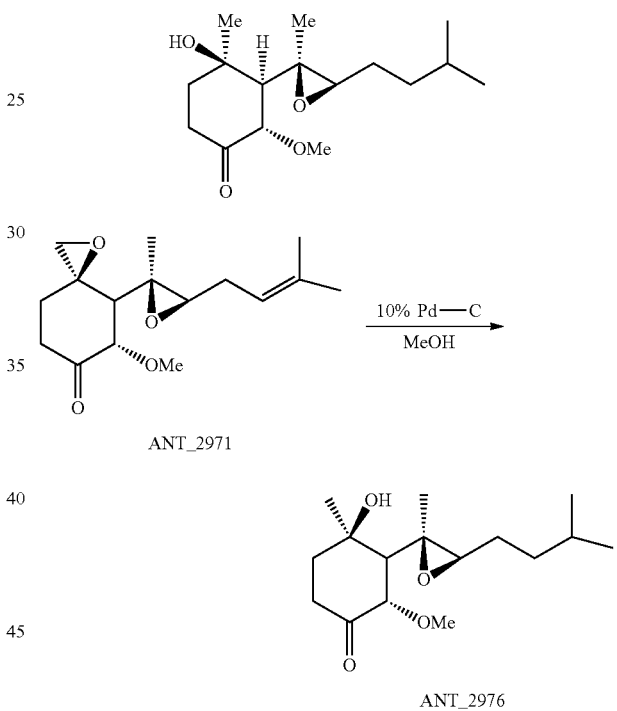

ANT_2976

(2S,4R)-4-hydroxy-3-((2R,3R)-3-isopentyl-2-methyloxiran-2-yl)-2-methoxy-4-methylcyclohexanone (ANT-2976)

ANT_2971 (50 mg, 0.178 mmol) was treated with MeOH (10 mL), 10% palladium on carbon (8 mg), and a balloon of $H_2$. The reaction mixture was stirred at RT for 3 h and LC/Mass showed that the olefin had been consumed. The reaction mixture was filtered and concentrated under reduced pressure. The crude product was purified on silica (50% EtOAc/hexanes) to provide ANT-2976 (17 mg, 51 mg theoretical, 33%). $^1$H NMR (300 MHz, CDCl$_3$) δ 0.992 (s, 3H), 0.994 (s, 3H), 1.35-1.38 (m, 1H), 1.39 (s, 3H), 1.50 (s, 3H), 1.52-1.75 (m, 4H), 1.96 (m, 1H), 1.99 (m, 1H), 2.21 (m, 1H), 2.23 (m, 1H), 2.81 (m, 1H), 3.01 (t, 1H), 3.43 (s, 3H), 3.86 (d, 1H), 3.98 (bs, 1H); LC-MS 285 (M+1).

Example 55

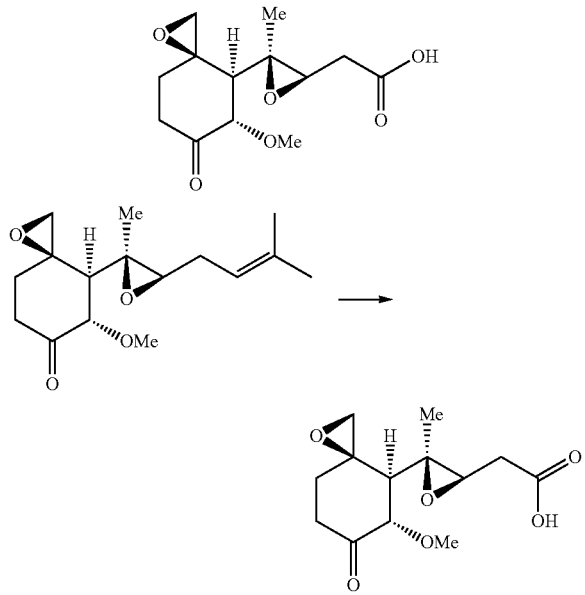

To the ketone starting material (100 mg, 0.36 mmol) in EtOAc (2 mL) was added a catalytic amount of benzyltriethylammonium chloride (4 mg), RuCl$_3$ (1 mg). A solution of NaIO$_4$ (381.5 mg, 1.78 mmol) in H$_2$O (2 mL) was then added slowly over 2 min. The reaction mixture was then stirred overnight. H$_2$O (5 mL) was added and the mixture was extracted with EtOAc (3×5 mL). The combined organic layer was dried over Na$_2$SO$_4$ and concentrated under reduced pressure to give the desired acid (59.2 mg, 61%). MS ES$^+$(M+H)$^+$ m/e 271; $^1$H NMR (400 MHz, CDCl$_3$); 4.11 (dd, J=9.2 Hz, 1H), 3.51 (s, 3H), 3.16 (d, J=4.0 Hz, 1H), 3.06 (t, J=6.0 Hz, 1H), 2.52-2.80 (m, 5H), 2.05-2.13 (m, 1H), 1.96 (d, J=10.4 Hz, 1H), 1.72-1.78 (m, 1H), 1.29 (s, 3H).

Example 56

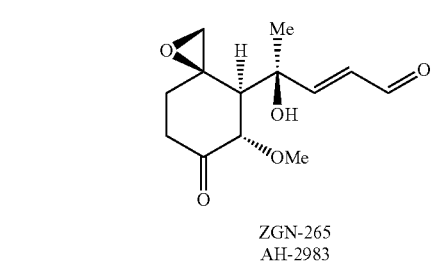

ZGN-265
AH-2983

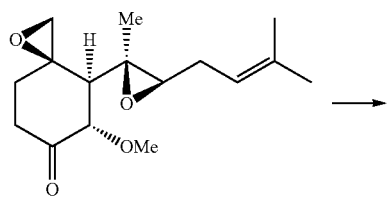

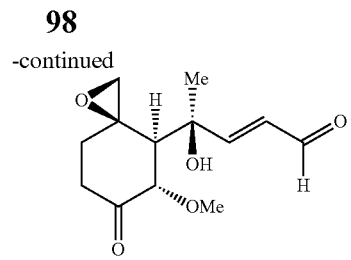

To the ketone starting material (100 mg, 0.36 mmol) in 3 mL of THF/H$_2$O (3:1) was added NMO-H$_2$O (96.4 mg, 0.71 mmol) and of 4 wt. % OsO$_4$ in H2O (50 □g). The reaction mixture was then stirred at room temperature for 3 h. LCMS showed that the starting material had been consumed and the diol intermediate was formed. NaIO$_4$ (152.6 mg, 0.71 mmol) was then added and the reaction mixture was stirred for 12 h. H$_2$O (10 mL) was added and the reaction mixture was extracted with ethylacetate (3×10 mL). The combined organic layer was dried over Na$_2$SO$_4$ and concentrated under reduced pressure. Flash chromatography using hexanes/EtOAc (1:1) gave the desired product (73.7 mg, 81%). MS ES$^+$(M+Na)$^+$ m/e 277; $^1$H NMR (400 MHz, CDCl$_3$); 9.62 (d, J=7.6 Hz, 1H), 6.81 (d, J=15.6 Hz, 1H), 6.49 (dd, J=7.6 Hz, 1H), 3.70 (dd, J=2.8 Hz, 1H), 3.42 (s, 3H), 3.03 (s, 1H), 2.71 (d, J=4.8 Hz, 1H), 2.63 (dd, J=3.2 Hz, 1H), 2.38-2.47 (m, 1H), 2.18-2.26 (m, 1H), 1.88 (d, J=4.4 Hz, 1H), 1.74-1.80 (m, 1H), 1.58 (s, 3H), 1.42-1.47 (m, 1H).

Example 57

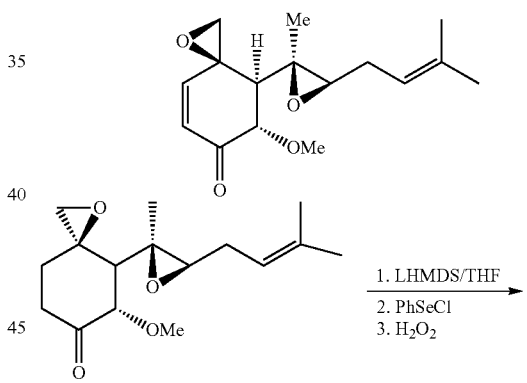

ANT_2971

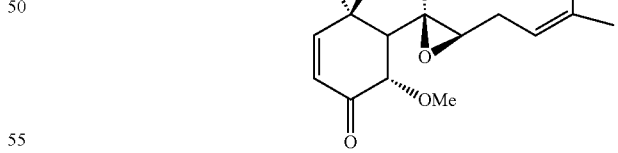

ANT_3090

(3R,S)-7-methoxy-8-((2R,3R)-2-methyl-3-(3-methylbut-2-enyl)oxiran-2-yl)-1-oxaspiro[2.5]oct-4-en-6-one (ANT-3090)

ANT_2971 (197 mg, 0.704 mmol) was treated with THF (2 mL) and cooled to −78° C. under N$_2$. The reaction mixture was then treated with lithium bis(trimethylsilyl)amide (LHMDS, 1.0 M in THF, 1.4 mL, 2.1 equiv.) and stirred at −78° C. for 3 h. The reaction mixture was then treated with a solution of PhSeCl (400 mg, 3 equiv.) in 1 mL of THF and the reaction mixture was gradually warmed to RT over a 2 h period and stirred at RT for 10 h. The reaction mixture was treated with saturated NH₄Cl solution in H₂O (5 mL) and extracted with EtOAc (3×5 mL). The combined organic layer was dried over anhydrous Na₂SO₄ and concentrated under reduced pressure. The crude product was purified on a Biotage (EtOAc/hexanes) to provide ANT-3090 (34 mg, 196 mg theoretical, 17%). $^1$H NMR (300 MHz, CDCl₃) δ 1.25 (s, 6H), 1.47 (s, 3H), 1.74 (m, 1H), 2.92 (d, 1H), 3.08 (d, 1H), 3.41 (s, 3H), 3.58 (m, 1H), 3.88 (m, 1H), 5.19 (m, 1H), 6.15 (d, 1H), 6.24 (q, 2H), 6.52 (d, 1H); LC-MS 279 (M+1).

Example 58

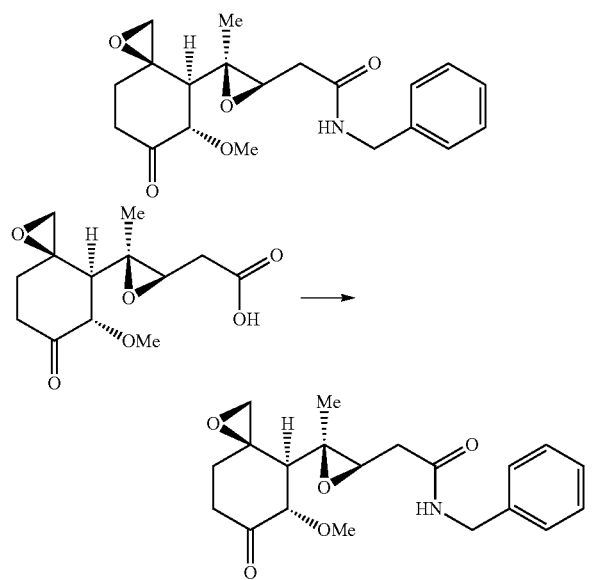

To the acid (59.2 mg, 0.22 mmol) in DCM (2 mL) was added triethylamine (61 L, 0.44 mmol), EDCI (42 mg, 0.22 mmol) and benzylamine (24 L, 0.22 mmol). The reaction mixture was stirred overnight and then diluted with DCM (5 mL) and washed with saturated NaHCO₃ (aq). The aqueous layer was extracted with DCM (2×5 mL) and the combined organic layer was dried over Na₂SO₄ and then concentrated under reduced pressure. Flash chromatography using 10:1 DCM/MeOH gave the desired product (15 mg, 20%). MS ES⁺(M+H)⁺ m/e 360; $^1$H NMR (300 MHz, CDCl₃); 7.24-7.32 (m, 5H), 6.30 (bs, 1H), 4.43 (dd, J=3.3 Hz, 2H), 4.09-4.13 (m, 1H), 3.11 (d, J=3.6 Hz), 2.98 (dd, J=2.4 Hz, 1H), 2.76 (d, J=3.9 Hz, 1H), 2.42-2.72 (m, 4H), 2.05-2.52 (m, 1H), 1.87 (d, J=10.5 Hz, 1H), 1.64-1.72 (m, 2H).

Example 59

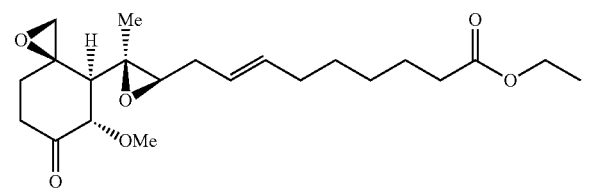

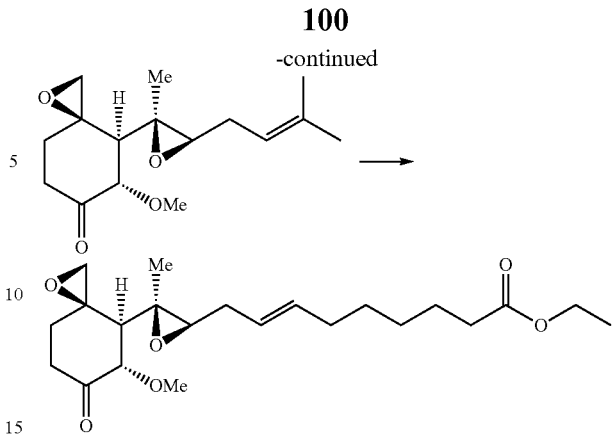

To the ketone starting material (35 mg, 0.125 mmol) in DCM (5 mL) was added ethyl-oct-7-enoate (340 mg, 3.6 mmol) and Grubbs-Hoveyda catalyst (5.58 mg, 0.009 mmol). The reaction mixture was refluxed for 12 h. It was then concentrated under reduced pressure. The residue was partitioned between EtOAc (10 mL) and saturated NaHCO₃ (aq) (10 mL). The aqueous layer was extracted with EtOAc (2×10 mL). The combined organic layer was dried over Na₂SO₄ and concentrated under reduced pressure. Flash chromatography using EtOAc/hexanes (1:1) gave the desired product (3.4 mg, 6.9%). MS ES⁺(M+H)⁺ m/e 395; $^1$H NMR (400 MHz, CDCl₃); 5.40-5.62 (m, 1H), 4.08-4.15 (m, 3H), 3.51 (s, 3H), 3.05 (d, J=4.4 Hz, 1H), 2.75 (d, J=4.4 Hz, 1H), 2.61-2.72 (m, 3H), 2.49-2.55 (m, 1H), 2.01-2.31 (m, 5H), 1.89 (d, J=10.4 Hz, 1H), 1.52-1.75 (m, 4H), 1.24-1.41 (m, 12H).

Example 60

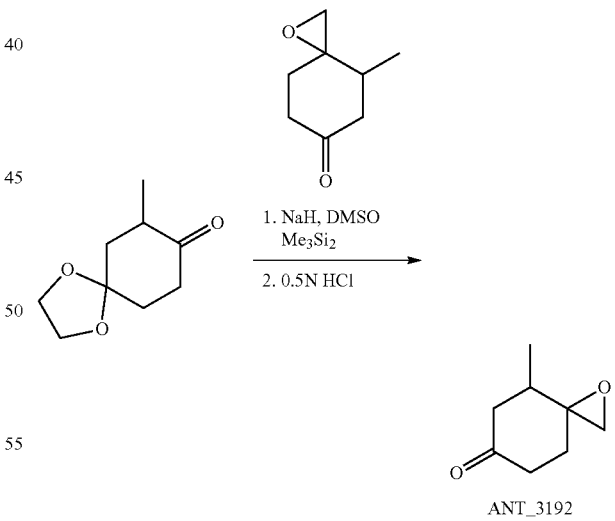

4-methyl-1-oxaspiro[2.5]octan-6-one (ANT-3192)

Me₃Si₂ (1.22, 6.0 mmol, 2 equiv.) was treated with DMSO (12 mL), NaH (60% dispersion, 240 mg, 6.0 mmol, 2 equiv.), and stirred at RT for 2 h. The reaction mixture was then treated with 7-methyl-1,4-dioxaspiro[4.5]decan-8-one (500 mg, 2.94 mmol) as a solution in DMSO (5 mL) and stirred at RT for 12 h. The mixture was treated with EtOAc (20 mL) and H$_2$O (20 mL) and the layers were separated. The organic layer was washed with and sat. NaCl (2×15 mL) and the combined organic layer was dried over anhydrous Na$_2$SO$_4$ and concentrated under reduced pressure. The crude product was purified on a Biotage (EtOAc/hexanes) to provide the ketal protected ANT-3192, which was dissolved in THF (5 mL) and treated with 1 N HCl (2 mL). The reaction was stirred for 1 h at RT and then extracted with EtOAc (3×20 mL). The combined organic layer was dried over anhydrous Na$_2$SO$_4$ and concentrated under reduced pressure to provide pure ANT-3192 (195 mg, 412 mg theoretical, 47%). $^1$H NMR (300 MHz, CDCl$_3$) δ 1.01 (dd, 3H), 1.89 (m, 1H), 2.04-2.45 (m, 4H), 2.51-2.78 (m, 2H), 3.52-3.78 (m, 2H); LC-MS 141 (M+1).

Example 61

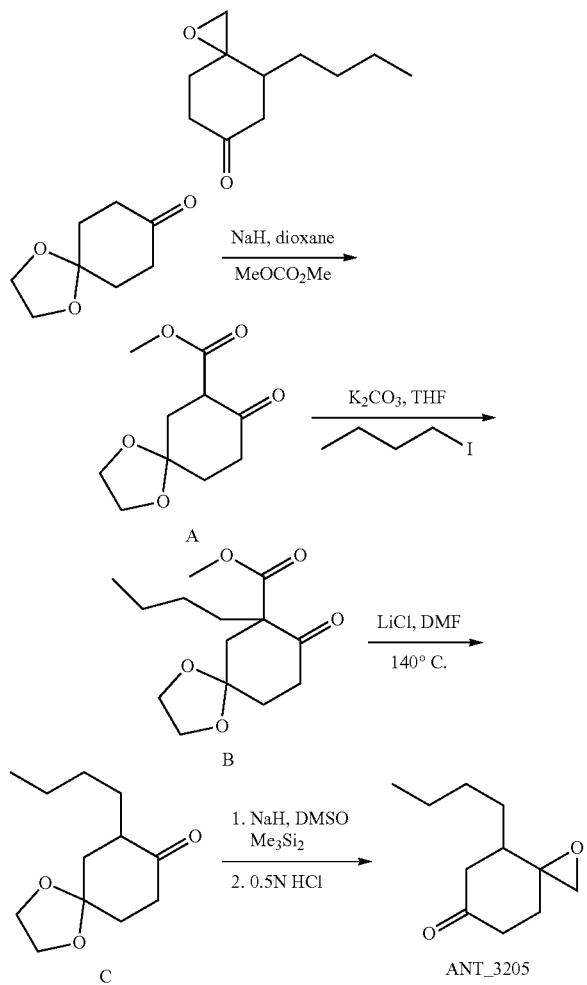

4-butyl-1-oxaspiro[2.5]octan-6-one (ANT-3205)

MeOCO$_2$Me (15 mL) was treated with 1,4-dioxaspiro[4.5]decan-8-one (38 g, 19.2 mmol) and then NaH (60% dispersion, 1.2 g, 25 mmol, 1.3 equiv.). The reaction mixture was allowed to stir at RT for 1 h. The reaction mixture was then treated with toluene (40 mL) and stirred at RT for 12 h. The reaction mixture was partitioned between H$_2$O (50 mL) and Et$_2$O (50 mL). The H$_2$O layer was extracted with Et$_2$O (3×15 mL). The combined organic layer was dried over anhydrous Na$_2$SO$_4$ and concentrated under reduced pressure. The crude product was purified on a Biotage (EtOAc/hexanes) to provide the intermediate keto ester A (26 g, 52 g theoretical, 50%).

Keto ester A (700 mg, 3.27 mmol) was treated with THF (10 mL), K$_2$CO$_3$ (1.39 g, 10 mmol, 3.1 equiv.), and n-butyl iodide (1.1 g, 6 mmol, 1.8 equiv.). The reaction mixture was heated to reflux and allowed to stir for 12 h. The reaction mixture was then treated with toluene (40 mL) and stirred at RT for 12 h. The reaction mixture was partitioned between H$_2$O (50 mL) and EtOAc (50 mL). The H$_2$O layer was extracted with EtOAc (3×20 mL). The combined organic layer was dried over anhydrous Na$_2$SO$_4$ and concentrated under reduced pressure. The crude intermediate B was dissolved in DMF (10 mL) and treated with LiCl (4.24 g, 10 mmol, 3.1 equiv.). The reaction mixture was heated to 140° C. and stirred for 12 h. The reaction mixture was then partitioned between H$_2$O (50 mL) and EtOAc (50 mL). The H$_2$O layer was extracted with EtOAc (3×20 mL). The combined organic layer was dried over anhydrous Na$_2$SO$_4$ and concentrated under reduced pressure. The crude product was purified on a Biotage (EtOAc/hexanes) to provide the desired intermediate C (218 mg, 883 mg theoretical, 25%).

Me$_3$Si$_2$ (408 mg, 2 mmol, 2 equiv.) was treated with DMSO (5 mL), NaH (60% dispersion, 48 mg, 2 mmol, 2 equiv.), and stirred at RT for 2 h. The reaction mixture was then treated with intermediate C (210 mg, 1 mmol) and stirred at RT for 12 h. The mixture was then treated with EtOAc (20 mL) and H$_2$O (20 mL) and the layers were separated. The water layer was extracted with EtOAc (3×15 mL) and the combined organic layer was dried over anhydrous Na$_2$SO$_4$ and concentrated under reduced pressure. The crude product was purified on a Biotage (EtOAc/hexanes) to provide ANT_3205 (80 mg, 180 mg theoretical, 44%). $^1$H NMR (300 MHz, CDCl$_3$) δ 0.89 (m, 2H), 1.24 (m, 6H), 1.92 (m, 2H), 2.10-2.40 (m, 4H), 2.60-2.95 (m, 2H), 3.55-3.95 (m, 2H); LC-MS 183 (M+1).

Example 62

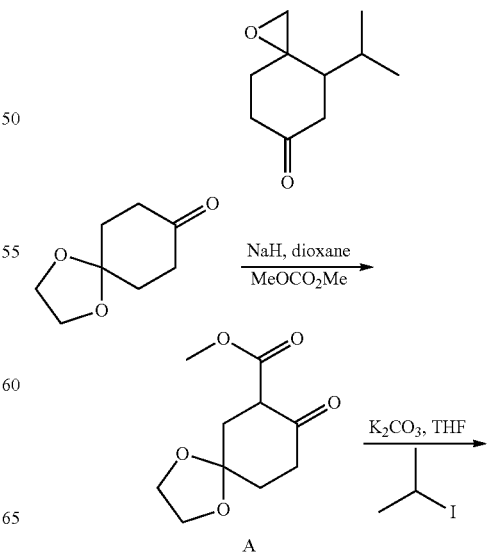

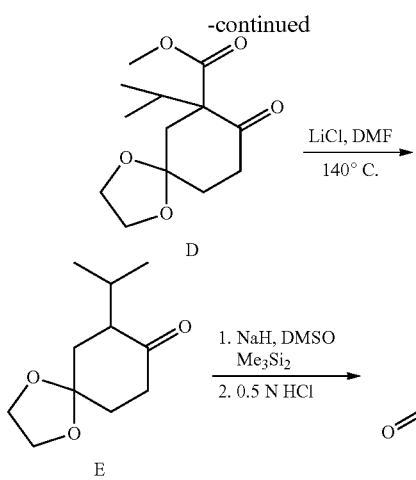

4-isopropyl-1-oxaspiro[2.5]octan-6-one (ANT-3241)

MeOCO₂Me (15 mL) was treated with 1,4-dioxaspiro[4.5]decan-8-one (38 g, 19.2 mmol) and then NaH (60% dispersion, 1.2 g, 25 mmol, 1.3 equiv.). The reaction mixture was allowed to stir at RT for 1 h. The reaction mixture was then treated with toluene (40 mL) and stirred at RT for 12 h. The reaction mixture was partitioned between H₂O (50 mL) and Et₂O (50 mL). The H₂O layer was extracted with Et₂O (3×15 mL). The combined organic layer was dried over anhydrous Na₂SO₄ and concentrated under reduced pressure. The crude product was purified on a Biotage (EtOAc/hexanes) to provide the intermediate keto ester A (26 g, 52 g theoretical, 50%).

Keto ester A (700 mg, 3.27 mmol) was treated with THF (10 mL), K₂CO₃ (1.39 g, 10 mmol, 3.1 equiv.), and isopropyl iodide (1.02 g, 6 mmol, 1.8 equiv.). The reaction mixture was heated to reflux and allowed to stir for 12 h. The reaction mixture was then treated with toluene (40 mL) and stirred at RT for 12 h. The reaction mixture was partitioned between H₂O (50 mL) and EtOAc (50 mL). The H₂O layer was extracted with EtOAc (3×20 mL). The combined organic layer was dried over anhydrous Na₂SO₄ and concentrated under reduced pressure. The crude intermediate D was dissolved in DMF (10 mL) and treated with LiCl (424 mg, 10 mmol, 3.1 equiv.). The reaction mixture was heated to 140° C. and stirred for 12 h. The reaction mixture was then partitioned between H₂O (50 mL) and EtOAc (50 mL). The H₂O layer was extracted with EtOAc (3×20 mL). The combined organic layer was dried over anhydrous Na₂SO₄ and concentrated under reduced pressure. The crude product was purified on a Biotage (EtOAc/hexanes) to provide the desired intermediate E (190 mg, 883 mg theoretical, 22%).

Me₃Si₂ (408 mg, 2 mmol, 4 equiv.) was treated with DMSO (5 mL), NaH (60% dispersion, 48 mg, 2 mmol, 4 equiv.), and stirred at RT for 2 h. The reaction mixture was then treated with intermediate E (100 mg, 0.5 mmol) and stirred at RT for 12 h. The mixture was treated with EtOAc (20 mL) and H₂O (20 mL) and the layers were separated. The water layer was extracted with EtOAc (3×15 mL) and the combined organic layer was dried over anhydrous Na₂SO₄ and concentrated under reduced pressure. The crude product was purified on a Biotage (EtOAc/hexanes) to provide ANT_3241 major (27 mg, 85 mg theoretical, 32%). ¹H NMR (300 MHz, CDCl₃) δ 0.91 (d, 3H), 0.97 (d, 3H), 1.81-1.91 (m, 3H), 2.06-2.34 (m, 3H), 2.61-2.74 (m, 2H), 3.59 (d, 1H), 3.84 (d, 1H); LC-MS 169 (M+). ANT_3267 minor (5 mg, 85 mg theoretical, 6%). ¹H NMR (300 MHz, CDCl₃) δ 0.82 (d, 3H), 0.99 (d, 3H), 1.90-2.16 (m, 4H), 2.26-2.34 (m, 2H), 2.58-2.65 (m, 2H), 3.79 (q, 2H); LC-MS 169 (M+).

Example 63

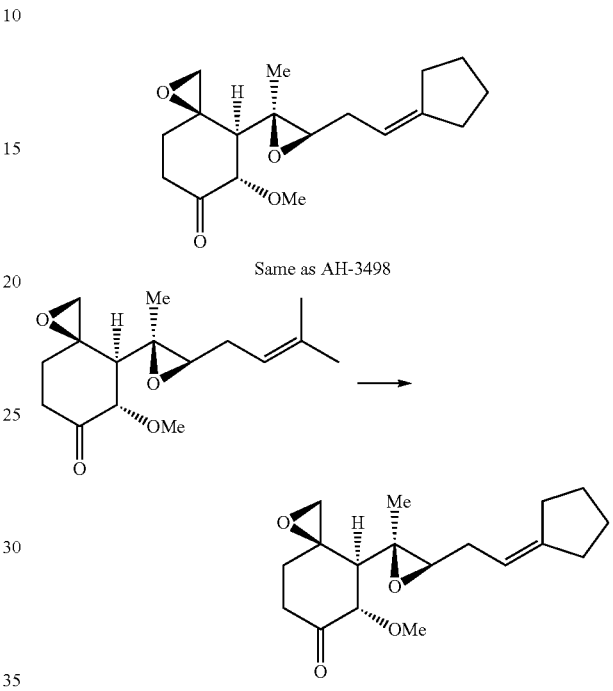

To the starting material (79 mg, 0.28 mmol) in DCM (2 mL) was added methylenecyclopentane (365 mg, 4.45 mmol) and Grubbs-Hoveyda catalyst (5.58 mg, 0.009 mmol). The reaction mixture was refluxed for 12 h. The reaction mixture was then concentrated under reduced pressure. The residue was partitioned between EtOAc (10 mL) and saturated NaHCO₃ (aq) (10 mL). The aqueous layer was extracted with EtOAc (2×10 mL). The combined organic layer was dried over Na₂SO₄ and concentrated under reduced pressure. Flash chromatography using EtOAc/hexanes (1:1) gave the desired product (4 mg, 4.7%). MS ES⁺(M+H)⁺ m/e 307; ¹H NMR (300 MHz, CDCl₃) δ: 5.27-5.33 (m, 1H), 4.08 (dd, J=9.3 Hz, 1H), 3.50 (s, 3H), 3.07 (d, J=4.2 Hz, 1H), 2.61-2.78 (m, 2H), 2.47-2.57 (m, 1H), 2.01-2.43 (m, 7H), 1.88 (d, J=10.8 Hz, 1H), 1.60-1.76 (m, 6H), 1.25-1.28 (m, 3H).

Example 64

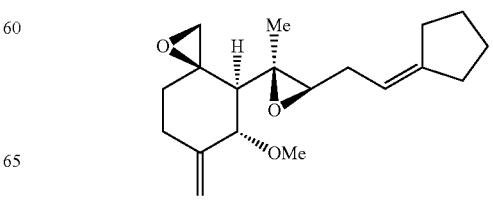

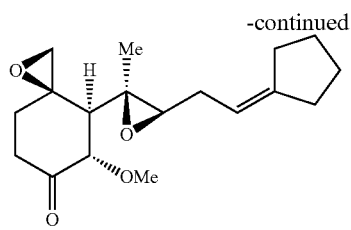

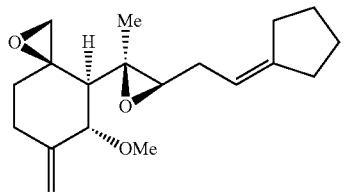

To a solution of Ph₃PCH₃Br (714 mg, 2 mmol) in THF (1 mL) was added nBuLi (2 mmol) at −78° C. The reaction mixture was stirred for 20 min at −78° C. The reaction mixture was then added to a solution of ketone (150 mg, ~0.5 mmol) in THF (1 mL) at −78° C. and stirred for 20 min and then stirred at room temperature for 2 h. EtOAc (10 mL) was then added and the mixture was washed with saturated NaHCO₃ (aq) (10 mL). The combined organic layer was dried over Na₂SO₄ and concentrated under reduced pressure. The crude was purified by reverse phase HPLC. MS ES⁺ (M+H)⁺ m/e 305; ¹H NMR (300 MHz, CDCl₃) □□ 5.29-5.35 (m, 1H), 5.07 (bs, 1H), 4.98 (bs, 1H), 3.93 (d, J=8.1 Hz, 1H), 3.39 (s, 3H), 2.87 (d, J=4.5 Hz, 1H), 2.62 (t, J=4.5 Hz, 1H), 2.57 (d, J=4.5 Hz, 1H), 2.14-2.44 (m, 7H), 1.48-1.70 (m, 8H), 1.25-1.29 (m, 3H).

Example 65

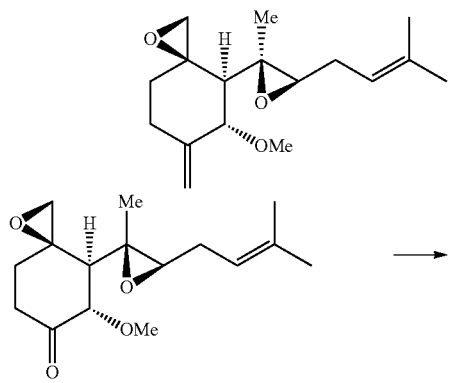

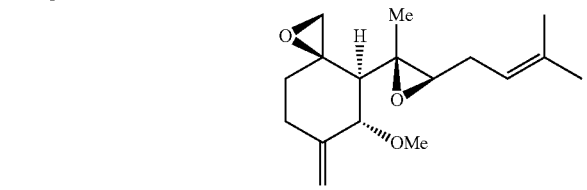

To a solution of Ph₃PCH₃Br (714 mg, 2 mmol) in THF (1 mL) was added nBuLi (2 mmol) at −78° C. The reaction mixture was stirred for 20 min at −78° C. The reaction mixture was then added to a solution of ketone (150 mg, ~0.5 mmol) in THF (1 mL) at −78° C. and stirred for 20 min and then stirred at room temperature for 2 h. EtOAc (10 mL) was then added and the mixture was washed with saturated NaHCO₃ (aq) (10 mL). The combined organic layer was dried over Na₂SO₄ and concentrated under reduced pressure. The crude was purified by reverse phase HPLC. MS ES⁺ (M+H)⁺ m/e 279; ¹H NMR (300 MHz, CDCl₃) □□ 5.16-5.23 (m, 1H), 5.06 (bs, 1H), 4.98 (bs, 1H), 3.93 (d, J=8.1 Hz, 1H), 3.38 (s, 3H), 2.85 (d, J=4.8 Hz, 1H), 2.59 (t, J=5.1 Hz, 1H), 2.56 (d, J=4.8 Hz, 1H), 2.27-2.45 (m, 3H), 2.12-2.22 (m, 1H), 1.73 (s, 3H), 1.54-1.66 (5H), 1.49 (d, J=8.1 Hz, 1H), 1.29 (s, 3H).

Example 66

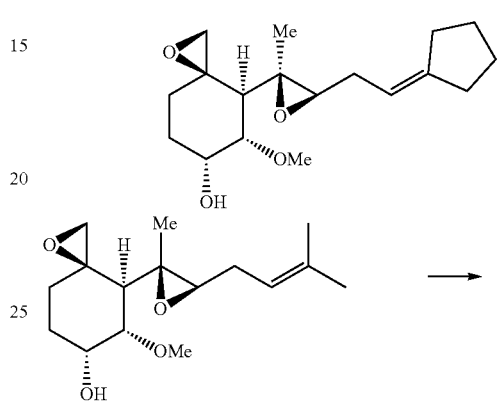

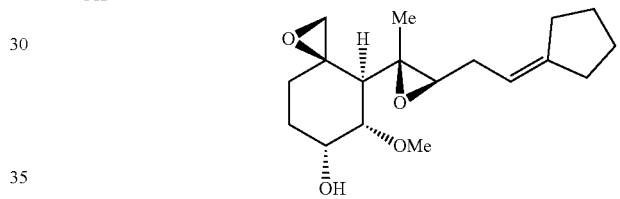

To the starting material (79 mg, 0.28 mmol) in DCM (2 mL) was added methylenecyclopentane (365 mg, 4.45 mmol) and Grubbs-Hoveyda catalyst (5.58 mg, 0.009 mmol). The reaction mixture was refluxed for 12 h. The reaction mixture was then concentrated under reduced pressure. The residue was partitioned between EtOAc (10 mL) and saturated NaHCO₃ (aq) (10 mL). The aqueous layer was extracted with EtOAc (2×10 mL). The combined organic layer was dried over Na₂SO₄ and concentrated under reduced pressure. Flash chromatography using EtOAc/hexanes (1:1) gave the desired product. MS ES⁺(M+H)⁺ m/e 309; ¹H NMR (300 MHz, CDCl₃) □□ 5.26-5.35 (m, 1H), 4.35-4.36 (m, 1H), 3.64 (dd, J=8.4 Hz, 1H), 3.48 (s, 3H), 2.95 (d, J=4.5 Hz, 1H), 2.60 (t, J=5.4 Hz, 1H), 2.52 (d, J=4.2 Hz, 1H), 2.10-2.39 (m, 6H), 1.95-2.03 (m, 1H), 1.92 (d, J=11.1 Hz, 1H), 1.58-1.81 (m, 5H), 1.21 (s, 3H), 0.94-1.00 (m, 1H).

Example 67

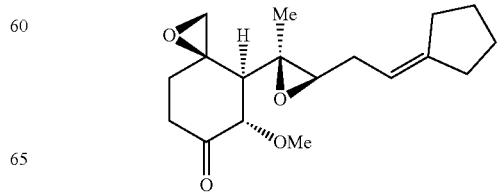

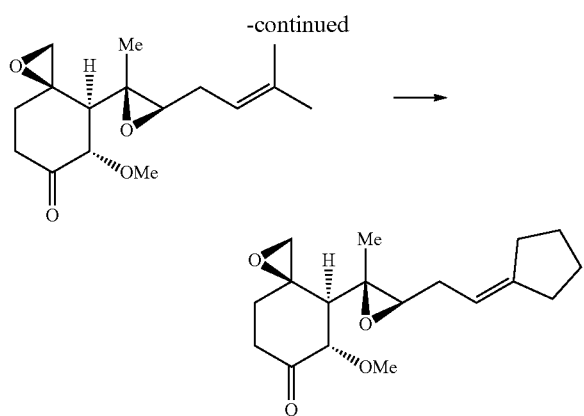

To the starting material (79 mg, 0.28 mmol) in DCM (2 mL) was added methylenecyclopentane (365 mg, 4.45 mmol) and Grubbs-Hoveyda catalyst (5.58 mg, 0.009 mmol). The reaction mixture was refluxed for 12 h. The reaction mixture was then concentrated under reduced pressure. The residue was partitioned between EtOAc (10 mL) and saturated NaHCO$_3$ (aq) (10 mL). The aqueous layer was extracted with EtOAc (2×10 mL). The combined organic layer was dried over Na$_2$SO$_4$ and concentrated under reduced pressure. Flash chromatography using EtOAc/hexanes (1:1) gave the desired product (4 mg, 4.7%). MS ES$^+$(M+H)$^+$ m/e 307; $^1$H NMR (300 MHz, CDCl$_3$); 5.27-5.33 (m, 1H), 4.08 (dd, J=9.3 Hz, 1H), 3.50 (s, 3H), 3.07 (d, J=4.2 Hz, 1H), 2.61-2.78 (m, 2H), 2.47-2.57 (m, 1H), 2.01-2.43 (m, 7H), 1.88 (d, J=10.8 Hz, 1H), 1.60-1.76 (m, 6H), 1.25-1.28 (m, 3H).

Example 68

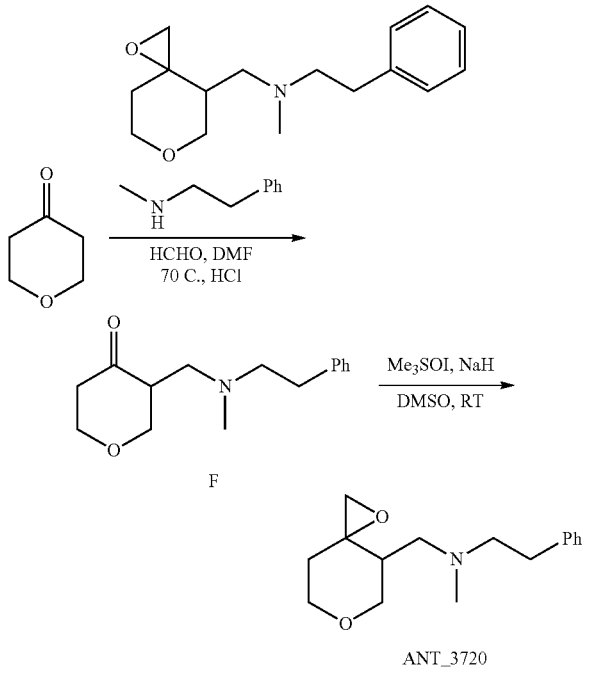

A mixture of tetrahydro-4H-pyran-4-one (400 mg, 4 mmol), paraformaldehyde (100 mg, 3.3 mmol), N,N-methylphenethylamine (541 mg, 4 mmol) and two drops of concentrated HCl in DMF (2 mL) was heated at 70° C. for 15 hours. The reaction solvent was removed under reduced pressure and the residue diluted with water and then extracted with EtOAc (3×3 mL). The combined organic layer was dried over MgSO$_4$ and concentrated in vacuo. The residue was purified by reverse-phase HPLC (5-50% MeCN in water with 0.1% TFA) to provide 344 mg of intermediate F (24% yield as a TFA salt), LC-MS 248 (M+1).

To a mixture of trimethylsufonium iodide (710 mg, 3.5 mmol) in anhydrous DMSO (21 mL) under a nitrogen atmosphere was added sodium hydride (60% dispersion, 130 mg, 3.5 mmol). The reaction mixture was stirred at room temperature for 3 hours, then treated with neat intermediate F (214 mg, 0.59 mmol as a TFA salt) and stirred at room temperature for 15 hours. The reaction mixture was diluted with water and extracted with EtOAc (3×10 mL). The solvent was removed in vacuo and the residue purified by reverse-phase HPLC (5-50% MeCN in water with 0.1% TFA). Sodium bicarbonate was added to the HPLC fractions and the product was extracted with EtOAc (3×10 mL). The solvent was removed in vacuo to provide 6.7 mg of the desired epoxide ANT_3720 (9% yield). $^1$H NMR (400 MHz, CD$_3$OD) δ 7.27-7.12 (m, 5H), 3.92-3.80 (m, 1H), 3.71-3.65 (m, 3H); 2.86 (d, 1H), 2.78-2.70 (m, 2H), 2.65-2.49 (m, 4H), 2.34-2.30 (m, 1H), 2.28 (s, 3H), 1.76-1.68 (m, 2H), 1.58-1.53 (m, 1H); LC-MS 262 (M+1).

Example 69

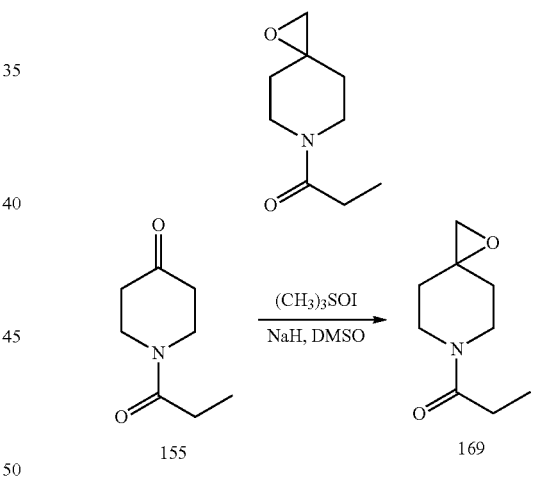

Trimethylsulfoxonium iodide (771 mg, 3.5 mmol) was dissolved in anhydrous dimethyl sulfoxide (4 mL) under the protection of argon, and then sodium hydride (134 mg, 3.4 mmol) was added. The reaction mixture was stirred violently at room temperature for 30 min. A solution made by dissolving 155 (500 mg, 2.9 mmol) in dimethyl sulfoxide (0.5 mL) was added slowly to the reaction mixture by a syringe. The reaction temperature was then allowed to increase to 60 and stirred for 40 min. After cooled to room temperature, water was added to quench the reaction and the mixture was extracted with ethyl acetate (30 mL×3). The combined organic layer was dried over Na$_2$SO$_4$ and the solvent was removed under reduced pressure. The residue was purified through a flash silica gel chromatography (petroleum ether/ethyl acetate=8:1) to afford a colorless oil (300 mg, 55%). $^1$H NMR: 4.05 (q, J=7.5 Hz, 2H), 3.55 (m, 2H), 3.42 (m, 2H), 2.66 (s, 2H), 1.66 (m, 2H), 1.41 (m, 2H), 1.19 (t, J=7.0 Hz, 2H). MS (m/z): 186 (M+NH₃).

Example 70

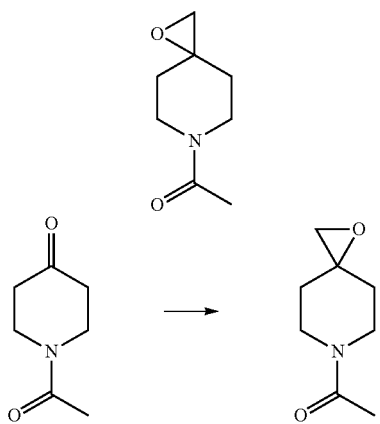

Trimethylsulfoxonium iodide (550 mg, 2.5 mmol) was dissolved in anhydrous dimethyl sulfoxide (4 mL) under the protection of argon, and then sodium hydride (100 mg, 2.5 mmol) was added. The reaction mixture was stirred violently at room temperature for 30 min. A solution made by dissolving 1-acetylpiperidin-4-one (141 mg, 1.0 mmol) in dimethyl sulfoxide (0.5 mL) was added slowly to the reaction mixture by a syringe. The reaction temperature was then allowed to increase to 60□ and stirred for 40 min. Water was added to quench the reaction and the mixture was extracted with ethyl acetate (30 mL×2). The combined organic layer was dried over Na₂SO₄ and the solvent was removed under reduced pressure. The residue was purified through a flash silica gel chromatography (petroleum ether/ethyl acetate=5:1) to afford a colorless oil (93 mg, 60%). ¹H NMR (500 MHz, CD₃OD), δ1.48 (m, 1H), 1.55 (m, 1H), 1.82 (m, 1H), 1.91 (m, 1H), 2.16 (s, 3H), 2.75 (s, 2H), 3.48 (m, 1H), 3.62 (s, 1H), 3.74 (m, 1H), 3.98 (m, 1H); EM(IES-EM): m/z 156[M⁺+1].

Example 71: Experimental Procedures for the Synthesis of Piperidin-4-One Analogs General Procedure

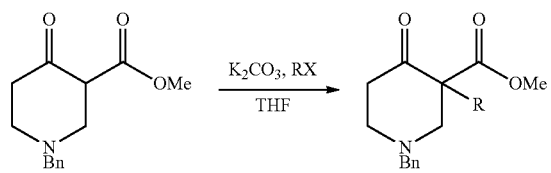

To methyl 1-benzyl-4-oxopiperidine-3-carboxylate (2 g, 8.09 mmol) in THF (15 mL) was added potassium carbonate (4.47 g, 32.35 mmol) and n-butyl iodide (1.84 mL, 16.18 mmol). The reaction mixture was heated to reflux for 24-48 h until starting material was consumed. It was then cooled to room temperature. The reaction mixture was then partitioned between water (50 mL) and ethylacetate (50 mL). The aqueous layer was extracted with ethylacetate (3×50 mL). The combined organic layer was dried over Na₂SO₄ and concentrated under reduced pressure. The crude material was then purified by column chromatography using 10-20% ethylacetate (0.5% triethylamine)/hexanes to give the desired product (1.62 g, 66%).

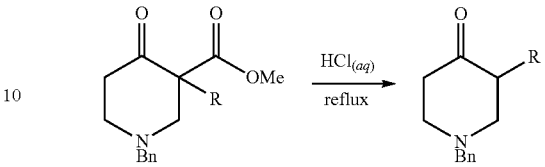

To methyl 1-benzyl-3-butyl-4-oxopiperidine-3-carboxylate (1 g, 3.29 mmol) was added 6 N HCl (10 mL). The reaction mixture was refluxed for 24 h. The reaction mixture was then cooled to room temperature and basified with sat. NaHCO₃(aq). The resulting mixture was extracted with dichloromethane (3×25 mL). The combined organic layer was dried over Na₂SO₄ and concentrated under reduced pressure. The crude material was purified by column chromatography using 10-20% ethylacetate (0.5% triethylamine)/hexanes to give the desired product (775 mg, 96%).

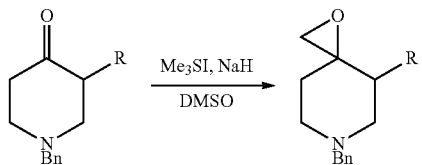

To trimethylsulfonium iodide (2.32 g, 11.4 mmol) in DMSO (7 mL) was added 60% NaH (456.4 mg, 11.4 mmol) slowly at room temperature. The reaction mixture was stirred for 2 h. A solution of 1-benzyl-3-butylpiperidin-4-one (700 mg, 2.85 mmol) in DMSO (3 mL) was added slowly. The resulting mixture was stirred for 16 h. Ice water (10 mL) was then added slowly and the reaction mixture was extracted with ethylacetate (3×25 mL). The combined organic layer was washed with brine (50 mL), dried over Na₂SO₄ and then concentrated under reduced pressure. The crude product was purified with column chromatography using 10-20% ethylacetate (0.5% triethylamine)/hexanes to give the desired product as two separable isomers (434 mg, 59% and 150 mg, 20%).

General Procedure

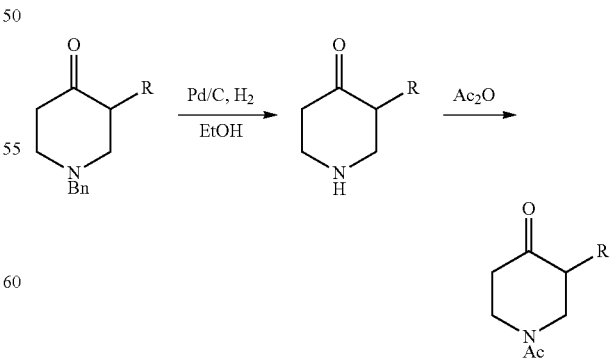

To 1-benzyl-3-(cyclopentylmethyl)piperidin-4-one (300 mg, 1.1 mmol) in EtOH (7 mL) was flushed with N₂. 10% Pd/C (300 mg) was then added and the reaction mixture was stirred under H$_2$ atmosphere for 16 h. LCMS showed complete consumption of the starting material. Ac$_2$O (226 mg, 2.21 mmol) was then added and stirred under N$_2$ atmosphere for 3 h. The reaction mixture was then filtered and concentrated under reduced pressure. The crude material was purified on silica gel using 25-50% ethylacetate (0.5% triethylamine)/hexanes to give the desired product (142.5 mg, 58%).

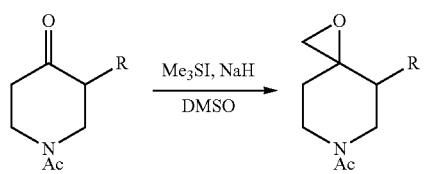

To trimethylsulfonium iodide (521 mg, 2.55 mmol) in DMSO (3 mL) was added 60% NaH (102 mg, 2.55 mmol) slowly at room temperature. The reaction mixture was stirred for 2 h. A solution of 1-acetyl-3-(cyclopentylmethyl) piperidin-4-one (142.5 mg, 0.64 mmol) in DMSO (3 mL) was added slowly. The resulting mixture was stirred for 16 h. Ice water (10 mL) was then added slowly and the reaction mixture was extracted with ethylacetate (3×25 mL). The combined organic layer was washed with brine (50 mL), dried over Na$_2$SO$_4$ and then concentrated under reduced pressure. The crude product was purified with column chromatography using 25-50% ethylacetate (0.5% triethylamine)/hexanes to give the desired product as two separable isomers (46.2 mg, 31% and 18 mg, 12%).

General Procedure

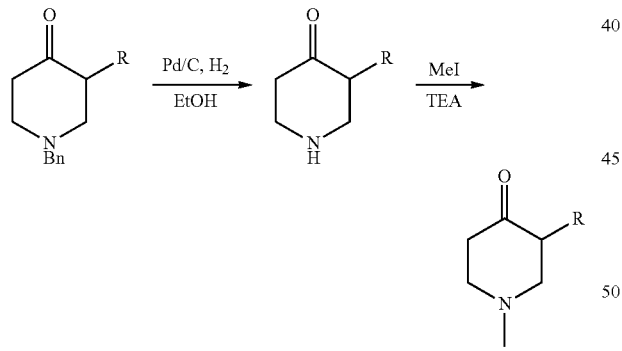

To 1-benzyl-3-(3-phenylpropyl)piperidin-4-one (308 mg, 1.0 mmol) in EtOH (7 mL) was flushed with N$_2$. 10% Pd/C (300 mg) was then added and the reaction mixture was stirred under H$_2$ atmosphere for 16 h. LCMS showed complete consumption of starting material. The reaction mixture was then filtered and concentrated under reduced pressure. DCM (5 mL) was then added followed by triethylamine (280 µl, 2.0 mmol) and 2 M MeI (2 ml, 4.0 mmol) in DCM. The reaction mixture was then stirred for 16 h. LCMS showed the reaction was complete. The reaction mixture was then concentrated under reduced pressure and purified on silica gel using 25-50% ethylacetate (0.5% triethylamine)/ hexanes to give the desired product (50.8 mg, 21%).

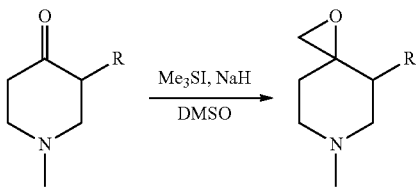

To trimethylsulfonium iodide (180 mg, 0.88 mmol) in DMSO (2 mL) was added 60% NaH (35.1 mg, 0.88 mmol) slowly at room temperature. The reaction mixture was stirred for 2 h. A solution of 1-benzyl-3-(3-phenylpropyl) piperidin-4-one (50.8 mg, 0.22 mmol) in DMSO (1 mL) was added slowly. The resulting mixture was stirred for 16 h. Ice water (5 mL) was then added slowly and the reaction mixture was extracted with ethylacetate (3×10 mL). The combined organic layer was washed with brine (10 mL), dried over Na$_2$SO$_4$ and then concentrated under reduced pressure. The crude product was purified with column chromatography using 25-50% ethylacetate (0.5% triethylamine)/hexanes to give the desired product as two separable isomers (36.6 mg, 68%).

The following compounds were yielded using the above protocol:

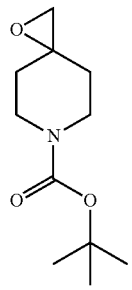

MS ES$^+$(M+H)$^+$ m/e 214; $^1$H NMR (400 MHz, CDCl$_3$) δ 3.70-3.74 (m, 2H), 3.40-3.46 (m, 2H), 2.69 (s, 2H), 1.76-1.83 (m, 2H), 1.48 (s, 9H), 1.42-1.50 (m, 2H).

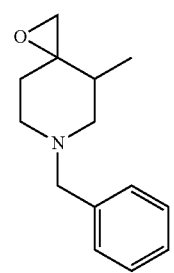 [SMILES: CC1CN(Cc2ccccc2)CCC12CO2]

MS ES$^+$(M+H)$^+$ m/e 218; $^1$H NMR (300 MHz, CDCl$_3$) δ 7.24-7.33 (m, 5H), 3.53 (dd, 2H), 2.69-2.75 (m, 3H), 2.52 (d, J=4.5 Hz, 1H), 2.39-248 (m, 2H), 2.13-2.19 (m, 1H), 1.70-1.87 (m, 3H), 0.89 (d, J=6.9 Hz, 3H).

113

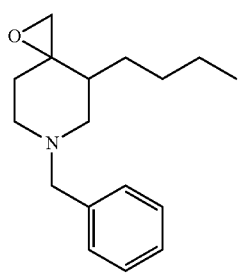 [SMILES: CCCCC1CN(Cc2ccccc2)CCC12CO2]

MS ES⁺(M+H)⁺ m/e 260; ¹H NMR (400 MHz, CDCl₃) δ 7.23-7.35 (m, 5H), 3.53 (dd, 2H), 2.73 (d, J=4.8 Hz, 1H), 2.61-2.67 (m, 1H), 2.56 (d, J=4.4 Hz, 1H), 2.46-2.49 (m, 3H), 1.81 (bs, 1H), 1.54-1.60 (m, 3H), 1.09-1.49 (m 7H), 0.86 (t, J=7.2 Hz, 3H).

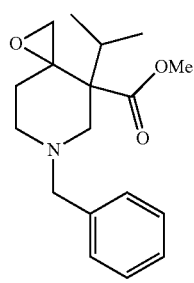 [SMILES: COC(=O)C1(C(C)C)CN(Cc2ccccc2)CCC12CO2]

MS ES⁺(M+H)⁺ m/e 304; ¹H NMR (300 MHz, CDCl₃) δ 7.24-7.33 (m, 5H), 3.68 (s, 3H), 3.55 (dd, 2H), 2.97 (d, J=11.4 Hz, 1H), 2.84 (d, J=5.7 Hz, 1H), 2.38-2.61 (m, 4H), 1.98-2.18 (m, 2H), 1.42-1.50 (m, 1H), 0.90 (d, J=7.2 Hz, 3H), 0.80 (d, J=6.9 Hz, 3H).

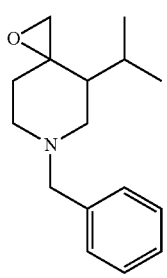

MS ES⁺(M+H)⁺ m/e 246; ¹H NMR (300 MHz, CDCl₃) δ 7.24-7.33 (m, 5H), 3.50 (dd, 2H), 2.81-2.90 (m, 2H), 2.48-2.54 (m, 2H), 2.08-2.31 (m, 4H), 1.18-1.25 (m, 1H), 0.91-1.01 (m, 4H), 0.785 (d, J=6 Hz, 3H).

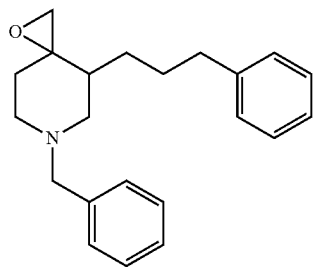 [SMILES: c1ccc(CCCC2CN(Cc3ccccc3)CCC23CO3)cc1]

114

MS ES⁺(M+H)⁺ m/e 322; ¹H NMR (300 MHz, CDCl₃) δ 7.24-7.34 (m, 7H), 7.12-7.19 (m, 3H), 3.53 (dd, 2H), 2.71 (dd, 1H), 2.55-2.60 (m, 4H), 2.47 (d, broad, 3H), 1.80-1.84 (m, 1H), 1.48-1.59 (m, 6H).

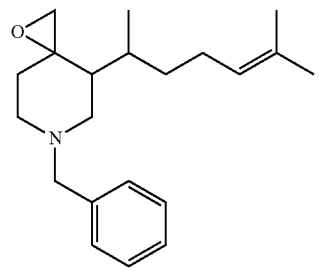 [SMILES: CC(C)=CCCC(C)C1CN(Cc2ccccc2)CCC12CO2]

MS ES⁺(M+H)⁺ m/e 314; mixtures of isomers ~3:1

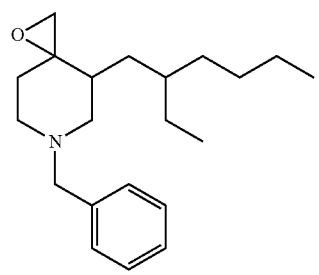 [SMILES: CCCCC(CC)CC1CN(Cc2ccccc2)CCC12CO2]

MS ES⁺(M+H)⁺ m/e 316; ¹H NMR (300 MHz, CDCl₃) δ 7.20-7.33 (m, 5H), 3.53 (dd, 2H), 2.74 (d, J=4.5 Hz, 1H), 2.34-2.66 (m, 5H), 1.58-1.80 (m, 3H), 1.13-1.40 (m, 12H), 0.75-0.91 (m, 6H).

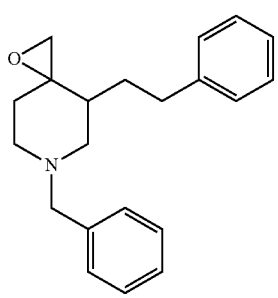 [SMILES: c1ccc(CCC2CN(Cc3ccccc3)CCC23CO3)cc1]

MS ES⁺(M+H)+m/e 308; ¹H NMR (400 MHz, CDCl₃) δ 7.11-7.36 (m, 10H), 3.54 (dd, 2H), 2.72 (dd, 1H), 2.44-2.58 (m, 6H), 1.70-1.1.95 (m, 3H), 1.46-1.63 (m, 3H).

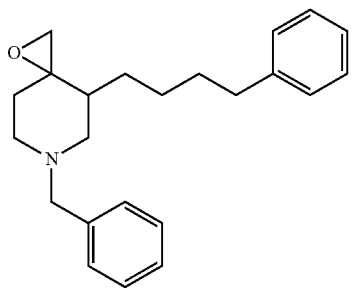 [SMILES: c1ccc(CCCCC2CN(Cc3ccccc3)CCC23CO3)cc1]

MS ES⁺(M+H)⁺ m/e 336; ¹H NMR (400 MHz, CDCl₃) δ 7.15-7.33 (m, 10H), 3.53 (dd, 2H), 2.72 (d, J=4.8 Hz, 1H), 2.46-2.65 (m, 7H), 1.82 (bs, 1H), 1.16-1.63 (m, 8H).

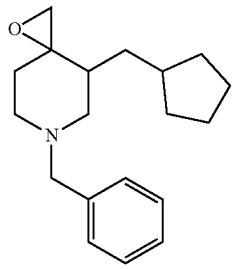 [SMILES: c1ccc(CN2CCC3(CO3)C(CC3CCCC3)C2)cc1]

MS ES⁺(M+H)⁺ m/e 286; ¹H NMR (400 MHz, CDCl₃) δ 7.25-7.35 (m, 5H), 3.54 (dd, 2H), 2.74 (d, J=4.4 Hz, 1H), 2.41-2.62 (m, 5H), 1.44-1.74 (m, 10H), 1.25-1.30 (m, 1H), 0.97-1.05 (m, 2H).

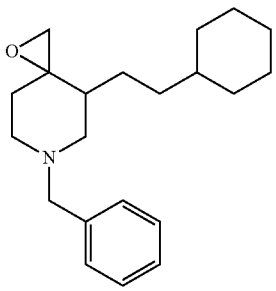 [SMILES: c1ccc(CN2CCC3(CO3)C(CCC3CCCCC3)C2)cc1]

MS ES⁺(M+H)⁺ m/e 314; ¹H NMR (400 MHz, CDCl₃) δ 7.23-7.35 (m, 5H), 3.52 (dd, 2H), 2.67 (d, J=4.4 Hz, 1H), 2.40-2.61 (m, 5H), 1.95 (bs, 1H), 1.65-1.67 (m, 5H), 1.24-1.47 (m, 4H), 1.00-1.22 (m, 5H), 0.79-0.92 (m, 2H).

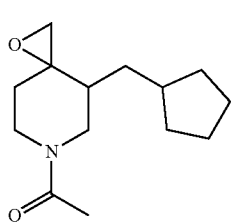 [SMILES: CC(=O)N1CCC2(CO2)C(CC2CCCC2)C1]

MS ES⁺(M+H)⁺ m/e 238; ¹H NMR (400 MHz, CDCl₃) δ: 3.86-3.91 (m, 1H), 3.74 (dd, 1H), 3.40-3.66 (m, 6H), 2.82 (dd, 2H), 2.62 (t, J=4.4 Hz, 2H), 2.11-2.13 (m, 6H), 1.45-1.92 (m, 20H), 1.16-1.33 (m, 4H), 0.89-1.10 (m, 4H).

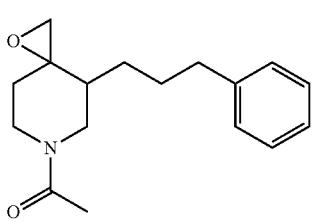 [SMILES: CC(=O)N1CCC2(CO2)C(CCCc2ccccc2)C1]

MS ES⁺(M+H)⁺ m/e 274; ¹H NMR (300 MHz, CDCl₃) δ: 7.13-7.29 (m, 10H), 4.32-4.36 (m, 1H), 4.08-4.13 (m, 1H), 3.41-3.70 (m, 5H), 3.32-3.37 (m, 1H), 3.09-3.19 (m, 1H), 2.56-2.72 (m, 9H), 2.13 (s, 3H), 2.04 (s, 3H), 1.93-2.01 (m, 2H), 1.20-1.84 (m, 10H).

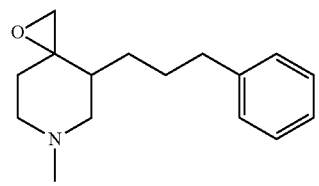 [SMILES: CN1CCC2(CO2)C(CCCc2ccccc2)C1]

MS ES⁺(M+H)⁺ m/e 246.

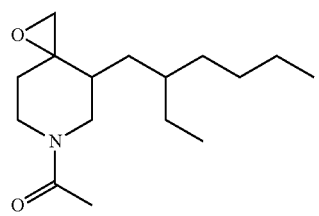 [SMILES: CCCCC(CC)CC1CN(C(C)=O)CCC12CO2]

MS ES⁺(M+H)⁺ m/e 268; ¹H NMR (400 MHz, CDCl₃) δ: 3.76-3.89 (m, 1H), 3.48-3.69 (m, 2H), 3.31-3.44 (m, 1H), 2.80-2.86 (m, 1H), 2.59-2.62 (m, 1H), 2.12-2.13 (m, 3H), 1.55-1.72 (m, 4H), 1.707-1.34 (m, 12H), 0.79-0.90 (m, 6H).

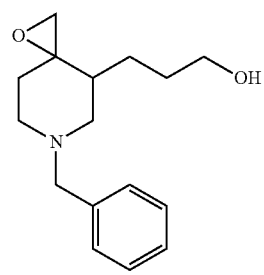 [SMILES: OCCCC1CN(Cc2ccccc2)CCC12CO2]

MS ES⁺(M+H)⁺ m/e 262; ¹H NMR (400 MHz, CDCl₃) δ 7.25-7.33 (m, 5H), 3.44-3.60 (m, 4H), 2.70 (d, J=4.4 Hz, 1H), 2.58-2.63 (m, 3H), 1.91-1.93 (d, broad, 1H), 1.40-1.53 (m, 7H).

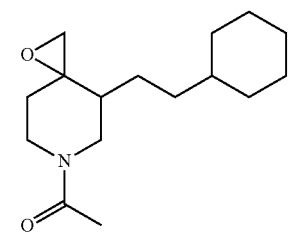 [SMILES: CC(=O)N1CCC2(CO2)C(CCC2CCCCC2)C1]

MS ES⁺(M+H)⁺ m/e 266; ¹H NMR (300 MHz, CDCl₃) δ: 3.95-4.03 (m, 1H), 3.74 (dd, 1H), 3.41-3.67 (m, 6H), 2.81 (dd, 2H), 2.62 (dd, 2H), 1.61-1.75 (m, 16H), 1.44-1.52 (m, 5H), 1.12-1.32 (m, 17H), 0.83-0.94 (m, 4H).

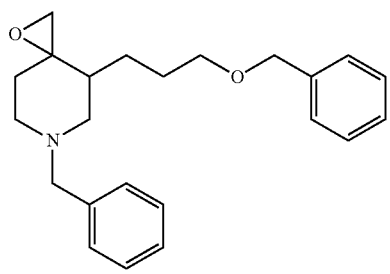 [SMILES: c1ccc(COCCCC2CN(Cc3ccccc3)CCC23CO3)cc1]
MS ES+(M+H)+ m/e 352; ¹H NMR (300 MHz, CDCl₃) δ 7.22-7.35 (m, 10H), 4.47 (s, 2H), 3.40-3.60 (m, 4H), 2.73 (d, J=4.5 Hz, 1H), 2.61-2.68 (m, 1H), 2.55 (d, J=3.6 Hz, 1H), 2.45-2.48 (m, 3H), 1.49-1.60 (m, 7H).
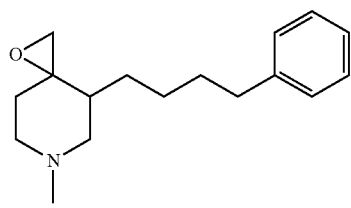 [SMILES: CN1CCC2(CO2)C(CCCCc2ccccc2)C1]
MS ES+(M+H)+ m/e 260; ¹H NMR (300 MHz, CDCl₃) δ 7.14-7.29 (m, 5H), 2.50-2.78 (m, 8H), 2.29 (d, J=2.7 Hz, 3H), 1.26-1.70 (m, 9H).
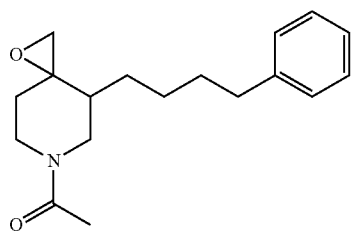 [SMILES: CC(=O)N1CCC2(CO2)C(CCCCc2ccccc2)C1]
MS ES+(M+H)+ m/e 260.
Example 72: Reaction Schemes
I. Scheme
Scheme 1. Synthesis of Key Intermediates
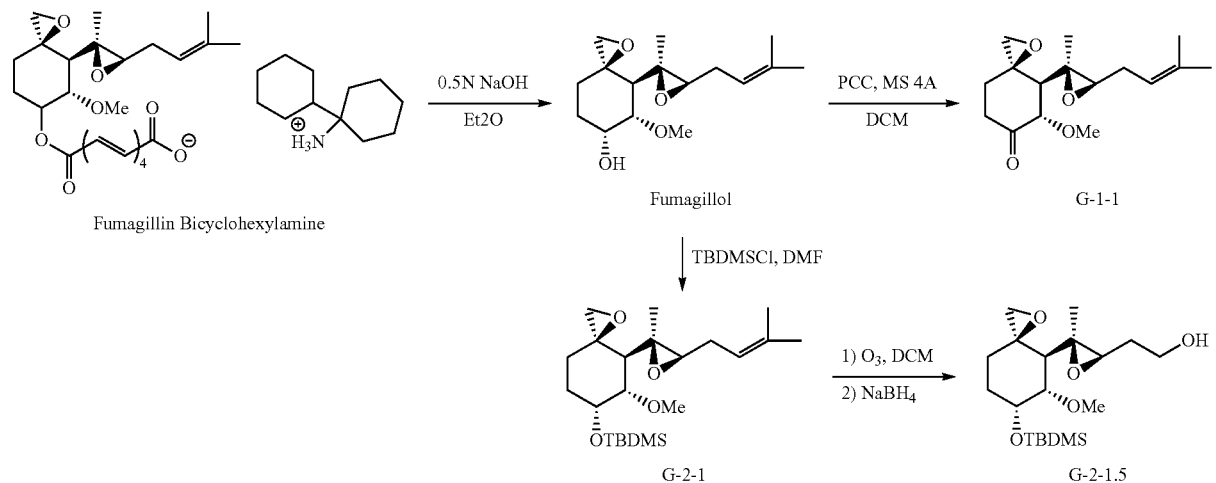
Scheme 2. Synthesis of A-1, A-5, A-1-C and A-5-C
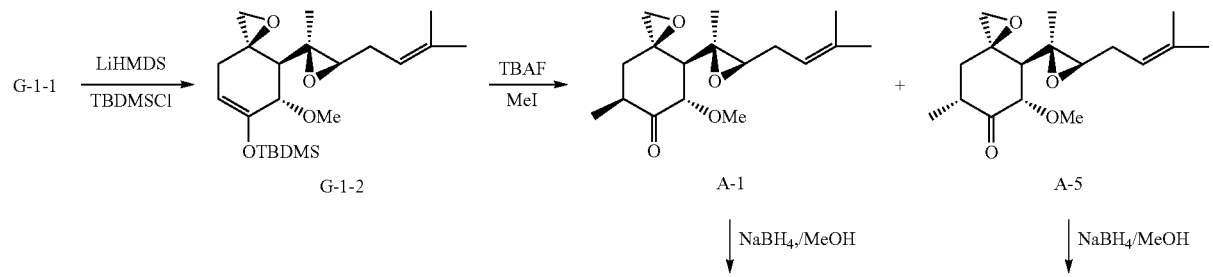

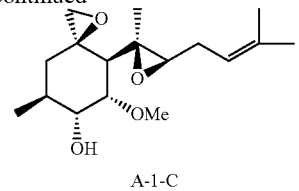
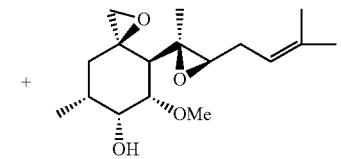
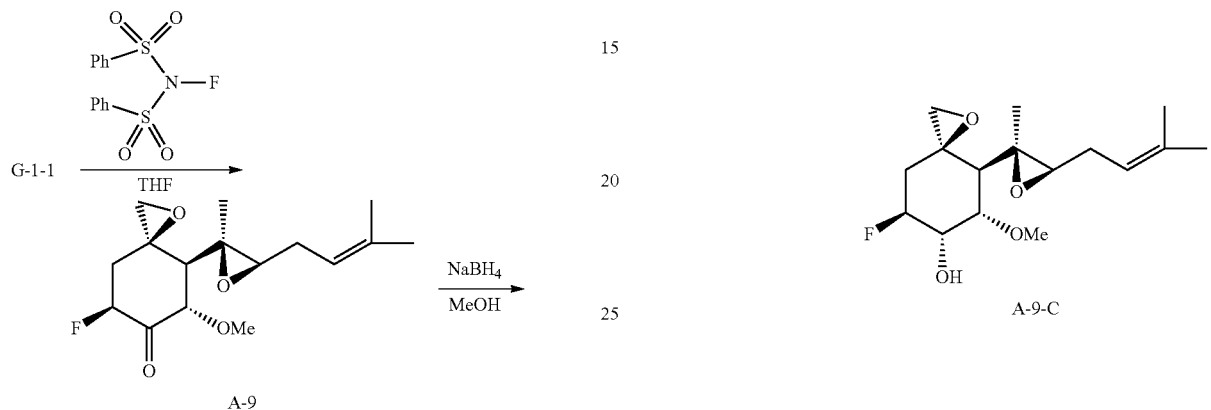
Scheme 3. Synthesis of A-9 and A-9-C
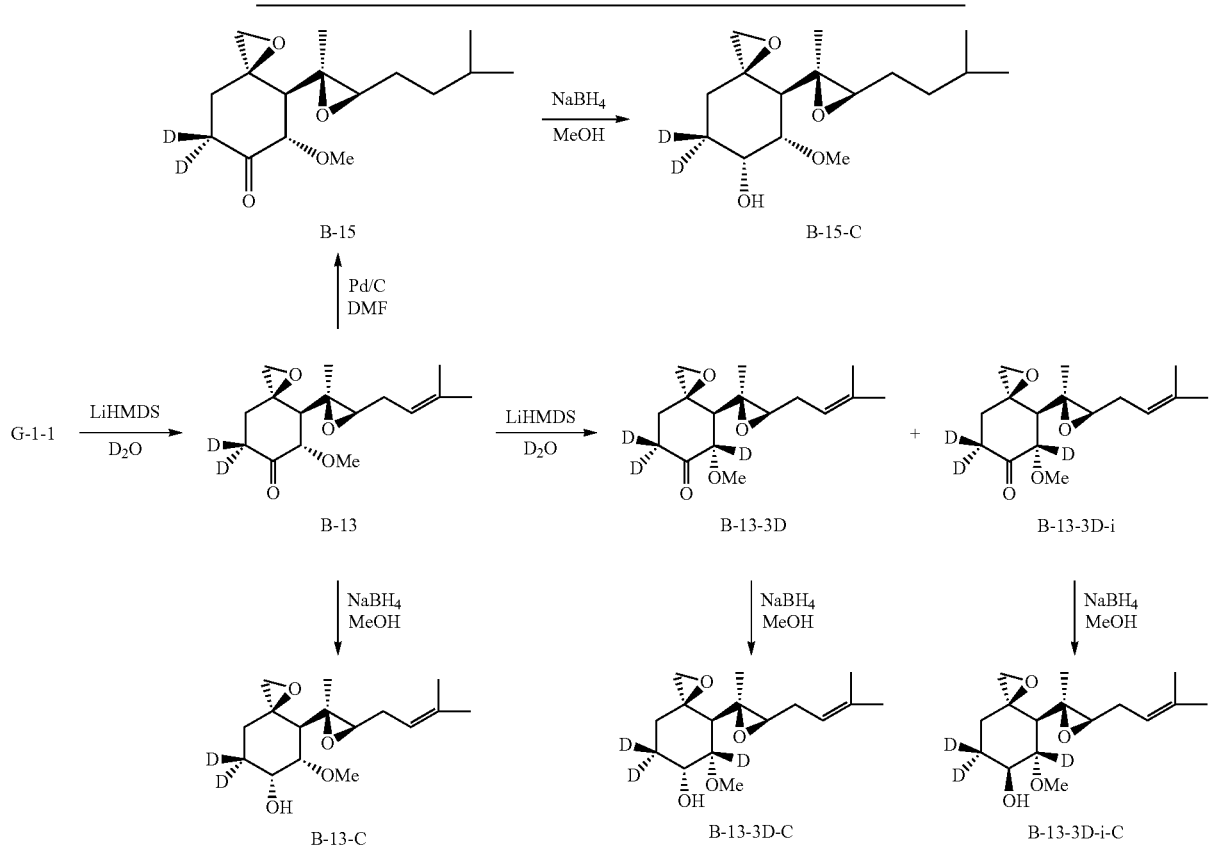
Scheme 4. Synthesis of B-13, B-13-3D, B-13-3D-i, B-15, B-13-C, B-13-3D-C, B-13-3D-i-C and B-15-C Scheme 5. Synthesis of B-1-D, B-3-D and B-1-2D
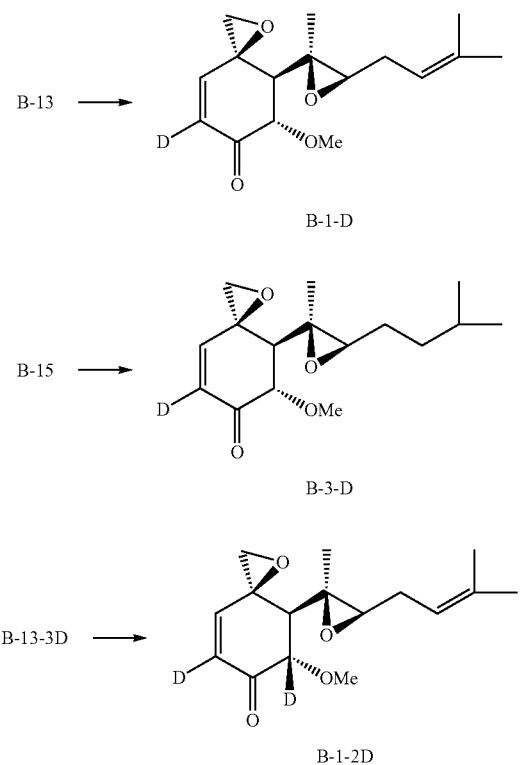
Scheme 6. Synthesis of G-3-2 and G-3-3
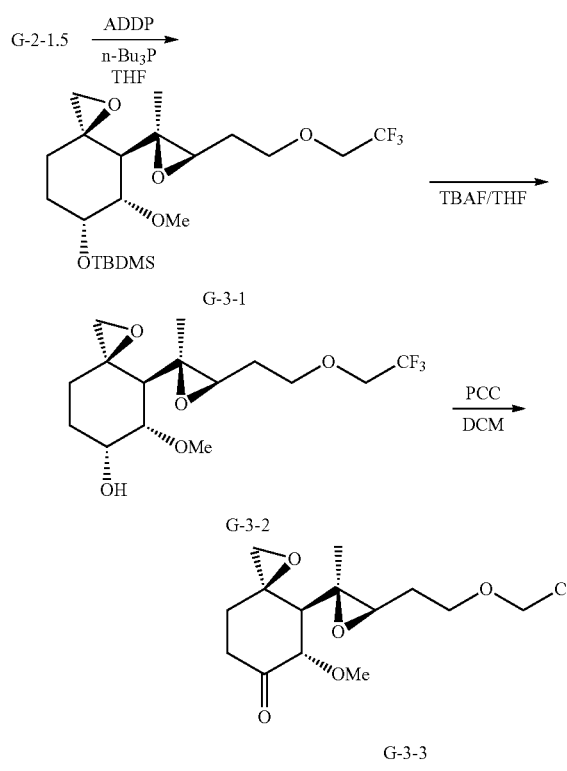
Scheme 7. Synthesis of G-4-2 and G-4-3
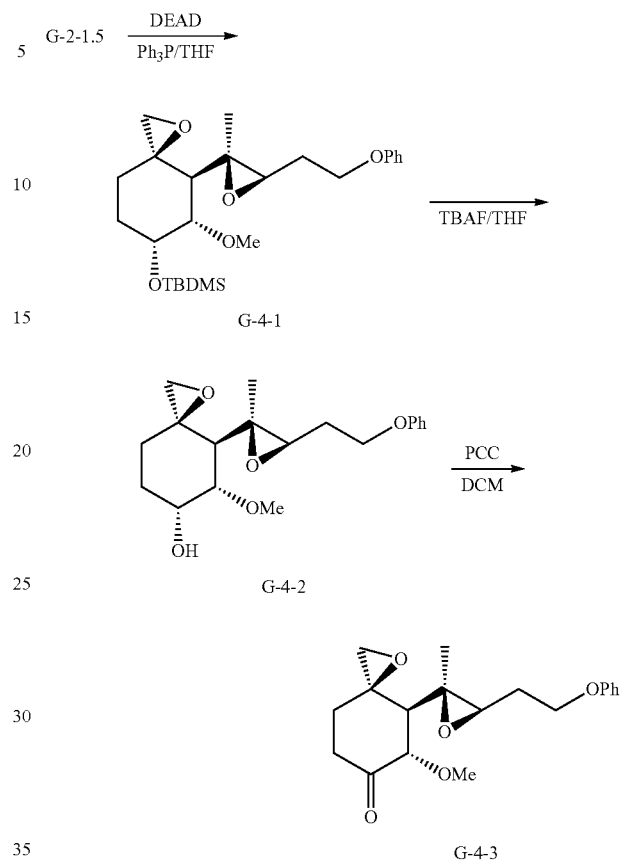
Scheme 8. Synthesis of A-11, A-11-C
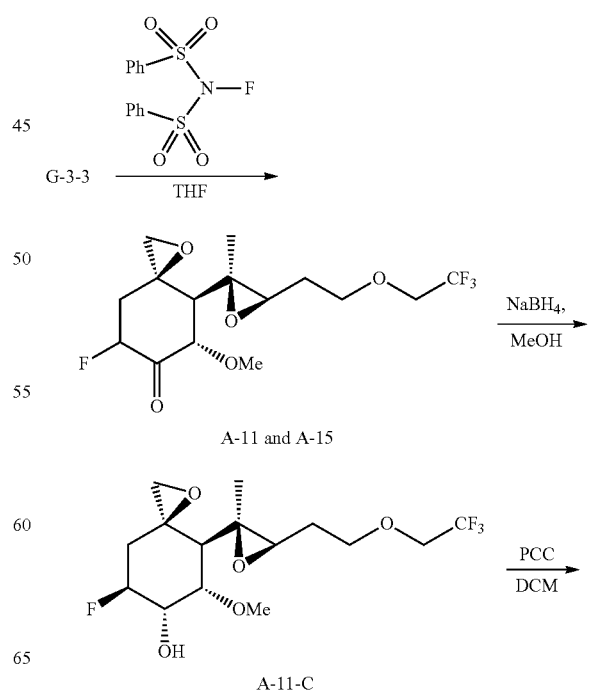

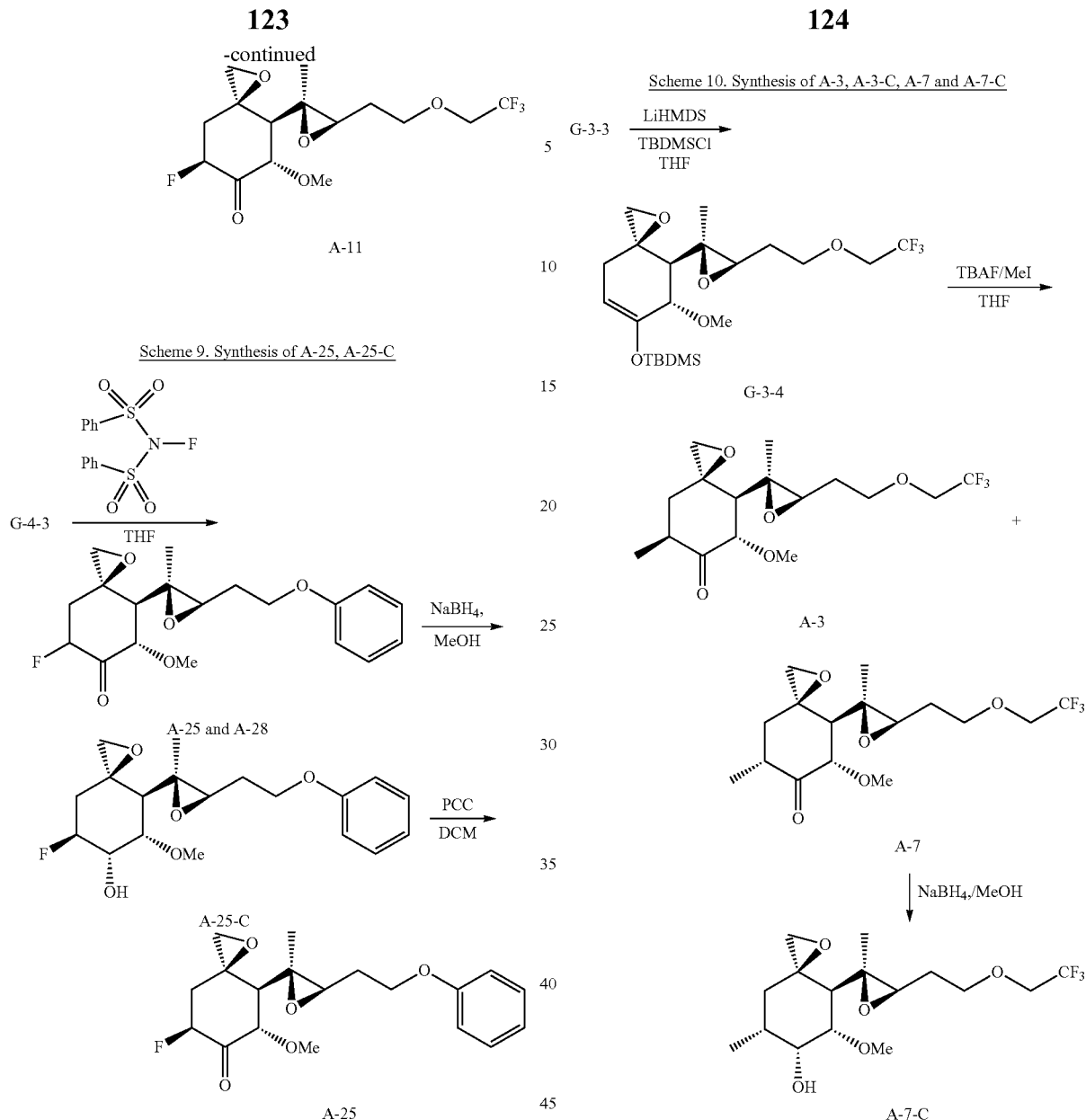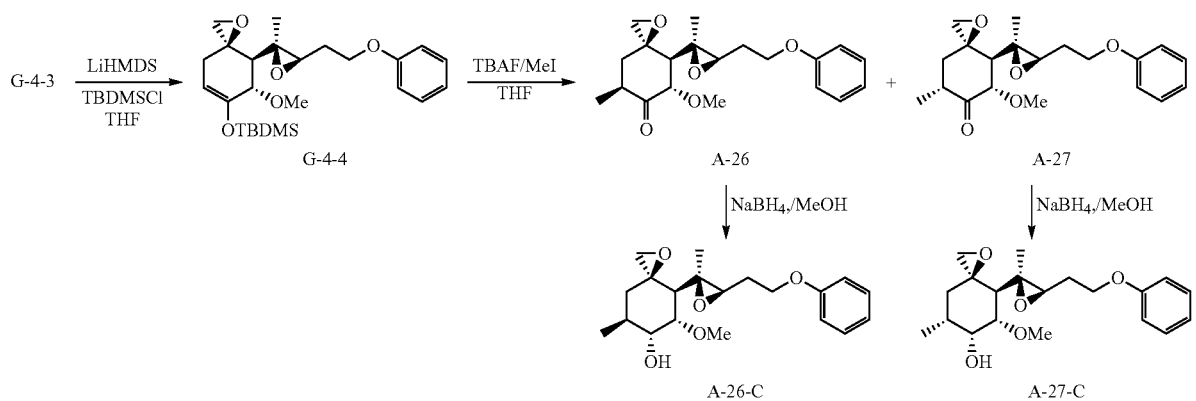

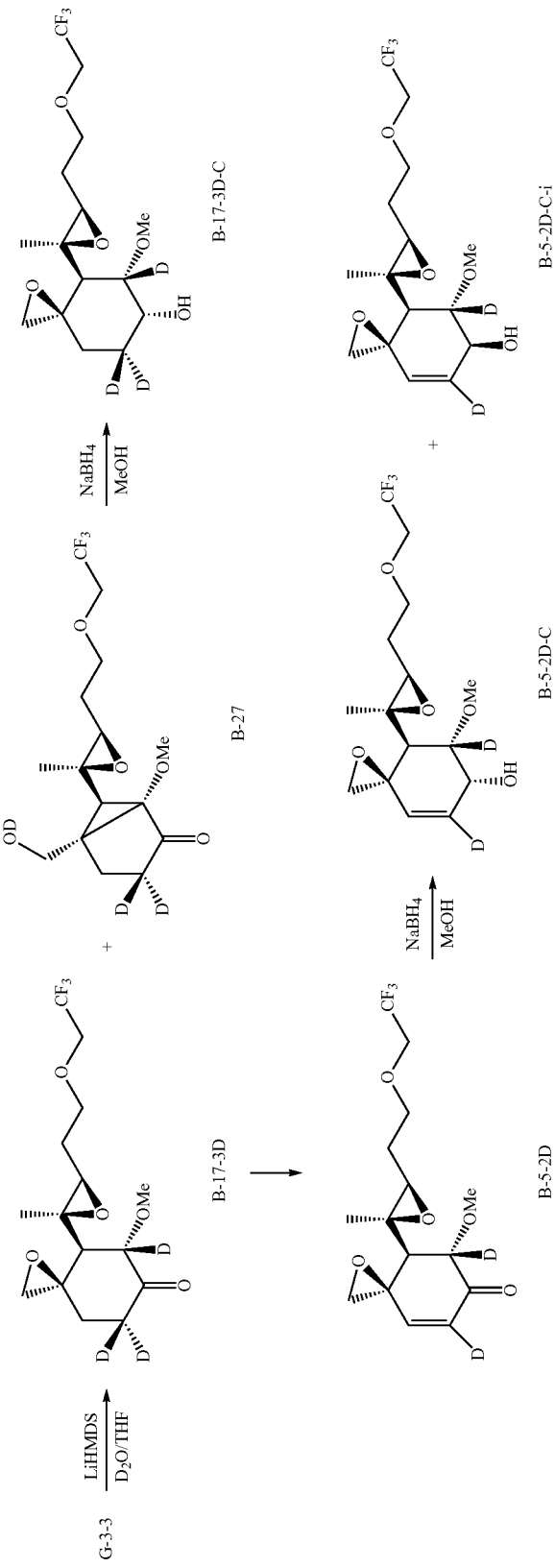

Scheme 13. Synthesis of B-25-3D, B-28 and B-26-2D
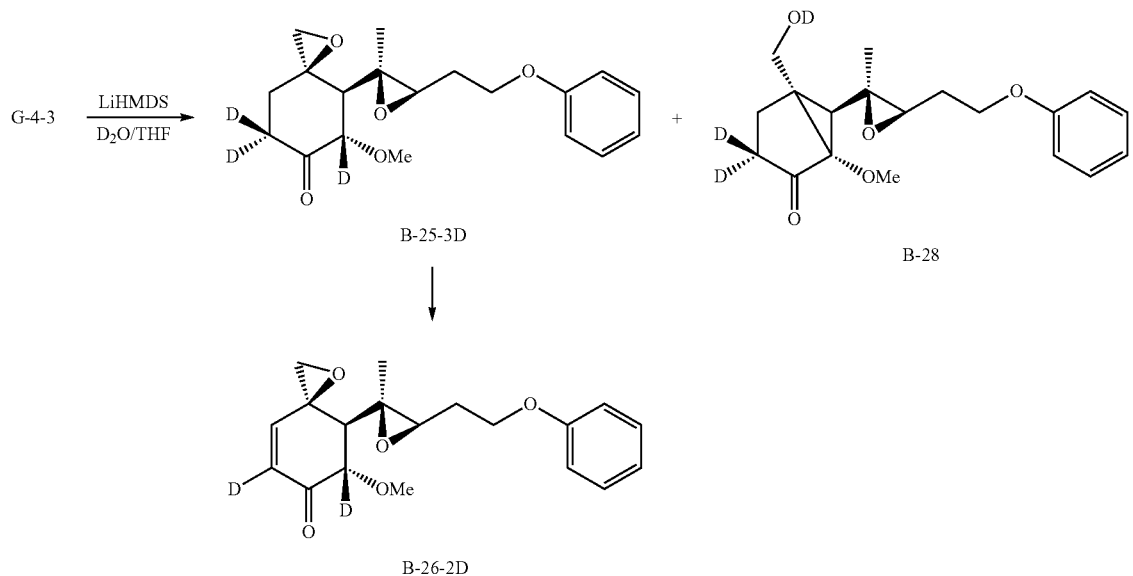
Scheme 14. Synthesis of Fumagillol-D6
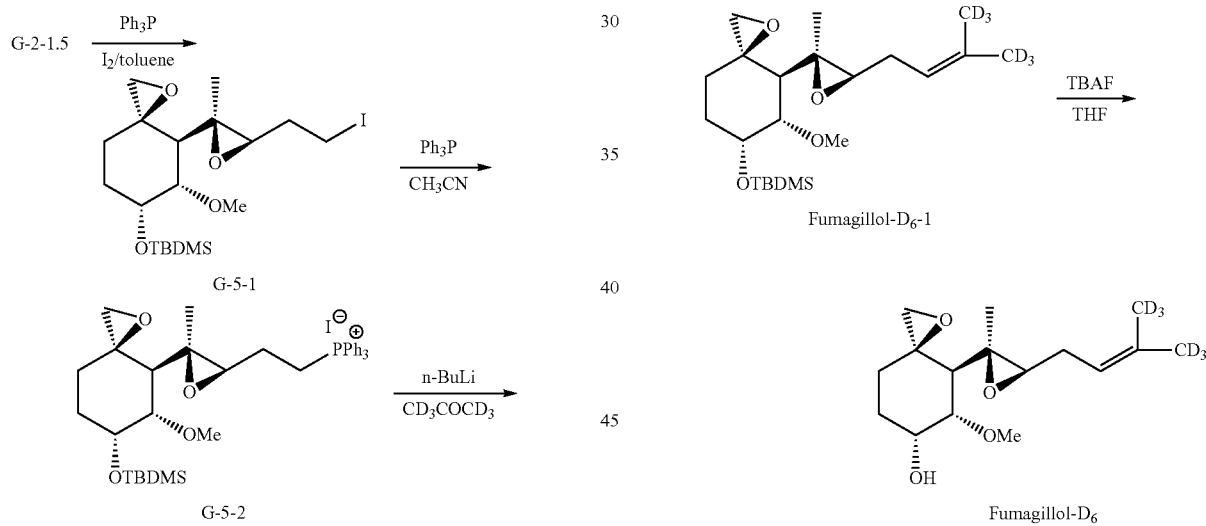
Scheme 15. Synthesis of G-5-3-E, G-5-3-Z and G-5-4-E
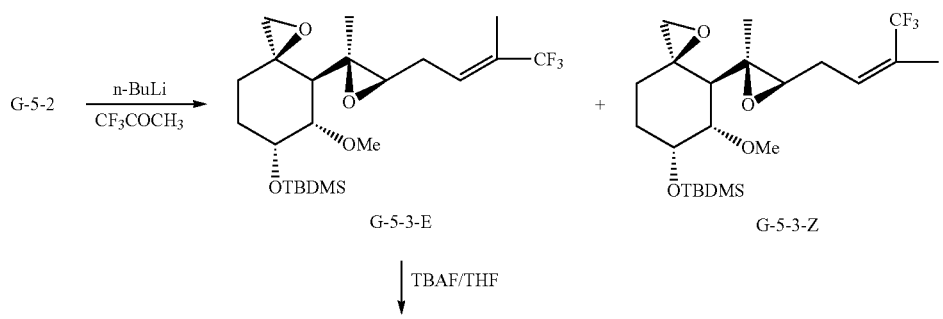

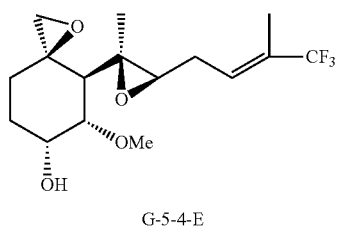
G-5-4-E
Scheme 16. Synthesis of G-2-4
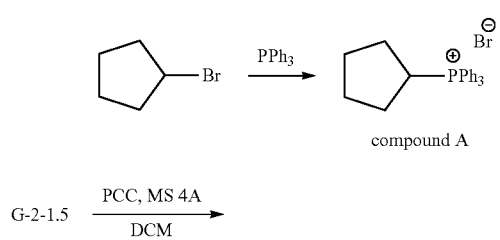
compound A
G-2-1.5 —PCC, MS 4A/DCM→
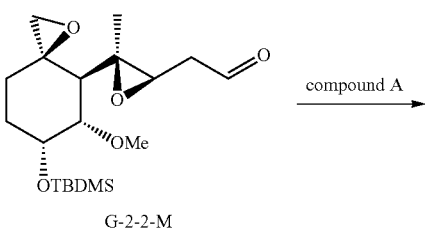
G-2-2-M
—compound A→
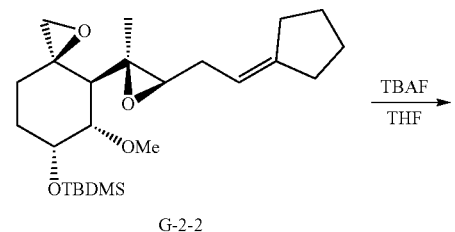
G-2-2
—TBAF/THF→
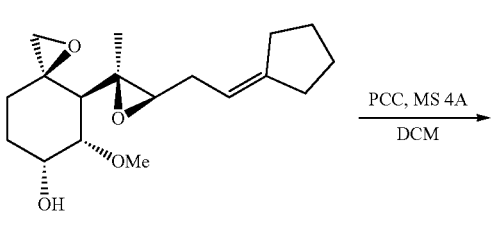
G-2-3
—PCC, MS 4A/DCM→
G-2-4
Scheme 17. Synthesis of A-12 and A-12-C
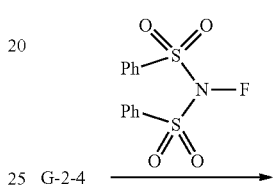
G-2-4 →
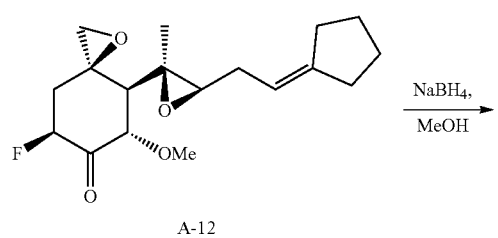
A-12
—NaBH₄, MeOH→
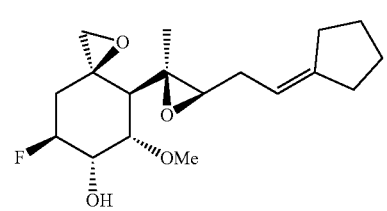
A-12-C
Scheme 18. Synthesis of B-18-3D
G-2-4 —LiHMDS, THF/D₂O→
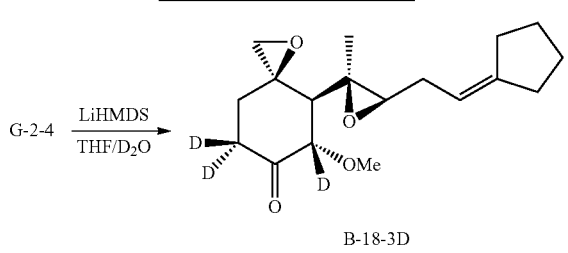
B-18-3D

Scheme 19. Synthesis of A-13-i, A-Two-OMe and A-29

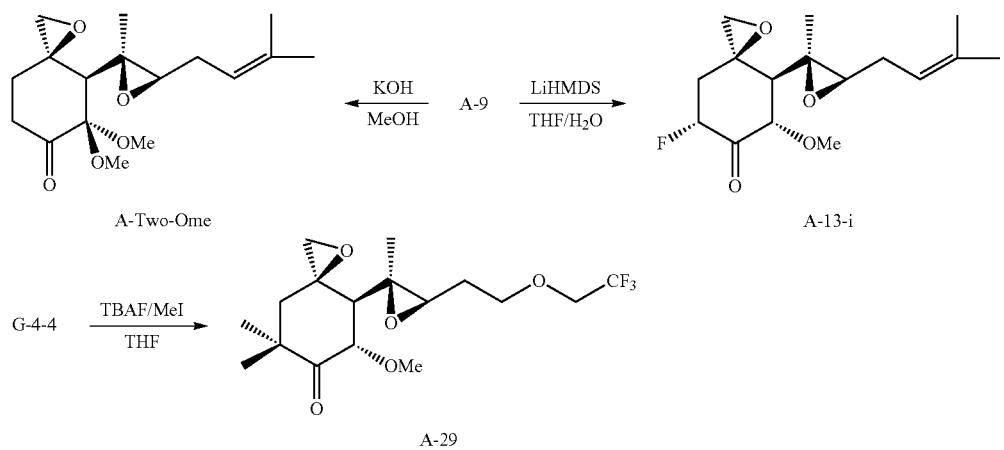

Scheme 20. G-3-2B and G-3-1B

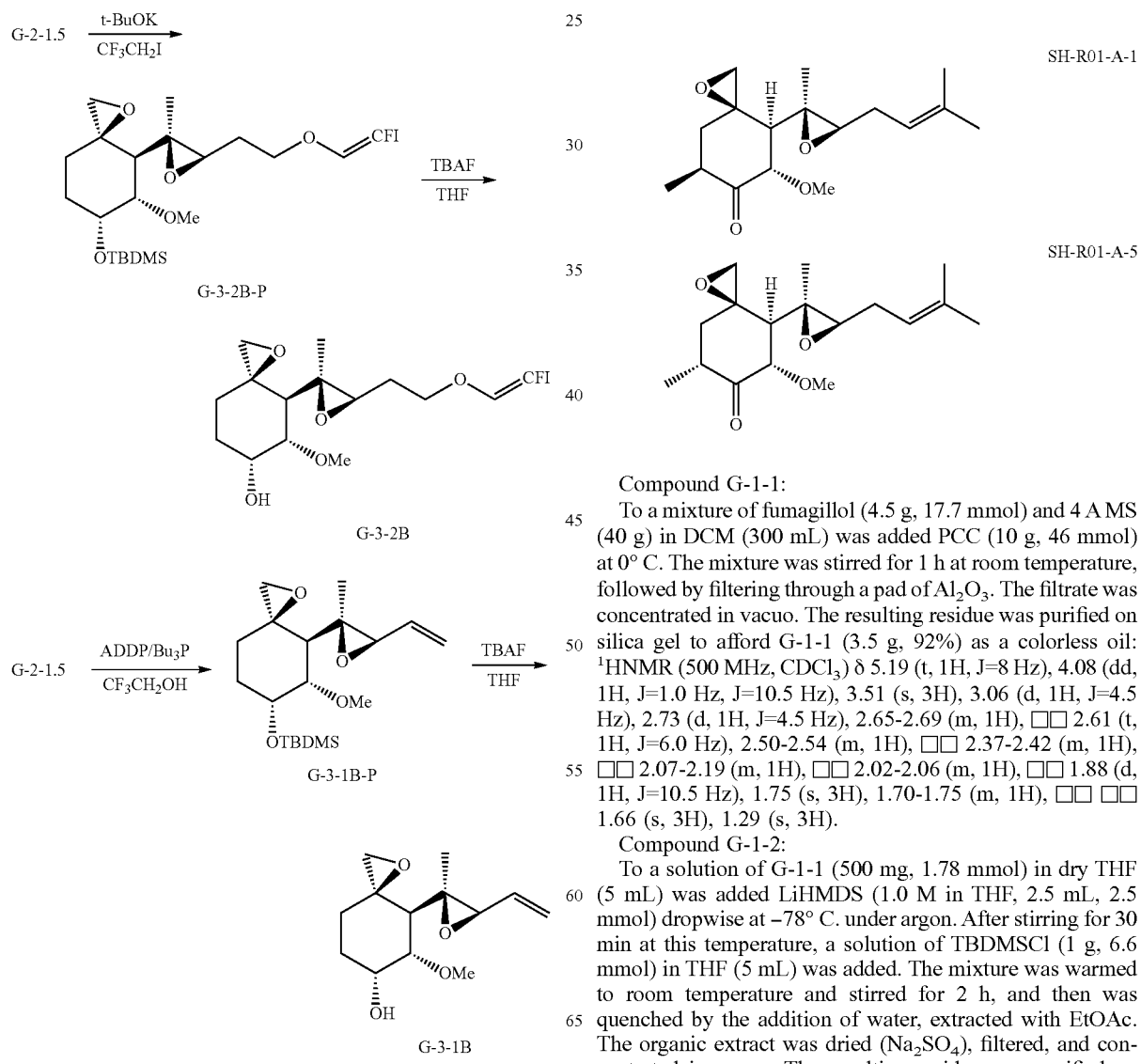

Example 73

Compound G-1-1:

To a mixture of fumagillol (4.5 g, 17.7 mmol) and 4 A MS (40 g) in DCM (300 mL) was added PCC (10 g, 46 mmol) at 0° C. The mixture was stirred for 1 h at room temperature, followed by filtering through a pad of $Al_2O_3$. The filtrate was concentrated in vacuo. The resulting residue was purified on silica gel to afford G-1-1 (3.5 g, 92%) as a colorless oil: $^1$HNMR (500 MHz, $CDCl_3$) δ 5.19 (t, 1H, J=8 Hz), 4.08 (dd, 1H, J=1.0 Hz, J=10.5 Hz), 3.51 (s, 3H), 3.06 (d, 1H, J=4.5 Hz), 2.73 (d, 1H, J=4.5 Hz), 2.65-2.69 (m, 1H), □□ 2.61 (t, 1H, J=6.0 Hz), 2.50-2.54 (m, 1H), □□ 2.37-2.42 (m, 1H), □□ 2.07-2.19 (m, 1H), □□ 2.02-2.06 (m, 1H), □□ 1.88 (d, 1H, J=10.5 Hz), 1.75 (s, 3H), 1.70-1.75 (m, 1H), □□ □□ 1.66 (s, 3H), 1.29 (s, 3H).

Compound G-1-2:

To a solution of G-1-1 (500 mg, 1.78 mmol) in dry THF (5 mL) was added LiHMDS (1.0 M in THF, 2.5 mL, 2.5 mmol) dropwise at −78° C. under argon. After stirring for 30 min at this temperature, a solution of TBDMSCl (1 g, 6.6 mmol) in THF (5 mL) was added. The mixture was warmed to room temperature and stirred for 2 h, and then was quenched by the addition of water, extracted with EtOAc. The organic extract was dried ($Na_2SO_4$), filtered, and concentrated in vacuo. The resulting residue was purified on silica gel to afford G-1-2 (350 mg, 50%) as a colorless oil: $^1$HNMR (500 MHz, CDCl$_3$) δ 5.20 (t, 1H, J=1.0 Hz), 4.90 (t, 1H, J=3.5 Hz), 3.81 (d, 1H, J=3.5 Hz), 3.37 (s, 3H), 2.81 (t, 1H, J=6.5 Hz), 2.69 (d, 1H, J=4.5 Hz), 2.61 (d, 1H, J=5.5 Hz), 2.40 (dd, 1H, J=3.5 Hz, J=17.5 Hz), 2.02-2.06 (m, 2H), 1 OD 2.04 (dd, 1H, J=4.5 Hz, J=17.5 Hz), 1.72 (s, 3H), 1.63 (s, 3H), 1.40 (d, 1H, J=3.0 Hz), 1.32 (s, 3H), 0.93 (s, 9H), 0.17 (s, 3H), 0.16 (s, 3H).

Compound A-1 and A-5:

The mixture of TBAF (1.0 M in THF, 0.3 mL, 0.3 mmol) and 4 A MS (200 mg) in dry THF (2 mL) was stirred overnight at room temperature under argon. The suspension was cooled to 0° C., and a solution of G-1-2 (100 mg, 0.25 mmol) and CH$_3$I (36 mg, 0.25 mmol) was added. The mixture was warmed up to r.t. and stirred for 1 h. The mixture was then filtered and diluted with H$_2$O and EtOAc, and extracted with EtOAc. The organic extract was washed with brine, dried (Na$_2$SO$_4$), filtered, and concentrated in vacuo. The crude residue was purified twice on silica gel to afford A-1 (10 mg, 9.5%) as a yellow oil and A-5 (9 mg, 8.6%) as a yellow oil.

For A-1:
$^1$HNMR (500 MHz, CDCl$_3$) δ 5.11-5.14 (m, 1H), 4.14 (dd, 1H, J=1.0 Hz, J=12.0 Hz), 3.47 (s, 3H), 3.04 (d, 1H, J=4.0 Hz), 2.74-2.80 (m, 1H), □□ 2.65 (d, 1H, J=4.5 Hz), 2.47 (dd, 1H, J=6.0 Hz, J=7.0 Hz), 2.31-2.36 (m, 1H), 2.05-2.11 (m, 1H), 1.77-1.83 (m, 2H), 1.68 (s, 3H), 1.60 (s, 3H), 1.46-1.50 (m, 1H), 1.19 (s, 3H), 1.00 (d, 6H, J=7.0 Hz); $^{13}$CNMR (500 MHz, CDCl$_3$) δ 12.4, 17.0, 24.7, 26.4, 39.5, 41.7, 50.0, 53.2, 57.2, 57.3, 57.8, 59.7, 82.4, 117.3, 134.1, 207.5.

For A-5:
$^1$HNMR (500 MHz, CDCl$_3$) δ 5.06-5.09 (m, 1H), 3.60 (d, 1H, J=4.5 Hz), 3.23 (s, 3H), 2.73-2.77 (m, 3H), □□ 2.65 (d, 1H, J=5.0 Hz), 2.25-2.30 (m, 1H), 2.15-2.20 (m, 1H), 2.04-2.10 (m, 1H), 1.84 (dd, 1H, J=2.0 Hz, J=4.5 Hz), 1.66 (s, 3H), 1.55-1.59 (m, 4H), 1.31 (s, 3H), 1.07 (d, 6H, J=7.0 Hz).

Example 74

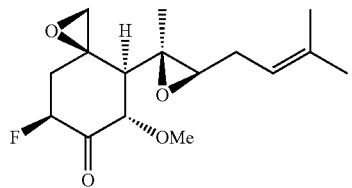

SH-R01-A-9

Compound A-9:

To a solution of G-1-1 (100 mg, 0.36 mmol) in dry THF (2 mL) was added LiHMDS (1.0 M in THF, 0.5 mL, 0.5 mmol) at −78° C. under argon. After stirring for 10 min, the solution was warmed to room temperature and stirred for 0.5 h, followed by addition of the solution of NFSi (147 mg, 0.47 mmol) in dry THF (2 mL) at −78° C. Stirring was continued for 2 h at room temperature. The mixture was diluted with H$_2$O and EtOAc, and extracted with EtOAc. The organic extract was washed with brine, dried (Na$_2$SO$_4$), filtered, and concentrated in vacuo. The resulting crude residue was purified twice on silica gel to afford A-9 (48 mg, 44.7%) as a yellow oil: $^1$HNMR (500 MHz, CDCl$_3$) δ 5.10-5.13 (m, 2H), 4.16 (d, 1H, J=12.5 Hz), 3.50 (s, 3H), 3.07 (dd, 1H, J=0.5 Hz, J=4.0 Hz), 2.69 (d, 1H, J=4.0 Hz), 2.49 (dd, 1H, J=6.0 Hz, J=7.5 Hz), 2.23-2.37 (m, 2H), □□ 2.05-2.10 (m, 1H), 1.83-1.98 (m, 1H), □□ 1.82 (d, 1H, J=12.5 Hz), 1.69 (s, 3H), 1.59 (s, 3H), 1.17 (s, 3H).

Example 75

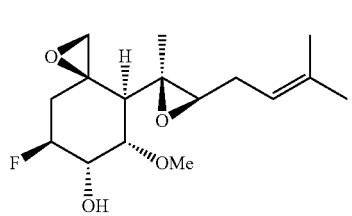

SH-R01-A-9-C

Compound A-9-C:

To a solution of A-9 (60 mg, 0.20 mmol) in MeOH (3 mL) was added NaBH$_4$ (50 mg, 1.4 mmol) at 0° C., then warmed to room temperature, and stirred for 0.5 h. The mixture was condensed under reduced pressure to give crude A-9-C, which was column chromatographed on silica gel to give A-9-C (31 mg, 52%) as a colorless oil: $^1$HNMR (500 MHz, CDCl$_3$) δ 5.12 (t, 1H, J=7.0 Hz), 4.63-4.77 (m, 1H), 4.56 (d, 1H, J=10.5 Hz), 3.54 (dd, 1H, J=1.5 Hz, J=11.0 Hz), 3.43 (s, 3H), 2.88 (d, 1H, J=4.5 Hz), 2.44-2.53 (m, 3H), 2.29-2.34 (m, 1H), 2.05-2.10 (m, 1H), □□ 1.89 (d, 1H, J=11.0 Hz), 1.68 (s, 3H), 1.59 (s, 3H), 1.37-1.41 (m, 1H), 1.13 (s, 3H).

Example 76

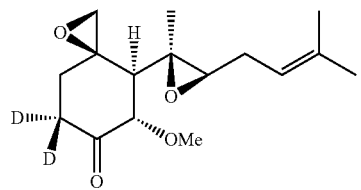

SH-R01-B-13

Compound B-13:

To a solution of G-1-1 (100 mg, 0.36 mmol) in dry THF (3 mL) was added LiHMDS (1.0 M in THF, 0.5 mL, 0.5 mmol) dropwise at −78° C. under argon. After stirring for 30 min at this temperature, the mixture was warmed to room temperature and stirred for 2 h, and then quenched with D$_2$O. The mixture was kept stirring for 2 h at room temperature. The mixture was diluted with EtOAc and extracted with EtOAc. The organic extract was, dried (Na$_2$SO$_4$), filtered, and concentrated in vacuo. The resulting crude residue was purified on silica gel to afford B-13 (48 mg, 48%) as a yellow oil: $^1$HNMR (500 MHz, CDCl$_3$) δ 5.19 (t, 1H, J=8.0 Hz), 4.08 (dd, 1H, J=1.0 Hz, J=10.5 Hz), 3.51 (s, 3H), 3.06 (d, 1H, J=4.5 Hz), 2.73 (d, 1H, J=4.5 Hz), 2.61 (t, 1H, J=6.0 Hz), 2.37-2.42 (m, 1H), □□ 2.07-2.19 (m, 1H), □□ 2.05 (d, 1H, J=13.5 Hz), □□ 1.88 (d, 1H, J=10.5 Hz), 1.75 (s, 3H), 1.70-1.75 (m, 1H), □□ □□ 1.66 (s, 3H), 1.29 (s, 3H).

Example 77

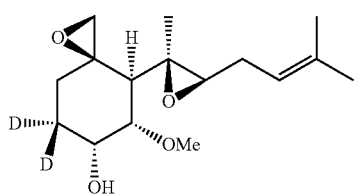

SH-R01-B-13-C

Compound B-13-C:

To a solution of B-13 (40 mg, 0.14 mmol) in MeOH (1 mL) was added NaBH$_4$ (32 mg, 0.85 mmol) at 0° C., then warmed to room temperature and stirred for 0.5 h. The mixture was evaporated under reduced pressure to give crude B-13-C, which was purified through silica gel chromatography to give B-13-C (13 mg, 32%) as a colorless oil: $^1$HNMR (500 MHz, CDCl$_3$) δ 5.21 (t, 1H, J=6.5 Hz), 4.37 (t, 1H, J=2.5 Hz), 3.62 (dd, 1H, J=3.0 Hz, J=11.0 Hz), 3.49 (s, 3H), 2.94 (d, 1H, J=4.5 Hz), 2.57 (t, 1H, J=7.0 Hz), ☐☐ 2.54 (d, 1H, J=4.0 Hz), 2.35-2.39 (m, 2H), ☐☐ 2.17-2.21 (m, 2H), ☐☐ 1.93 (d, 1H, J=11.0 Hz), 1.74 (s, 3H), 1.66 (s, 3H), 1.22 (s, 3H), 0.97-0.99 (m, 1H).

Example 78

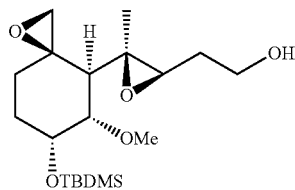

SH-R01-G-2-1.5

Compound G-2-1.5:

A solution of G-2-1 (2 g, 5.0 mmol) in dichloromethane (15 mL) was cooled to −78° C. using a dry ice/acetone bath. The cooled solution was bubbled with ozone gas for 45 min until a blue color persisted. The reaction was then bubbled with O$_2$ for 5 min. The solution was then treated with NaBH$_4$ (1.9 g, 50 mmol) at −78° C., and then gradually increased to −20° C. over a 1 h period. Additional NaBH$_4$ (1.9 g, 50 mmol) was added. The reaction mixture was stirred for another 1 h, and then filtered. The filtrate was evaporated under reduced pressure to give crude G-2-1.5, which was column chromatographed on silica gel to give G-2-1.5 (1.45 g, 80%) as a white solid: $^1$HNMR (500 MHz, CDCl$_3$) δ 4.35 (t, 1H, J=2.0 Hz), 3.84-3.90 (m, 2H), 3.45 (dd, 1H, J=2.0 Hz, J=10.5 Hz), 3.42 (s, 3H), 2.89 (d, 1H, J=4.0 Hz), 2.74-2.76 (m, 1H), ☐☐ 2.57 (d, 1H, J=4.5 Hz), 2.17-2.21 (m, 1H), ☐☐ 2.06 (d, 1H, J=4.0 Hz), 1.68-1.93 (m, 5H), ☐☐ 1.20 (s, 3H), 0.99-1.02 (m, 1H), 0.91 (s, 9H), 0.11 (s, 3H), 0.08 (s, 3H). MS (ESI) m/z 373 [M+H]$^+$.

Example 79

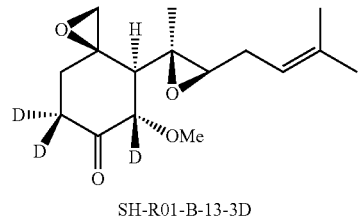

SH-R01-B-13-3D

B-13-3D and B-13-3D-i:

To a solution of G-1-1 (100 mg, 0.36 mmol) in dry THF (3 mL) was added LiHMDS (1.0 M in THF, 0.5 mL, 0.5 mmol) dropwise at −78° C. under argon. After stirring for 30 min at this temperature, the mixture was warmed to room temperature and stirred for 2 h, and then was quenched with D$_2$O. The mixture was stirred overnight at room temperature. The mixture was diluted with EtOAc and extracted with EtOAc. The organic extract was washed dried (Na$_2$SO$_4$), filtered, and concentrated in vacuo. The resulting crude residue was purified on silica gel to afford B-13-3D (30 mg, 30%) as a yellow oil and B-13-3D-i (30 mg, 30%) as a yellow oil.

For B-13-3D:

$^1$HNMR (500 MHz, CDCl$_3$) δ 5.12 (t, 1H, J=8.0 Hz), 3.43 (s, 3H), 2.99 (d, 1H, J=4.0 Hz), 2.67 (d, 1H, J=4.0 Hz), 2.54 (t, 1H, J=7.0 Hz), 2.30-2.39 (m, 1H), ☐☐ 2.05-2.15 (m, 1H), ☐☐ 1.98 (d, 1H, J=14.0 Hz), ☐☐ 1.80 (s, 1H), 1.67 (s, 3H), 1.64 (d, 1H, J=13.5 Hz), ☐☐ ☐☐ 1.59 (s, 3H), 1.22 (s, 3H).

Example 80

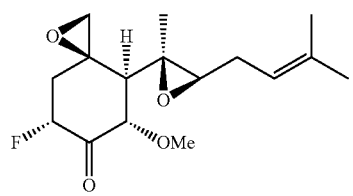

SH-R01-A-13-i

Compound A-13-i:

To a solution of A-9 (50 mg, 0.17 mmol) in dry THF (2 mL) was added LiHMDS (1.0 M in THF, 0.25 mL, 0.25 mmol) dropwise at −78° C. under argon. After stirring for 30 min at this temperature, the mixture was warmed to room temperature and stirred for 2 h, and then was quenched with H$_2$O. The mixture was stirred overnight at room temperature. The mixture was dried (Na$_2$SO$_4$), filtered, and concentrated in vacuo. The resulting crude residue was purified on silica gel to afford A-9 (23 mg, 46%) as a yellow oil and A-13-i (20 mg, 40%) as a colorless oil: $^1$HNMR (500 MHz, CDCl$_3$) δ 5.17-5.23 (m, 0.5H), 5.07-5.11 (m, 1.5H), 3.89 (t, 1H, J=5.5 Hz), 3.30 (s, 3H), 2.77 (dd, 1H, J=1.0 Hz, J=4.5 Hz), 2.72 (t, 1H, J=6.5 Hz), 2.66 (d, 1H, J=4.5 Hz), 2.57-2.63 (m, 1H), 2.26-2.29 (m, 1H), ☐☐ 1.97-2.10 (m, 2H), 1.85 (d, 1H, J=5.0 Hz), 1.66 (s, 3H), 1.54 (s, 3H), 1.33 (s, 3H).

Example 81

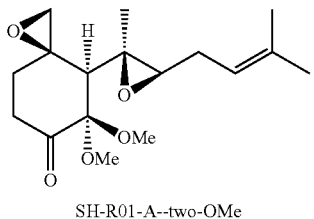

SH-R01-A--two-OMe

Compound A-Two-OMe:

To a solution of A-9 (50 mg, 0.17 mmol) in MeOH (5.5 mL) was added KOH (2N in H₂O, 0.25 mL, 1.82 mmol) dropwise at room temperature. After stirring for 8 h at this temperature, the mixture was diluted with H₂O and EtOAc, and extracted with EtOAc. The organic extract was washed with brine, dried (Na₂SO₄), filtered, and concentrated in vacuo. The resulting crude residue was purified on silica gel to afford A-Two-OMe (17 mg, 32%) as a yellow oil: $^1$HNMR (500 MHz, CDCl₃) δ 5.11 (t, 1H, J=5.0 Hz), 3.25 (s, 3H), 3.18 (t, 1H, J=6.5 Hz), 3.02 (s, 3H), 2.72 (dd, 1H, J=1.5 Hz, J=5.0 Hz), 2.68 (d, 1H, J=5.0 Hz), 2.53-2.67 (m, 2H), 2.43-2.49 (m, 1H), ☐☐ 2.22-2.28 (m, 1H), 2.05-2.13 (m, 1H), 1.83 (d, 1H, J=1.5 Hz), 1.65 (s, 3H), 1.57 (s, 3H), 1.41-1.45 (m, 1H), 1.32 (s, 3H); $^{13}$CNMR (500 MHz, CDCl₃) δ 16.3, 17.0, 24.7, 26.2, 29.1, 35.0, 47.8, 48.3, 54.1, 55.3, 57.1, 58.2, 58.8, 98.8, 117.5, 133.3, 202.6.

Example 82

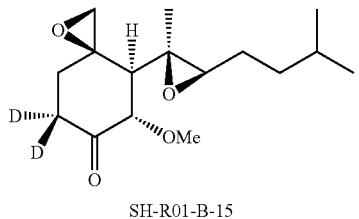

SH-R01-B-15

Compound B-15:

B-13 (40 mg, 0.14 mmol) in DMF (1 mL) was hydrogenated under atmospheric hydrogen with 10% Pd/C (5 mg) at ambient temperature for 2 h. The reaction mixture was filtered and concentrated; the residue was column chromatographed on silica gel to give B-15 (40 mg, 99%) as a yellow oil: $^1$HNMR (500 MHz, CDCl₃) δ 4.00 (d, 1H, J=13.0 Hz), 3.43 (s, 3H), 2.91 (d, 1H, J=5.5 Hz), 2.71 (d, 1H, J=5.5 Hz), 2.52 (t, 1H, J=3.0 Hz), ☐☐ 1.93-1.99 (m, 1H), ☐☐ 1.80-1.82 (m, 1H), ☐☐ 1.62-1.70 (m, 1H), ☐☐ 1.55 (s, 3H), 1.19-1.55 (m, 5H), ☐☐ 1.19 (s, 3H), 0.84 (d, 6H, J=8.0 Hz).

Example 83

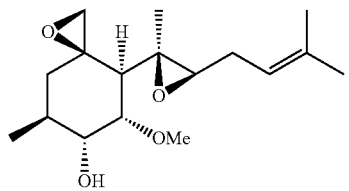

SH-R01-A-1-C

Compound A-1-C:

To a solution of A-1 (70 mg, 0.23 mmol) in MeOH (3 mL) was added NaBH₄ (55 mg, 1.4 mmol) at 0° C. The solution was then warmed to room temperature and stirred for 0.5 h. The mixture was concentrated under reduced pressure to give crude A-1-C, which was purified through a silica gel column chromatography to give A-1-C (50 mg, 71%) as a yellow solid: $^1$HNMR (500 MHz, CDCl₃) δ 5.11-5.16 (m, 1H), 4.09 (s, 1H), 3.52-3.57 (m, 2H), 3.43 (s, 3H), 2.88 (d, 1H, J=5.0 Hz), 2.49 (d, 1H, J=8.0 Hz), 2.45 (d, 1H, J=5.0 Hz), 2.26-2.33 (m, 1H), ☐☐ 2.16 (s, 1H), 2.06-2.13 (m, 1H), 1.94 (d, 1H, J=16.5 Hz), 1.81 (d, 1H, J=14.0 Hz), 1.67 (s, 3H), 1.59 (s, 3H), 1.18 (s, 1H), 1.15 (s, 3H), 1.01 (d, 3H, J=8.0 Hz).

Example 84

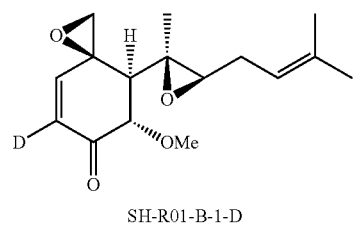

SH-R01-B-1-D

Compound B-1-D:

To a solution of B-13 (110 mg, 0.39 mmol) in dry THF (3 mL) was added LiHMDS (1.0 M in THF, 0.6 mL, 0.6 mmol) dropwise at −78° C. under argon. After stirring for 10 min, the solution was warmed to room temperature and stirred for 1 h, followed by addition of the solution of N-tert-butyl-benzene-sulfinimidoylchloride (252 mg, 1.17 mmol) in dry THF (2 mL) at −78° C. Stirring was continued for 2 h at room temperature. The mixture was diluted with H₂O and EtOAc, and extracted with EtOAc. The organic extract was washed with brine, dried (Na₂SO₄), filtered, and concentrated in vacuo. The resulting crude residue was purified on silica gel, followed by Prep-TLC twice to afford B-1-D (18 mg, 16%) as a colorless oil: $^1$HNMR (500 MHz, CDCl₃) δ 6.23 (s, 1H), 5.12 (t, 1H, J=7.5 Hz), 3.81 (d, 1H, J=4.5 Hz), ☐☐ 3.36 (s, 3H), 3.03 (d, 1H, J=5.0 Hz), ☐☐ 2.87 (d, 1H, J=5.0 Hz), ☐☐ 2.62 (t, 1H, J=6.5 Hz), 2.23-2.28 (m, 1H), ☐☐ 2.10-2.15 (m, 1H), ☐☐ 1.90 (d, 1H, J=4.5 Hz), ☐☐ 1.67 (s, 3H), ☐☐ 1.57 (s, 3H), ☐☐ 1.20 (s, 3H).

Example 85

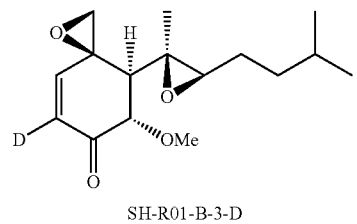

SH-R01-B-3-D

Compound B-3-D:

To a solution of B-15 (50 mg, 0.18 mmol) in dry THF (3 mL) was added LiHMDS (1.0 M in THF, 0.3 mL, 0.3 mmol) dropwise at −78° C. under argon. After stirring for 10 min, the solution was warmed to room temperature and stirred for 1 h, followed by addition of the solution of N-tert-butyl-benzenesulfinimidoylchloride (114 mg, 0.53 mmol) in dry THF (2 mL) at −78° C. Stirring was continued for 2 h at room temperature. The mixture was diluted with H$_2$O and EtOAc, and extracted with EtOAc. The organic extract was washed with brine, dried (Na$_2$SO$_4$), filtered, and concentrated in vacuo. The resulting crude residue was purified on silica gel, followed by Prep-TLC twice to afford B-3-D (9 mg, 16%) as a colorless oil: $^1$HNMR (500 MHz, CDCl$_3$) δ 6.23 (s, 1H), 3.78 (s, 1H), □□ 3.40 (s, 3H), 3.00 (d, 1H, J=5.0 Hz), □□ 2.89 (d, 1H, J=5.0 Hz), □□ 2.59 (t, 1H, J=8.0 Hz), 1.85 (s, 1H), □□ 1.40-1.48 (m, 3H), □□ 1.20-1.38 (m, 2H), □□ 1.15 (s, 3H), □□ 0.83 (dd, 6H, J=1.5 Hz, J=6.5 Hz).

Example 86

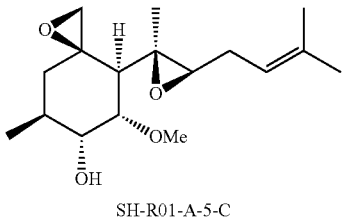

SH-R01-A-5-C

Compound A-5-C:

To a solution of A-5 (70 mg, 0.23 mmol) in MeOH (3 mL) was added NaBH$_4$ (55 mg, 1.4 mmol) at 0° C., The solution was then warmed to room temperature and stirred for 0.5 h. The mixture was concentrated under reduced pressure to give crude A-5-C, which was purified through a silica gel chromatography to give A-5-C (40 mg, 57%) as a yellow solid: $^1$HNMR (500 MHz, CDCl$_3$) δ 5.20-5.21 (m, 1H), 3.93 (s, 1H), 3.67-3.69 (m, 1H), 3.50-3.52 (m, 1H), 3.45 (s, 3H), 2.66-2.74 (m, 1H), 2.57-2.72 (m, 1H), 2.42-2.43 (m, 1H), □□ 2.33-2.36 (m, 1H), 2.14-2.22 (m, 2H), 2.00-2.03 (m, 1H), 1.89-1.91 (m, 1H), 1.74 (s, 3H), 1.65 (s, 3H), 1.31 (s, 3H), 1.21-1.26 (m, 1H), 1.10-1.12 (m, 3H).

Example 87

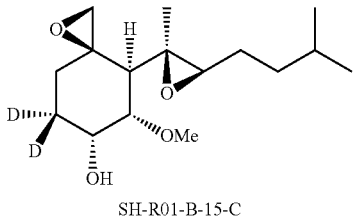

SH-R01-B-15-C

Compound B-15-C:

To a solution of B-15 (40 mg, 0.14 mmol) in MeOH (1 mL) was added NaBH$_4$ (32 mg, 0.85 mmol) at 0° C., followed by warming to room temperature, and stirred for 0.5 h. The mixture was evaporated under reduced pressure to give crude B-15-C, which was column chromatographed on silica gel to give B-15-C (13 mg, 32%) as a colorless oil: $^1$HNMR (500 MHz, CDCl$_3$) δ 4.29 (d, 1H, J=3.0 Hz), 3.55 (dd, 1H, J=3.0 Hz, J=11.0 Hz), 3.43 (s, 3H), 2.78 (d, 1H, J=4.0 Hz), 2.52 (d, 1H, J=4.5 Hz), □□ 2.48-2.51 (m, 1H), □□ 2.31 (s, 1H), 2.12 (d, 1H, J=19.0 Hz), □□ 1.86-1.88 (m, 1H), □□ 1.53-1.58 (m, 1H), □□ 1.32-1.38 (m, 3H), □□ 1.18-1.26 (m, 1H), □□ 1.12 (s, 3H), 0.92 (d, 1H, J=14.5 Hz), 0.84 (dd, 6H, J=1.5 Hz, J=6.5 Hz).

Example 88

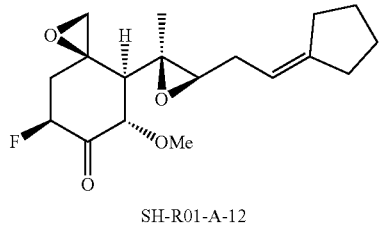

SH-R01-A-12

Compound A:

A mixture of PPh$_3$ (5 g, 33.6 mmol) and cyclopentyl bromide (8.8 g, 33.6 mmol) was heated for 24 h at 160-200° C., then cooled to room temperature. The solvent was removed and the residue was recrystalized from EtOAc and MeOH to obtain compound A (9 g, 65%) as a white solid: $^1$HNMR (500 MHz, DMSO) δ 7.88-7.92 (m, 9H), 7.75-7.79 (m, 6H), 4.50-4.60 (m, 1H), 2.28-2.39 (m, 2H), 1.62-1.64 (m, 4H), □□ 1.20-1.29 (m, 2H).

Compound G-2-2-M:

To a mixture of G-2-1.5 (782 mg, 2.1 mmol) and 4 A MS (2 g) in DCM (40 mL) was added PCC (743 mg, 3.4 mmol) at 0° C. After 10 min the reaction mixture was filtered through a pad of active carbon. The filtrate was concentrated in vacuo to afford G-2-2-M (800 mg) as a white solid. The crude compound was used to next step.

Compound G-2-2:

To a suspension mixture of A (1.2 g, 3.2 mmol) in dry THF (15 mL) was added dropwise a solution n-BuLi (2.5 M in hexane, 0.24 mL, 0.24 mmol) at −78° C. The reaction mixture was warmed gradually to 0° C., followed addition of a solution of crude G-2-2-M (800 mg) in dry THF, and warmed to room temperature. The mixture was stirred overnight at room temperature, diluted with H$_2$O and EtOAc, and extracted with EtOAc. The organic extract was washed with brine, dried (Na$_2$SO$_4$), filtered, and concentrated in vacuo. The resulting crude residue was purified on silica gel to afford G-2-2 (100 mg, 12%) as a white solid. $^1$HNMR (500 MHz, CDCl$_3$) δ 5.26 (t, 1H, J=8.0 Hz), 4.29 (s, 1H), □□ 3.37 (d, 1H, J=1.5 Hz), 3.34 (s, 3H), □□ 2.90 (d, 1H, J=4.5 Hz), 3.50 (t, 1H, J=6.0 Hz), 2.44 (d, 1H, J=4.0 Hz), 2.06-2.24 (m, 6H), □□ 1.96 (d, 1H, J=10.5 Hz), 1.53-1.68 (m, 7H), 1.12 (s, 3H), 0.88-0.91 (m, 1H), 0.82 (s, 9H), 0.02 (d, 6H, J=16.5 Hz).

Compound G-2-3:

To a solution of G-2-2 (500 mg, 1.18 mmol) in dry THF (10 mL) was added dropwise a solution of TBAF (1.0 M in THF, 5 mL, 5 mmol) at 0° C. The mixture was stirred at room temperature overnight, then diluted with H$_2$O and EtOAc, and extracted with EtOAc. The organic extract was washed with brine, dried (Na$_2$SO$_4$), filtered, and concentrated in vacuo. The resulting crude G-2-3 (470 mg, 100%) was used to next step.

Compound G-2-4:

To a mixture of G-2-3 (470 mg) and 4 A MS (2 g) in DCM (30 mL) was added PCC (700 mg, 3.2 mmol) at 0° C. and stirred for 30 min. The reaction mixture was filtered through a pad of Al$_2$O$_3$. The filtrate was concentrated in vacuo. The resulting residue was purified on silica gel to afford G-2-4 (200 mg, 52% in two steps) as a colorless oil: $^1$HNMR (500 MHz, CDCl$_3$) δ 5.30 (t, 1H, J=7.0 Hz), 4.09 (d, 1H, J=10.5

Hz), ☐☐ 3.51 (s, 3H), ☐☐ 3.08 (d, 1H, J=5.0 Hz), 2.73 (d, 1H, J=4.0 Hz), 2.65-2.72 (m, 1H), ☐☐ 2.63 (t, 1H, J=6.5 Hz), 2.49-2.53 (m, 1H), 2.35-2.40 (m, 1H), 2.04-2.28 (m, 6H), 1.88 (d, 1H, J=10.5 Hz), 1.59-1.73 (m, 5H), 1.28 (s, 9H).

Compound A-12:

To a solution of G-2-4 (100 mg, 0.33 mmol) in dry THF (3 mL) was added LiHMDS (1.0 M in THF, 0.57 mL, 0.57 mmol) at −78° C. under argon. After stirring for 10 min, the solution was warmed to room temperature and stirred for additional 0.5 h, followed by addition of the solution of NFSi (180 mg, 0.57 mmol) in dry THF (2 mL) at −78° C. Stirring was continued for 2 h at room temperature. The mixture was diluted with $H_2O$ and EtOAc, and extracted with EtOAc. The organic extract was washed with brine, dried ($Na_2SO_4$), filtered, and concentrated in vacuo. The resulting crude residue was purified twice on silica gel to afford A-12 (35 mg, 33%) as a yellow oil: $^1$HNMR (500 MHz, $CDCl_3$) δ 5.21-5.24 (m, 1.5H), 5.11-5.13 (m, 0.5H), 4.16 (d, 1H, J=12.5 Hz), 3.51 (s, 3H), 3.09 (d, 1H, J=4.0 Hz), 2.70 (d, 1H, J=4.0 Hz), 2.52 (d, 1H, J=6.5 Hz), 2.30-2.36 (m, 1H), ☐☐ 2.27 (d, 1H, J=11.5 Hz), 2.03-2.23 (m, 5H), 1.93-1.98 (m, 1H), ☐☐ 1.82 (d, 1H, J=12.0 Hz), 1.51-1.65 (m, 4H), 1.18 (s, 3H).

Example 89

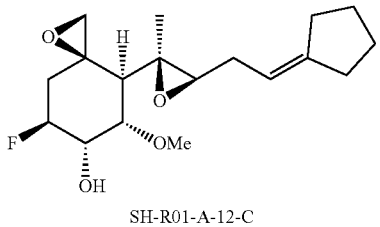

SH-R01-A-12-C

Compound A-12-C:

To a solution of A-12 (18 mg, 0.06 mmol) in MeOH (2 mL) was added $NaBH_4$ (12 mg, 0.34 mmol) at 0° C., then warmed to room temperature, and stirred for 0.5 h. The mixture was condensed under reduced pressure to give crude A-12-C, which was column chromatographied on silica gel to give A-12-C (14 mg, 78%) as a colorless oil: $^1$HNMR (500 MHz, $CDCl_3$) δ 5.24 (t, 1H, J=3.0 Hz), 4.61-4.63 (m, 0.5H), 4.76-4.75 (m, 0.5H), 4.56 (d, 1H, J=12.0 Hz), 3.53-3.57 (m, 1H), 3.44 (s, 3H), 2.91 (d, 1H, J=5.0 Hz), 2.55 (t, 1H, J=8.0 Hz), 2.46-2.52 (m, 2H), 2.36 (s, 1H), 2.28-2.36 (m, 1H), 2.05-2.21 (m, 5H), ☐☐ 1.89 (d, 1H, J=13.5 Hz), 1.54-1.64 (m, 1H), 1.54 (s, 3H), 1.37-1.41 (m, 1H), 1.13 (s, 3H).

Example 90

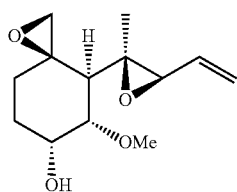

SH-R01-G-3-1B

Compound G-3-1B-P:

To a solution of G-2-1.5 (10 g, 26.9 mmol), $CF_3CH_2OH$ (26.8 g, 268.8 mmol) and n-$Bu_3P$ (10.9 g, 53.8 mmol) in dry THF (100 mL) was added dropwise a solution of ADDP (13.5 g, 53.8 mmol) in THF at 0° C. The mixture was stirred overnight at room temperature, and then filtered and concentrated in vacuo. The resulting crude residue was purified on silica gel to afford G-3-1 (6.9 g, 58%) as a white solid and G-3-1B-P (100 mg, 1%) as a white solid: $^1$HNMR (500 MHz, $CDCl_3$) δ 5.70-5.77 (m, 1H), 5.47 (d, 1H, J=17.0 Hz), 5.35 (d, 1H, J=10.5 Hz), 4.38 (t, 1H, J=2.0 Hz), 3.44 (dd, 1H, J=2.0 Hz, J=11.0 Hz), 3.42 (s, 3H), 3.03 (d, 1H, J=12.0 Hz), Q 2.86 (d, 1H, J=4.0 Hz), 2.57 (d, 1H, J=4.0 Hz), ☐☐ 2.20-2.18 (m, 1H), 2.12 (d, 1H, J=11.0 Hz), ☐☐ 1.70-1.80 (m, 2H), ☐☐ 1.17 (s, 3H), ☐☐ 0.95-0.98 (m, 1H), ☐☐ 0.89 (s, 9H), ☐☐ 0.09 (d, 6H, J=17.5 Hz).

Compound G-3-1B:

To a solution of G-3-1B-P (100 mg, 0.28 mmol) in dry THF (5 mL) was added dropwise a solution of TBAF (1.0 M in THF, 2 mL, 2 mmol) at 0° C. The mixture was stirred overnight at room temperature, diluted with $H_2O$ and EtOAc, and extracted with EtOAc. The organic extract was washed with brine, dried ($Na_2SO_4$), filtered, and concentrated in vacuo. The resulting crude residue was purified on silica gel to afford G-3-2B (45 mg, 67%) as a white solid: $^1$HNMR (500 MHz, $CDCl_3$) δ 5.71-5.75 (m, 1H), 5.50 (d, 1H, J=17.0 Hz), 5.40 (d, 1H, J=10.0 Hz), 4.39 (d, 1H, J=3.0 Hz), 3.63 (dd, 1H, J=3.0 Hz, J=11.0 Hz), 3.51 (s, 3H), 3.05 (d, 1H, J=7.5 Hz), ☐☐ 2.83 (d, 1H, J=3.5 Hz), 2.60 (d, 1H, J=4.5 Hz), ☐☐ 2.35 (s, 1H), 2.20-2.26 (m, 1H), ☐☐ 2.00-2.05 (m, 2H), ☐☐ 1.74-1.81 (m, 1H), ☐☐ 1.20 (s, 3H), ☐☐ 0.99-1.02 (m, 1H).

Example 91

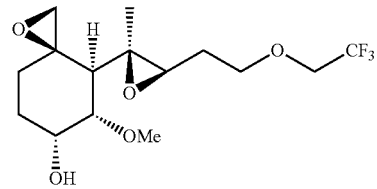

SH-R01-G-3-2

Compound G-3-1:

To a solution of G-2-1.5 (10 g, 26.9 mmol), $CF_3CH_2OH$ (26.8 g, 268.8 mmol) and n-$Bu_3P$ (10.9 g, 53.8 mmol) in dry THF (100 mL) was added dropwise a solution of ADDP (13.5 g, 53.8 mmol) in THF at 0° C. The mixture was stirred overnight at room temperature, and then filtered and concentrated in vacuo. The resulting crude residue was purified on silica gel to afford G-3-1 (6.9 g, 58%) as a white solid: $^1$HNMR (500 MHz, $CDCl_3$) δ 4.29 (t, 1H, J=2.0 Hz), 3.69-3.81 (m, 4H), ☐☐ 3.34-3.38 (m, 4H), 2.82 (d, 1H, J=4.0 Hz), ☐☐ 2.62 (t, 1H, J=4.5 Hz), 2.47 (d, 1H, J=4.5 Hz), ☐☐ 2.11-2.15 (m, 1H), 1.98 (d, 1H, J=11.0 Hz), ☐☐ 1.87-1.90 (m, 1H), ☐☐ 1.59-1.70 (m, 3H), ☐☐ 1.18 (s, 3H), ☐☐ 0.85-0.95 (m, 1H), ☐☐ 0.80 (s, 9H), ☐☐ 0.01 (d, 6H, J=10.0 Hz).

Compound G-3-2:

To a solution of G-3-1 (100 mg, 0.28 mmol) in dry THF (1 mL) was added dropwise a solution of TBAF (1.0 M in THF, 2 mL, 2 mmol) at 0° C. The mixture was stirred overnight at room temperature, then diluted with $H_2O$ and EtOAc, and extracted with EtOAc. The organic extract was washed with brine, dried (Na$_2$SO$_4$), filtered, and concentrated in vacuo. The resulting crude residue was purified on silica gel to afford G-3-2 (45 mg, 67%) as a colorless oil: $^1$HNMR (500 MHz, CDCl$_3$) δ 4.37-4.38 (m, 1H), 3.77-3.86 (m, 4H), ☐☐ 3.64 (dd, 1H, J=3.0 Hz, J=11.5 Hz), 3.50 (s, 3H), 2.89 (d, 1H, J=4.0 Hz), ☐☐ 2.74-2.76 (m, 1H), 2.58 (d, 1H, J=4.0 Hz), ☐☐ 2.32 (s, 1H), 2.18-2.22 (m, 1H), 1.95-2.05 (m, 3H), 1.68-1.82 (m, 2H), ☐☐ 1.20 (s, 3H), ☐☐ 0.95-1.05 (m, 1H).

Example 92

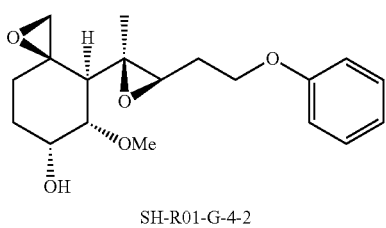

SH-R01-G-4-2

Compound G-4-1:

To a solution of G-2-1.5 (50 mg, 0.13 mmol), phenol (61 mg, 0.65 mmol) and Ph$_3$P (79 mg, 0.3 mmol) in dry THF (100 mL) was added dropwise a solution of DEAD (45 mg, 0.26 mmol) in THF at 0° C. The mixture was stirred for 3 h at room temperature, then diluted with H$_2$O and EtOAc, and extracted with EtOAc. The organic extract was washed with brine, dried (Na$_2$SO$_4$), filtered, and concentrated in vacuo. The resulting crude residue was purified on silica gel to afford G-4-1 (41 mg, 70%) as a white solid: $^1$HNMR (500 MHz, CDCl$_3$) δ 7.19-7.24 (m, 2H), ☐☐ 6.84-6.88 (m, 3H), ☐☐ 4.30 (s, 1H), 4.07-4.08 (m, 2H), ☐☐ 3.38 (dd, 1H, J=2.0 Hz, J=10.5 Hz), ☐☐ 3.35 (s, 3H), 2.92 (d, 1H, J=4.0 Hz), 0 D 2.71 (dd, 1H, J=4.5 Hz, J=7.0 Hz), ☐☐ 2.45 (d, 1H, J=4.5 Hz), 2.12-2.18 (m, 1H), ☐☐ 2.00-2.08 (m, 2H), ☐☐ 1.81-1.87 (m, 1H), ☐☐ 1.65-1.71 (m, 2H), ☐☐ 1.15 (s, 3H), ☐☐ 0.87-0.91 (m, 1H), ☐☐ 0.82 (s, 9H), ☐☐ 0.01 (d, 6H, J=10.0 Hz).

Compound G-4-2:

To a solution of G-4-1 (10 g, 22.3 mmol) in dry THF (100 mL) was added dropwise a solution of TBAF (1.0 M in THF, 200 mL, 200 mmol) at 0° C. The mixture was stirred at room temperature overnight, then diluted with H$_2$O and EtOAc, and extracted with EtOAc. The organic extract was washed with brine, dried (Na$_2$SO$_4$), filtered, and concentrated in vacuo. The resulting crude residue was purified on silica gel to afford G-4-2 (6.0 g, 80%) as a colorless oil: $^1$HNMR (500 MHz, CDCl$_3$) δ 7.29-7.31 (m, 2H), ☐☐ 6.90-6.98 (m, 3H), ☐☐ 4.38 (d, 1H, J=2.5 Hz), 4.12-4.16 (m, 2H), ☐☐ 3.64 (dd, 1H, J=2.5 Hz, J=11.0 Hz), 3.49 (s, 3H), 2.98 (d, 1H, J=4.0 Hz), ☐☐ 2.83 (dd, 1H, J=5.0 Hz, J=7.0 Hz), 2.52 (d, 1H, J=4.0 Hz), ☐☐ 2.45 (s, 1H), 2.18-2.24 (m, 1H), 2.10-2.13 (m, 1H), 1.91-2.04 (m, 3H), ☐☐ 1.76-1.77 (m, 1H), ☐☐ 1.24 (s, 3H), ☐☐ 0.97-0.99 (m, 1H).

Example 93

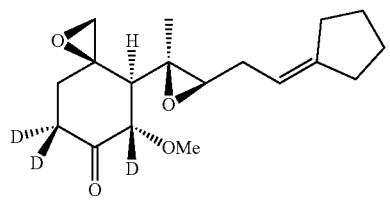

SH-R01-B-18-3D

Compound B-18-3D:

To a solution of G-2-4 (70 mg, 0.23 mmol) in dry THF (3 mL) was added LiHMDS (1.0 M in THF, 0.4 mL, 0.4 mmol) dropwise at −78° C. under argon. After stirring for 30 min at this temperature, the mixture was warmed to room temperature and stirred for 2 h, and then was quenched with D$_2$O. The mixture was stirred for 2 h at room temperature. The mixture was dried (Na$_2$SO$_4$), filtered, and concentrated in vacuo. The resulting crude residue was purified on silica gel to afford B-18-3D (35 mg, 50%) as a colorless oil: $^1$HNMR (500 MHz, CDCl$_3$) δ 5.31 (m, 1H), 3.51 (s, 3H), 3.08 (d, 1H, J=4.5 Hz), 2.74 (d, 1H, J=4.0 Hz), 2.63 (t, 1H, J=6.5 Hz), 2.36-2.74 (m, 1H), ☐☐ 2.13-2.28 (m, 5H), ☐☐ 2.05 (d, 1H, J=14.0 Hz), ☐☐ 1.88 (s, 1H), 1.60-1.71 (m, 4H), 1.29 (s, 3H).

Example 94

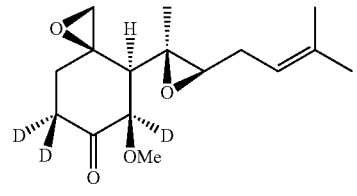

SH-R01-B-13-3D-i

B-13-3D and B-13-3D-i:

To a solution of G-1-1 (100 mg, 0.36 mmol) in dry THF (3 mL) was added LiHMDS (1.0 M in THF, 0.5 mL, 0.5 mmol) dropwise at −78° C. under argon. After stirring for 30 min at this temperature, the mixture was warmed to room temperature and stirred for 2 h, and then was quenched with D$_2$O. The mixture was stirred overnight at room temperature. The mixture was diluted with EtOAc and extracted with EtOAc. The organic extract was washed dried (Na$_2$SO$_4$), filtered, and concentrated in vacuo. The resulting crude residue was purified on silica gel to afford B-13-3D (30 mg, 30%) as a yellow oil and B-13-3D-i (30 mg, 30%) as a yellow oil.

For B-13-3D-i:

$^1$HNMR (500 MHz, CDCl$_3$) δ 5.14 (t, 1H, J=7.0 Hz), 3.41 (s, 3H), 3.17-3.20 (m, 1H), 2.76 (d, 1H, J=4.5 Hz), 2.69 (d, 1H, J=5.0 Hz), 2.45 (d, 1H, J=13.5 Hz), ☐☐ 2.30-2.33 (m, 1H), DD 2.11-2.14 (m, 1H), ☐☐ 1.99 (s, 1H), DD 1.72 (s, 3H), 1.63-1.66 (m, 4H), 1.41 (s, 3H).

Example 95

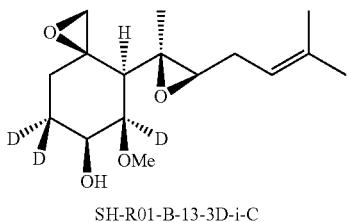

SH-R01-B-13-3D-i-C

Compound B-13-3D-i-C:

To a solution of B-13-3D-i (15 mg, 0.05 mmol) in MeOH (1 mL) was added NaBH$_4$ (12 mg, 0.32 mmol) at 0° C., followed by warming to room temperature, and stirred for 0.5 h. The mixture was evaporated under reduced pressure to give crude B-13-3D-i-C, which was column chromatographed on silica gel to give B-13-3D-i-C (15 mg, 99%) as a colorless oil: $^1$HNMR (500 MHz, CDCl$_3$) δ 5.18 (t, 1H, J=2.5 Hz), 3.63 (d, 1H, J=9.0 Hz), □□ 3.60 (s, 3H), 2.78 (t, 1H, J=6.5 Hz), 2.66 (d, 1H, J=5.0 Hz), □□ 2.42 (d, 1H, J=5.0 Hz), □□ 2.36-2.39 (m, 1H), □□ 2.27 (d, 1H, J=9.0 Hz), □□ 2.12-2.15 (m, 1H), □□ 1.86-1.88 (m, 1H), □□ 1.74 (s, 3H), □□ 1.72 (s, 1H), □□ 1.65 (s, 3H), □□ 1.58 (s, 3H), 1.38 (s, 3H), 1.36 (s, 1H).

Example 96

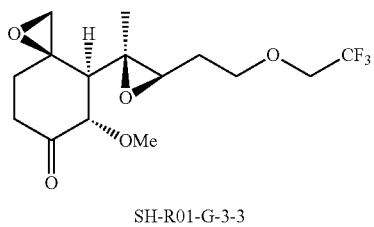

SH-R01-G-3-3

Compound G-3-3:

To a mixture of G-3-2 (6.5 g, 19.1 mmol) and 4 A MS (10 g) in DCM (100 mL) was added PCC (10.7 g, 50 mmol) at 0° C. The mixture was stirred for 1 h at room temperature, then filtered through a pad of Al$_2$O$_3$. The filtrate was concentrated in vacuo. The resulting crude residue was purified on silica gel to afford G-3-3 (5.2 g, 80%) as a white solid: $^1$HNMR (500 MHz, CDCl$_3$) δ 4.10-4.13 (m, 1H), 3.77-3.88 (m, 4H), □□ 3.52 (s, 3H), 3.05 (d, 1H, J=4.0 Hz), □□ 2.76-2.78 (m, 2H), 2.68-2.70 (m, 1H), 2.52-2.55 (m, 2H), 2.04-2.11 (m, 1H), 1.95-1.96 (m, 1H), 1.90 (d, 1H, J=10.5 Hz), 1.70-1.78 (m, 2H), □□ 1.26 (s, 3H).

Example 97

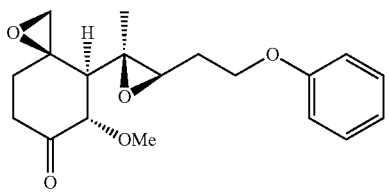

SH-R01-G-4-3

Compound G-4-3:

To a mixture of G-4-2 (6.0 g, 18 mmol) and 4 A MS (10 g) in DCM (100 mL) was added PCC (11.3 g, 53 mmol) at 0° C. The mixture was stirred for 1 h at room temperature, then filtered through a pad of Al$_2$O$_3$. The filtrate was concentrated in vacuo. The resulting crude residue was purified on silica gel to afford G-4-3 (4.0 g, 67%) as a white solid: $^1$HNMR (500 MHz, CDCl$_3$) δ 7.27-7.31 (m, 2H), □□ 6.91-6.98 (m, 3H), 4.12-4.16 (m, 3H), 3.77-3.88 (m, 4H), □□ 3.52 (s, 3H), 3.14 (d, 1H, J=4.0 Hz), Q 2.85 (t, 1H, J=6.5 Hz), 2.67-2.73 (m, 2H), 2.50-2.53 (m, 1H), 2.00-2.12 (m, 3H), 1.92 (d, 1H, J=11.0 Hz), 1.63-1.74 (m, 1H), □□ 1.32 (s, 3H). MS (ESI) m/z 333 [M+H]$^+$

Example 98

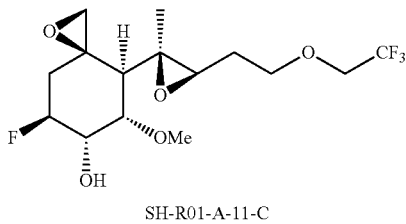

SH-R01-A-11-C

Compound A-11-C:

To a solution of A-11 and A-15 (50 mg, 0.14 mmol) in MeOH (2 mL) was added NaBH$_4$ (32 mg, 1.4 mmol) at 0° C., then warmed to room temperature, and stirred for 0.5 h. The mixture was condensed under reduced pressure to give crude A-11-C, which was column chromatographied on silica gel to give A-11-C (23 mg, 46%) as a colorless oil: $^1$HNMR (500 MHz, CDCl$_3$) δ 4.70-4.74 (m, 1H), 4.61-4.65 (m, 1H), 4.54 (d, 1H, J=10.0 Hz), 3.67-3.78 (m, 4H), 3.53 (d, 1H, J=11.5 Hz), 3.41 (s, 3H), 2.86 (d, 1H, J=4.0 Hz), 2.69 (dd, 1H, J=4.5 Hz, J=7.0 Hz), 2.54 (d, 1H, J=4.5 Hz), 2.42-2.52 (m, 1H), 2.34 (s, 1H), 1.93 (d, 1H, J=5.5 Hz), 1.87-1.94 (m, 1H), □□ 1.58-1.66 (m, 1H), 1.36-1.40 (m, 1H), □□ 1.08 (s, 3H).

Example 99

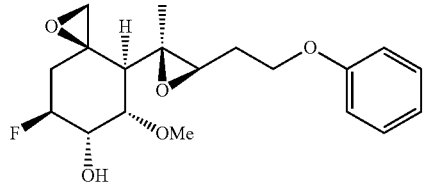

SH-R01-A-25-C

Compound A-25-C:

To a solution of A-25 and A-28 (231 mg, 0.66 mmol) in MeOH (2 mL) was added NaBH$_4$ (150 mg, 3.96 mmol) at 0° C., then warmed to room temperature, and stirred for 0.5 h. The mixture was condensed under reduced pressure to give crude A-25-C, which was column chromatographied on silica gel to give A-25-C (236 mg, 100%) as a yellow oil: $^1$HNMR (500 MHz, CDCl$_3$) δ 7.22 (t, 2H, J=8.0 Hz), 6.90 (t, 1H, J=7.0 Hz), 6.84 (d, 2H, J=8.5 Hz), 4.73-4.77 (m, 1H), 4.64-4.68 (m, 1H), 4.58 (d, 1H, J=9.5 Hz), 4.03-4.11 (m, 2H), 3.58 (d, 1H, J=12.5 Hz), 3.45 (s, 3H), 2.97 (d, 1H, J=4.0 Hz), 2.78 (t, 1H, J=6.0 Hz), 2.45-2.52 (m, 2H), 2.33 (s, 1H), 1.58-2.07 (m, 3H), ☐☐ 1.38-1.41 (m, 1H), 1.18 (s, 3H).

1.93-1.99 (m, 1H), ☐☐ 1.89 (s, 1H), ☐☐ 1.72-1.79 (m, 1H), ☐☐ 1.71 (d, 1H, J=14.0 Hz), 1.27 (s, 3H).

Example 100

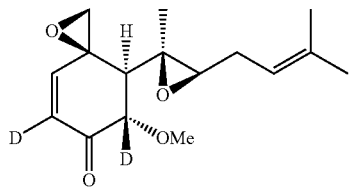

SH-R01-B-1-2D

Compound B-1-2D:

To a solution of B-13-3D (110 mg, 0.39 mmol) in dry THF (3 mL) was added LiHMDS (1.0 M in THF, 0.6 mL, 0.6 mmol) dropwise at −78° C. under argon. After stirring for 10 min, the solution was warmed to room temperature and stirred for 1 h, followed by addition of the solution of N-tert-butylbenzene-sulfinimidoylchloride (252 mg, 1.17 mmol) in dry THF (2 mL) at −78° C. Stirring was continued for 2 h at room temperature. The mixture was diluted with H$_2$O and EtOAc, and extracted with EtOAc. The organic extract was washed with brine, dried (Na$_2$SO$_4$), filtered, and concentrated in vacuo. The resulting crude residue was purified on silica gel, followed by Prep-TLC twice to afford B-1-2D (15 mg, 13%) as a colorless oil: $^1$HNMR (500 MHz, CDCl$_3$) δ 6.23 (s, 1H), 5.16-5.19 (m, 1H), 3.40 (s, 3H), 3.09 (d, 1H, J=5.0 Hz), ☐☐ 2.93 (d, 1H, J=4.5 Hz), ☐☐ 2.68 (t, 1H, J=6.5 Hz), 2.31-2.34 (m, 1H), ☐☐ 2.17-2.19 (m, 1H), ☐☐ 1.96 (s, 1H), ☐☐ 1.73 (s, 3H), ☐☐ 1.63 (s, 3H), ☐☐ 1.25 (s, 3H).

Example 101

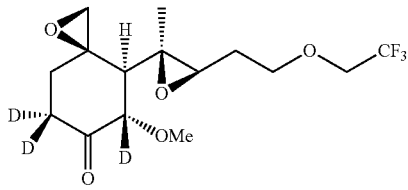

SH-R01-B-17-3D

Compound B-17-3D and B-27:

To a solution of G-3-3 (100 mg, 0.30 mmol) in dry THF (3 mL) was added LiHMDS (1.0 M in THF, 0.5 mL, 0.5 mmol) dropwise at −78° C. under argon. After stirring for 30 min at this temperature, the mixture was warmed to room temperature and stirred for 2 h, and then quenched with D$_2$O. The mixture was kept stirring overnight. The mixture was dried (Na$_2$SO$_4$), filtered, and concentrated in vacuo. The resulting crude residue was purified on silica gel to afford B-17-3D (20 mg, 20%) as a yellow solid and B-27 (10 mg, 10%) as a colorless oil.

For B-17-3D:

$^1$HNMR (500 MHz, CDCl$_3$) δ 3.85 (dd, 2H, J=1.0 Hz, J=8.5 Hz), 3.80-3.84 (m, 2H), 3.51 (s, 3H), 3.05 (d, 1H, J=4.5 Hz), 2.76-2.77 (m, 2H), 2.07 (d, 1H, J=13.5 Hz),

Example 102

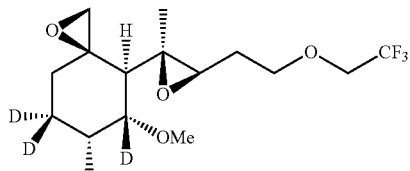

SH-R01-B-17-3D-C

Compound B-17-3D-C:

To a solution of B-17-3D (21 mg, 0.06 mmol) in MeOH (2 mL) was added NaBH$_4$ (14 mg, 0.37 mmol) at −78° C., then warmed to 0° C. and stirred for 0.5 h. The mixture was evaporated under reduced pressure to give crude B-17-3D-C, which was purified through silica gel chromatography to give B-17-3D-C (18 mg, 86%) as a colorless oil: $^1$HNMR (500 MHz, CDCl$_3$) δ 4.37 (s, 1H), 3.77-3.88 (m, 4H), 3.49 (s, 3H), 2.88 (d, 1H, J=4.5 Hz), 2.75 (dd, 1H, J=4.0 Hz, J=7.0 Hz), 2.58 (d, 1H, J=4.0 Hz), ☐☐ 2.34 (s, 1H), 2.20 (d, 1H, J=14.0 Hz), 1.95-2.00 (m, 1H), ☐☐ 1.68-1.72 (m, 1H), ☐☐ 1.19 (s, 3H), 0.98 (d, 1H, J=14.0 Hz).

Example 103

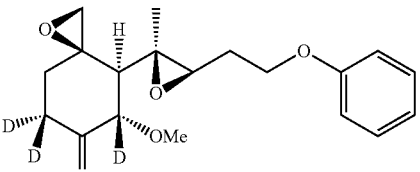

SH-R01-B-25-3D

Compound B-25-3D and B-28:

To a solution of G-4-3 (400 mg, 1.2 mmol) in dry THF (5 mL) was added LiHMDS (1.0 M in THF, 1.8 mL, 1.8 mmol) dropwise at −78° C. under argon. After stirring for 30 min at this temperature, the mixture was warmed to room temperature and stirred for 2 h, and then quenched with D$_2$O. The mixture was kept stirring overnight. The mixture was dried (Na$_2$SO$_4$), filtered, and concentrated in vacuo. The resulting crude residue was purified on silica gel to afford B-17-3D (60 mg, 15%) as a white solid and B-28 (35 mg, 9%) as a colorless oil.

For B-25-3D:

$^1$HNMR (500 MHz, CDCl$_3$) δ 7.30 (t, 2H, J=8.0 Hz), 6.97 (t, 1H, J=7.5 Hz), 6.91 (d, 2H, J=7.5 Hz), 4.13-4.16 (m, 2H), 3.52 (s, 3H), 3.14 (d, 1H, J=4.0 Hz), 2.85 (t, 1H, J=6.0 Hz), 2.73 (d, 1H, J=4.0 Hz), 2.00-2.12 (m, 3H), ☐☐ 1.91 (s, 1H), ☐☐ 1.64-1.69 (m, 1H), ☐☐ 1.32 (s, 3H).

Example 104

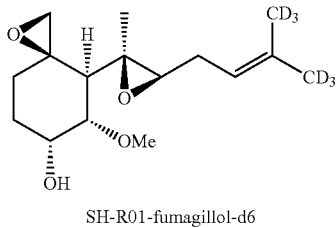

SH-R01-fumagillol-d6

Compound G-5-1:

To a reaction mixture of G-2-1.5 (5 g, 13.4 mmol), PPh$_3$ (8.7 g, 33.5 mmol) and imidazole (2.4 g, 33.5 mmol) in dry toluene (150 mL) was added I$_2$ (6.8 g, 26.8 mmol) at 0° C. under argon. The mixture was warmed to room temperature and stirred for 2 h, and then was quenched by the addition of sat. NaHCO$_3$, extracted with EtOAc. The organic extract was dried (Na$_2$SO$_4$), filtered, and concentrated in vacuo. The resulting crude residue was purified on silica gel to afford G-5-1 (3.88 g, 60%) as a colorless oil: $^1$HNMR (500 MHz, CDCl$_3$) δ 4.30 (t, 1H, J=2.5 Hz), 3.36 (dd, 1H, J=2.5 Hz, J=13.5 Hz), 3.34 (s, 3H), 3.16-3.23 (m, 2H), 2.75 (d, 1H, J=5.5 Hz), 2.58-2.61 (m, 1H), □□ 2.51 (d, 1H, J=5.5 Hz), 2.12-2.15 (m, 2H), □□ 1.99 (d, 1H, J=13.5 Hz), 1.85-1.96 (m, 1H), □□ 1.68-1.69 (m, 2H), □□ 1.18 (s, 3H), 0.91-0.98 (m, 1H), □□ 0.82 (s, 9H), 0.15 (d, 1H, J=15.0 Hz).

Compound G-5-2:

A reaction mixture of G-5-1 (150 mg, 0.3 mmol), PPh$_3$ (81 mg, 0.3 mmol) in CH$_3$CN (1 mL) was refluxed for 3 h, and then concentrated in vacuo. The resulting crude residue was washed with EtOAc/PE to obtain G-5-2 (150 mg, 64%) as white solid. MS (ESI) m/z 617.3 [M−I]$^-$ Compound Fumagillol-D$_6$-1:

n-BuLi (2.5 M in hexane, 0.03 mL, 0.067 mmol) was added dropwise to a solution of G-5-2 (50 mg, 0.067 mmol) in dry THF (0.5 mL) at −78° C. under argon. Keeping this temperature for 40 min, and then CD$_3$COCD$_3$ (4.3 mg, 0.067 mmol) was added. The reaction was gradually warmed to room temperature over a 2 h period, followed by addition sat. NH$_4$Cl, and then extracted with EtOAc. The organic extract was washed with brine, dried (Na$_2$SO$_4$), filtered, and concentrated in vacuo. The resulting crude residue was purified on silica gel to afford Fumagillol-D$_6$-1 (16 mg, 60%) as a white solid: $^1$HNMR (500 MHz, CDCl$_3$) δ 5.22 (t, 1H, J=7.5 Hz), 4.36 (s, 1H), 3.41-3.44 (m, 4H), 2.95 (d, 1H, J=4.0 Hz), 2.54 (t, 1H, J=6.5 Hz), □□ 2.50 (d, 1H, J=4.5 Hz), 2.32-2.34 (m, 1H), □□ 2.14-2.21 (m, 2H), □□ 2.03 (d, 1H, J=11.0 Hz), 1.73-1.74 (m, 1H), □□ 1.19 (s, 3H), □□ 0.91-0.92 (m, 1H), □□ 0.88 (s, 9H), 0.09 (d, 1H, J=15.0 Hz)

Compound Fumagillol-D$_6$:

To a solution of Fimagillol-D$_6$-1 (100 mg, 0.25 mmol) in dry THF (1 mL) was added dropwise a solution TBAF (1.0 M in THF, 2 mL, 2 mmol) at 0° C. The mixture was stirred overnight at room temperature, diluted with H$_2$O and EtOAc, and extracted with EtOAc. The organic extract was washed with brine, dried (Na$_2$SO$_4$), filtered, and concentrated in vacuo. The resulting crude residue was purified on silica gel to afford Fumagillol-D$_6$ (62 mg, 86%) as a white solid: $^1$HNMR (500 MHz, CDCl$_3$) δ 5.20 (t, 1H, J=8.0 Hz), 4.37 (d, 1H, J=3.5 Hz), 3.63 (dd, 1H, J=2.5 Hz, J=11.0 Hz), 3.50 (s, 3H), 2.94 (d, 1H, J=4.0 Hz), 2.58 (t, 1H, J=6.0 Hz), □□ 2.54 (d, 1H, J=4.5 Hz), 2.34-2.39 (m, 2H), □□ 2.14-2.24 (m, 2H), □□ 1.98-2.02 (m, 1H), □□ 1.93 (d, 1H, J=11.0 Hz), 1.22 (s, 3H), 0.97-1.00 (m, 1H).

Example 105

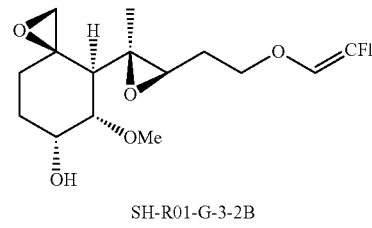

SH-R01-G-3-2B

Compound G-3-2B-P:

To a mixture of G-2-1.5 (100 mg, 0.26 mmol) and t-BuOK (60 mg, 0.54 mmol) in dry THF (5 mL) was added 2-iodo-1,1,1-trifluorothane (68 mg, 0.32 mmol) at 0° C. The reaction mixture was warmed gradually to room temperature and stirred overnight, followed by being filtered and concentrated in vacuo. The resulting crude residue was purified on silica gel to afford G-3-2B-P (40 mg, 33%) as a white solid: $^1$HNMR (500 MHz, CDCl$_3$) δ 4.60 (d, 1H, J=4.5 Hz), 4.27 (t, 1H, J=2.0 Hz), 4.09-4.12 (m, 2H), □□ 3.34 (dd, 1H, J=2.0 Hz, J=10.5 Hz), 3.31 (s, 3H), □□ 2.77 (d, 1H, J=4.0 Hz), 2.70 (dd, 1H, J=4.0 Hz, J=8.0 Hz), 2.48 (d, 1H, J=4.5 Hz), 2.10-2.11 (m, 1H), □□ 1.98 (dd, 2H, J=3.5 Hz, J=7.5 Hz), 1.61-1.67 (m, 3H), 1.09 (s, 3H), 0.87-0.90 (m, 1H), 0.78 (s, 9H), 0.00 (d, 6H, J=16.5 Hz).

Compound G-3-2B:

To a solution of G-3-2B-P (40 mg, 0.07 mmol) in dry THF (5 mL) was added dropwise a solution TBAF (1.0 M in THF, 0.5 mL, 0.5 mmol) at 0° C. The mixture was stirred overnight at room temperature, diluted with H$_2$O and EtOAc, and extracted with EtOAc. The organic extract was washed with brine, dried (Na$_2$SO$_4$), filtered, and concentrated in vacuo. The resulting crude residue was purified on silica gel to afford G-3-2B (20 mg, 67%) as a colorless oil: $^1$HNMR (500 MHz, CDCl$_3$) δ 4.72 (d, 1H, J=4.0 Hz), 4.38 (d, 1H, J=2.5 Hz), 4.20-4.23 (m, 2H), □□ 3.64 (dd, 1H, J=3.0 Hz, J=11.0 Hz), 3.50 (s, 3H), □□ 2.85-2.87 (m, 1H), 2.63 (d, 1H, J=4.0 Hz), 2.35 (s, 1H), □□ 2.20-2.24 (m, 1H), 2.08-2.17 (m, 1H), 1.98-2.05 (m, 2H), 1.75-1.80 (m, 2H), 1.21 (s, 3H), 0.09-1.05 (m, 1H). MS (ESI) m/z 429 [M+H]$^+$.

Example 106

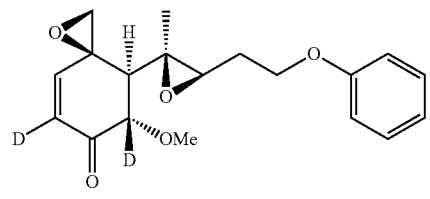

SH-R01-B-26-2D

Compound B-26-2D:

To a solution of B-25-3D (120 mg, 0.36 mmol) in dry THF (3 mL) was added LiHMDS (1.0 M in THF, 0.54 mL, 0.54 mmol) dropwise at −78° C. under argon. After stirring for 10 min, the solution was warmed to room temperature and stirred for 1 h, followed by addition of the solution of N-tert-butylbenzene-sulfinimidoylchloride (231 mg, 1.07 mmol) in dry THF (2 mL) at −78° C. Stirring was continued for 2 h at room temperature. The mixture was diluted with H$_2$O and EtOAc, and extracted with EtOAc. The organic extract was washed with brine, dried (Na$_2$SO$_4$), filtered, and concentrated in vacuo. The resulting crude residue was purified on silica gel, followed by Prep-TLC to afford B-26-2D (45 mg, 37.5%) as a colorless oil: $^1$HNMR (500 MHz, CDCl$_3$) δ 7.22 (t, 2H, J=7.5 Hz), 6.89 (t, 1H, J=7.0 Hz), 6.85 (d, 2H, J=8.0 Hz), 6.22 (s, 1H), 4.04-4.07 (m, 2H), 3.36 (s, 3H), 3.05 (d, 1H, J=5.0 Hz), □□ 2.85-2.87 (m, 2H), 2.00-2.05 (m, 1H), 1.95 (s, 1H), □□ 1.90-1.95 (m, 1H), □□ 1.22 (s, 3H).

Example 107

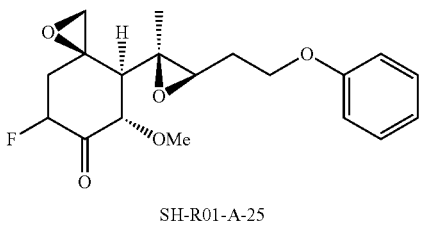

SH-R01-A-25

Compound A-25:

To a solution of G-4-3 (530 mg, 1.60 mmol) in dry THF (4 mL) was added LiHMDS (1.0 M in THF, 2.24 mL, 2.24 mmol) at −78° C. under argon. After stirring for 45 min, the solution was warmed to 0° C. and stirred for 0.5 h, followed by addition of the solution of NFSi (756 mg, 2.40 mmol) in dry THF (2 mL) at −78° C. Stirring was continued for 2 h at room temperature. The mixture was diluted with H$_2$O and EtOAc, and extracted with EtOAc. The organic extract was washed with brine, dried (Na$_2$SO$_4$), filtered, and concentrated in vacuo. The resulting crude residue was purified on silica gel to afford A-25 and A-28 (231 mg, 41.3%) as a yellow oil.

Compound A-25:

To a mixture of A-25-C (50 mg, 0.14 mmol) and 4 A MS (1 g) in DCM (5 mL) was added PCC (90 mg, 0.42 mmol) at 0° C. The mixture was stirred for 1 h at room temperature, then filtered through a pad of Al$_2$O$_3$. The filtrate was concentrated in vacuo. The resulting crude residue was purified on silica gel to afford A-25 (30 mg, 61%) as a yellow oil: $^1$HNMR (500 MHz, CDCl$_3$) δ 7.31 (t, 2H, J=8.5 Hz), 6.98 (t, 1H, J=7.5 Hz), 6.91 (d, 2H, J=8.0 Hz), 5.28-4.32 (m, 1H), 5.09-5.13 (m, 1H), 4.27 (d, 1H, J=12.5 Hz), 4.13-4.16 (m, 2H), 3.59 (s, 3H), 3.26 (d, 1H, J=4.5 Hz), 2.82 (t, 1H, J=6.0 Hz), 2.75 (d, 1H, J=4.0 Hz), 2.31-2.37 (m, 1H), 2.00-2.10 (m, 3H), 1.94 (d, 1H, J=12.5 Hz), 1.28 (s, 3H).

Example 108

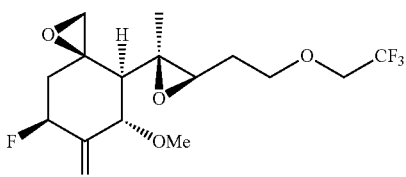

SH-R01-A-11

Compound A-11:

To a mixture of A-11-C (50 mg, 0.14 mmol) and 4 A MS (1 g) in DCM (5 mL) was added PCC (78 mg, 0.36 mmol) at 0° C. The mixture was stirred for 1 h at room temperature, then filtered through a pad of Al$_2$O$_3$. The filtrate was concentrated in vacuo. The resulting crude residue was purified on silica gel to afford A-11 (30 mg, 60%) as a yellow oil: $^1$HNMR (500 MHz, CDCl$_3$) δ 5.28-5.32 (m, 1H), 5.12-5.23 (m, 1H), □□ 4.25 (d, 1H, J=11.5 Hz), □□ 3.78-3.88 (m, 4H), 3.58 (s, 3H), 3.14 (d, 1H, J=3.5 Hz), □□ 2.80 (d, 1H, J=3.5 Hz), □□2.73 (t, 1H, J=6.0 Hz), 2.32-2.39 (m, 1H), 1.91-2.06 (m, 3H), 1.74-1.80 (m, 2H), 1.22 (s, 3H).

Compound A-11:

To a solution of G-3-3 (500 mg, 1.48 mmol) in dry THF (4 mL) was added LiHMDS (1.0 M in THF, 2.1 mL, 2.1 mmol) at −78° C. under argon. After stirring for 45 min, the solution was warmed to 0° C. and stirred for 0.5 h, followed by addition of the solution of NFSi (699 mg, 2.22 mmol) in dry THF (2 mL) at −78° C. Stirring was continued for 2 h at room temperature. The mixture was diluted with H$_2$O and EtOAc, and extracted with EtOAc. The organic extract was washed with brine, dried (Na$_2$SO$_4$), filtered, and concentrated in vacuo. The resulting crude residue was purified on silica gel to afford A-11 and A-15 (143 mg, 27%) as a yellow oil.

Example 109

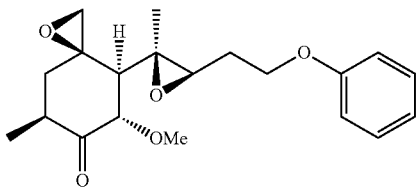

SH-R01-A-26

Compound G-4-4:

To a solution of G-4-3 (500 mg, 0.15 mmol) in dry THF (5 mL) was added LiHMDS (1.0 M in THF, 2.5 mL, 2.5 mmol) dropwise at −78° C. under argon. After stirring for 30 min at this temperature, a solution of TBDMSCl (840 mg, 5.0 mmol) in THF (5 mL) was added. The mixture was warmed to room temperature and stirred for 2 h, and then quenched by the addition of water, extracted with EtOAc. The organic extract was dried (Na$_2$SO$_4$), filtered, and concentrated in vacuo. The resulting residue was purified on silica gel to afford G-4-4 (400 mg, 61%) as a yellow solid: $^1$HNMR (500 MHz, CDCl$_3$) δ 7.27-7.30 (m, 2H), 6.92-6.97 (m, 3H), 4.93 (t, 1H, J=3.5 Hz), 4.13-4.17 (m, 2H), 3.85 (t, 1H, J=3.5 Hz), 3.41 (s, 3H), 3.05 (t, 1H, J=5.5 Hz), 2.74 (d, 1H, J=4.5 Hz), 2.64 (d, 1H, J=5.0 Hz), 2.44 (dd, 1H, J=3.5 Hz, J=17.5 Hz), 2.13-2.20 (m, 1H), 2.07 (dd, 1H, J=4.0 Hz, J=17.0 Hz), 1.95-2.02 (m, 1H), 1.46 (d, 1H, J=3.0 Hz), 1.37 (s, 3H), 0.95 (s, 9H), 0.18 (d, 6H, J=6.0 Hz).

Compound A-26 and A-27:

The mixture of TBAF (1.0 M in THF, 0.27 mL, 0.27 mmol) and 4 A MS (200 mg) in dry THF (3 mL) was stirred overnight at room temperature under argon. The suspension was cooled to 0° C., and a solution of G-4-4 (100 mg, 0.22 mmol) and CH$_3$I (37 mg, 0.27 mmol) was added. The mixture was warmed up to r.t. and stirred for 1 h. The mixture was then filtered and diluted with H$_2$O and EtOAc, then extracted with EtOAc. The organic extract was washed with brine, dried (Na$_2$SO$_4$), filtered, and concentrated in vacuo. The residue was purified twice on silica gel to afford A-26 (5 mg, 5%) as a colorless oil and A-27 (5 mg, 5%) as a colorless oil.

For A-26:

$^1$HNMR (500 MHz, CDCl$_3$) δ 7.27-7.31 (m, 2H), 6.96 (t, 1H, J=7.5 Hz), 6.91 (d, 2H, J=8.0 Hz), 4.10-4.13 (m, 3H), 3.72 (d, 1H, J=5.0 Hz), 3.31 (s, 3H), □□ 3.03 (t, 1H, J=6.5 Hz), 2.84-2.88 (m, 1H), □□ 2.83 (d, 1H, J=4.0 Hz), 2.72 (d, 1H, J=4.5 Hz), 2.21 (t, 1H, J=17.5 Hz), 1.99-2.09 (m, 2H), 1.92 (dd, 1H, J=1.5 Hz, J=4.5 Hz), 1.65-1.69 (m, 1H), 1.40 (s, 3H), 1.15 (d, 6H, J=6.5 Hz).

Example 110

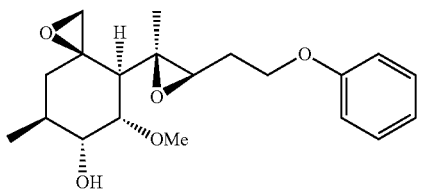

SH-R01-A-26-C

Compound A-26-C:

To a solution of A-26 (58 mg, 0.18 mmol) in MeOH (3 mL) was added NaBH$_4$ (39 mg, 1.08 mmol) at −78° C. The solution was stirred for 0.5 h, and then concentrated under reduced pressure. The residue was purified through a silica gel chromatography to give A-26-C (30 mg, 50%) as a colorless oil: $^1$HNMR (500 MHz, CDCl$_3$) δ 7.29 (t, 2H, J=8.5 Hz), 6.96 (t, 1H, J=7.5 Hz), 6.91 (d, 2H, J=8.0 Hz), 4.13-4.16 (m, 2H), 3.70-3.72 (m, 2H), 3.55 (s, 3H), 2.96 (t, 1H, J=6.5 Hz), 2.78 (d, 1H, J=4.5 Hz), 2.41 (d, 1H, J=4.5 Hz), 2.20-2.17 (m, 1H), 2.08-2.18 (m, 1H), 1.96-2.10 (m, 1H), 1.76 (dd, 1H, J=4.0 Hz, J=14.0 Hz), 1.67 (d, 1H, J=8.0 Hz), 1.41 (s, 3H), 1.11 (d, 6H, J=7.0 Hz).

Example 111

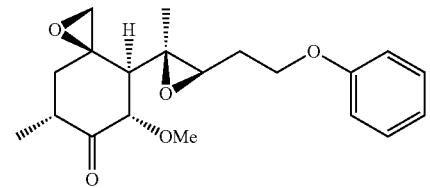

SH-R01-A-27

Compound G-4-4:

To a solution of G-4-3 (500 mg, 0.15 mmol) in dry THF (5 mL) was added LiHMDS (1.0 M in THF, 2.5 mL, 2.5 mmol) dropwise at −78° C. under argon. After stirring for 30 min at this temperature, a solution of TBDMSCl (840 mg, 5.0 mmol) in THF (5 mL) was added. The mixture was warmed to room temperature and stirred for 2 h, and then quenched by the addition of water, extracted with EtOAc. The organic extract was dried (Na$_2$SO$_4$), filtered, and concentrated in vacuo. The resulting residue was purified on silica gel to afford G-4-4 (400 mg, 61%) as a yellow solid: $^1$HNMR (500 MHz, CDCl$_3$) δ 7.27-7.30 (m, 2H), 6.92-6.97 (m, 3H), 4.93 (t, 1H, J=3.5 Hz), 4.13-4.17 (m, 2H), 3.85 (t, 1H, J=3.5 Hz), 3.41 (s, 3H), 3.05 (t, 1H, J=5.5 Hz), 2.74 (d, 1H, J=4.5 Hz), 2.64 (d, 1H, J=5.0 Hz), 2.44 (dd, 1H, J=3.5 Hz, J=17.5 Hz), 2.13-2.20 (m, 1H), 2.07 (dd, 1H, J=4.0 Hz, J=17.0 Hz), 1.95-2.02 (m, 1H), 1.46 (d, 1H, J=3.0 Hz), 1.37 (s, 3H), 0.95 (s, 9H), 0.18 (d, 6H, J=6.0 Hz).

Compound A-26 and A-27:

The mixture of TBAF (1.0 M in THF, 0.27 mL, 0.27 mmol) and 4 A MS (200 mg) in dry THF (3 mL) was stirred overnight at room temperature under argon. The suspension was cooled to 0° C., and a solution of G-4-4 (100 mg, 0.22 mmol) and CH$_3$I (37 mg, 0.27 mmol) was added. The mixture was warmed up to r.t. and stirred for 1 h. The mixture was then filtered and diluted with H$_2$O and EtOAc, then extracted with EtOAc. The organic extract was washed with brine, dried (Na$_2$SO$_4$), filtered, and concentrated in vacuo. The residue was purified twice on silica gel to afford A-26 (5 mg, 5%) as a colorless oil and A-27 (5 mg, 5%) as a colorless oil.

For A-27:

$^1$HNMR (500 MHz, CDCl$_3$) δ 7.30 (t, 2H, J=8.0 Hz), 6.97 (t, 1H, J=7.5 Hz), 6.91 (d, 2H, J=8.0 Hz), 4.24 (d, 1H, J=12.0 Hz), 4.11-4.17 (m, 2H), 3.55 (s, 3H), 3.20 (d, 1H, J=4.0 Hz), 2.83-2.88 (m, 1H), □□ 2.80 (t, 1H, J=6.0 Hz), 2.71 (d, 1H, J=4.0 Hz), 1.97-2.14 (m, 2H), 1.86-1.92 (m, 2H), 1.53-1.57 (m, 1H), 1.30 (s, 3H), 1.07 (d, 6H, J=6.0 Hz).

Example 112

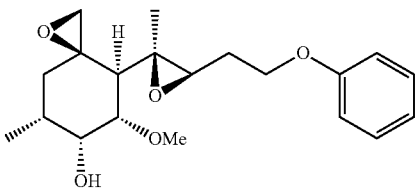

SH-R01-A-27-C

Compound A-27-C:

To a solution of A-27 (58 mg, 0.18 mmol) in MeOH (4 mL) was added NaBH$_4$ (39 mg, 1.08 mmol) at −78° C. The solution was stirred for 0.5 h. The mixture was concentrated under reduced pressure to give crude A-27-C, which was purified through a silica gel chromatography to give A-27-C (32 mg, 55%) as a colorless oil: $^1$HNMR (500 MHz, CDCl$_3$) δ 7.20-7.24 (m, 2H), 6.89 (t, 1H, J=9.5 Hz), 6.84 (d, 2H, J=11.0 Hz), 4.04-4.10 (m, 3H), 3.57 (dd, 1H, J=3.5 Hz, J=14.5 Hz), 3.44 (s, 1H), 2.93 (d, 1H, J=5.5 Hz), 2.75 (dd, 1H, J=6.5 Hz, J=9.0 Hz), 2.45 (d, 1H, J=5.5 Hz), 2.18 (s, 1H), 1.84-2.10 (m, 5H), 1.19 (s, 3H), □□ 1.01 (d, 6H, J=8.0 Hz), 0.81 (dd, 1H, J=4.5 Hz, J=16.0 Hz).

Example 113

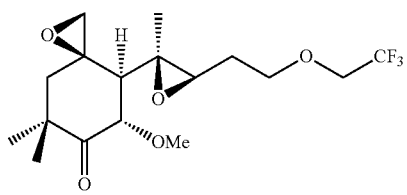

SH-R01-A-29

Compound A-29:

A mixture of TBAF (1.0 M in THF, 0.30 mL, 0.30 mmol) and 4 A MS (200 mg) in dry THF (5 mL) were stirred overnight at room temperature under argon. The suspension was cooled to 0° C., and a solution of G-3-4 (90 mg, 0.20 mmol) and CH$_3$I (33 mg, 0.24 mmol) was added. The mixture was warmed up to room temperature and stirred for 1 h. The mixture was then filtered and diluted with H$_2$O and EtOAc, and extracted with EtOAc. The organic extract was washed with brine, dried (Na$_2$SO$_4$), filtered, and concentrated in vacuo. The crude residue was purified twice on silica gel to afford A-3 (5 mg, 5%) as a colorless oil and A-29 (10 mg, 11%) as a yellow oil: $^1$HNMR (500 MHz, CDCl$_3$) δ 4.37 (d, 1H, J=11.5 Hz), 3.76-3.87 (m, 4H), 3.50 (s, 3H), 2.93 (d, 1H, J=4.0 Hz), 2.73 (t, 1H, J=5.0 Hz), 2.61 (d, 1H, J=4.0 Hz), 1.93-1.98 (m, 2H), 1.87 (d, 1H, J=11.5 Hz), 1.73-1.78 (m, 1H), 1.58 (s, 1H), 1.33 (s, 3H), 1.28 (s, 3H), 1.25 (s, 1H), 1.12 (s, 3H).

Example 114

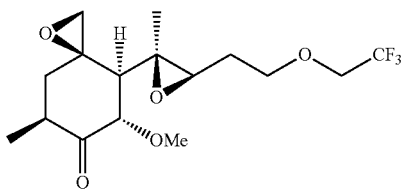

SH-R01-A-3

Compound G-3-4:

To a solution of G-3-3 (100 mg, 0.30 mmol) in dry THF (2 mL) was added LiHMDS (1.0 M in THF, 0.5 mL, 0.5 mmol) dropwise at −78° C. under argon. After stirring for 30 min at this temperature, a solution of TBDMSCl (165 mg, 3.7 mmol) in THF (1 mL) was added. The mixture was warmed to room temperature and stirred for 2 h, and then quenched by the addition of water, extracted with EtOAc. The organic extract was dried (Na$_2$SO$_4$), filtered, and concentrated in vacuo. The resulting residue was purified on silica gel to afford G-3-4 (90 mg, 67.6%) as a yellow oil: $^1$HNMR (500 MHz, CDCl$_3$) δ 4.74-4.76 (m, 1H), 3.60-3.71 (m, 1H), 3.22 (s, 3H), 2.77 (t, 1H, J=6.5 Hz), 2.52 (d, 1H, J=5.5 Hz), 2.47 (d, 1H, J=5.0 Hz), 2.28 (dd, 1H, J=3.5 Hz, J=18.0 Hz), 1.86 (dd, 1H, J=4.5 Hz, J=17.5 Hz), 1.76-1.79 (m, 1H), 1.64-1.67 (m, 1H), 1.41 (s, 1H), 1.22 (d, 1H, J=3.0 Hz), 1.15 (s, 3H), 0.77 (s, 9H), 0.07 (d, 6H, J=6.0 Hz).

Compound A-3 and A-7:

The mixture of TBAF (1.0 M in THF, 0.40 mL, 0.40 mmol) and 4 A MS (200 mg) in dry THF (5 mL) was stirred overnight at room temperature under argon. The suspension was cooled to 0° C., and a solution of G-3-4 (150 mg, 0.33 mmol) and CH$_3$I (55 mg, 0.40 mmol) was added. The mixture was warmed up to room temperature and stirred for 1 h. The mixture was then filtered, diluted with H$_2$O and EtOAc, and extracted with EtOAc. The organic extract was washed with brine, dried (Na$_2$SO$_4$), filtered, and concentrated in vacuo. The crude residue was purified twice on silica gel to afford A-3 (29 mg, 19%) as a colorless oil and A-7 (30 mg, 19%) as a yellow solid.

For A-3:

$^1$HNMR (500 MHz, CDCl$_3$) δ 3.67-3.80 (m, 4H), 3.64 (d, 1H, J=4.0 Hz), 3.24 (s, 3H), 2.87 (t, 1H, J=6.0 Hz), 2.80-2.83 (m, 1H), □□ 2.74 (d, 1H, J=5.0 Hz), 2.66 (d, 1H, J=5.0 Hz), 2.14 (t, 1H, J=12.0 Hz), 1.74-1.83 (m, 3H), 1.59-1.61 (m, 1H), 1.28 (s, 3H), 1.08 (d, 6H, J=7.0 Hz).

Example 115

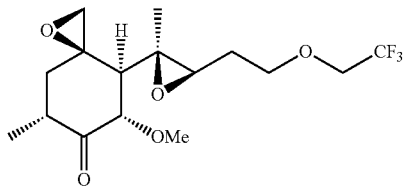

SH-R01-A-7

Compound G-3-4:

To a solution of G-3-3 (100 mg, 0.30 mmol) in dry THF (2 mL) was added LiHMDS (1.0 M in THF, 0.5 mL, 0.5 mmol) dropwise at −78° C. under argon. After stirring for 30 min at this temperature, a solution of TBDMSCl (165 mg, 3.7 mmol) in THF (1 mL) was added. The mixture was warmed to room temperature and stirred for 2 h, and then quenched by the addition of water, extracted with EtOAc. The organic extract was dried (Na$_2$SO$_4$), filtered, and concentrated in vacuo. The resulting residue was purified on silica gel to afford G-3-4 (90 mg, 67.6%) as a yellow oil: $^1$HNMR (500 MHz, CDCl$_3$) δ 4.74-4.76 (m, 1H), 3.60-3.71 (m, 1H), 3.22 (s, 3H), 2.77 (t, 1H, J=6.5 Hz), 2.52 (d, 1H, J=5.5 Hz), 2.47 (d, 1H, J=5.0 Hz), 2.28 (dd, 1H, J=3.5 Hz, J=18.0 Hz), 1.86 (dd, 1H, J=4.5 Hz, J=17.5 Hz), 1.76-1.79 (m, 1H), 1.64-1.67 (m, 1H), 1.41 (s, 1H), 1.22 (d, 1H, J=3.0 Hz), 1.15 (s, 3H), 0.77 (s, 9H), 0.07 (d, 6H, J=6.0 Hz).

Compound A-3 and A-7:

The mixture of TBAF (1.0 M in THF, 0.40 mL, 0.40 mmol) and 4 A MS (200 mg) in dry THF (5 mL) was stirred overnight at room temperature under argon. The suspension was cooled to 0° C., and a solution of G-3-4 (150 mg, 0.33 mmol) and CH$_3$I (55 mg, 0.40 mmol) was added. The mixture was warmed up to room temperature and stirred for 1 h. The mixture was then filtered, diluted with H$_2$O and EtOAc, and extracted with EtOAc. The organic extract was washed with brine, dried (Na$_2$SO$_4$), filtered, and concentrated in vacuo. The crude residue was purified twice on silica gel to afford A-3 (29 mg, 19%) as a colorless oil and A-7 (30 mg, 19%) as a yellow solid.

For A-7:

$^1$HNMR (500 MHz, CDCl$_3$) δ 4.22 (d, 1H, J=14.5 Hz), 3.77-3.89 (m, 4H), 3.55 (s, 3H), 3.09 (d, 1H, J=5.0 Hz), 2.82-2.87 (m, 1H), □□ 2.76 (d, 1H, J=5.0 Hz), 2.71 (d, 1H, J=6.5 Hz), 1.86-1.99 (m, 3H), 1.72-1.77 (m, 1H), 1.54-1.59 (m, 1H), 1.39 (s, 3H), 1.08 (d, 6H, J=8.0 Hz).

Example 116

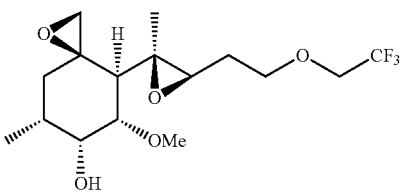

SH-R01-A-7-C

Compound A-7-C:

To a solution of A-7 (20 mg, 0.06 mmol) in MeOH (3 mL) was added NaBH$_4$ (13 mg, 0.34 mmol) at −78° C. The solution was stirred for 0.5 h. The mixture was concentrated under reduced pressure to give crude A-7-C, which was purified through a silica gel chromatography to give A-7-C (10 mg, 50%) as a yellow solid: $^1$HNMR (500 MHz, CDCl$_3$) δ 4.16 (s, 1H), 3.76-3.87 (m, 1H), 3.62 (dd, 1H, J=2.0 Hz, J=11.0 Hz), 3.50 (s, 1H), 2.88 (d, 1H, J=4.0 Hz), 2.73 (dd, 1H, J=4.0 Hz, J=7.0 Hz), 2.56 (d, 1H, J=4.0 Hz), 2.22 (s, 3H), 1.90-2.05 (m, 4H), 1.66-1.71 (m, 1H), 1.18 (s, 1H), □□ 1.08 (d, 6H, J=6.5 Hz), 0.89 (dd, 1H, J=3.5 Hz, J=8.0 Hz).

Example 117

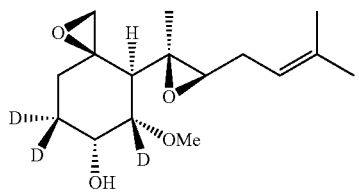

SH-R01-B-13-3D-C

Compound B-13-3D-C:

To a solution of B-13-3D (20 mg, 0.05 mmol) in MeOH (1 mL) was added NaBH$_4$ (12 mg, 0.32 mmol) at 0° C., followed by warming to room temperature and stirred for 0.5 h. The mixture was evaporated under reduced pressure to give crude B-13-3D-C, which was column chromatographied on silica gel to give B-13-3D-C (15 mg, 74%) as a colorless oil: $^1$HNMR (500 MHz, CDCl$_3$) δ 5.20 (t, 1H, J=9.0 Hz), 4.35 (s, 1H), 3.49 (s, 3H), 2.93 (d, 1H, J=5.5 Hz), □□ 2.57 (t, 1H, J=8.5 Hz), 2.52 (d, 1H, J=6.0 Hz), □□ 2.32-2.37 (m, 2H), □□ 2.15-2.20 (m, 2H), □□ □□ 1.92 (s, 1H), □□ 1.74 (s, 3H), □□ 1.65 (s, 3H), □□ 1.19 (s, 3H), 0.97 (d, 1H, J=17.0 Hz).

Example 118

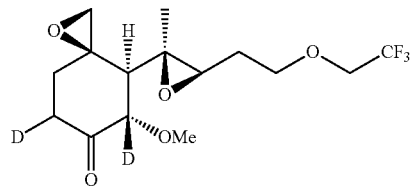

SH-R01-B-5-2D

Compound B-5-2D:

To a solution of B-17-3D (192 mg, 0.56 mmol) in dry THF (3 mL) was added LiHMDS (1.0 M in THF, 0.79 mL, 0.79 mmol) dropwise at −78° C. under argon. After stirring for 10 min, the solution was warmed to room temperature and stirred for 1 h, followed by addition of the solution of N-tert-butylbenzene-sulfinimidoylchloride (361 mg, 1.68 mmol) in dry THF (2 mL) at −78° C. Stirring was continued for 2 h at room temperature. The mixture was diluted with H$_2$O and EtOAc, and extracted with EtOAc. The organic extract was washed with brine, dried (Na$_2$SO$_4$), filtered, and concentrated in vacuo. The resulting crude residue was purified on silica gel, followed by Prep-TLC twice to afford B-5-2D (10 mg, 5%) as a colorless oil: $^1$HNMR (500 MHz, CDCl$_3$) δ 6.29 (s, 1H), 3.75-3.88 (m, 4H), 3.42 (s, 3H), 3.09 (d, 1H, J=5.5 Hz), □□ 2.95 (d, 1H, J=5.5 Hz), □□ 2.54 (t, 1H, J=5.5 Hz), 1.96 (s, 1H), □□ 1.89-1.95 (m, 2H), □□ 1.23 (s, 3H).

Example 119

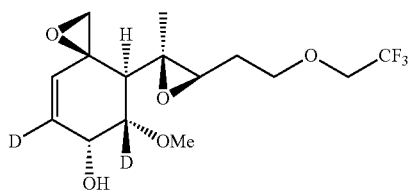

SH-R01-B-5-2D-C

Compound B-5-2D-C and B-5-2D-C-i:

To a solution of B-5-2D (35 mg, 0.10 mmol) in MeOH (3 mL) was added NaBH$_4$ (8 mg, 0.21 mmol) at −78° C., then stirred for 0.5 h. The mixture was evaporated under reduced pressure to give crude compound, which was purified through silica gel chromatography to give B-5-2D-C (8 mg, 23%) as a colorless oil and B-5-2D-C-i (11 mg, 31%) as a colorless oil.

For B-5-2D-C:

$^1$HNMR (500 MHz, CDCl$_3$) δ 5.27 (s, 1H), 4.44 (d, 1H, J=3.0 Hz), 3.49 (s, 3H), 3.69-3.81 (m, 4H), □□ 3.46 (s, 3H), 3.00 (d, 1H, J=4.0 Hz), 2.76 (t, 1H, J=6.5 Hz), 2.66 (d, 1H, J=4.0 Hz), □□ 2.56 (d, 1H, J=4.5 Hz), 2.05 (s, 1H), 1.82-1.87 (m, 1H), □□ 1.71-1.76 (m, 1H), □□ 1.26 (s, 3H).

Example 120

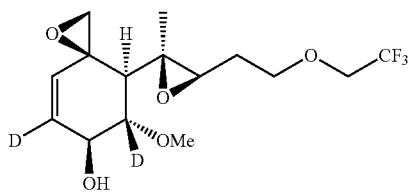

SH-R01-B-5-2D-C-i

Compound B-5-2D-C and B-5-2D-C-i:

To a solution of B-5-2D (35 mg, 0.10 mmol) in MeOH (3 mL) was added NaBH$_4$ (8 mg, 0.21 mmol) at −78° C., then stirred for 0.5 h. The mixture was evaporated under reduced pressure to give crude compound, which was purified through silica gel chromatography to give B-5-2D-C (8 mg, 23%) as a colorless oil and B-5-2D-C-i (11 mg, 31%) as a colorless oil.

For B-5-2D-C-i:

$^1$HNMR (500 MHz, CDCl$_3$) δ 5.12 (s, 1H), 4.25 (d, 1H, J=3.5 Hz), 3.70-3.81 (m, 4H), 3.60 (s, 3H), 3.01 (d, 1H, J=4.0 Hz), 2.75 (t, 1H, J=6.5 Hz), □□ 2.64 (d, 1H, J=4.5 Hz), 2.36 (s, 1H), □□ 1.76-1.83 (m, 3H), 1.30 (s, 3H).

Example 121

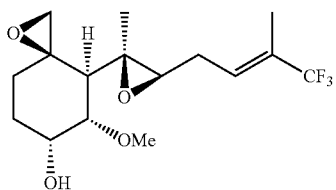

SH-R01-G-5-4-E

Compound G-5-3-E and G-5-3-Z:

n-BuLi (2.5 M in hexane, 0.03 mL, 0.067 mmol) was added dropwise to a solution of G-5-2 (50 mg, 0.067 mmol) in dry THF (0.5 mL) at −78° C. under argon. Keeping this temperature for 40 min, and then $CF_3COCH_3$ (7.5 mg, 0.067 mmol) was added. The reaction was gradually warmed to room temperature over a 2 h period, followed by addition sat. $NH_4Cl$, and then extracted with EtOAc. The organic extract was washed with brine, dried ($Na_2SO_4$), filtered, and concentrated in vacuo. The resulting crude residue was purified on silica gel to afford G-5-3-E (15 mg, 50%) as a colorless oil and G-5-3-Z (4 mg, 13%) as a colorless oil.

For G-5-3-E:
$^1$HNMR (500 MHz, $CDCl_3$) δ 6.20 (t, 1H, J=8.0 Hz), 4.37 (s, 1H), 3.44 (dd, 1H, J=2.0 Hz, J=11.0 Hz), 3.41 (s, 3H), 2.80 (d, 1H, J=4.5 Hz), 2.62 (t, 1H, J=6.5 Hz), □□ 2.56 (d, 1H, J=5.0 Hz), 2.35-2.36 (m, 2H), □□ 2.18-2.23 (m, 1H), □□ 2.06 (d, 1H, J=11.0 Hz), 1.81 (s, 3H), □□ 1.72-1.81 (m, 2H), □□ 1.23 (s, 3H), 0.96-0.99 (m, 1H), □□ 0.89 (s, 9H), 0.09 (d, 1H, J=15.0 Hz). MS (ESI) m/z 473 $[M+Na]^+$

For G-5-3-Z:
$^1$HNMR (500 MHz, $CDCl_3$) δ 5.75 (t, 1H, J=11.5 Hz), 4.27 (s, 1H), 3.33 (dd, 1H, J=2.0 Hz, J=11.0 Hz), 3.31 (s, 3H), 2.72 (d, 1H, J=4.5 Hz), 2.45-2.53 (m, 3H), □□ 2.08-2.21 (m, 2H), □□ 1.94 (d, 1H, J=11.0 Hz), 1.78 (s, 3H), □□ 1.62-1.68 (m, 2H), □□ 1.08 (s, 3H), 0.85-0.88 (m, 1H), □□ 0.79 (s, 9H), 0.01 (d, 1H, J=15.0 Hz). MS (ESI) m/z 473 $[M+Na]^+$

Compound G-5-4-E:

To a solution of G-5-3-E (140 mg, 0.32 mmol) in dry THF (1 mL) was added dropwise a solution of TBAF (1.0 M in THF, 0.26 mL, 0.26 mmol) at 0° C. The mixture was stirred overnight at room temperature, diluted with $H_2O$ and EtOAc, and extracted with EtOAc. The organic extract was washed with brine, dried ($Na_2SO_4$), filtered, and concentrated in vacuo. The resulting crude residue was purified on silica gel to afford G-5-4-E (12 mg, 11%) as a colorless oil:
$^1$HNMR (500 MHz, $CDCl_3$) δ 6.18 (t, 1H, J=7.0 Hz), 4.38 (s, 1H), 3.62 (dd, 1H, J=2.5 Hz, J=11.0 Hz), 3.49 (s, 3H), 2.78 (d, 1H, J=4.0 Hz), 2.66 (t, 1H, J=6.5 Hz), □□ 2.59 (d, 1H, J=4.0 Hz), 2.34-2.38 (m, 2H), □□ 2.17-2.23 (m, 1H), □□ 1.94-2.02 (m, 2H), □□ 1.73-1.81 (m, 4H), 1.25 (s, 3H), 0.97-1.00 (m, 1H).

Example 122: Expression and Purification of Recombinant Human MetAP2

Exemplary procedures for expression and purification of MetAP2 are shown in Griffith et al. (PNAS (1998) 95(26): 15183-15188). Briefly, recombinant His-tagged human MetAP2 is expressed by using a Bac-to-Bac baculovirus expression system (GIBCO/BRL). Recombinant baculovirus stocks are generated and amplified as per the manufacturer's instructions. Protein is harvested 36 hr after baculovirus infection of two 15-cm plates of High Five cells.

The cell pellet are weighed and lysed (in 5 ml/g of wet pellet) in pre-chilled lysis buffer [buffer B+1% Nonidet P-40/1 mM phenymethylsulfonyl fluoride (PMSF)/2 µg/ml leupeptin/2 µg/ml aprotinin/1 µg/ml pepstatin]. The lysate is incubated on ice for 10 min and centrifuged at 10,000×g for 10 min. The supernatant is diluted to 6 ml in buffer B and incubated for 1 hr at 4° C. with 1 ml of pre-equilibrated Talon resin (CLONTECH). The Talon resin is pelleted by centrifugation at 1,200×g for 3 min and washed with 4×10 ml of buffer B. During the final wash, the resin is slurried into a Bio-Rad Econo column. The 6×His-tagged MetAP2 is eluted with 6 ml of 50 mM imidazole in buffer B, and 0.5 ml fractions are collected. The amount and purity of recombinant MetAP2 is analyzed by the absorbance at 280 nm and SDS/PAGE (10% gel). The fractions containing the highest amounts of MetAP2 are pooled and dialyzed against 3 liters of buffer B overnight before storage at 4° C.

Example 123: Assay of Inhibition of Compounds Against MetAP2

An enzyme assay is performed in a 96-well format as described in Griffith et al. (PNAS (1998) 95(26):15183-15188). Various concentrations of compounds of the invention herein and a solvent control are incubated with 1 nM recombinant MetAP2 in buffer A (20 mM Hepes, pH 7.5/40 mM KCl/1.5 mM $CoCl_2$) for 1 hr at 4° C. To begin the enzymatic reaction, Met-Gly-Met-Met is added to a final concentration of 4 mM and incubated at 37° C. The reaction is quenched after 20 min by adding EDTA to a concentration of 10 mM. Released methionine is quantitated as described in Ben-Bassat et al. (J Bacteriol (1987) 169:751-757).

$IC_{50}$ values are calculated and compounds herein are determined to be active inhibitors of MetAP2, with some having nanomolar activities. The compounds provided herein are found to have $IC_{50}$ values for MetAP2 inhibition in the range from about 0.005 to about 100 µM, or about 0.002 to about 50 µM, including, for example, the range from about 0.001 to about 2 µM or lower. Results are indicated in Table Q.

Example 124: Weight Loss without Substantial Reduction of Lean Body Mass

Lean body mass is important to normal function in subjects. Substantial loss of lean body mass is not a desirable consequence of a therapy for an overweight or obese subject. A study is undertaken to analyze weight loss with respect to lean body mass.

Mice are divided into two groups, a diet-induced obese group and a lean group (control). For the diet-induced obese group, C57BL/6NTac mice maintained prior to and during the study on a diet containing 60% fat on a kilocalorie basis are further divided into two groups, fifteen mice per group. Average body weight of these diet-induced obese mice is 40 g at the start of the study. For the lean group, fifteen C57BLI6NTac mice are maintained on a diet containing 4.3% by weight fat prior to and during the study. Average body weight of these lean mice is 33 g at the start of the study. Daily food consumption is also recorded.

Compounds of the invention are administered to one of the diet-induced obese mice groups by oral gavage as a solution in 10% DMSO, at dose of 1 mg/kg/day, 7 days. The other diet-induced obese mice group and the lean mice group are not administered anything.

Results shown in Table A.

| 1 hr 200 nM | 1 hr 50 nM | 2 hr 200 nM | 2 hr 50 nM | 4 hr 200 nM | 4 hr 50 nM | Cell Based Assay Inhibition Range | Mice Wt Loss 7 day % WL 1 mpk | Example # |
|---|---|---|---|---|---|---|---|---|
| 100% | 42% | 100% | 65% | 100% | 79% | <10 nM | 10.8 | |
| 100% | 62% | 100% | 90% | 100% | 100% | <10 nM | 5. | 3 |
| 50% | 46% | 53% | 58% | 94% | 94% | 10-100 nM | 12.5 | 4 |
| 58% | 15% | 75% | 30% | 93% | 50% | <10 nM | 9.5 | 5 |
| 12% | 0% | 15% | 0% | 57% | 0% | >1 uM | 1.7 | 6 |
| 0% | 0% | 0% | 0% | 0% | 0% | >1 uM | 0.5 | 7 |
| 89% | 46% | 100% | 65% | 100% | 93% | <10 nM | 11.3 | 8 |
| 27% | 12% | 45% | 35% | 64% | 50% | 0.1-1 uM | 3.3 | 9 |
| 89% | 0% | 100% | 5% | 100% | 21% | <10 nM | 8.3 | 10 |
| | | | | | | ND | ND | 11 |
| 31% | 0% | 45% | 5% | 79% | 29% | 0.1-1 uM | 8.4 | 12 |
| 36% | 26% | 40% | 32% | 60% | 40% | 0.1-1 uM | 7.9 | 15 |
| 7% | 0% | 0% | 0% | 0% | 0% | >1 uM | 5.4 | 16 |
| 42% | 29% | 48% | 44% | 60% | 40% | >1 uM | 0.1 | 17 |
| 0% | 0% | 0% | 0% | 0% | 0% | >1 uM | 0 | 18 |
| 0% | 0% | 0% | 0% | 0% | 0% | >1 uM | −0.9 | 19 |
| 0% | 0% | 0% | 0% | 0% | 0% | >1 uM | 0.4 | 20 |
| 0% | 0% | 0% | 0% | 0% | 0% | >1 uM | | 21 |
| 0% | 0% | 0% | 0% | 0% | 0% | >1 uM | | 22 |
| 29% | 23% | 34% | 28% | 40% | 27% | 10-100 nM | −0.33 | 23 |
| 0% | 0% | 0% | 0% | 0% | 0% | 10-100 nM | | 24 |
| 29% | 19% | 34% | 40% | 80% | 40% | 10-100 nM | 0.1 | 25 |
| 0% | 0% | 0% | 0% | 33% | 0% | | | 26 |
| | | | | 89% | 48% | 10-100 nM | 4.4 (0.3) | 27 |
| | | | | 100% | 63% | <10 nM | 5.7 | 29 |
| | | | | 96% | 30% | <10 nM | −0.9 | 30 |
| | | | | 0% | 0% | | | 31 |
| | | | | 100% | 54% | <10 nM | 0.3 | 32 |
| | | | | 100% | 43% | <10 nM | 2.1 | 33 |
| | | | | 100% | 64% | <10 nM | | 36 |
| | | | | | | | | 38 |
| | | | | 93% | 96% | <10 nM | | 37 |
| 44% | 0% | 100% | 44% | 100% | 78% | | | 51 |
| 0% | 0% | 28% | 0% | 61% | 17% | | | 52 |
| 0% | 0% | 11% | 0% | 67% | 28% | | | 53 |
| 0% | 0% | 0% | 0% | 0% | 0% | | | 54 |
| | | | | 0% | 0% | | | 55 |
| | | | | 89% | 37% | | | 57 |
| | | | | 0% | 0% | | | 58 |
| | | | | 4% | 0% | 10-100 nM | | 59 |

Example 125: Weight Loss and Thioredoxin 1 (THX1)

Figure 2:
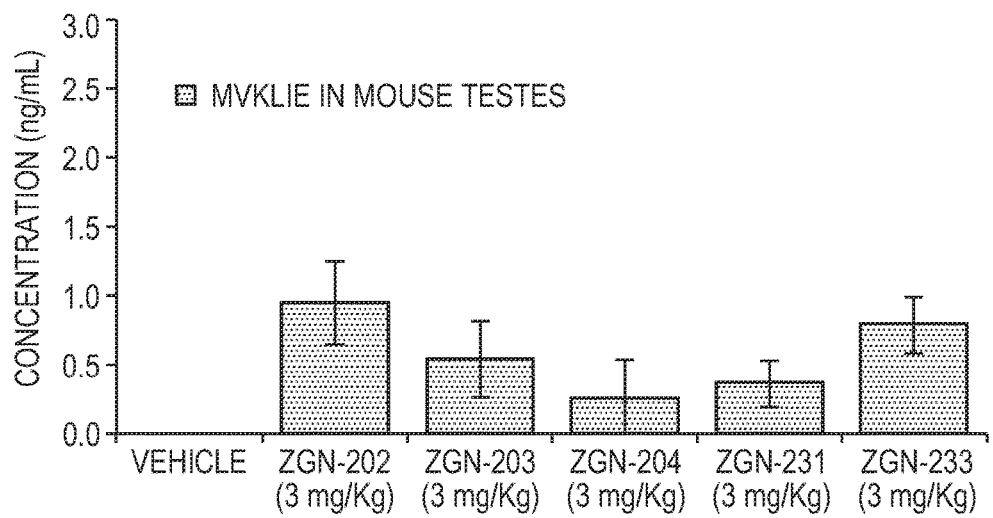
FIG. 2. shows the amount of THX1 N-terminal peptide in the testes of mice dosed PO once a day for 10 days with 3 mg/kg of compound 202, 203, 204, 231 or 233.
Figure 2:
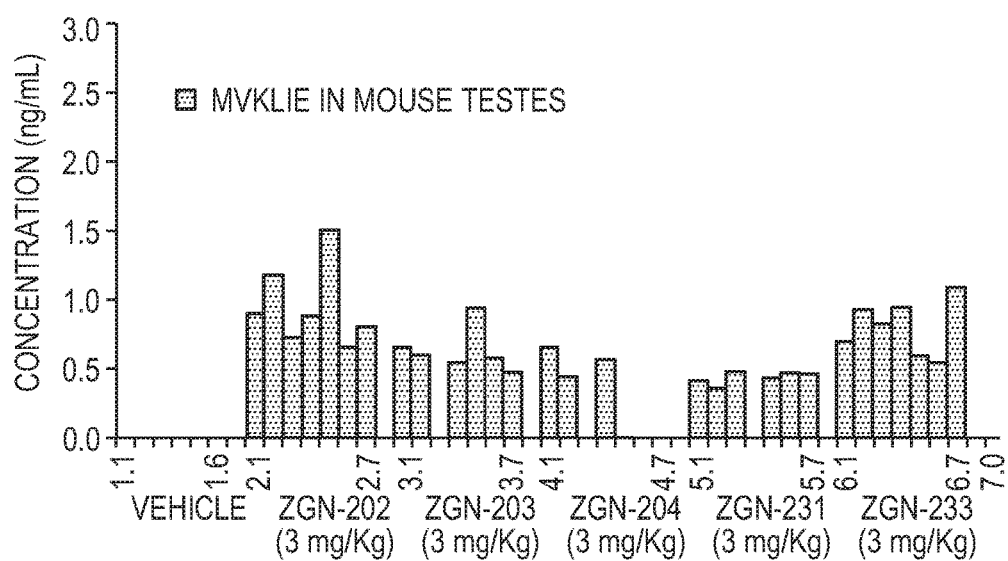
Figure 3:
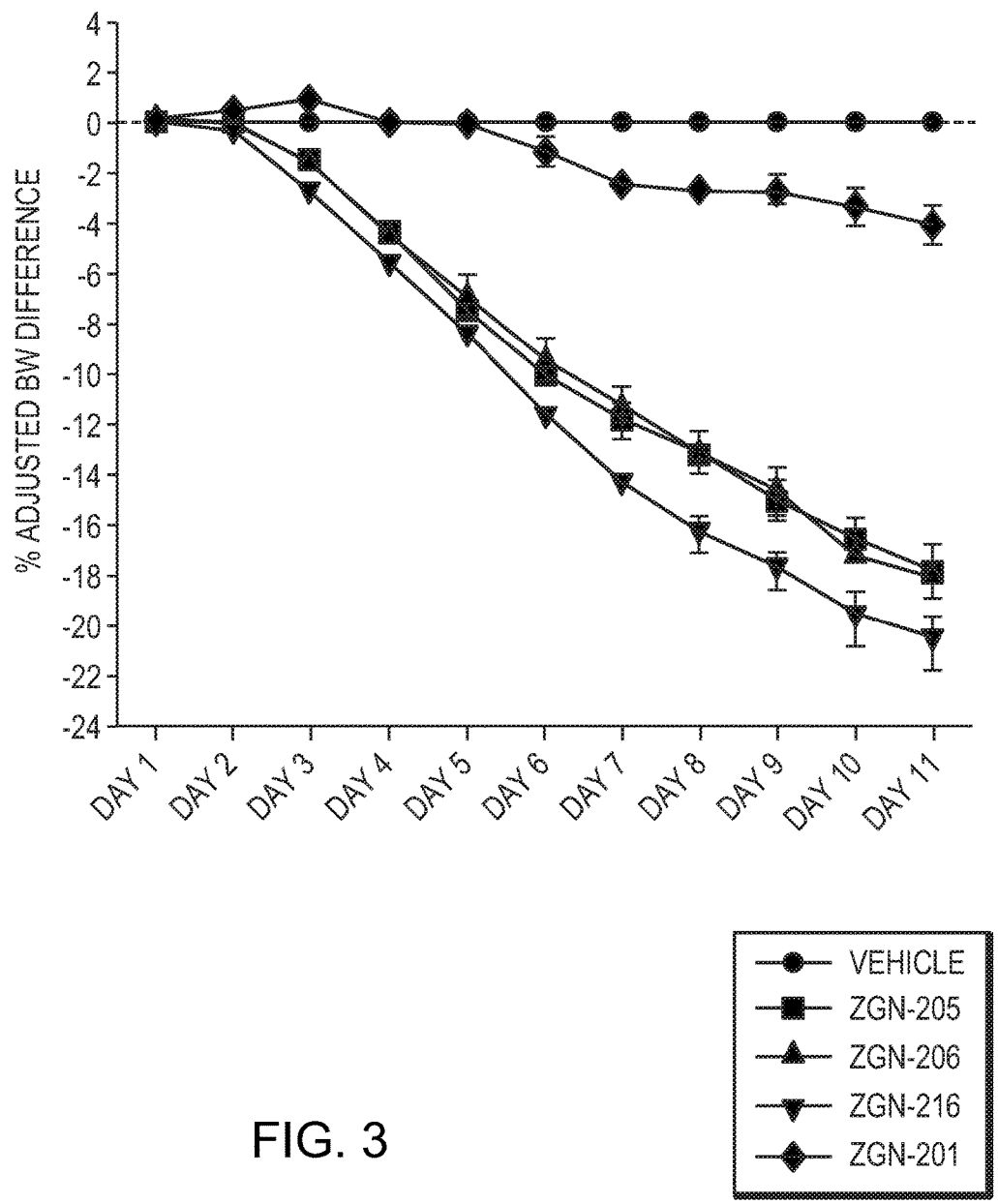
FIG. 3. depicts body weight % difference in mice dosed PO once a day for 10 days with 3 mg/kg of compound 201, 205, 206 or 216.
Figure 4:
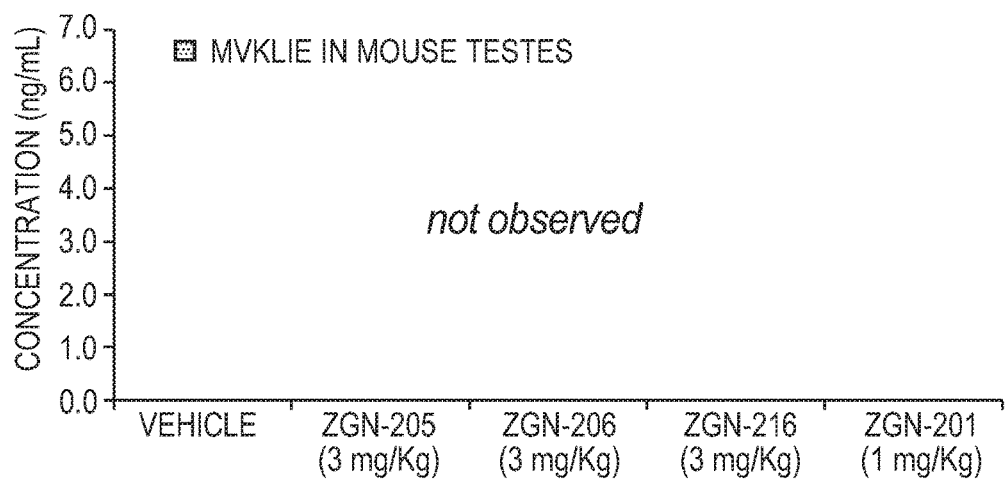
FIG. 4. shows the amount of THX1 N-terminal peptide in the testes of mice dosed PO once a day for 10 days with 3 mg/kg of compound 201, 205, 206 or 216.
Figure 4:
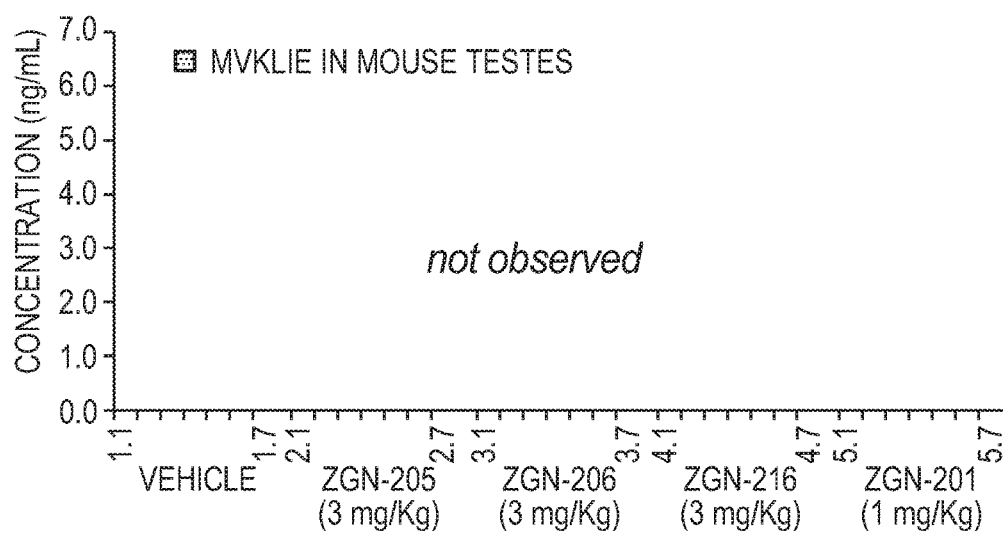

Diet-induced obese mice, C57BL/6NTac mice, were dosed PO once a day for 10 days with 3 mg/kg of compound 201 (fumagillin), 202, 203, 231 and 233. Body weight % difference from day 1 is shown in FIG. 1 for each analogue. On day 11, 24 hours after the last dose the mice are sacrificed and the testes are dissected out and frozen. The frozen testes are subsequently homogenized and subjected to endoproteinase Glu-C digestion. The resulting digest mixture is analyzed by LC-MS/MS to quantitate the level of the N-terminal peptide of thioredoxin (Thrx), amino acid 1-6. Thioredoxin is a selective substrate of the MetAP2 enzyme and the degree of unprocessed thioredoxin (amino acid 1-6 rather than the processed des-Met thioredoxin amino acid 2-6) is indicative of the level of MetAP2 inhibition in a given tissue. FIG. 2 shows the amount of THX1 N-terminal peptide in the mouse testes after such a Glu-C digestion and indicates the degree to which these analogues inhibit the enzyme in the testes. FIGS. 3 and 4 shows the same experiment with compounds 201, 205, 206 and 216. No inhibition of the enzyme is observed with these analogues meaning that testicular exposure is minimized with these analogues despite robust weight loss over this 10 days of treatment.

What is claimed is:
1. A compound selected from the group consisting of:

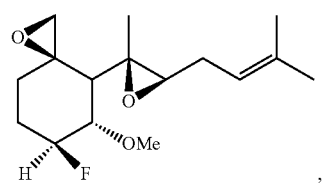

,

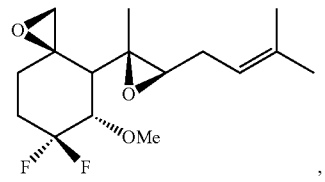

,

163
-continued

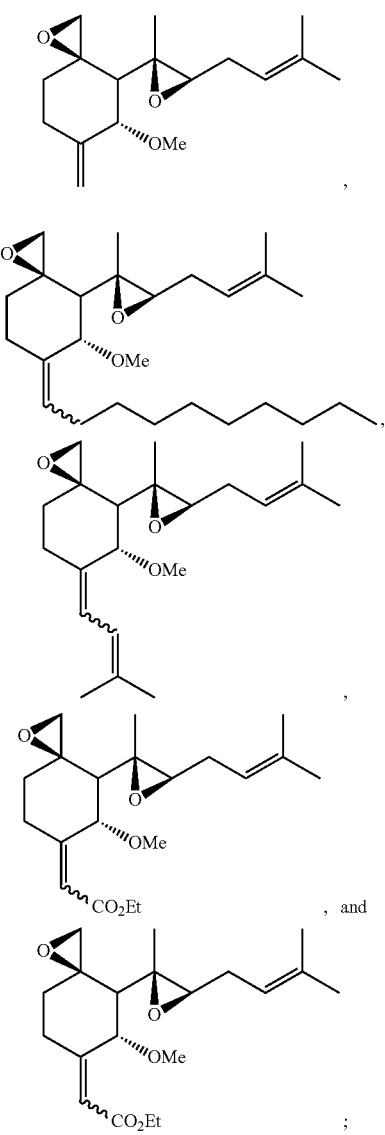

and a pharmaceutically acceptable salt or stereoisomer thereof.

164

2. A compound selected from the group consisting of:

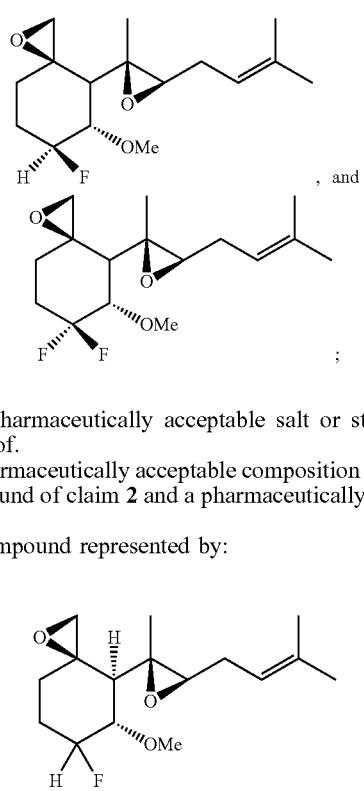

and a pharmaceutically acceptable salt or stereoisomer thereof.

3. A pharmaceutically acceptable composition comprising the compound of claim 2 and a pharmaceutically acceptable excipient.

4. A compound represented by:

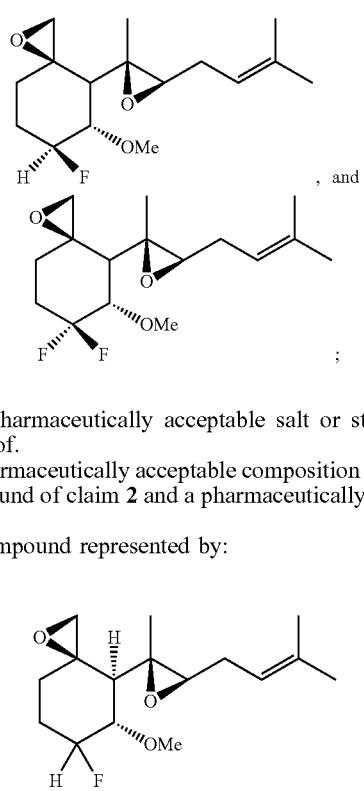

or a pharmaceutically acceptable salt thereof.

5. A pharmaceutically acceptable composition comprising the compound of claim 4, and a pharmaceutically acceptable excipient.

6. A method of treating and/or controlling obesity, comprising administering to a patient in need thereof an effective amount of the compound of claim 2.

7. The method of claim 6, wherein the patient is a human.

8. The method of claim 7, wherein the patient has a body mass index greater than or equal to about 25 kg/m² before the administration.

9. The method of claim 6, wherein after administration, thioredoxin 1 is not significantly present in the testes of a male patient.

* * * * *